US011209412B2

(12) United States Patent
Hasty et al.

(10) Patent No.: US 11,209,412 B2
(45) Date of Patent: Dec. 28, 2021

(54) MICROBIAL MICROFLUIDIC BIOSENSOR

(71) Applicant: The Regents of the University of California, Oakland, CA (US)

(72) Inventors: Jeff Hasty, Encinitas, CA (US); Leo Alexander Baumgart, San Diego, CA (US); Scott Cookson, Encinitas, CA (US); Michael Ferry, San Diego, CA (US); Garrett Graham, San Diego, CA (US); Ramon Huerta, San Diego, CA (US); Ryan Johnson, San Diego, CA (US); Lev Tsimring, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 733 days.

(21) Appl. No.: 15/551,124

(22) PCT Filed: Feb. 12, 2016

(86) PCT No.: PCT/US2016/017889
§ 371 (c)(1),
(2) Date: Jan. 26, 2018

(87) PCT Pub. No.: WO2016/133830
PCT Pub. Date: Aug. 25, 2016

(65) Prior Publication Data
US 2018/0149633 A1    May 31, 2018

Related U.S. Application Data

(60) Provisional application No. 62/116,888, filed on Feb. 16, 2015.

(51) Int. Cl.
*G01N 33/18* (2006.01)
*C12Q 1/02* (2006.01)
(Continued)

(52) U.S. Cl.
CPC ...... *G01N 33/1813* (2013.01); *B01L 3/50273* (2013.01); *C12M 23/16* (2013.01);
(Continued)

(58) Field of Classification Search
CPC ........... B01L 3/50273; B01L 2300/023; B01L 2300/0654; B01L 2400/0481;
(Continued)

(56) References Cited

U.S. PATENT DOCUMENTS

2010/0092955 A1    4/2010    Harriman
2010/0304379 A1    12/2010    Daunert et al.

FOREIGN PATENT DOCUMENTS

EP          2947155           11/2015
WO     WO2004078925           9/2004
(Continued)

OTHER PUBLICATIONS

King et al "A high-throughput microfluidic real-time gene expression living cell array" Lab on a Chip, 2007, 7: 77-85. (Year: 2007).*
(Continued)

*Primary Examiner* — Jeremy C Flinders
(74) *Attorney, Agent, or Firm* — Fish & Richardson P.C.

(57) ABSTRACT

Provided are a microfluidic biosensors that are suitable for continuously monitoring toxin levels in water supplies.

18 Claims, 78 Drawing Sheets

Specification includes a Sequence Listing.

(51) Int. Cl.
   *B01L 3/00*    (2006.01)
   *C12Q 1/6897*  (2018.01)
   *C12M 3/06*    (2006.01)
   *C12M 1/34*    (2006.01)
(52) U.S. Cl.
   CPC ............... *C12M 41/00* (2013.01); *C12Q 1/02* (2013.01); *C12Q 1/6897* (2013.01); *B01L 2300/023* (2013.01); *B01L 2300/0654* (2013.01); *B01L 2400/0481* (2013.01)
(58) Field of Classification Search
   CPC ......... C12M 23/16; C12M 41/00; C12Q 1/02; C12Q 1/6897; G01N 33/1813
   See application file for complete search history.

(56) References Cited

FOREIGN PATENT DOCUMENTS

| WO | WO2009036070 | 3/2009 |
| WO | WO2010092539 | 8/2010 |
| WO | WO2013090818 | 6/2013 |

OTHER PUBLICATIONS

Daunertetal. (Chemical Reviews, 2000, 100(7):2705-2737) (Year: 2000).*
San Francisco et al. (Nucleic Acids Research, 1990, 18:619-624). (Year: 1990).*
Aguilar-Barajas et al., "An lrp-type transcriptional regulator controls expression of the Bacillus subtilis chromate transporter," Antonie Van Leeuwenhoek, Dec. 2013, 104(6):941-948.
Anders et al., "Count-based differential expression analysis of RNA sequencing data using R and Bioconductor," Nat Protoc, Sep. 2013, 8(9):1765-1786.
Anders et al., "Differential expression analysis for sequence count data," Genome Biol, Oct. 2010, 11(10):R106.
Anders et al., "HTSeq—a Python framework to work with high-throughput sequencing data," bioinformatics, Sep. 2014, 31(2):166-169.
Branco et al., "Highly sensitive, highly specific whole-cell bioreporters for the detection of chromate in environmental samples," PLoS One, Jan. 2013, 8(1):e54005.
Branco et al., "The chromate-inducible chrbacf operon from the transposable element tnotchr confers resistance to chromium(vi) and superoxide," J Bacteriol, Nov. 2008, 190(21):6996-7003.
Busenlehner et al., "The smtb/arsr family of metalloregulatory transcriptional repressors: Structural insightsinto prokaryotic metal resistance," FEMS Microbiol Rev, Jun. 2003, 27(2-3):131-143.
Chu et al., "Regulation of the *Staphylococcus aureus* plasmid pi258 mercury resistance operon," J Bacteriol, Nov. 1992, 174(21):7044-7047.
Cortes et al., "Support-vector networks," Machine learning, Sep. 1995, 20(3):273-297.
Endo et al., "Cadc, the transcriptional regulatory protein of the cadmium resistance system of *Staphylococcus aureus* plasmid pi258," J Bacteriol, Aug. 1995, 177(15):4437-4441.
Hobman et al., "Cysteine coordination of pb(ii) is involved in the pbrr-dependent activation of the lead-resistance promoter, ppbra, from Cupriavidus metallidurans ch34," BMC Microbiol, Jun. 2012, 12:109.
Huerta et al., "Inhibition in multiclass classification," Neural computation, Sep. 2012, 24(9):2473-2507.
International Preliminary Report on Patentability for corresponding International Application No. PCT/US16/17889, dated Aug. 22, 2017, 6 pages.
International Search Report for corresponding International Application No. PCT/US16/17889, dated Jun. 24, 2016, 4 pages.
Ivask et al., "Detection of organomercurials with sensor bacteria," Anal Chem, Nov. 2001, 73(21):5168-5171.
Jaroslawiecka et al., "Lead resistance in microorganisms," Microbiology, Jan. 2014, 160(Pt 1):12-25.
Karlin et al., "Methods for assessing the statistical significance of molecular sequence features by using general scoring schemes," Proc. Natl. Acad. Sci. (U.S.A.), Mar. 1990, 87:2264-2268.
Langmead et al., "Ultrafast and memory-efficient alignment of short DNA sequences to the human genome," Genome Biol, Mar 2009, 10(3):R25.
Lee et al., "Chromosomal locus for cadmium resistance in pseudomonas putida consisting of a cadmium-transporting atpase and a merr family response regulator," Appl Environ Microbiol, Apr. 2001, 67(4):1437-1444.
Needleman et al., "A general method applicable to the search for similarities in the amino acid sequence of two proteins," J. Mol. Biol., Mar. 1970, 48(3):443-453.
Norseth, "The carcinogenicity of chromium," Environmental health perspectives, Aug. 1981, 40:121.
Nucifora et al., "Mercury operon regulation by the men gene of the organomercurial resistance system of plasmid pdu1358," J Bacteriol, Aug. 1989, 171(8):4241-4247.
Park et al., "Genetic analysis of the tn21 mer operatorpromoter," J Bacteriol, Apr. 1992, 174(7):2160-2171.
Paustenbach et al., "Human health risk and exposure assessment of chromium (vi) in tap water," J. Toxicol Environ Health A, Jul. 2003, 66(14):1295-1339.
Pearson et al., "Improved tools for biological sequence comparison," Proc. Natl. Acad. Sci. (U.S.A.), Apr. 1988, 85(8):2444-2448.
Permina et al., "Comparative genomics of regulation of heavy metal resistance in eubacteria," BMC Microbiol, Jun. 2006, 6(1):49.
Quinlan et al., "BEDTools: a flexible suite of utilities for comparing genomic features," Bioinformatics, Mar. 2010, 26(6):841-842.
Rensing et al., "*Escherichia coli* mechanisms of copper homeostasis in a changing environmen," FEMS Microbiol Rev, Jun. 2003, 27(2-3):197-213.
Rodriguez-Lujan et al., "Quadratic programming feature selection," The Journal of Machine Learning Research, Apr. 2010, 11:1491-1516.
Rother et al., "Purification and characterization of men the regulator of the broad-spectrum mercury resistance genes in streptomyces lividans 1326," Mol Gen Genet, Aug. 1999, 262(1):154-162.
Smith et al., "Comparison of biosequences," Advances in applied mathematics, Dec. 1981, 2(4):482-489.
Stocker et al., "Development of a set of simple bacterial biosensors for quantitative and rapid measurements of arsenite and arsenate in potable water," Environ Sci Technol, Oct. 2003, 37(20):4743-4750.
Stout et al., "Hexavalent chromium is carcinogenic to f344/n rats and b6c3f1 mice after chronic oral exposure," Environ Health Perspect, May 2009, 117(5):716-722.
Vergara et al., "Chemical gas sensor drift compensation using classifier ensembles," Sensors and Actuators B: Chemical, May 2012, 166:320-329.
Vergara et al., "On the performance of gas sensor arrays in open sampling systems using inhibitory support vector machines," Sensors and Actuators B: Chemical, Aug. 2013, 185:462-477.
Written Opinion for corresponding International Application No. PCT/US16/17889, dated Jun. 24, 2016, 5 pages.
Wu et al., "Metalloregulated expression of the ars operon," J Biol Chem, Jan. 1993, 268(1):52-58.
Xu et al., "The chromosomal arsr gene of *Escherichia coli* encodes a trans-acting metalloregulatory protein," J Biol Chem, Feb. 1996, 271(5):2427-2432.
Bereza-Malcolm et al., "Environmental Sensing of Heavy Metals Through Whole Cell Microbial Biosensors: A Synthetic Biology Approach", ACS Synthetic Biology, vol. 4, No. 5, pp. 535-546, 2014.
Extended European Search Report in European Application No. PCT/US2016017889, dated Aug. 13, 2018, 9 pages.
CN Office Action in Chinese Appln. No. 201680022244.7, dated Jan. 25, 2021, 3 pages.
EP Office Action in European Appln. No. 16752856.1, date Dec. 22, 2020, 5 pages.

* cited by examiner

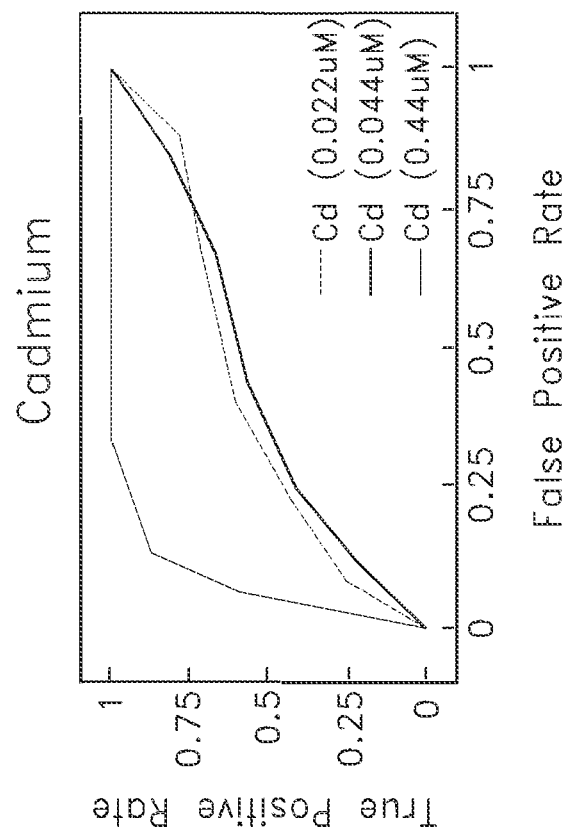
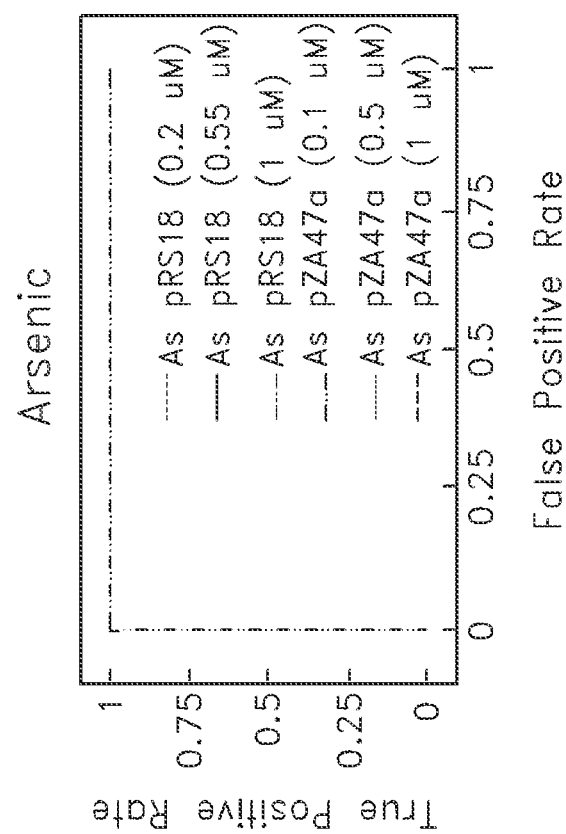
FIG. 8B
FIG. 8A

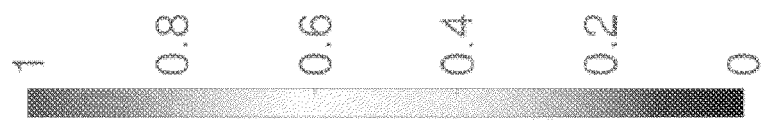
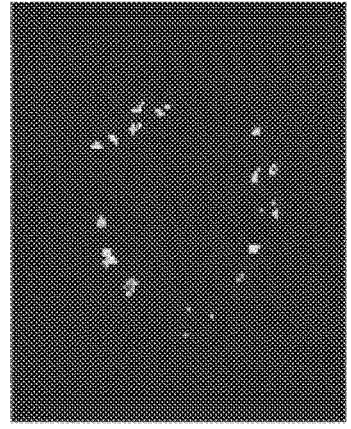
FIG. 11A
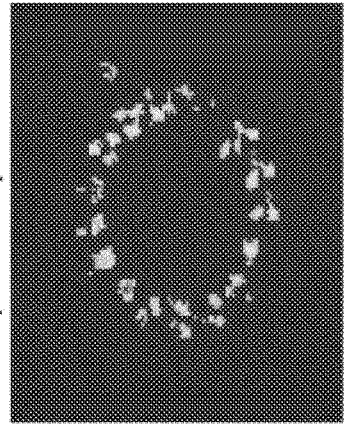
FIG. 11B
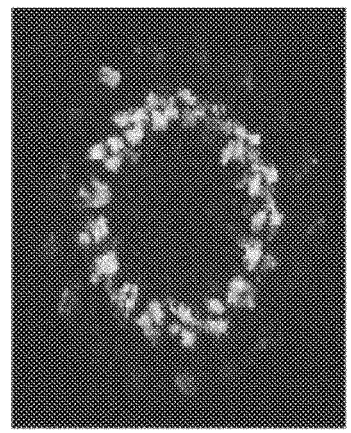
FIG. 11C
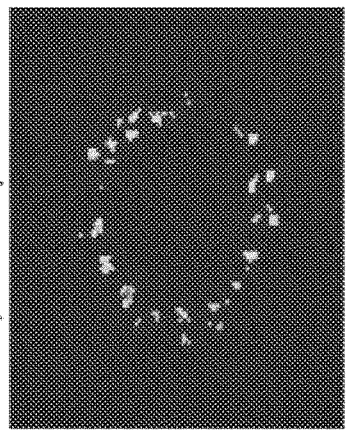
FIG. 11D FIG. 17
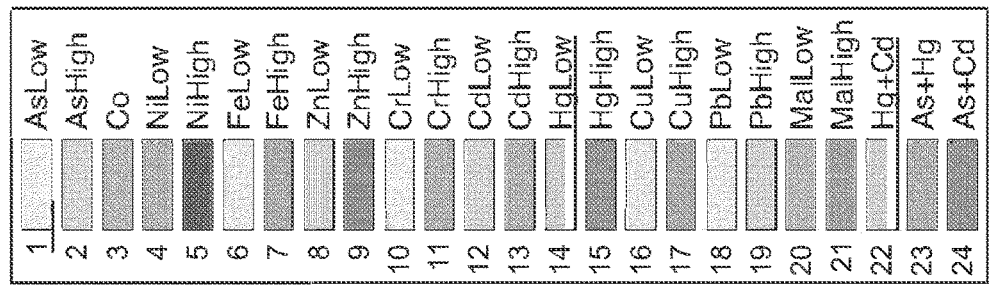
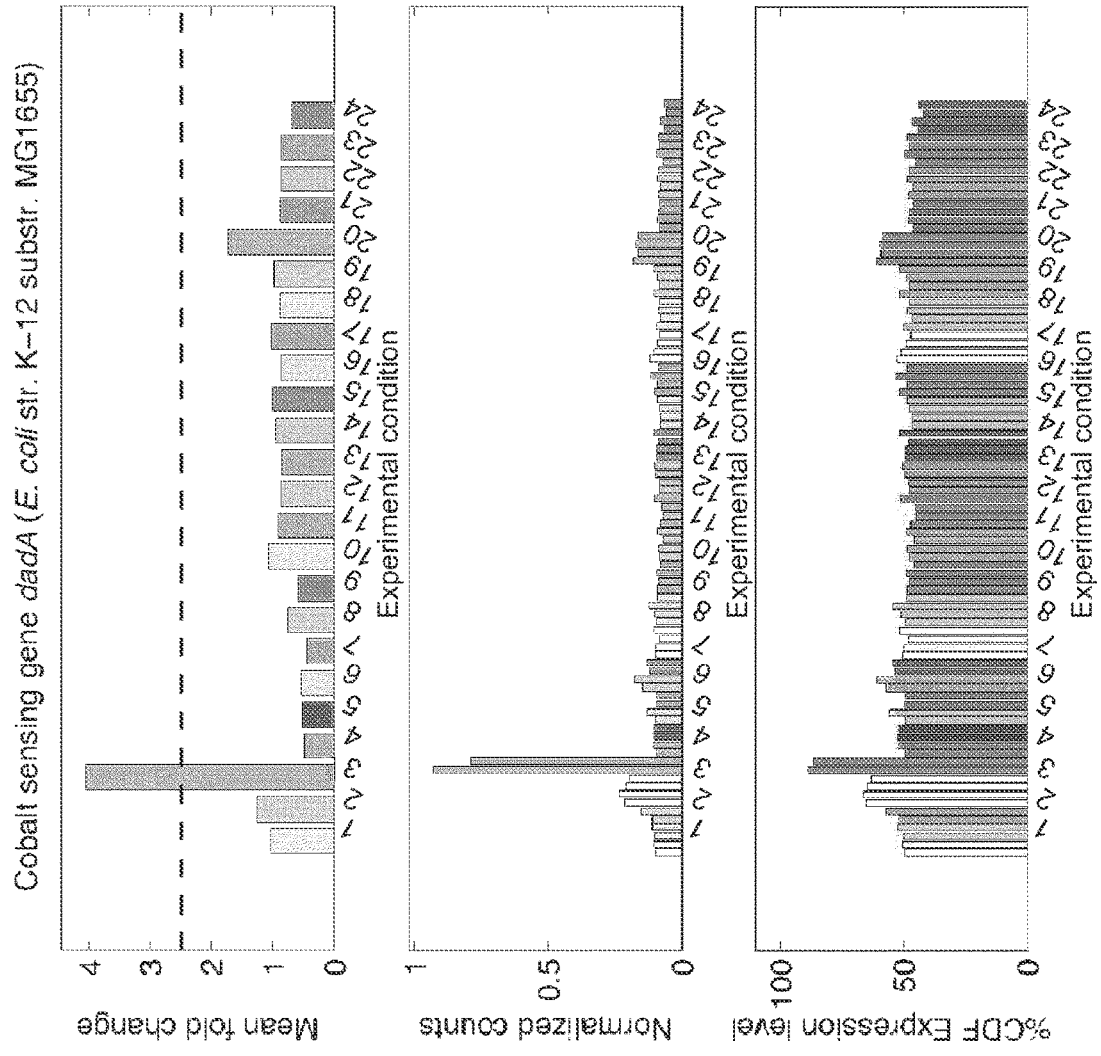

FIG. 41A Ammonium
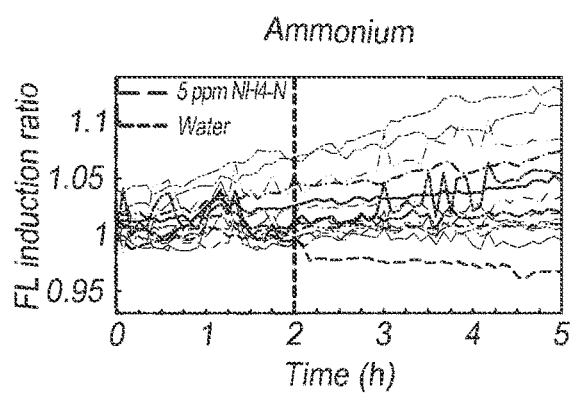
FIG 41B Ammonium
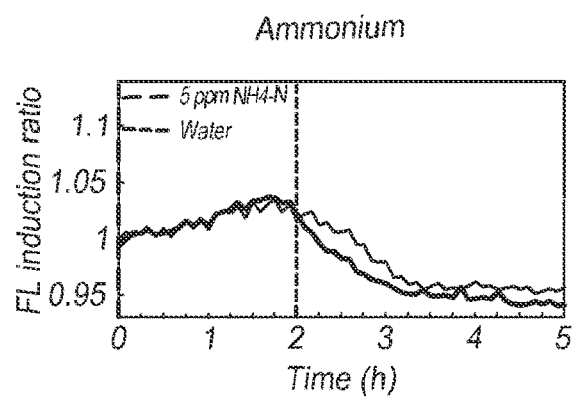
FIG. 41G Cobalt
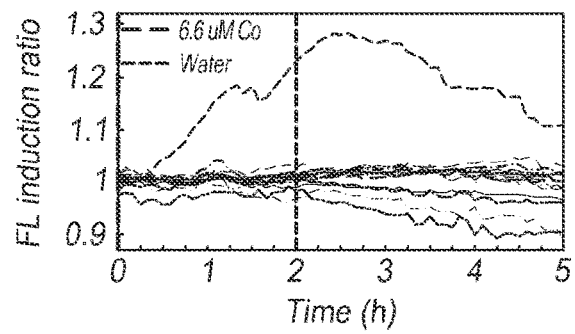
FIG. 41D Cobalt
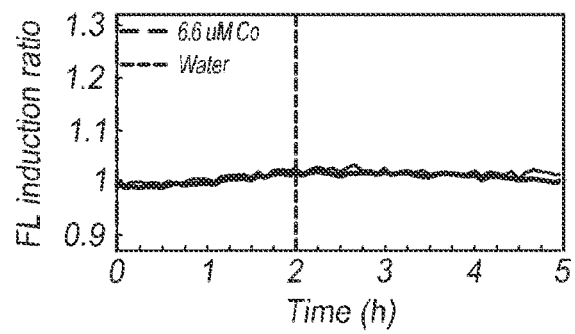
FIG. 41E Lead
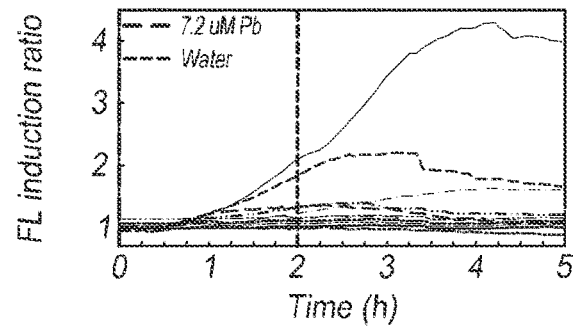
FIG. 41F Lead
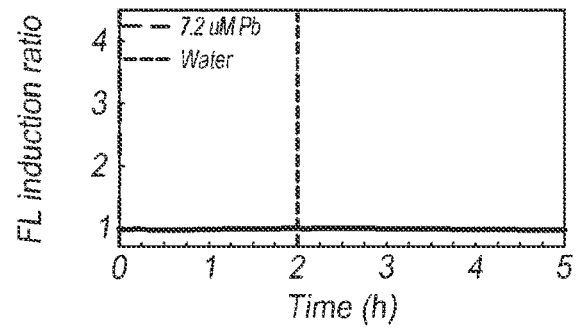
E. coli MG1655 strains:
— As7  — Cd1  — Cu1  — Hg3+  — Pb7  — Co2  — Co3
— As7  — Cd1  — Co7  — Cr11  — Cu1  — Pb7  — Hg3
B. subtilis NCIB 3610 strains:
— Amm3
— Amm3

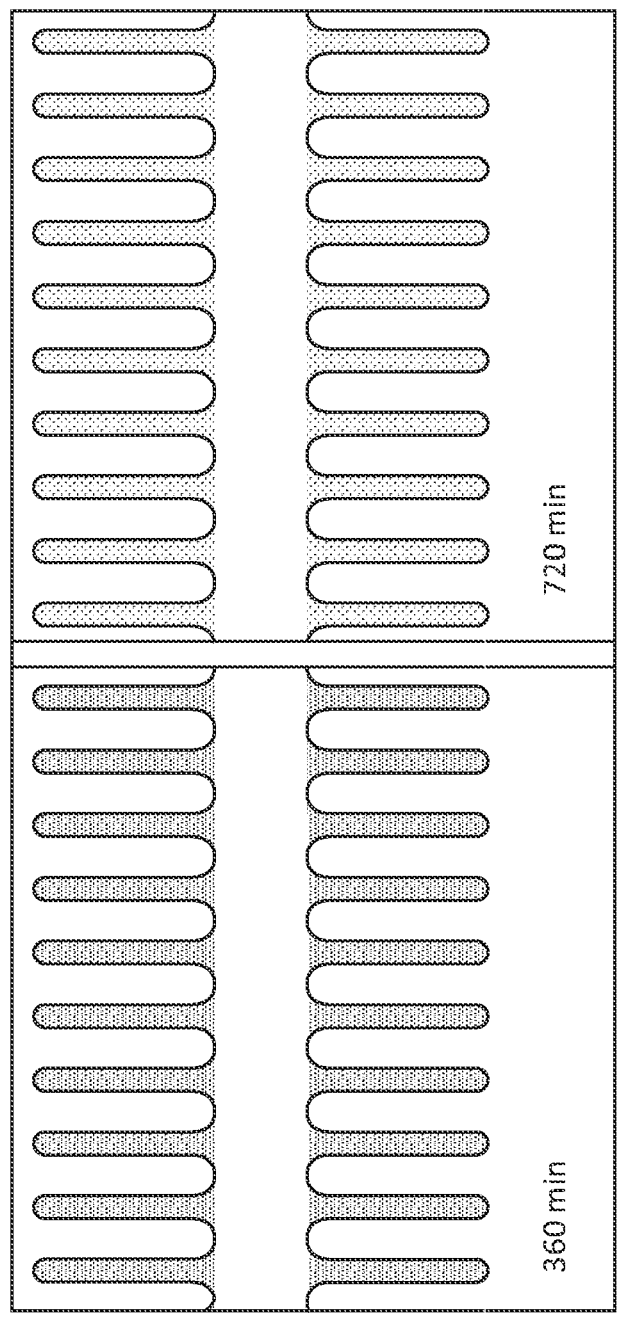

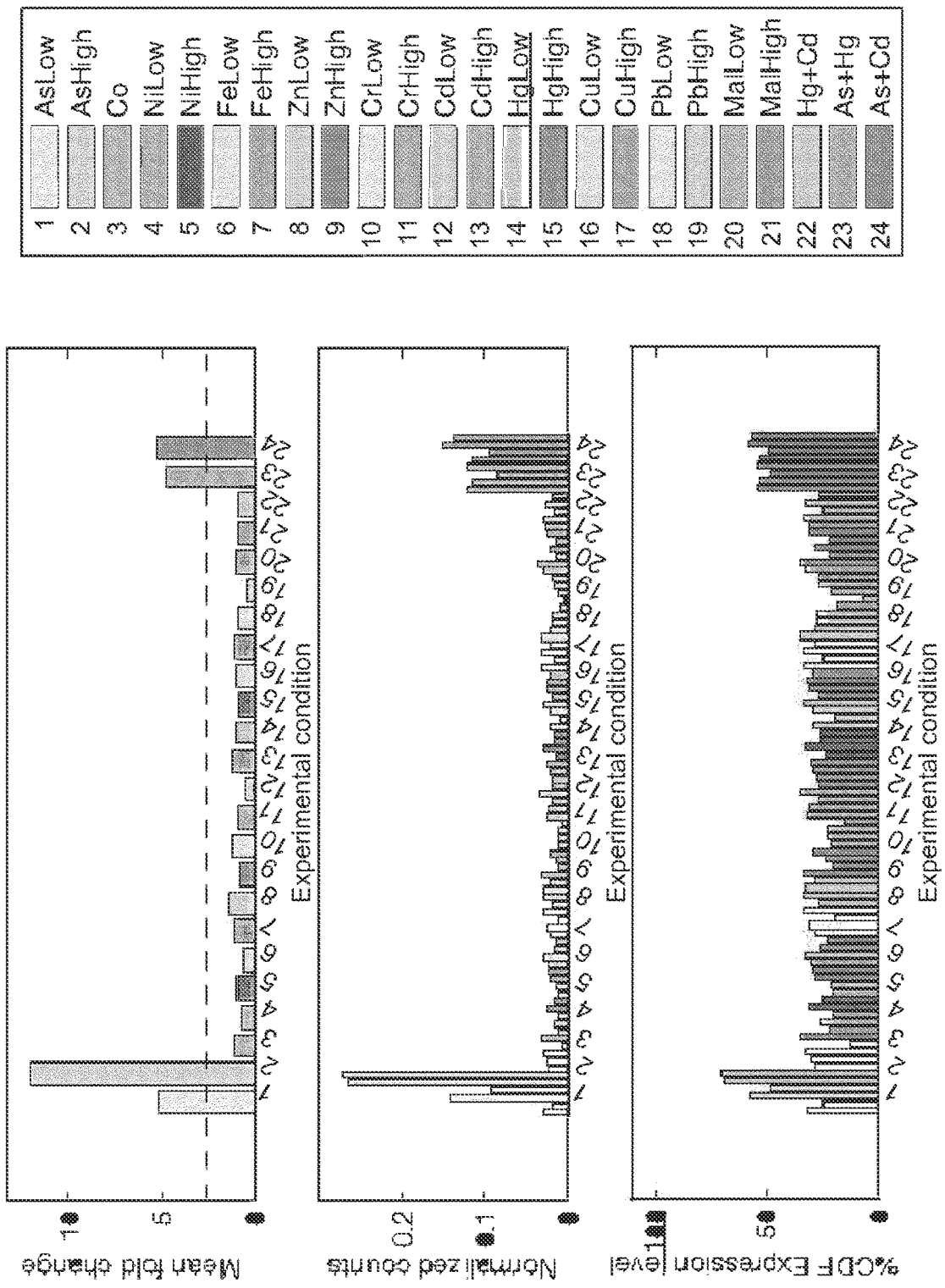

SEQUENCE LISTING

<160> NUMBER OF SEQ ID NOS: 43

<210> SEQ ID NO 1
<211> LENGTH: 125
<212> TYPE: DNA
<213> ORGANISM: Artificial Sequence
<220> FEATURE:
<223> OTHER INFORMATION: pLB-Amm3, promoter and operator and RBS driving
      the detectable protein

<400> SEQUENCE: 1
atgtgtaagt ttttgtgaca cgtttaatgc gttaacaatg cattgtgaca taatttttaa      60
taggagaaaa cttacgagct tcgccaaagg aggtctgata catggattca atagaaaagg     120
taagc                                                                 125

<210> SEQ ID NO 2
<211> LENGTH: 523
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-As7, promoter and operator and RBS driving
      the detectable protein, polynucleotide encoding
      regulatory protein arsR

<400> SEQUENCE: 2
gtaatagtgt gattaatcat atgcgttttt ggttatgtgt tgtttgactt aatatcagag      60
ccgagagata cttgttttct acaaaggaga gggaaatgtt gcaactaaca ccacttcagt     120
tatttaaaaa cctgtccgat gaaacccgtt tgggtatcgt gttgttgctc agggagatgg     180
gagagttgtg cgtgtgtgat ctttgcatgg cactggatca atcacagccc aaaatatccc     240
gtcatctggc gatgctacgg gaaagtggaa tccttctgga tcgtaaacag ggaaaatggg     300
ttcactaccg cttatcaccg catattcctt catgggctgc ccagattatt gagcaggcct     360
ggttaagcca acaggacgac gttcaggtca tcgcacgcaa gctggcttca gttaactgct     420
ccggtagcag taaggctgtc tgcatctaaa aaatttgcct gaacatatat gttttatcaa     480
atgcgaggta tttaaggaat tcattaaaga ggagaaaggt acc                       523

```
<210> SEQ ID NO 3
<211> LENGTH: 95
<212> TYPE: DNA
<213> ORGANISM: Artificial Sequence
<220> FEATURE:
<223> OTHER INFORMATION: pLB-As7, promoter and operator and RBS driving
      the detectable protein

<400> SEQUENCE: 3
gtaatagtgt gattaatcat atgcgttttt ggttatgtgt tgtttgactt aatatcagag     60
ccgagagata cttgttttct acaaaggaga gggaa                                95

<210> SEQ ID NO 4
<211> LENGTH: 354
<212> TYPE: DNA
<213> ORGANISM: Escherichia coli
<220> FEATURE:
<221> NAME/KEY: misc_feature
<222> LOCATION: (0)...(0)
<223> OTHER INFORMATION: 4 polynucleotide encoding regulatory protein
      arsR

<400> SEQUENCE: 4
atgttgcaac taacaccact tcagttattt aaaaacctgt ccgatgaaac ccgtttgggt     60
atcgtgttgt tgctcaggga gatgggagag ttgtgcgtgt gtgatctttg catggcactg    120
gatcaatcac agcccaaaat atcccgtcat ctggcgatgc tacgggaaag tggaatcctt    180
ctggatcgta acagggaaa  atgggttcac taccgcttat caccgcatat tccttcatgg    240
gctgcccaga ttattgagca ggcctggtta agccaacagg acgacgttca ggtcatcgca    300
cgcaagctgg cttcagttaa ctgctccggt agcagtaagg ctgtctgcat ctaa          354

<210> SEQ ID NO 5
<211> LENGTH: 469
<212> TYPE: DNA
<213> ORGANISM: Staphylococcus aureus
<220> FEATURE:
<221> NAME/KEY: misc_feature
<222> LOCATION: (0)...(0)
<223> OTHER INFORMATION: pLB-Cd1, promoter and operator and RBS driving
      the detectable protein, polynucleotide encoding
      regulatory protein CadC

<400> SEQUENCE: 5
cttacttctt ttattttcat tcaaatattt gcttgcatga tgagtcgaaa atggttataa     60
tacactcaaa taaatatttg aatgaagatg ggatgataat atgaaaaaaa aagatacctg    120
cgaaattttt tgctacgatg aagaaaaagt gaaccgtatt cagggagact tgcagaccgt    180
ggatatctcc ggtgtatccc agattctgaa ggcgatcgcg gatgaaaatc gtgccaagat    240
cacttatgcg ctgtgccagg atgaagaact ttgtgtttgt gatattgcga atattctcgg    300
ggtgactatc gcgaatgcat cacaccacct gcgcacattg tacaaacaag gtgtggttaa    360
ctttcgcaaa gaaggtaaat tggctctttta ttcgcttgga gacgaacaca tccgccaaat    420
tatgatgatc gcgctggccc ataaaaaaga agtaaaagtg aacgtctaa                469

<210> SEQ ID NO 6
<211> LENGTH: 100
<212> TYPE: DNA
<213> ORGANISM: Artificial Sequence
<220> FEATURE:
<223> OTHER INFORMATION: pLB-Cd1, promoter and operator and RBS driving
      the detectable protein

<400> SEQUENCE: 6
```

```
cttacttctt ttattttcat tcaaatattt gcttgcatga tgagtcgaaa atggttataa      60
tacactcaaa taaatatttg aatgaagatg ggatgataat                           100

<210> SEQ ID NO 7
<211> LENGTH: 369
<212> TYPE: DNA
<213> ORGANISM: Staphylococcus aureus
<220> FEATURE:
<221> NAME/KEY: misc_feature
<222> LOCATION: (0)...(0)
<223> OTHER INFORMATION: Polynucleotide encoding regulatory protein CadC

<400> SEQUENCE: 7
atgaaaaaaa aagatacctg cgaaattttt tgctacgatg aagaaaaagt gaaccgtatt      60
cagggagact tgcagaccgt ggatatctcc ggtgtatccc agattctgaa ggcgatcgcg     120
gatgaaaatc gtgccaagat cacttatgcg ctgtgccagg atgaagaact ttgtgtttgt     180
gatattgcga atattctcgg ggtgactatc gcgaatgcat cacaccacct gcgcacattg     240
tacaaacaag gtgtggttaa cttcgcaaa gaaggtaaat tggctcttta ttcgcttgga     300
gacgaacaca tccgccaaat tatgatgatc gcgctggccc ataaaaaaga agtaaaagtg     360
aacgtctaa                                                            369

<210> SEQ ID NO 8
<211> LENGTH: 429
<212> TYPE: DNA
<213> ORGANISM: Mycobacterium tuberculosis
<220> FEATURE:
<221> NAME/KEY: misc_feature
<222> LOCATION: (0)...(0)
<223> OTHER INFORMATION: Promoter and operator and RBS driving the
      detectable protein, polynucleotide encoding
      regulatory protein nmtR

<400> SEQUENCE: 8
ccggccaaca tatcagaata tatgatcata tgttcattta tttctttggg gataggctgc      60
ctaaccatgg gacatggtgt ggaagggcgc aatcggccga cgccccgtt ggattcccag     120 gcggcagcgc aagttgcctc cacgctgcag gctctggcaa ccccgtctcg cctgatgatc     180
ctgacccagc tgcgcaacgg gccttttaccc gttacggatc tggccgaggc gattgggatg     240
gaacagagtg cggtgtctca ccagctgcgt gtgctgcgca atttaggtct tgtggtgggc     300
gaccgcgcgg gtcggtccat tgtctactct ctgtatgata cacacgttgc gcagctcctg     360
gacgaagcaa tctatcattc tgaacatctg caccttgggc tgtctgaccg ccatccctcg     420
gcgggttaa                                                            429

<210> SEQ ID NO 9
<211> LENGTH: 66
<212> TYPE: DNA
<213> ORGANISM: Mycobacterium tuberculosis
<220> FEATURE:
<221> NAME/KEY: misc_feature
<222> LOCATION: (0)...(0)
<223> OTHER INFORMATION: Promoter and operator and RBS driving the
      detectable protein

<400> SEQUENCE: 9
ccggccaaca tatcagaata tatgatcata tgttcattta tttctttggg gataggctgc      60
ctaacc                                                                66
```

<210> SEQ ID NO 10
<211> LENGTH: 363
<212> TYPE: DNA
<213> ORGANISM: Mycobacterium tuberculosis
<220> FEATURE:
<221> NAME/KEY: misc_feature
<222> LOCATION: (0)...(0)
<223> OTHER INFORMATION: Polynucleotide encoding regulatory protein nmtR

<400> SEQUENCE: 10

```
atgggacatg gtgtggaagg gcgcaatcgg ccgagcgccc cgttggattc ccaggcggca    60
gcgcaagttg cctccacgct gcaggctctg gcaaccccgt ctcgcctgat gatcctgacc   120
cagctgcgca acgggccttt acccgttacg gatctggccg aggcgattgg gatggaacag   180
agtgcggtgt ctcaccagct gcgtgtgctg cgcaatttag gtcttgtggt gggcgaccgc   240
gcgggtcggt ccattgtcta ctctctgtat gatacacacg ttgcgcagct cctgacgaa    300 gcaatctatc attctgaaca tctgcacctt gggctgtctg accgccatcc ctcggcgggt   360
taa                                                                 363
```

<210> SEQ ID NO 11
<211> LENGTH: 200
<212> TYPE: DNA
<213> ORGANISM: Artificial Sequence
<220> FEATURE:
<223> OTHER INFORMATION: pLB-Co3, promoter and operator and RBS driving
      the detectable protein

<400> SEQUENCE: 11

```
gttaatcatt tcaggggaag aagcgaacgg cgagttcttg atgctggttc cgggaaagat    60
gctgttttgc agcttttgcg tgatgcttat gaagcaagta cgcaaaattg tatcggttgg   120
ctaacccttc ttctttggag tcatagtgcc ctttaagatt aagatgtaat ataaatacat   180
cttaatgagg tggaggcagc                                               200
```

<210> SEQ ID NO 12
<211> LENGTH: 210
<212> TYPE: DNA
<213> ORGANISM: Artificial Sequence
<220> FEATURE:
<223> OTHER INFORMATION: pLB-Co4, promoter and operator and RBS driving
      the detectable protein

<400> SEQUENCE: 12

```
gttaatcatt tcaggggaag aagcgaacgg cgagttcttg atgctggttc cgggaaagat    60
gctgttttgc agcttttgcg tgatgcttat gaagcaagta cgcaaaattg tatcggttgg   120
ctaacccttc ttctttggag tcatagtgcc ctttaagatt aagatgtaat ataaatacat   180
cttgaattca ttaaagagga gaaaggtacc                                    210
```

<210> SEQ ID NO 13
<211> LENGTH: 142
<212> TYPE: DNA
<213> ORGANISM: Artificial Sequence
<220> FEATURE:
<223> OTHER INFORMATION: pLB-Co6, promoter and operator and RBS driving
      the detectable protein

<400> SEQUENCE: 13

```
cggttaaaaa ttctgaataa ataatcctaa gccaaattgc tgactacact taatctcacg    60
ttcagaagaa aagtgaacgt actctcattc acaacctaac gatgaggtct tgattgaatt   120
cattaaagag gagaaaggta cc                                            142
```

<210> SEQ ID NO 14
<211> LENGTH: 234
<212> TYPE: DNA
<213> ORGANISM: Artificial Sequence
<220> FEATURE:
<223> OTHER INFORMATION: pLB-Co8, promoter and operator and RBS driving the detectable protein

<400> SEQUENCE: 14

```
gatctcatat cagggacttg ttcgcacctt ccggaggcgt tatgagctgg cggccctttt      60
tgtatctgat tattaatccc cacccgctat taagcgcccg gcgcgggcat ctgcgtctgg     120
tgcagggttg actttgcatt ctgttaacaa acgcggtata acaaaccttc tttggatgtt     180
tagatgtcca tacgtttaga aggttatgaa ttcattaaag aggagaaagg tacc           234
```

<210> SEQ ID NO 15
<211> LENGTH: 251
<212> TYPE: DNA
<213> ORGANISM: Artificial Sequence
<220> FEATURE:
<223> OTHER INFORMATION: pLB-Cr11, promoter and operator and RBS driving the detectable protein

<400> SEQUENCE: 15

```
ataacataaa agaatgattc acattaacgg atccgttaac tacgaaaata ggcaacttat      60
tcttaagggg caagattaat ttatgttttc ccgtcaccaa cgacaaaatt tgcgaggctc     120
tttccgaaaa tagggttgat cttgttgtc actggatgta ctgtacatcc atacagtaac     180 tcacagggggc tggattgatt atgtacactt caggctatgc acatgaattc attaaagagg     240
agaaaggtac c                                                          251
```

<210> SEQ ID NO 16
<211> LENGTH: 208
<212> TYPE: DNA
<213> ORGANISM: Artificial Sequence
<220> FEATURE:
<223> OTHER INFORMATION: pLB-Cr12, promoter and operator and RBS driving the detectable protein

<400> SEQUENCE: 16

```
tattctatt tttagccggg tgatattttt catttctgct ggatgagcgt cgtcgccaga      60
aggccacgtg agcacaagat aagagaacga aaaatcagca gcctatgcag cgacaaatat     120
tgatagcctg aatcagtatt gatctgctgg caagaacaga ctactgtata taaaaacagt     180
agaattcatt aaagaggaga aggtacc                                         208
```

<210> SEQ ID NO 17
<211> LENGTH: 1102
<212> TYPE: DNA
<213> ORGANISM: Ochrobactrum tritici
<220> FEATURE:
<221> NAME/KEY: misc_feature
<222> LOCATION: (0)...(0)
<223> OTHER INFORMATION: pLB-Cr13, promoter and operator and RBS driving the detectable protein, polynucleotide encoding regulatory protein chrB

<400> SEQUENCE: 17

```
ttgacaatta atcatccggc tcgtataatg tgtggatgtg ctgcttccat tgtgattgcg      60
caaatgtccg tttttgcaat ctactcaaga ctttatttcg tagatcttat ctcattattg     120
tagtaacatc tacgacatga atcttctcag cccgatcttg tcactcccga cggaaaacgc     180
```

```
cactgtgcgc cagcgcacgt ggcgcgcgct gaaagcgagc ggagcggccg tgctgcgtga   240
cggcgtgtac ctgatgccgg accgtgacga atgccgcgca gttctggata acctggcttc   300
ggacgtgcgc gaaggcggtg gggtagcgca tgtgcttcgc atggaagacc cggagggtgt   360
caactttgta gccttattcg atcgctcaaa tgattttgct gccctgctgg tggatgtcca   420
tcatctgcgt caaaccctca ccctggacac tgtgcaggat gtcctgcgcc aagtgcgtaa   480
gctgcgcaaa tcctttacta cccttgtgga aattgatttc tatccgggtg aagcacagcg   540
ccaggcggat agcgcgcttt gtgagttgga gcaggcttgt gctcgtacac tctccccgga   600
tgagccgcat gcagtggaag gcaccattac gcgtctggac cgccttgact accaggcccg   660
tacctgggca actcgtgcac gcccctgggt tgatcgtctc gcgtcggcat ggttaattcg   720
tcgctttatt gatccgcagg cacgcatctt gtggctcgcc acgccggcag actgtccccc   780
agacgctctg ggcttcgatt ttgacggtgc aacctttagc catgtcgggt cgcgcgtcac   840
cttcgaggtg ctggcggctt cgtttggttt ggaacagccg gcaatcacgc gcatcgggtt   900
agtcgtgcat tatctggatg ttggcggcat ccaaccaccg gaggcgacag gtatcgaaag   960
tgttttggcc ggcctgcgtg aaaccgtcga ccatgatgac caactgttag cgattgcgtc  1020
aactgtattt gatggtctcc tggcctcttt tgaaaagggg accttgacag tgtaagaatt  1080
cattaaagag gagaaaggta cc                                            1102

<210> SEQ ID NO 18
<211> LENGTH: 136
<212> TYPE: DNA
<213> ORGANISM: Artificial Sequence
<220> FEATURE:
<223> OTHER INFORMATION: pLB-Cr13, promoter and operator and RBS driving
      the detectable protein

<400> SEQUENCE: 18
ttgacaatta atcatccggc tcgtataatg tgtggatgtg ctgcttccat tgtgattgcg    60
caaatgtccg ttttgcaat ctactcaaga ctttatttcg tagatcttat ctcattattg    120
tagtaacatc tacgac                                                   136

<210> SEQ ID NO 19
<211> LENGTH: 939
<212> TYPE: DNA
<213> ORGANISM: Ochrobactrum tritici
<220> FEATURE:
<221> NAME/KEY: misc_feature
<222> LOCATION: (0)...(0)
<223> OTHER INFORMATION: Polynucleotide encoding regulatory protein chrB

<400> SEQUENCE: 19
atgaatcttc tcagcccgat cttgtcactc ccgacggaaa acgccactgt gcgccagcgc    60
acgtggcgcg cgctgaaagc gagcggagcg gccgtgctgc gtgacggcgt gtacctgatg   120
ccggaccgtg acgaatgccg cgcagttctg gataacctgg cttcggacgt gcgcgaaggc   180 ggtgggtag cgcatgtgct tcgcatggaa gacccggagg gtgtcaactt tgtagcctta   240
ttcgatcgct caaatgattt tgctgccctg ctggtggatg tccatcatct gcgtcaaacc   300
ctcaccctgg acactgtgca ggatgtcctg cgccaagtgc gtaagctgcg caaatccttt   360
actacccttg tggaaattga tttctatccg ggtgaagcac agcgccaggc ggatagcgcg   420
ctttgtgagt tggagcaggc ttgtgctcgt acactctccc cggatgagcc gcatgcagtg   480
gaaggcacca ttacgcgtct ggaccgcctt gactaccagg cccgtacctg gcaactcgt   540
```

```
gcacgcccct gggttgatcg tctcgcgtcg gcatggttaa ttcgtcgctt tattgatccg    600
caggcacgca tcttgtggct cgccacgccg gcagactgtc ccccagacgc tctgggcttc    660
gattttgacg gtgcaacctt tagccatgtc gggtcgcgcg tcaccttcga ggtgctggcg    720
gcttcgtttg gttggaaca gccggcaatc acgcgcatcg ggttagtcgt gcattatctg    780
gatgttggcg gcatccaacc accggaggcg acaggtatcg aaagtgtttt ggccggcctg    840
cgtgaaaccg tcgaccatga tgaccaactg ttagcgattg cgtcaactgt atttgatggt    900
ctcctggcct cttttgaaaa agggaccttg acagtgtaa                          939
```

<210> SEQ ID NO 20
<211> LENGTH: 608
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Cu1, promoter and operator and RBS driving
    the detectable protein, polynucleotide encoding
    regulatory protein cueR

<400> SEQUENCE: 20

```
aaaacactcc tttaagacag ttttgactgg ctgtgataaa ggttaaacct tccagcaagg     60
ggaaggtcaa gaaattaata aaccaggcgg gtaaaagtcc tgtattattg tggtggcggt    120
cgatattcgc actggcaaaa aaacgtgctt gaatatctgt tgaaaccctt taacaaagca    180
caggaggcgt tgcgcgaacg atgaacatca gcgatgtagc aaaaattacc ggcctgacca    240
gcaaagccat tcgcttctat gaagagaagg ggctggtgac gccgccgatg cgcagcgaaa    300
acggttatcg cacctacacg cagcagcatc tcaacgaact gaccttactg cgccaggcac    360
ggcaggtggg cttaaacctg gaagagagcg gcgagctggt gaatctgttt aacgacccgc    420
agcggcacag cgccgacgtc aaacggcgca cgctggagaa ggtggcggag atcgaacgac    480
acattgagga gctgcaatcc atgcgcgacc agctgctggc actggcgaat gcctgccctg    540
gcgatgacag cgccgactgc ccgattatcg aaaatctctc cggctgctgt catcatcggg    600
cagggtga                                                            608
```

<210> SEQ ID NO 21
<211> LENGTH: 200
<212> TYPE: DNA
<213> ORGANISM: Artificial Sequence
<220> FEATURE:
<223> OTHER INFORMATION: pLB-Cu1, promoter and operator and RBS driving
    the detectable protein

<400> SEQUENCE: 21

```
aaaacactcc tttaagacag ttttgactgg ctgtgataaa ggttaaacct tccagcaagg     60
ggaaggtcaa gaaattaata aaccaggcgg gtaaaagtcc tgtattattg tggtggcggt    120
cgatattcgc actggcaaaa aaacgtgctt gaatatctgt tgaaaccctt taacaaagca    180
caggaggcgt tgcgcgaacg                                               200
```

<210> SEQ ID NO 22
<211> LENGTH: 408
<212> TYPE: DNA
<213> ORGANISM: Escherichia coli
<220> FEATURE:
<221> NAME/KEY: misc_feature
<222> LOCATION: (0)...(0)
<223> OTHER INFORMATION: Polynucleotide encoding regulatory protein cueR

<400> SEQUENCE: 22

```
atgaacatca gcgatgtagc aaaaattacc ggcctgacca gcaaagccat tcgcttctat       60
gaagagaagg ggctggtgac gccgccgatg cgcagcgaaa acggttatcg cacctacacg      120
cagcagcatc tcaacgaact gaccttactg cgccaggcac ggcaggtggg ctttaacctg      180
gaagagagcg gcgagctggt gaatctgttt aacgacccgc agcggcacag cgccgacgtc      240
aaacggcgca cgctggagaa ggtggcggag atcgaacgac acattgagga gctgcaatcc      300
atgcgcgacc agctgctggc actggcgaat gcctgccctg gcgatgacag cgccgactgc      360
ccgattatcg aaaatctctc cggctgctgt catcatcggg cagggtga                   408
```

<210> SEQ ID NO 23
<211> LENGTH: 522
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Hg3+, regulatory protein merR

<400> SEQUENCE: 23

```
ggtacctttc tcctctttaa tgaattcttt gaatttggat tggatagcgt aaccttactt       60
ccgtactcat gtacggagtc aagcgatatg gagaacaacc tggaaaacct gacgattggg      120
gtgtttgcca aagcagctgg ggtgaacgta gaaacgatcc gttttttacca gcggaaaggt     180 ttgctgcggg agcctgataa gccatacggc tcgattcggc gttatggcga agccgacgtc     240
gtgcgtgtta aattcgtgaa aagcgcgcaa cggctgggct tttcgctgga tgaaattgca     300
gagttactgc gtttggatga cggcacccat tgtgaagagg cgtcaagcct cgcggaacac     360
aaactgaaag atgtccgtga gaaatggcg gacctggcgc gtatggagac ggtgctctct     420
gaattggtgt gcgcttgtca cgctcggaag ggaaacgtgt cttgccctct gattgcgtca     480
ctgcaaggtg aggcgggctt ggcgcgtagt gccatgccgt aa                        522
```

<210> SEQ ID NO 24
<211> LENGTH: 435
<212> TYPE: DNA
<213> ORGANISM: Escherichia coli
<220> FEATURE:
<221> NAME/KEY: misc_feature
<222> LOCATION: (0)...(0)
<223> OTHER INFORMATION: Regulatory protein merR from Escherichia coli
       transposon Tn21

<400> SEQUENCE: 24

```
atggagaaca acctggaaaa cctgacgatt ggggtgtttg ccaaagcagc tggggtgaac       60
gtagaaacga tccgtttttta ccagcggaaa ggtttgctgc gggagcctga taagccatac    120
ggctcgattc ggcgttatgg cgaagccgac gtcgtgcgtg ttaaattcgt gaaaagcgcg     180
caacggctgg gcttttcgct ggatgaaatt gcagagttac tgcgtttgga tgacggcacc     240
cattgtgaag aggcgtcaag cctcgcggaa cacaaactga agatgtccg tgagaaatg      300 gcggacctgg cgcgtatgga gacggtgctc tctgaattgg tgtgcgcttg tcacgctcgg     360
aagggaaacg tgtcttgccc tctgattgcg tcactgcaag gtgaggcggg cttggcgcgt     420
agtgccatgc cgtaa                                                      435
```

<210> SEQ ID NO 25
<211> LENGTH: 702

<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Hg3+, merT and merP

<400> SEQUENCE: 25

| | | | | | |
|---|---|---|---|---|---|
| tttacggcta | gctcagtcct | aggtatagtg | ctagcgaatt | cattaaagag | gagaaaggta | 60 |
| ccatgtctga | accacaaaac | gggcgcggtg | cgctcttcgc | cggcgggctg | gccgccattc | 120 |
| ttgcatcgac | ctgctgcctg | gggccgctag | tactggtcgc | cctgggcttc | tccggtgctt | 180 |
| ggatcggcaa | cctgacggtg | ctggaaccct | atcgaccgtt | gttcatcggc | gcggcgctag | 240 |
| tggcgctgtt | cttcgcctgg | aagcggattt | accggcccgt | gcaggcatgc | aagccaggtg | 300 |
| aggtctgcgc | gattccgcag | gtgcgcgcca | cctacaagct | gattttctgg | atcgtggccg | 360 |
| tgctggtcct | ggtcgcgctt | ggatttccct | atgtcgttcc | attttctat | taaccaggag | 420 |
| ttcatcatga | agaaactgtt | tgcctccctt | gccctcgccg | ccgctgttgc | cccggtgtgg | 480 |
| gccgctaccc | agaccgtcac | gctagcggtt | cccggcatga | cttgcgccgc | ctgcccgatc | 540 |
| acagtcaaga | aagcgctctc | caaggtcgaa | ggcgtgagca | aggtcgatgt | gggcttcgag | 600 |
| aagcgcgagg | ccgtcgtcac | ttttgacgac | accaaggcca | gcgtacagaa | gctgaccaag | 660 |
| gccaccgcag | acgccggcta | tccgtccagc | gtcaagcagt | ga | | 702 |

<210> SEQ ID NO 26
<211> LENGTH: 351
<212> TYPE: DNA
<213> ORGANISM: Artificial Sequence
<220> FEATURE:
<223> OTHER INFORMATION: merT importer protein

<400> SEQUENCE: 26

| | | | | | |
|---|---|---|---|---|---|
| atgtctgaac | cacaaaacgg | gcgcggtgcg | ctcttcgccg | gcgggctggc | cgccattctt | 60 |
| gcatcgacct | gctgcctggg | gccgctagta | ctggtcgccc | tgggcttctc | cggtgcttgg | 120 |
| atcggcaacc | tgacggtgct | ggaaccctat | cgaccgttgt | tcatcggcgc | ggcgctagtg | 180 |
| gcgctgttct | tcgcctggaa | gcggatttac | cggcccgtgc | aggcatgcaa | gccaggtgag | 240 |
| gtctgcgcga | ttccgcaggt | gcgcgccacc | tacaagctga | ttttctggat | cgtggccgtg | 300 |
| ctggtcctgg | tcgcgcttgg | atttccctat | gtcgttccat | ttttctatta | a | 351 |

<210> SEQ ID NO 27
<211> LENGTH: 276
<212> TYPE: DNA
<213> ORGANISM: Artificial Sequence
<220> FEATURE:
<223> OTHER INFORMATION: merP importer protein

<400> SEQUENCE: 27

| | | | | | |
|---|---|---|---|---|---|
| atgaagaaac | tgtttgcctc | ccttgccctc | gccgccgctg | ttgccccggt | gtgggccgct | 60 |
| acccagaccg | tcacgctagc | ggttcccggc | atgacttgcg | ccgcctgccc | gatcacagtc | 120 |
| aagaaagcgc | tctccaaggt | cgaaggcgtg | agcaaggtcg | atgtgggctt | cgagaagcgc | 180 |
| gaggccgtcg | tcacttttga | cgacaccaag | gccagcgtac | agaagctgac | caaggccacc | 240 |
| gcagacgccg | gctatccgtc | cagcgtcaag | cagtga | | | 276 |

<210> SEQ ID NO 28
<211> LENGTH: 215
<212> TYPE: DNA

<213> ORGANISM: Artificial Sequence
<220> FEATURE:
<223> OTHER INFORMATION: pLB-Pb3, promoter and operator and RBS driving the detectable protein

<400> SEQUENCE: 28

```
gctatgttgt gtatggaagc tgaaagttat gtaaatgtgc taacattaaa cataaccata    60
acattcaagt catcaatctt ttcgtagtca taatcctggt ctatcagaga aatcaccaca   120
atccatttaa atgaatttga taatcattct cgtttggcat agcatgaaac atagcaaagg   180
ctatgtttga attcattaaa gaggagaaag gtacc                              215
```

<210> SEQ ID NO 29
<211> LENGTH: 199
<212> TYPE: DNA
<213> ORGANISM: Artificial Sequence
<220> FEATURE:
<223> OTHER INFORMATION: pLB-Pb7, promoter and operator and RBS driving the detectable protein

<400> SEQUENCE: 29

```
gctgtttatc agtaactttg tctggctggg gagccactat cgccgacgct tccgtgcgga    60
taacgcgatt gctgcggcct gctactttgc cggtcacttc ctgatcgtcc gctcgctgta   120
tctctgataa aacttgactc tggagtcgac tccagagtgt atccttcggt tagaattcat   180
taaagaggag aaaggtacc                                                199
```

<210> SEQ ID NO 30
<211> LENGTH: 673
<212> TYPE: DNA
<213> ORGANISM: Cupriavidus metallidurans
<220> FEATURE:
<221> NAME/KEY: misc_feature
<222> LOCATION: (0)...(0)
<223> OTHER INFORMATION: pLB-Pb8, promoter and operator and RBS driving the detectable protein, polynucleotide encoding regulatory protein pbrR

<400> SEQUENCE: 30

```
ggtaccttc tcctctttaa tgaattcggc aaccccttgt gtgtattcat ctcgcgttgc     60
cgatttaaca ccctctagtt actatagagt caagacatct cccatccgac gccttgacaa   120
ttaatcatcc ggctcgtata atgtgtggaa gggcccaagt tcacttaaaa aggagatcaa   180
caatgaaagc aattttcgta ctgaaacatc ttaatcatgc tggggagggt ttctaatgca   240
tatccaaatt ggtgaactgg cgaaacgtac ggcgtgtccg gtagtcacaa ttcgtttcta   300
cgagcaggaa ggattgctgc ctccacccgg acgcagccgt gggaattttc gtttgtacgg   360
tgaggagcat gtggaacgct tgcaatttat ccgccactgc cgcagcctcg atatgccttt   420
aagcgacgtt cgtactctgt taagctatcg caaacgtccg gatcaggatt gcggggaggt   480
gaatatgttg cttgatgaac atattcgcca ggtcgagagc cgcatcggtg cactgttgga   540
actcaaacac catctggttg aactgcgtga ggcatgttcg ggcgctcgtc cggcccaatc   600
ttgcggtatt ttacaaggcc tgtctgattg cgtgtgtgat acccgtggca ccacggccca   660
cccgagcgac taa                                                      673
```

<210> SEQ ID NO 31
<211> LENGTH: 234
<212> TYPE: DNA
<213> ORGANISM: Artificial Sequence
<220> FEATURE:
<223> OTHER INFORMATION: pLB-Pb8, promoter and operator and RBS driving the detectable protein

<400> SEQUENCE: 31

```
ggtacctttc tcctctttaa tgaattcggc aaccccttgt gtgtattcat ctcgcgttgc      60
cgatttaaca ccctctagtt actatagagt caagacatct cccatccgac gccttgacaa     120
ttaatcatcc ggctcgtata atgtgtggaa gggcccaagt tcacttaaaa aggagatcaa     180
caatgaaagc aattttcgta ctgaaacatc ttaatcatgc tggggagggt ttct           234
```

<210> SEQ ID NO 32
<211> LENGTH: 438
<212> TYPE: DNA
<213> ORGANISM: Cupriavidus metallidurans
<220> FEATURE:
<221> NAME/KEY: misc_feature
<222> LOCATION: (0)...(0)
<223> OTHER INFORMATION: Polynucleotide encoding regulatory protein pbrR

<400> SEQUENCE: 32

```
atgcatatcc aaattggtga actggcgaaa cgtacggcgt gtccggtagt cacaattcgt      60
ttctacgagc aggaaggatt gctgcctcca cccggacgca gccgtgggaa ttttcgtttg     120
tacggtgagg agcatgtgga acgcttgcaa tttatccgcc actgccgcag cctcgatatg     180
cctttaagcg acgttcgtac tctgttaagc tatcgcaaac gtccggatca ggattgcggg     240
gaggtgaata tgttgcttga tgaacatatt cgccaggtcg agagccgcat cggtgcactg     300
ttggaactca acaccatct ggttgaactg cgtgaggcat gttcgggcgc tcgtccggcc     360
caatcttgcg gtattttaca aggcctgtct gattgcgtgt gtgataccg tggcaccacg     420 gcccacccga gcgactaa                                                   438
```

<210> SEQ ID NO 33
<211> LENGTH: 204
<212> TYPE: DNA
<213> ORGANISM: Artificial Sequence
<220> FEATURE:
<223> OTHER INFORMATION: pLB-Zn6, promoter and operator and RBS driving the detectable protein

<400> SEQUENCE: 33

```
aatcatgcca tcttttatca gcgcttaccc tgcgctgtaa cacaaaggct taagtttcaa      60
tgagtaaaaa tgactcgcta cccgcagcag gcgagtcatt tttactcgtt tatcatgcca     120
gattacccgt catatcagcg tttcatcgtt ggcacggaag atgcaatacc cgaagtagaa     180
ttcattaaag aggagaaagg tacc                                            204
```

<210> SEQ ID NO 34
<211> LENGTH: 3459
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Hg3, merR

<400> SEQUENCE: 34

```
gaattcaaaa gatcttaagt aagtaagagt atacgtatat cggctaataa cgtattaagg      60
cgcttcggcg cctttttta tgggggtatt ttcatcccaa tccacacgtc caacgcacag     120
caaacaccac gtcgaccta tcagctgcgt gctttctatg agtcgttgct gcataactta     180
cggcatggca ctacgcgcca agcccgcctc accttgcagt gacgcaatca gagggcaaga     240
```

```
cacgtttccc ttccgagcgt gacaagcgca caccaattca gagagcaccg tctccatacg    300
cgccaggtcc gccatttttct cacggacatc tttcagtttg tgttccgcga ggcttgacgc    360
ctcttcacaa tgggtgccgt catccaaacg cagtaactct gcaatttcat ccagcgaaaa    420
gcccagccgt tgcgcgcttt tcacgaattt aacacgcacg acgtcggctt cgccataacg    480
ccgaatcgag ccgtatggct tatcaggctc ccgcagcaaa cctttccgct ggtaaaaacg    540 gatcgttttct acgttcaccc cagctgcttt ggcaaacacc ccaatcgtca ggttttccag    600
gttgttctcc atatcgcttg actccgtaca tgagtacgga agtaaggtta cgctatccaa    660
tccaaattca agaattcat taaagaggag aaaggtacca tgcgtaaagg cgaagagctg    720
ttcactggtg tcgtccctat tctggtggaa ctggatggtg atgtcaacgg tcataagttt    780
tccgtgcgtg gcgagggtga aggtgacgca actaatggta aactgacgct gaagttcatc    840
tgtactactg gtaaactgcc ggtaccttgg ccgactctgg taacgacgct gacttatggt    900
gttcagtgct ttgctcgtta tccggaccat atgaagcagc atgacttctt caagtccgcc    960
atgccggaag gctatgtgca ggaacgcacg atttccttta aggatgacgg cacgtacaaa   1020
acgcgtgcgg aagtgaaatt tgaaggcgat accctggtaa accgcattga gctgaaaggc   1080
attgacttta aagaagacgg caatatcctg ggccataagc tggaatacaa ttttaacagc   1140
cacaatgttt acatcaccgc cgataaacaa aaaaatggca ttaaagcgaa ttttaaaatt   1200
cgccacaacg tggaggatgg cagcgtgcag ctggctgatc actaccagca aaacactcca   1260
atcggtgatg gtcctgttct gctgccagac aatcactatc tgagcacgca aagcgttctg   1320
tctaaagatc cgaacgagaa acgcgatcat atggttctgc tggagttcgt aaccgcagcg   1380
ggcatcacgc atggtatgga tgaactgtac aaatgacttg gactcctgtt gatagatcca   1440
gtaatgacct cagaactcca tctggatttg ttcagaacgc tcggttgccg ccgggcgttt   1500
tttattggtg agaatccacc agccaggaca gaaatgcctc gacttcgctg ctgcccaagg   1560
ttgccgggtg acgcacaccg tggaaacgga tgaaggcacg aacccagtgg acataagcct   1620
gttcggttcg taagctgtaa tgcaagtagc gtatgcgctc acgcaactgg tccagaacct   1680
tgaccgaacg cagcggtggt aacggcgcag tggcggtttt catggcttgt tatgactgtt   1740
tttttggggt acagtctatg cctcgggcat ccaagcagca agcgcgttac gccgtgggtc   1800
gatgtttgat gttatggagc agcaacgatg ttacgcagca gggcagtcgc cctaaaacaa   1860
agttaaacat catgagggaa gcggtgatcg ccgaagtatc gactcaacta tcagaggtag   1920
ttggcgtcat cgagcgccat ctcgaaccga cgttgctggc cgtacatttg tacggctccg   1980
cagtggatgg cggcctgaag ccacacagtg atattgattt gctggttacg gtgaccgtaa   2040
ggcttgatga aacaacgcgg cgagctttga tcaacgacct tttggaaact tcggcttccc   2100
ctggagagag cgagattctc cgcgctgtag aagtcaccat tgttgtgcac gacgacatca   2160
ttccgtggcg ttatccagct aagcgcgaac tgcaatttgg agaatggcag cgcaatgaca   2220
ttcttgcagg tatcttcgag ccagccacga tcgacattga tctggctatc ttgctgacaa   2280
aagcaagaga acatagcgtt gccttggtag gtccagcggc ggaggaactc tttgatccgg   2340
ttcctgaaca ggatctattt gaggcgctaa atgaaacctt aacgctatgg aactcgccgc   2400
ccgactgggc tggcgatgag cgaaatgtag tgcttacgtt gtcccgcatt tggtacagcg   2460
cagtaaccgg caaaatcgcg ccgaaggatg tcgctgccga ctgggcaatg gagcgcctgc   2520
cggcccagta tcagcccgtc atacttgaag ctagacaggc ttatcttgga caagaagaag   2580
atcgcttggc ctcgcgcgca gatcagttgg aagaatttgt ccactacgtg aaaggcgaga   2640
```

```
tcaccaaggt agtcggcaaa taagatatat tccgcttcct cgctcactga ctcgctacgc    2700
tcggtcgttc gactgcggcg agcggaaatg cttacgaac ggggcggaga tttcctggaa     2760
gatgccagga agatacttaa cagggaagtg agagggccgc ggcaaagccg ttttccata    2820 ggctccgccc ccctgacaag catcacgaaa tctgacgctc aaatcagtgg tggcgaaacc    2880
cgacaggact ataaagatac caggcgtttc ccctggcgg ctccctcgtg cgctctcctg    2940
ttcctgcctt tcggtttacc ggtgtcattc cgctgttatg gccgcgtttg tctcattcca    3000
cgcctgacac tcagttccgg gtaggcagtt cgctccaagc tggactgtat gcacgaaccc    3060
cccgttcagt ccgaccgctg cgccttatcc ggtaactatc gtcttgagtc caacccggaa    3120
agacatgcaa agcaccact ggcagcagcc actggtaatt gatttagagg agttagtctt    3180
gaagtcatgc gccggttaag gctaaactga aggacaagt tttggtgact gcgctcctcc    3240
aagccagtta cctcggttca aagagttggt agctcagaga accttcgaaa aaccgccctg    3300
caaggcggtt ttttcgtttt cagagcaaga gattacgcgc agaccaaaac gatctcaaga    3360
agatcatctt attaatcaga taaaatattt ctagatttca gtgcaattta tctcttcaaa    3420
tgtagcacct gaagtcagcc ccatacgata taagttgtt                          3459

<210> SEQ ID NO 35
<211> LENGTH: 435
<212> TYPE: DNA
<213> ORGANISM: Escherichia coli
<220> FEATURE:
<221> NAME/KEY: misc_feature
<222> LOCATION: (0)...(0)
<223> OTHER INFORMATION: merR

<400> SEQUENCE: 35
atggagaaca acctggaaaa cctgacgatt ggggtgtttg ccaaagcagc tggggtgaac     60
gtagaaacga tccgttttta ccagcggaaa ggtttgctgc gggagcctga taagccatac    120
ggctcgattc ggcgttatgg cgaagccgac gtcgtgcgtg ttaaattcgt gaaaagcgcg    180
caacggctgg gctttttcgct ggatgaaatt gcagagttac tgcgtttgga tgacggcacc    240
cattgtgaag aggcgtcaag cctcgcggaa acaaactga aagatgtccg tgagaaaatg    300
gcggacctgg cgcgtatgga gacggtgctc tctgaattgg tgtgcgcttg tcacgctcgg    360
aagggaaacg tgtcttgccc tctgattgcg tcactgcaag gtgaggcggg cttggcgcgt    420
agtgccatgc cgtaa                                                     435

<210> SEQ ID NO 36
<211> LENGTH: 717
<212> TYPE: DNA
<213> ORGANISM: Artificial Sequence
<220> FEATURE:
<223> OTHER INFORMATION: sfGFP coding sequence

<400> SEQUENCE: 36
atgcgtaaag gcgaagagct gttcactggt gtcgtcccta ttctggtgga actggatggt     60
gatgtcaacg tcataagtt tccgtgcgt ggcgagggtg aaggtgacgc aactaatggt    120
aaactgacgc tgaagttcat ctgtactact ggtaaactgc cggtaccttg gccgactctg    180
gtaacgacgc tgacttatgg tgttcagtgc tttgctcgtt atccggacca tatgaagcag    240
catgacttct tcaagtccgc catgccggaa ggctatgtgc aggaacgcac gatttccttt    300
aaggatgacg gcacgtacaa aacgcgtgcg gaagtgaaat ttgaaggcga tacccctggta    360
```

| | |
|---|---|
| aaccgcattg agctgaaagg cattgacttt aaagaagacg gcaatatcct gggccataag | 420 |
| ctggaataca attttaacag ccacaatgtt tacatcaccg ccgataaaca aaaaaatggc | 480 |
| attaaagcga attttaaaat tcgccacaac gtggaggatg gcagcgtgca gctggctgat | 540 |
| cactaccagc aaaacactcc aatcggtgat ggtcctgttc tgctgccaga caatcactat | 600 |
| ctgagcacgc aaagcgttct gtctaaagat ccgaacgaga aacgcgatca tatggttctg | 660 |
| ctggagttcg taaccgcagc gggcatcacg catggtatgg atgaactgta caaatga | 717 |

<210> SEQ ID NO 37
<211> LENGTH: 87
<212> TYPE: DNA
<213> ORGANISM: Artificial Sequence
<220> FEATURE:
<223> OTHER INFORMATION: Promoter and operator and RBS driving
      the fluorescent protein

<400> SEQUENCE: 37

| | |
|---|---|
| atcgcttgac tccgtacatg agtacggaag taaggttacg ctatccaatc caaattcaaa | 60 |
| gaattcatta aagaggagaa aggtacc | 87 |

<210> SEQ ID NO 38
<211> LENGTH: 3041
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Cu3

<400> SEQUENCE: 38

| | |
|---|---|
| gaattcaaaa gatcttaagt aagtaagagt atacgtatat cggctaataa cgtattaagg | 60 |
| cgcttcggcg cctttttta tgggggtatt ttcatcccaa tccacacgtc caacgcacag | 120 |
| caaacaccac gtcgacccta tcagctgcgt gctttctatg agtcgttgct gcataactcg | 180 |
| cttattggca aaatgacaat tttgtcattt ttctgtcacc ggaaaatcag agcctggcga | 240 |
| gtaaagttgg cggcgaattc attaaagagg agaaaggtac catgcgtaaa ggcgaagagc | 300 |
| tgttcactgg tgtcgtccct attctggtgg aactggatgg tgatgtcaac ggtcataagt | 360 |
| tttccgtgcg tggcgagggt gaaggtgacg caactaatgg taaactgacg ctgaagttca | 420 |
| tctgtactac tggtaaactg ccggtacctt ggccgactct ggtaacgacg ctgacttatg | 480 |
| gtgttcagtg ctttgctcgt tatccggacc atatgaagca gcatgacttc ttcaagtccg | 540 |
| ccatgccgga aggctatgtg caggaacgca cgatttcctt taaggatgac ggcacgtaca | 600 |
| aaacgcgtgc ggaagtgaaa tttgaaggcg ataccctggt aaaccgcatt gagctgaaag | 660 |
| gcattgactt taagaagac ggcaatatcc tgggccataa gctggaatac aattttaaca | 720 |
| gccacaatgt ttacatcacc gccgataaac aaaaaaatgg cattaaagcg aattttaaaa | 780 |
| ttcgccacaa cgtggaggat ggcagcgtgc agctggctga tcactaccag caaaacactc | 840 |
| caatcggtga tggtcctgtt ctgctgccag acaatcacta tctgagcacg caaagcgttc | 900 |
| tgtctaaaga tccgaacgag aaacgcgatc atatggttct gctggagttc gtaaccgcag | 960 |
| cgggcatcac gcatggtatg gatgaactgt acaaatgact ggactcctg ttgatagatc | 1020 |
| cagtaatgac ctcagaactc catctggatt tgttcagaac gctcggttgc cgccgggcgt | 1080 |
| tttttattgg tgagaatcca ccagccagga cagaaatgcc tcgacttcgc tgctgcccaa | 1140 |
| ggttgccggg tgacgcacac cgtggaaacg gatgaaggca cgaacccagt ggacataagc | 1200 |

| | |
|---|---|
| ctgttcggtt cgtaagctgt aatgcaagta gcgtatgcgc tcacgcaact ggtccagaac | 1260 |
| cttgaccgaa cgcagcggtg gtaacggcgc agtggcggtt ttcatggctt gttatgactg | 1320 |
| ttttttttggg gtacagtcta tgcctcgggc atccaagcag caagcgcgtt acgccgtggg | 1380 |
| tcgatgtttg atgttatgga gcagcaacga tgttacgcag cagggcagtc gccctaaaac | 1440 |
| aaagttaaac atcatgaggg aagcggtgat cgccgaagta tcgactcaac tatcagaggt | 1500 |
| agttggcgtc atcgagcgcc atctcgaacc gacgttgctg gccgtacatt tgtacggctc | 1560 |
| cgcagtggat ggcggcctga agccacacag tgatattgat ttgctggtta cggtgaccgt | 1620 |
| aaggcttgat gaaacaacgc ggcgagcttt gatcaacgac cttttggaaa cttcggcttc | 1680 |
| ccctggagag agcgagattc tccgcgctgt agaagtcacc attgttgtgc acgacgacat | 1740 |
| cattccgtgg cgttatccag ctaagcgcga actgcaattt ggagaatggc agcgcaatga | 1800 |
| cattcttgca ggtatcttcg agccagccac gatcgacatt gatctggcta tcttgctgac | 1860 |
| aaaagcaaga gaacatagcg ttgccttggt aggtccagcg gcggaggaac tctttgatcc | 1920 |
| ggttcctgaa caggatctat ttgaggcgct aaatgaaacc ttaacgctat ggaactcgcc | 1980 |
| gcccgactgg gctggcgatg agcgaaatgt agtgcttacg ttgtcccgca tttggtacag | 2040 |
| cgcagtaacc ggcaaaatcg cgccaagga tgtcgctgcc gactgggcaa tggagcgcct | 2100 |
| gccggcccag tatcagcccg tcatacttga agctagacag gcttatcttg acaagaaga | 2160 |
| agatcgcttg gcctcgcgcg cagatcagtt ggaagaattt gtccactacg tgaaaggcga | 2220 |
| gatcaccaag gtagtcggca aataagatat attccgcttc ctcgctcact gactcgctac | 2280 |
| gctcggtcgt tcgactgcgg cgagcggaaa tggcttacga acggggcgga gatttcctgg | 2340 |
| aagatgccag gaagatactt aacagggaag tgagagggcc gcggcaaagc cgttttttcca | 2400 |
| taggctccgc ccccctgaca gcatcacga aatctgacgc tcaaatcagt ggtggcgaaa | 2460 |
| cccgacagga ctataaagat accaggcgtt tcccctggc ggctccctcg tgcgctctcc | 2520 |
| tgttcctgcc tttcggttta ccggtgtcat tccgctgtta tggccgcgtt tgtctcattc | 2580 |
| cacgcctgac actcagttcc gggtaggcag ttcgctccaa gctggactgt atgcacgaac | 2640 |
| cccccgttca gtccgaccgc tgcgccttat ccggtaacta tcgtcttgag tccaacccgg | 2700 |
| aaagacatgc aaaagcacca ctggcagcag ccactggtaa ttgatttaga ggagttagtc | 2760 |
| ttgaagtcat cgccggtta aggctaaact gaaaggacaa gttttggtga ctgcgctcct | 2820 |
| ccaagccagt tacctcggtt caaagagttg gtagctcaga gaaccttcga aaaccgccc | 2880 |
| tgcaaggcgg ttttttcgtt ttcagagcaa gagattacgc gcagaccaaa acgatctcaa | 2940 |
| gaagatcatc ttattaatca gataaaatat ttctagattt cagtgcaatt tatctcttca | 3000 |
| aatgtagcac ctgaagtcag ccccatacga tataagttgt t | 3041 |

<210> SEQ ID NO 39
<211> LENGTH: 7729
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Hg-i, merT and merP

<400> SEQUENCE: 39

| | |
|---|---|
| tttacggcta gctcagtcct aggtatagtg ctagcgaatt cattaaagag gagaaaggta | 60 |
| ccatgtctga accacaaaac gggcgcggtg cgctcttcgc cggcgggctg gccgccattc | 120 |
| ttgcatcgac ctgctgcctg gggccgctag tactggtcgc cctgggcttc tccggtgctt | 180 |

```
ggatcggcaa cctgacggtg ctggaaccct atcgaccgtt gttcatcggc gcggcgctag    240
tggcgctgtt cttcgcctgg aagcggattt accggcccgt gcaggcatgc aagccaggtg    300
aggtctgcgc gattccgcag gtgcgcgcca cctacaagct gattttctgg atcgtggccg    360
tgctggtcct ggtcgcgctt ggatttccct atgtcgttcc attttctat taaccaggag    420 ttcatcatga agaaactgtt tgcctccctt gccctcgccg ccgctgttgc cccggtgtgg    480
gccgctaccc agaccgtcac gctagcggtt cccggcatga cttgcgccgc ctgcccgatc    540
acagtcaaga aagcgctctc caaggtcgaa ggcgtgagca aggtcgatgt gggcttcgag    600
aagcgcgagg ccgtcgtcac ttttgacgac accaaggcca cgtacagaa gctgaccaag    660 gccaccgcag acgccggcta tccgtccagc gtcaagcagt gaaaataata aaaaagccgg    720
attaataatc tggcttttta tattctctct ctagtatata aacgcagaaa ggcccacccg    780
aaggtgagcc agtgtgatca ttagcctcca atcttatagt gaaactccgc aaacttcgtt    840
tcctcaatat tgggaatact cgataacttt tgttcagctt tttcataaaa agaaattgct    900
ttaacataat tttttttaaa aaactcataa tcccctgcaa acaattcaaa ataaaatttt    960
attaaaagat catgacttcc cttacttaac atattaacga catcacccat agatgcctct   1020
tgatcaaaac aaaggctatg acgatgatcc agtagaataa aataatcaac caggtcctta   1080
ttatcttcag cctgacttaa caattgcttt atttcagttc ttttctctat agactcatga   1140
accttctcct gcataatata gtcatgccat ttattcaaca gattgcctac ataggagac    1200 ggtactttt ttactttgga caacatacac ttccctccag ctattcaaaa atcaaaacta    1260
gtcctaatac ttatcggcat catcaaacat tttaaaacac agaacattta gtacatagtg   1320
cttaatgttc aaatctcatt ttgatgctct gaacccaagc atgtactgat atcatactaa   1380
acggctcaaa cacaatctat acaagttttt aagataggcc aaagggaata acagtatacg   1440
ttagtgaaat cccacaggaa aaatatatta aaatactaat gttctatcaa acgaacaacc   1500
cttaaaaagg aacttaaaac ctctgggttt taaggaaatt cgcattttat ttagtgtttt   1560
tctcttgact ttgagaactt gaaactagca gaatagctga ctgttctagg aaacagggcg   1620
aatttcgatt gcctatgtct gtcgcgcaaa aaataaaaac ggacagacat aggcaatcga   1680
tcaggatttg aaactagcgt catagagacg tctgaggttt ccagctctgc cttgctatcg   1740
ccaggctttc gcctgccatg acctttttac atacaatgct tgtcctgtat gcaacttcta   1800
tggggtttgt ctcgtgttct ctcacacggt cacactcaat tgtgtgccgc tgcatagaag   1860
cttggccata gttgcccgca ccgtagtgcg ccaagcaacc tagtggttta tccacattct   1920
ccggaccgtt aatggccgtc ctcgccattc accacaagcg cagcaaggaa cgcttattgt   1980
ggtatatccc cgggtttgcg gtggacgggg caactcctga cgtcagttta ttttacaccc   2040
cttaacggca gctgggtgac aaacaaaaaa cgacagaaaa ccacggtttg ataccctcca   2100
aacagtggtt ttctgtcgtc caaaaatagc cgaaaagtgt tgacgtatac acttgttttc   2160
ggtaaaatga agacataact taaacattgt aagtgagggc ttacaaacca agtgttcgat   2220
gctgcaacat cggacacttt ttatttgtca ttctttattt gtattcaatt ttgcaaatag   2280
ctcgcaaaca aaatatgtat catcaaatct attaaccttg ttgtctgcaa acaacagggt   2340
tttttgttgt ttatttagaa taactagaac cagaattcaa tgccaaaact ttcacattga   2400
cttaacttga cttatcttta cacgattttt ttttgacgt aaagccccgg gcctgaaatc    2460 actttctct actgatttca ctgatttcat ttttattata taatcctcaa atagcctgta   2520
```

```
ttcactgatt ttaaatgtga tttcatttta ttgactttag tgatataaga tgctagtatt    2580
gaggaaagtg aaatcaaagg agagaataaa aatatgaata tttctcgtat gaacgtggac    2640
tttggaaaca gtatgtacat gaatttaatt gatggttatt tttttgaatt gcctacaaat    2700
gtagtagaga tatctaaaga agctgctgaa ggaaaattta cgagtatcgt tgaagatccg    2760
gcagatttaa aggaccggtt attagtttct acagttattg atgaaacaga gagatatttt    2820
ctagttggtg aacttgctga accagaagtg ttaggcaacc aacacatcaa gaagttacat    2880
aataaagtag agtcacatat tccatacgta acatttttag ctgcaactgc ttattaccaa    2940
gcgctaaaag gcaaacgtga agataatgaa gttactattg aatactttca acaatgcta     3000 ccaatttggc ttcttaaaaa attggataag ttcagtgaaa tgcagaaaag gatggcatct    3060
aaatttttgg gcactcacca agtaaaggtg ctgacattag gattagaaaa agagcttact    3120
ataaaagtgg aagatgcagc gtgcaggatc gaatctgaag tagcaagatg ggcaataaag    3180
aaaaactttg acctagaaga taaagactat gccgaacaat ttaaaaatta tgacgtagtt    3240
ttttgtgatt taggtggcgg aacagatgat ctagtattac taccagctgg attaaaaccg    3300
ccaaaaagtc gtgattcttt tgtttctaat accgaagcac cgttttagc gcacttagaa     3360 aaattgagaa aagaaaaact cctagagcac tttgatagcg ttagggagct tgaaaagttt    3420
atatactcaa atattggaaa aactaagatg gaacgaagag acgggaatac cggtcagaaa    3480
tttgatttaa ctgatatcat caaaaaatct cttaaagaat acacagaaat caaaatagcc    3540
caagctgaaa atacgttccc tgcaccaaaa gataaggttt acaaataccct ttattttggc   3600 ggtgttggcg aggtgcttga agaatcaatt agtgtggtta ctgaagagag atatggccgt    3660
gatatttctg aatcaaatca tatagttgct gaggatgcaa gactgctcaa cttatatggc    3720
cttgaagttt taagccgcgc tgaacaagta aagaaacagg caaatgaaaa agaggcacaa    3780
tcaatttagg tgattagaaa tggggaaaaa caaagaatt ccactcttta atgtccgaac      3840
aacacaaatg tctgatgaaa tgtacgattt tgttttagag cagattagta cattcagtaa    3900
aggtaagagt aagggtacct ttagagagta tgcctttcag ctcatagaaa gggacatgca    3960
acaacagaaa gaggaacagc aaaatagaga aaaagatcgt catgttcatg atgaattaat    4020
tgccatgaga gaagaaatga aaaagaatt tcgtgatttg aggaaaaaaa ttgatcaggg    4080
atcgatctac gtagaacaca aaacagctga tccaaagtca gcttcaaaaa cgattgaaga    4140
aggtcagtta atcactgaaa aaatcactgg aactattgaa gaagaatacg actatgattt    4200
ttaagagcct ggattaatct aggctctttt tttatgccat ttaagggagg attgcatgac    4260 aaacttttt tagttgcaac acagacgccc tgagcaacgc taggacaaca tcagcaagga    4320 gaaagggct accggcgaac cagcagcccc tttataaagg cgcttcagta gtcagaccag    4380
catcagtcct gaaaaggcgg gcctgcgccc gcctccaggt tgctacttac cggattcgta    4440
agccatgaaa gccgccacct ccctgtgtcc gtctctgtaa cgaatctcgc acagcgattt    4500
tcgtgtcaga taagtgaata tcaacagtgt gagacacacg atcaacacac accagacaag    4560
ggaacttcgt ggtagtttca tggccttctt ctccttgcgc aaagcgcggt aagaggctat    4620
cctgatgtgg actagacata gggatgcctc gtggtggtta atgaaaatta acttactacg    4680
gggctatctt cttctgcca cacaacacgg caacaaacca ccttcacgtc atgaggcaga     4740
aagcctcaag cgccgggcac atcatagccc atatacctgc acgctgacca cactcacttt    4800
ccctgaaaat aatccgctca ttcagaccgt tcacgggaaa tccgtgtgat tgttgccgca    4860
tcacgctgcc tcccggagtt tgttgctagg tctagggcgg cggatttgtc ctactcagga    4920
```

```
gagcgttcac cgacaaacaa cagataaaac gaaaggccca gtctttcgac tgagcctttc    4980
gttttatttg atgcctctag ttacgccccg ccctgccact catcgcagta ctgttgtaat    5040
tcattaagca ttctgccgac atggaagcca tcacagacgg catgatgaac ctgaatcgcc    5100
agcggcatca gcaccttgtc gccttgcgta taatatttgc ccatggtgaa aacggggggcg   5160 aagaagttgt ccatattggc cacgtttaaa tcaaaactgg tgaaactcac ccagggattg    5220
gctgagacga aaacatatt ctcaataaac cctttaggga ataggccag gttttcaccg      5280 taacacgcca catcttgcga atatatgtgt agaaactgcc ggaaatcgtc gtggtattca    5340
ctccagagcg atgaaaacgt ttcagtttgc tcatggaaaa cggtgtaaca agggtgaaca    5400
ctatcccata tcaccagctc accgtctttc attgccatac gaaattccgg atgagcattc    5460
atcaggcggg caagaatgtg aataaaggcc ggataaaact tgtgcttatt tttctttacg    5520
gtctttaaaa aggccgtaat atccagctga acggtctggt tataggtaca ttgagcaact    5580
gactgaaatg cctcaaaatg ttctttacga tgccattggg atatatcaac ggtggtatat    5640
ccagtgattt ttttctccat tttagcttcc ttagctcctg aaaatctcga taactcaaaa    5700
aatacgcccg gtagtgatct tatttcatta tggtgaaagt tggaacctct tacgtgccga    5760
tcaacgtctc attttcgcca aaagttggcc cagggcttcc cggtatcaac agggacacca    5820
ggatttattt attctgcgaa gtgatcttcc gtcacaggta tttattcggc gcctgtagtg    5880
ccatttaccc ccattcactg ccagagccgt gagcgcagcg aactgaatgt cacgaaaaag    5940
acagcgactc aggtgcctga tggtcggaga caaaaggaat attcagcgat ttgcccgagc    6000
ttgcgagggt gctacttaag cctttagggt tttaaggtct gttttgtaga ggagcaaaca    6060
gcgtttgcga catccttttg taatactgcg gaactgacta agtagtgag ttatacacag     6120 ggctgggatc tattctttt atcttttttt attctttctt tattctataa attataacca     6180
cttgaatata aacaaaaaaa acacacaaag gtctagcgga atttacagag ggtctagcag    6240
aatttacaag ttttccagca aaggtctagc agaatttaca gatacccaca actcaaagga    6300
aaaggactag taattatcat tgactagccc atctcaattg gtatagtgat taaaatcacc    6360
tagaccaatt gagatgtatg tctgaattag ttgttttcaa agcaaatgaa ctagcgatta    6420
gtcgctatga cttaacggag catgaaacca gctaattttt atgctgtgtg gcactactca    6480
accccacgat tgaaaccct acaaggaaag aacggacggt atcgttcact tataaccaat     6540
acgctcagat gatgaacatc agtagggaaa atgcttatgg tgtattagct aaagcaacca    6600
gagagctgat gacgagaact gtggaaatca ggaatccttt ggttaaaggc tttgagattt    6660
tccagtggac aaactatgcc aagttctcaa gcgaaaaatt agaattagtt tttagtgaag    6720
agatattgcc ttatcttttc cagttaaaaa aattcataaa atataatctg gaacatgtta    6780
agtcttttga aaacaaatac tctatgagga tttatgagtg gttattaaaa gaactaacac    6840
aaaagaaaac tcacaaggca aatatagaga ttagccttga tgaatttaag ttcatgttaa    6900
tgcttgaaaa taactaccat gagtttaaaa ggcttaacca atgggttttg aaaccaataa    6960
gtaaagattt aaacacttac agcaatatga aattggtggt tgataagcga ggccgcccga    7020
ctgatacgtt gattttccaa gttgaactag atagacaaat ggatctcgta accgaacttg    7080
agaacaacca gataaaaatg aatggtgaca aaataccaac aaccattaca tcagattcct    7140
acctacataa cggactaaga aaaacactac acgatgcttt aactgcaaaa attcagctca    7200
ccagttttga ggcaaaattt ttgagtgaca tgcaaagtaa gtatgatctc aatggttcgt    7260
```

| | | |
|---|---|---|
| tctcatggct cacgcaaaaa caacgaacca cactagagaa catactggct aaatacggaa | 7320 | |
| ggatctgagg ttcttatggc tcttgtatct atcagtgaag catcaagact aacaaacaaa | 7380 | |
| agtagaacaa ctgttcaccg ttacatatca aagggaaaac tgtccatatg cacagatgaa | 7440 | |
| aacggtgtaa aaagataga tacatcagag cttttacgag ttttggtgc attcaaagct | 7500 | |
| gttcaccatg aacagatcga caatgtaaca gatgaacagc atgtaacacc taatagaaca | 7560 | |
| ggtgaaacca gtaaacaaa gcaactagaa catgaaattg aacacctgag acaacttgtt | 7620 | |
| acagctcaac agtcacacat agacagcctg aaacaggcga tgctgcttat cgaatcaaag | 7680 | |
| ctgccgacaa cacgggagcc agtgacgcct cccgtgggga aaaaatcat | 7729 | |

<210> SEQ ID NO 40
<211> LENGTH: 351
<212> TYPE: DNA
<213> ORGANISM: Artificial Sequence
<220> FEATURE:
<223> OTHER INFORMATION: merT

<400> SEQUENCE: 40

| | | |
|---|---|---|
| atgtctgaac cacaaaacgg gcgcggtgcg ctcttcgccg gcgggctggc cgccattctt | 60 | |
| gcatcgacct gctgcctggg gccgctagta ctggtcgccc tgggcttctc cggtgcttgg | 120 | |
| atcggcaacc tgacggtgct ggaaccctat cgaccgttgt tcatcggcgc ggcgctagtg | 180 | |
| gcgctgttct tcgcctggaa gcggatttac cggcccgtgc aggcatgcaa gccaggtgag | 240 | |
| gtctgcgcga ttccgcaggt gcgcgccacc tacaagctga ttttctggat cgtggccgtg | 300 | |
| ctggtcctgg tcgcgcttgg atttccctat gtcgttccat ttttctatta a | 351 | |

<210> SEQ ID NO 41
<211> LENGTH: 276
<212> TYPE: DNA
<213> ORGANISM: Artificial Sequence
<220> FEATURE:
<223> OTHER INFORMATION: merP

<400> SEQUENCE: 41

| | | |
|---|---|---|
| atgaagaaac tgtttgcctc ccttgccctc gccgccgctg ttgccccggt gtgggccgct | 60 | |
| acccagaccg tcacgctagc ggttcccggc atgacttgcg ccgcctgccc gatcacagtc | 120 | |
| aagaaagcgc tctccaaggt cgaaggcgtg agcaaggtcg atgtgggctt cgagaagcgc | 180 | |
| gaggccgtcg tcactttga cgacaccaag gccagcgtac agaagctgac caaggccacc | 240 | |
| gcagacgccg gctatccgtc cagcgtcaag cagtga | 276 | |

<210> SEQ ID NO 42
<211> LENGTH: 9018
<212> TYPE: DNA
<213> ORGANISM: Escherichia coli
<220> FEATURE:
<221> NAME/KEY: misc_feature
<222> LOCATION: (0)...(0)
<223> OTHER INFORMATION: pLB-Pb-i, pbrT

<400> SEQUENCE: 42

| | | |
|---|---|---|
| tttacggcta gctcagtcct aggtatagtg ctagcgaatt cattaaagag gagaaaggta | 60 | |
| ccatgcaagc cctgcgtctc ctttcgattg ttctgctctc tctgttcgtg acggtctcga | 120 | |
| ccgcacaggc agatcctctc gccacgcaag acaaggccaa gcaaatctgg caagtactgg | 180 | |
| actaccttgc tgtcgactat ggccggtccg tcaaggatgg ccacgtcgcc aacgaagccg | 240 | |
| agtatgccga gatgcaggag ttcgcgcagg ccgctgaacg gcagctaacc gagttgccgc | 300 | |

```
cgacgccagc cgcgccagag ttggccaagg aagcggcggc gttgcgcgca tccattgcag    360
aaaaggcccc gcccgaatca gtcggcgagc aagctcgcaa actggccggc ggactcctcg    420
cagcctatcc ggtcccgatg ccccccggca agctgcccga tctgcaacaa ggggcaaagc    480
tgtatcaaag ccaatgtgct tcgtgccacg gcgtttccgg gcacgcggac ggcccactag    540
ctgcaaagct gagcccgcca ccgatcgccc tggctgatca cgagcgcgcc caggagcgca    600
gcgtcttcgc cctacagcaa atcatcacgc gcggggtaga agggacgtcg atgccggcat    660
ttgctcaact ctcggacgag gaacgctggg cgctcgccta ttttgcctcg accctttcgt    720
attcggatgc cgaccgccag gccggcgcca agctgtggac ctctcaaccg gctctccacg    780
cagccgtgcc cacgctggcc ttgttaagcc agacctccga ggctgcgctc gccaagaccg    840
tcggggcgga tgccgctcgc caactgaccg cgtacctcag gagcacgccg ggctcggtca    900
ccgcgtcaag caccgacagc ctgatgatcg ccagagacaa gctgaaggaa agcttggcca    960
ccctggacaa gggcgacagg cagttggctt cgcggctggc gttgtctgcc tatctcgacg   1020
gcttcgagcc cgtcgagccg gcgctggctg ccaagaacca ggcgctgttc caggatatcg   1080
agaagacgat ggggctctat cgcaatgctg tgacagcggg ccaggtggaa cgcgcccatg   1140
aaattgcgca gaagttgcaa tcgcagcttg acgacgcaca ggaggcgctg gcggcacca    1200 atgacgccat atcgaccttc ctcggcgccc tgacaatcct gctacgagaa gggcttgaag   1260
ccctgttggt ggtcgtcgcg atgatggcgt tcctgaagaa agcggatcgc accgatgtcc   1320
tgccctacgt gcatgcaggc tgggttactg cgctggcggc cggtgggctg acctgggcgg   1380
tagccaccta tgtcgtcgac ctgagtggcg ccagtcgcga gatgacggaa ggttttccg    1440 cagtgtttgc cgcaatcgtg ttgcttggcg tgggcatgtg gatgcaccag aagagtcttg   1500
cgggtcgctg gcaggcctat gtgaaggcga agctgtcctc ggcattgaac aagaaatcag   1560
cgctgatgct gttcctgctg tcgttcgtga ccgtctatcg agaagtgttt gaaacagtcc   1620
tcttttacgc tgccctgtgg acagagggca acggtgtatt tttgctcgca ggacttgcgt   1680
cgggtatcgc catcctggcc gcgatcgcca tcgtgctcct gcgctccacg gcgcgcctgc   1740
cgattggtca gttctttgcc ttcagctcag cattggtcgg cgtgttggcg gtcgttctga   1800
ttggtaaagg catagctgcg cttcagaaag tcggcttcct acaagttacg ccgatctcca   1860
tgcctcgtat cgacgtcctg ggcatttatc cgtccgtcca gaccgtcgta gcgcaagtcc   1920
tgattctgct cattatcgcc gcaagcgtcg tctacaattt gcggtcgcac cggccatcta   1980
cccaggtgta aaataataa aaagccgga ttaataatct ggcttttat attctctctc      2040 tagtatataa acgcagaaag gcccacccga aggtgagcca gtgtgatcat tagcctccaa   2100
tcttatagtg aaactccgca aacttcgttt cctcaatatt gggaatactc gataactttt   2160
gttcagcttt ttcataaaaa gaaattgctt taacataatt tttttaaaa aactcataat   2220 cccctgcaaa caattcaaaa taaaaattta ttaaaagatc atgacttccc ttacttaaca   2280
tattaacgac atcacccata gatgcctctt gatcaaaaca aaggctatga cgatgatcca   2340
gtagaataaa ataatcaacc aggtccttat tatcttcagc ctgacttaac aattgcttta   2400
tttcagttct tttctctata gactcatgaa ccttctcctg cataatatag tcatgccatt   2460
tattcaacag attgcctaca tagggagacg gtactttttt tactttggac aacatacact   2520
tccctccagc tattcaaaaa tcaaaactag tcctaatact tatcggcatc atcaaacatt   2580
ttaaaacaca gaacatttag tacatagtgc ttaatgttca aatctcattt tgatgctctg   2640
```

```
aacccaagca tgtactgata tcatactaaa cggctcaaac acaatctata caagtttta    2700
agataggcca aagggaataa cagtatacgt tagtgaaatc ccacaggaaa aatatattaa    2760
aatactaatg ttctatcaaa cgaacaaccc ttaaaaagga acttaaaacc tctgggtttt    2820
aaggaaattc gcattttatt tagtgttttt ctcttgactt tgagaacttg aaactagcag    2880
aatagctgac tgttctagga aacagggcga atttcgattg cctatgtctg tcgcgcaaaa    2940
aataaaaacg gacagacata ggcaatcgat caggatttga aactagcgtc atagagacgt    3000
ctgaggtttc cagctctgcc ttgctatcgc caggctttcg cctgccatga ccttttaca    3060
tacaatgctt gtcctgtatg caacttctat ggggtttgtc tcgtgttctc tcacacggtc    3120
acactcaatt gtgtgccgct gcatagaagc ttggccatag ttgcccgcac cgtagtgcgc    3180
caagcaacct agtggtttat ccacattctc cggaccgtta atggccgtcc tcgccattca    3240
ccacaagcgc agcaaggaac gcttattgtg gtatatcccc gggtttgcgg tggacggggc    3300
aactcctgac gtcagtttat tttacacccc ttaacggcag ctgggtgaca acaaaaaaac    3360
gacagaaaac cacggtttga taccctccaa acagtggttt tctgtcgtcc aaaaatagcc    3420
gaaaagtgtt gacgtataca cttgttttcg gtaaaatgaa gacataactt aaacattgta    3480
agtgagggct tacaaaccaa gtgttcgatg ctgcaacatc ggacactttt tatttgtcat    3540
tcttatttg tattcaattt tgcaaatagc tcgcaaacaa aatatgtatc atcaaatcta    3600
ttaaccttgt tgtctgcaaa caacagggtt ttttgttgtt tatttagaat aactagaacc    3660
agaattcaat gccaaaactt tcacattgac ttaacttgac tttatcttac acgattttt    3720
ttttgacgta aagcccgggg cctgaaatca cttttctcta ctgatttcac tgatttcatt    3780
tttattatat aatcctcaaa tagcctgtat tcactgattt taaatgtgat ttcattttat    3840
tgacttagt gatataagat gctagtattg aggaaagtga atcaaagga gagaataaaa    3900
atatgaatat ttctcgtatg aacgtggact ttggaaacag tatgtacatg aatttaattg    3960
atggttattt ttttgaattg cctacaaatg tagtagagat atctaaagaa gctgctgaag    4020
gaaaatttac gagtatcgtt gaagatccgg cagatttaaa ggaccggtta ttagtttcta    4080
cagttattga tgaaacagag agatattttc tagttggtga acttgctgaa ccagaagtgt    4140
taggcaacca acacatcaag aagttacata ataaagtaga gtcacatatt ccatacgtaa    4200
cattttagc tgcaactgct tattaccaag cgctaaaagg caaacgtgaa gataatgaag    4260
ttactattga atactttcaa acaatgctac caatttggct tcttaaaaaa ttggataagt    4320
tcagtgaaat gcagaaaagg atggcatcta aattttggg cactcaccaa gtaaggtgc    4380
tgacattagg attagaaaaa gagcttacta taaaagtgga agatgcagcg tgcaggatcg    4440
aatctgaagt agcaagatgg gcaataaaga aaaactttga cctagaagat aaagactatg    4500
ccgaacaatt taaaaattat gacgtagttt tttgtgattt aggtggcgga acagatgatc    4560
tagtattact accagctgga ttaaaaccgc caaaagtcg tgattctttt gtttctaata    4620
ccgaagcacc gtttttagcg cacttagaaa aattgagaaa agaaaaactc ctagagcact    4680
ttgatagcgt tagggagctt gaaaagttta tatactcaaa tattggaaaa actaagatgg    4740
aacgaagaga cgggaatacc ggtcagaaat ttgatttaac tgatatcatc aaaaaatctc    4800
ttaaagaata cacagaaatc aaaatagccc aagctgaaaa tacgttccct gcaccaaaag    4860
ataaggttta caaatacctt tattttggcg gtgttggcga ggtgcttgaa gaatcaatta    4920
gtgtggttac tgaagagaga tatggccgtg atatttctga atcaaatcat atagttgctg    4980
aggatgcaag actgctcaac ttatatggcc ttgaagtttt aagccgcgct gaacaagtaa    5040
```

```
agaaacaggc aaatgaaaaa gaggcacaat caatttaggt gattagaaat ggggaaaaac    5100
aaaagaattc cactctttaa tgtccgaaca acacaaatgt ctgatgaaat gtacgatttt    5160
gttttagagc agattagtac attcagtaaa ggtaagagta agggtacctt tagagagtat    5220
gcctttcagc tcatagaaag ggacatgcaa caacagaaag aggaacagca aaatagagaa    5280
aaagatcgtc atgttcatga tgaattaatt gccatgagag aagaaatgaa aaagaatttt    5340
cgtgatttga ggaaaaaaat tgatcaggga tcgatctacg tagaacacaa acagctgat    5400
ccaaagtcag cttcaaaaac gattgaagaa ggtcagttaa tcactgaaaa aatcactgga    5460
actattgaag aagaatacga ctatgatttt taagagcctg gattaatcta ggctcttttt    5520
ttatgccatt taagggagga ttgcatgaca aactttttt agttgcaaca cagacgccct    5580
gagcaacgct aggacaacat cagcaaggag aaagggcta ccggcgaacc agcagccct    5640
ttataaaggc gcttcagtag tcagaccagc atcagtcctg aaaaggcggg cctgcgcccg    5700
cctccaggtt gctacttacc ggattcgtaa gccatgaaag ccgccacctc cctgtgtccg    5760
tctctgtaac gaatctcgca cagcgatttt cgtgtcagat aagtgaatat caacagtgtg    5820
agacacacga tcaacacaca ccagacaagg gaacttcgtg gtagtttcat ggccttcttc    5880
tccttgcgca aagcgcggta agaggctatc ctgatgtgga ctagacatag ggatgcctcg    5940
tggtggttaa tgaaaattaa cttactacgg ggctatcttc tttctgccac acaacacggc    6000
aacaaaccac cttcacgtca tgaggcagaa agcctcaagc gccgggcaca tcatagccca    6060
tatacctgca cgctgaccac actcactttc cctgaaaata atccgctcat tcagaccgtt    6120
cacgggaaat ccgtgtgatt gttgccgcat cacgctgcct cccggagttt gttgctaggt    6180
ctagggcggc ggatttgtcc tactcaggag agcgttcacc gacaaacaac agataaaacg    6240
aaaggcccag tctttcgact gagcctttcg ttttatttga tgcctctagt tacgccccgc    6300
cctgccactc atcgcagtac tgttgtaatt cattaagcat tctgccgaca tggaagccat    6360
cacagacggc atgatgaacc tgaatcgcca gcggcatcag caccttgtcg ccttgcgtat    6420
aatatttgcc catggtgaaa acgggggcga agaagttgtc catattggcc acgtttaaat    6480
caaaactggt gaaactcacc cagggattgg ctgagacgaa aacatattc tcaataaacc    6540
ctttagggaa ataggccagg ttttcaccgt aacacgccac atcttgcgaa tatatgtgta    6600
gaaactgccg gaaatcgtcg tggtattcac tccagagcga tgaaaacgtt tcagtttgct    6660
catggaaaac ggtgtaacaa gggtgaacac tatcccatat caccagctca ccgtctttca    6720
ttgccatacg aaattccgga tgagcattca tcaggcgggc aagaatgtga ataaaggccg    6780
gataaaactt gtgcttattt ttctttacgg tctttaaaaa ggccgtaata tccagctgaa    6840
cggtctggtt ataggtacat tgagcaactg actgaaatgc ctcaaaatgt tctttacgat    6900
gccattggga tatatcaacg gtggtatatc cagtgatttt tttctccatt ttagcttcct    6960
tagctcctga aaatctcgat aactcaaaaa atacgcccgg tagtgatctt atttcattat    7020
ggtgaaagtt ggaacctctt acgtgccgat caacgtctca ttttcgccaa agttggccc    7080
agggcttccc ggtatcaaca gggacaccag gatttattta ttctgcgaag tgatcttccg    7140
tcacaggtat ttattcggcg cctgtagtgc catttacccc cattcactgc cagagccgtg    7200
agcgcagcga actgaatgtc acgaaaaaga cagcgactca ggtgcctgat ggtcggagac    7260
aaaaggaata ttcagcgatt tgcccgagct tgcgagggtg ctacttaagc ctttaggggtt    7320
ttaaggtctg ttttgtagag gagcaaacag cgtttgcgac atccttttgt aatactgcgg    7380
```

```
aactgactaa agtagtgagt tatacacagg gctgggatct attctttta tctttttta     7440
ttctttcttt attctataaa ttataaccac ttgaatataa acaaaaaaaa cacacaaagg   7500
tctagcggaa tttacagagg gtctagcaga atttacaagt tttccagcaa aggtctagca   7560
gaatttacag atacccacaa ctcaaaggaa aaggactagt aattatcatt gactagccca   7620
tctcaattgg tatagtgatt aaaatcacct agaccaattg agatgtatgt ctgaattagt   7680
tgttttcaaa gcaaatgaac tagcgattag tcgctatgac ttaacggagc atgaaaccaa   7740
gctaattta tgctgtgtgg cactactcaa ccccacgatt gaaaaccta caaggaaaga    7800
acggacggta tcgttcactt ataaccaata cgctcagatg atgaacatca gtagggaaaa   7860
tgcttatggt gtattagcta aagcaaccag agagctgatg acgagaactg tggaaatcag   7920
gaatcctttg gttaaaggct ttgagatttt ccagtggaca aactatgcca agttctcaag   7980
cgaaaaatta gaattagttt ttagtgaaga gatattgcct tatctttcc agttaaaaaa    8040
attcataaaa tataatctgg aacatgttaa gtcttttgaa aacaaatact ctatgaggat   8100
ttatgagtgg ttattaaaag aactaacaca aagaaaact cacaaggcaa atatagagat    8160
tagccttgat gaatttaagt tcatgttaat gcttgaaaat aactaccatg agtttaaaag   8220
gcttaaccaa tgggttttga aaccaataag taaagattta aacacttaca gcaatatgaa   8280
attggtggtt gataagcgag gccgcccgac tgatacgttg atttttccaag ttgaactaga   8340
tagacaaatg gatctcgtaa ccgaacttga gaacaaccag ataaaaatga atggtgacaa   8400
aataccaaca accattacat cagattccta cctacataac ggactaagaa aaacactaca   8460
cgatgcttta actgcaaaaa ttcagctcac cagttttgag gcaaaatttt tgagtgacat   8520
gcaaagtaag tatgatctca atggttcgtt ctcatggctc acgcaaaaac aacgaaccac   8580
actagagaac atactggcta aatacggaag gatctgaggt tcttatggct cttgtatcta   8640
tcagtgaagc atcaagacta acaaacaaaa gtagaacaac tgttcaccgt tacatatcaa   8700
agggaaaact gtccatatgc acagatgaaa acggtgtaaa aaagatagat acatcagagc   8760
ttttacgagt ttttggtgca ttcaaagctg ttcaccatga acagatcgac aatgtaacag   8820
atgaacagca tgtaacacct aatagaacag gtgaaaccag taaacaaag caactagaac    8880
atgaaattga acacctgaga caacttgtta cagctcaaca gtcacacata gacagcctga   8940
aacaggcgat gctgcttatc gaatcaaagc tgccgacaac acgggagcca gtgacgcctc   9000
ccgtggggaa aaaatcat                                                  9018
```

<210> SEQ ID NO 43
<211> LENGTH: 1929
<212> TYPE: DNA
<213> ORGANISM: Artificial Sequence
<220> FEATURE:
<223> OTHER INFORMATION: pbrT

<400> SEQUENCE: 43

```
atgcaagccc tgcgtctcct ttcgattgtt ctgctctctc tgttcgtgac ggtctcgacc     60
gcacaggcag atcctctcgc cacgcaagac aaggccaagc aaatctggca agtactggac    120
taccttgctg tcgactatgg ccggtccgtc aaggatggcc acgtcgccaa cgaagccgag    180
tatgccgaga tgcaggagtt cgcgcaggcc gctgaacggc agctaaccga gttgccgccg    240
acgccagccg cgccagagtt ggccaaggaa gcggcggcgt tgcgcgcatc cattgcagaa    300
aaggccccgc ccgaatcagt cggcgagcaa gctcgcaaac tggccggcgg actcctcgca    360
gcctatccgg tcccgatggc ccccggcaag ctgcccgatc tgcaacaagg ggcaaagctg    420
```

```
tatcaaagcc aatgtgcttc gtgccacggc gtttccgggc acgcggacgg cccactagct    480
gcaaagctga gcccgccacc gatcgccctg gctgatcacg agcgcgccca ggagcgcagc    540
gtctttgccc tacagcaaat catcacgcgc ggggtagaag ggacgtcgat gccggcattt    600
gctcaactct cggacgagga acgctgggcg ctcgcctatt ttgcctcgac cctttcgtat    660
tcggatgccg accgccaggc cggcgccaag ctgtggacct ctcaaccggc tctccacgca    720
gccgtgccca cgctggcctt gttaagccag acctccgagg ctgcgctcgc caagaccgtc    780
ggggcggatg ccgctcgcca actgaccgcg tacctcagga gcacgccggg ctcggtcacc    840
gcgtcaagca ccgacagcct gatgatcgcc agagacaagc tgaaggaaag cttggccacc    900
ctggacaagg gcgacaggca gttggcttcg cggctggcgt tgtctgccta tctcgacggc    960
ttcgagcccg tcgagccggc gctggctgcc aagaaccagg cgctgttcca ggatatcgag   1020
aagacgatgg ggctctatcg caatgctgtg acagcgggcc aggtggaacg cgcccatgaa   1080
attgcgcaga agttgcaatc gcagcttgac gacgcacagg aggcgctggg cggcaccaat   1140
gacgccatat cgaccttcct cggcgccctg acaatcctgc tacgagaagg gcttgaagcc   1200
ctgttggtgg tcgtcgcgat gatggcgttc ctgaagaaag cggatcgcac cgatgtcctg   1260
ccctacgtgc atgcaggctg ggttactgcg ctggcggccg gtgggctgac ctgggcggta   1320
gccacctatg tcgtcgacct gagtggcgcc agtcgcgaga tgacggaagg tttttccgca   1380
gtgtttgccg caatcgtgtt gcttggcgtg ggcatgtgga tgcaccagaa gagtcttgcg   1440
ggtcgctggc aggcctatgt gaaggcgaag ctgtcctcgg cattgaacaa gaaatcagcg   1500
ctgatgctgt tcctgctgtc gttcgtgacc gtctatcgag aagtgtttga aacagtcctc   1560
ttttacgctg ccctgtggac agagggcaac ggtgtatttt tgctcgcagg acttgcgtcg   1620
ggtatcgcca tcctggccgc gatcgccatc gtgctcctgc gctccacggc gcgcctgccg   1680
attggtcagt tctttgcctt cagctcagca ttggtcggcg tgttggcggt cgttctgatt   1740
ggtaaaggca tagctgcgct tcagaaagtc ggcttcctac aagttacgcc gatctccatg   1800
cctcgtatcg acgtcctggg catttatccg tccgtccaga ccgtcgtagc gcaagtcctg   1860
attctgctca ttatcgccgc aagcgtcgtc tacaatttgc ggtcgcaccg gccatctacc   1920
caggtgtaa                                                           1929
```

MICROBIAL MICROFLUIDIC BIOSENSOR

INCORPORATION BY REFERENCE TO ANY PRIORITY APPLICATIONS

This application is a National Stage application under 35 U.S.C. § 371 of International No. PCT/US2016/017889, filed Feb. 12, 2016, which claims priority to U.S. Provisional Application Ser. No. 62/116,888, entitled "Microbial Microfluidic Biosensor" filed Feb. 16, 2015, the contents of which are hereby expressly incorporated by referenced in their entirety.

STATEMENT REGARDING FEDERALLY SPONSORED R&D

This invention was made with government support under W911NF-14-2-0032, awarded by the United States Army. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled SEQ.TXT created Jan. 2, 2018, which is 54.4 kb in size. The information is the electronic format of the Sequence Listing is incorporated herein by reference in its entirety.

FIELD OF THE INVENTION

Provided are microfluidic biosensors that are suitable for continuously monitoring analyte levels.

BACKGROUND OF THE INVENTION

The existing art consists of using engineered biosensor strains in a well plate to test for water toxin levels. Alternatively, electronic testing devices not based on bacterial biosensors provide disposable test strips or cartridges to perform an individual test for a toxin of interest. Neither of these methods offer a cost-effective option for continuous monitoring of water toxin levels without human intervention.

SUMMARY OF THE INVENTION

In a first aspect, a microfluidic device comprising one or more colonies or cultures of microorganism cells at one or more predetermined addressable locations is provided, wherein each of the cells within the one or more colonies or cultures comprises an expression cassette comprising a biosensor or promoter operably linked to a polynucleotide encoding a detectable agent, wherein transcription of the biosensor or promoter is modulated by the presence of an analyte. In some embodiments, the detectable agent is a nucleic acid, detectable protein, antibody-linked reporter protein, enzymatic assay product, or electrochemical reaction product. In some embodiments, the detectable protein comprises an activity that is increased or decreased in the presence of an analyte. In some embodiments, the detectable agent is a detectable protein, wherein the detectable protein provides a detectable signal. In some embodiments, the detectable protein is a fluorescent protein or a luminescent protein. In some embodiments, the detectable agent is a detectable protein, wherein the detectable protein provides a detectable signal. In some embodiments, the nucleic acid is RNA or DNA. In some embodiments, the microfluidic device comprises microfluidic channels or lumens arranged in a rotationally symmetric gill cell trapping configuration. In some embodiments, the microfluidic channels or lumens are arranged in 16 or 18 rotationally symmetric gills. In some embodiments, the device comprises about 20,000 chambers or gill traps. In some embodiments, transcription of the biosensor or promoter is induced, promoted or increased by the presence of an analyte. In some embodiments, transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the biosensor or promoter comprises a polynucleotide having a sequence identity of at least about 90% to a polynucleotide sequence selected from the group consisting of SEQ ID NOs: 1-43. In some embodiments, the biosensor or promoter comprises a polynucleotide having a sequence identity of at least about 90% to a polynucleotide sequence selected from the group consisting of SEQ ID NOs: 2, 5, 8, 11, 12, 13, 14, 15, 16, 17, 20, 23, 25, 28, 29, 30 and 33. In some embodiments, transcription of the biosensor or promoter is decreased or inhibited by the presence of an analyte. In some embodiments, the biosensor or promoter is decreased or inhibited by the presence of ammonia. In some embodiments, the biosensor or promoter which is decreased or inhibited by the presence of ammonia is selected from the group consisting of PnasA (ammonia), PnasB (ammonia), Pspo1-tnrA1 (ammonia) and Pspo1-tnrA2 (ammonia). In some embodiments, the biosensor or promoter comprises a polynucleotide sequence having at least about 90% sequence identity to SEQ ID NO:1. In some embodiments, the device detects or monitors the presence or levels of one or more analytes at the following concentrations: a) at least about 0.2 nM arsenic; b) at least about 0.44 µM cadmium; c) at least about 2.5 µM chromium (VI); d) at least about 5 µM copper; e) at least about 1 µM mercury; f) at least about 1.8 µM lead; g) at least about 72.5 mg/l malathion; and/or h) at least about 1 ppm ammonia. In some embodiments, the microorganism cells are selected from the group consisting of bacteria, cyanobacteria, microalgae and fungi. In some embodiments, the microorganism cells comprise a bacteria selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans,* and *Staphylococcus aureus.* In some embodiments, the microorganism cells comprise a fungus selected from the group consisting of *Saccharomyces cerevisiae* and *Trichosporon cutaneum.* In some embodiments, the microorganism cells comprise *Synechocystis* sp. In some embodiments, the device is capable of culturing at least about 4,000 individual strains of microorganism cells. In some embodiments, the expression cassette is in a plasmid which has been introduced into the microorganism. In some embodiments, the expression cassette is integrated into the genome of the microorganism. In some embodiments, the one or more colonies or cultures of microorganisms are lyophilized (freeze-dried). In some embodiments, the one or more colonies or cultures of microorganisms are one or more different species. In some embodiments, the one or more colonies or cultures of microorganisms are the same species. In some embodiments, the detectable protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the detectable protein is a luminescent protein. In some embodiments, the luminescent protein is bacterial luciferase (Lux). In some embodiments, said microfluidic device comprises a plurality of said colonies or cultures and wherein each of said plurality of colonies or cultures comprises an expression cassette comprising a biosensor or promoter operably linked to a polynucleotide encoding a detectable protein wherein transcription of the biosensor or promoter is modulated by the presence of a different analyte than the biosensor or promoter in the other of said plurality of colonies or cultures. In some embodiments, the plurality of colonies or cultures comprises at least 2 colonies or cultures, 3 colonies or cultures, 4 colonies or cultures, 5 colonies or cultures, 6 colonies or cultures or 7 colonies or cultures. In some embodiments, the colonies or cultures comprise microorganism cells are selected from the group consisting of bacteria, cyanobacteria, microalgae and fungi. In some embodiments, the transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc)

In a second aspect, a system comprising the microfluidic device of any one of the embodiments, is provided. In some embodiments, the system further comprises a housing enclosing the device, comprising within the housing: i) a peristaltic pump in fluid communication with the microfluidic device; ii) a fluorescent or luminescent signal sensor or detector comprising a platform to accommodate the microfluidic device; and iii) electronics for acquiring and processing data in electronic communication with the fluorescent or luminescent signal sensor or detector. In some embodiments, the system is configured as depicted in FIG. 7. In some embodiments, the housing is temperature and/or humidity controlled.

In a third aspect, a method of detecting the presence or levels of an analyte in an aqueous sample is provided, wherein the method comprises a) inputting into the microfluidic lumens of a microfluidic device of any one of the embodiments provided herein an aqueous test sample suspected of comprising one or more analytes of interest such that the aqueous test sample contacts the one or more colonies or cultures of microorganism cells; b) measuring the amount of a detectable agent that can correspond to a quantifiable level of analyte. In some embodiments, the detectable protein is a fluorescent protein or a luminescent protein. In some embodiments, measuring comprises measuring the transcription and/or activation levels of the detectable agent, wherein the transcription and/or activation levels of the detectable protein expressed by the one or more colonies or cultures at the predetermined addressable locations correspond to a quantifiable level of analyte. In some embodiments, the method further comprises measuring the fluorescence and/or the luminescence of the one or more detectable proteins expressed by the one or more colonies or cultures at the predetermined addressable locations within the device.

In a fourth aspect a collection comprising a plurality of different nucleic acids is provided, wherein each nucleic acid within said collection comprises a first sequence comprising a promoter responsive to an analyte different from the analyte to which the other promoters in the other nucleic acids are responsive; and a second sequence comprising a reporter protein. In some embodiments, the promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the reporter protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG.

In a fifth aspect, a method of making a plurality of cell strains for the detection of an analyte, the method comprising: introducing into a plurality of cell strains the collection of anyone of the embodiments provided herein.

In a sixth aspect, cell strains for the detection of an analyte is provided, wherein the cell strains comprises the nucleic acid of anyone of the embodiments provided herein or made by the method of any of the embodiments provided herein. In some embodiments, the cell is of bacteria, cyanobacteria, microalgae and fungi. In some embodiments, the bacteria is selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans,* and *Staphylococcus aureus*. In some embodiments, the cell is a fungus selected from the group consisting of *Saccharomyces cerevisiae* and *Trichosporon cutaneum*. In some embodiments, the cell comprises *Synechocystis* sp.

In a seventh aspect, a microfluidic device comprising a plurality of lyophilized cell strains wherein each of said plurality of lyophilized cells strains has been genetically engineered to produce an increased or decreased amount of a detectable agent in the presence of an analyte relative to the amount produced in the absence of said analyte. In some embodiments, the detectable agent is a nucleic acid, detectable protein, antibody-linked reporter protein, enzymatic assay product, or electrochemical reaction product. In some embodiments, the detectable protein is a fluorescent protein or a luminescent protein. In some embodiments, the detectable protein comprises an activity that is increased or decreased in the presence of an analyte. In some embodiments, the detectable agent is a detectable protein, wherein the detectable protein provides a detectable signal. In some embodiments, the nucleic acid is RNA or DNA. In some embodiments, the microfluidic device comprises microfluidic channels or lumens arranged in a rotationally symmetric gill cell trapping configuration. In some embodiments, the microfluidic channels or lumens are arranged in 16 or 18 rotationally symmetric gills. In some embodiments, the device comprises about 20,000 chambers or gill traps. In some embodiments, transcription of the biosensor or promoter is induced, promoted or increased by the presence of an analyte. In some embodiments, transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the biosensor or promoter comprises a polynucleotide having a sequence identity of at least about 90% to a polynucleotide sequence selected from the group consisting of SEQ ID NOs: 1-43. In some embodiments, the biosensor or promoter comprises a polynucleotide having a sequence identity of at least about 90% to a polynucleotide sequence selected from the group consisting of SEQ ID NOs: 2, 5, 8, 11, 12, 13, 14, 15, 16, 17, 20, 23, 25, 28, 29, 30 and 33. In some embodiments, transcription of the biosensor or promoter is decreased or inhibited by the presence of an analyte. In some embodiments, the biosensor or promoter is decreased or inhibited by the presence of ammonia. In some embodiments, the biosensor or promoter which is decreased or inhibited by the presence of ammonia is selected from the group consisting of PnasA (ammonia), PnasB (ammonia), Pspo1-tnrA1 (ammonia) and Pspo1-tnrA2 (ammonia). In some embodiments, the biosensor or promoter comprises a polynucleotide sequence having at least about 90% sequence identity to SEQ ID NO:1. In some embodiments, the device detects or monitors the presence or levels of one or more analytes at the following concentrations: a) at least about 0.2 nM arsenic; b) at least about 0.44 µM cadmium; c) at least about 2.5 µM chromium (VI); d) at least about 5 µM copper; e) at least about 1 µM mercury; f) at least about 1.8 µM lead; g) at least about 72.5 mg/l malathion; and/or h) at least about 1 ppm ammonia. In some embodiments, the microorganism cells are selected from the group consisting of bacteria, cyanobacteria, microalgae and fungi. In some embodiments, the microorganism cells comprise a bacteria selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans*, and *Staphylococcus aureus*. In some embodiments, the microorganism cells comprise a fungus selected from the group consisting of *Saccharomyces cerevisiae* and *Trichosporon cutaneum*. In some embodiments, the microorganism cells comprise *Synechocystis* sp. In some embodiments, the device is capable of culturing at least about 4,000 individual strains of microorganism cells. In some embodiments, the expression cassette is in a plasmid which has been introduced into the microorganism. In some embodiments, the expression cassette is integrated into the genome of the microorganism. In some embodiments, the one or more colonies or cultures of microorganisms are one or more different species. In some embodiments, the one or more colonies or cultures of microorganisms are the same species. In some embodiments, the detectable protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the detectable protein is a luminescent protein. In some embodiments, the luminescent protein is bacterial luciferase (Lux).

BRIEF DESCRIPTION OF THE DRAWINGS

FIG. 17 shows the response of the dadA promoter in E. coli MG1655 for specifically sensing cobalt. The response of the dadA promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.

FIGS. 41 (41A, 41B, 41C, 41D, 41E and 41F) shows 18-strain chip induction data for three toxins, demonstrating the sensor-specific induction of *B. subtilis* NCIB 3610/Amm3 for ammonium and the unique combinations of responses allowing the identification of cobalt and lead.

FIG. 51 shows the response of the arsR promoter in *E. coli* MG1655 for specifically sensing arsenic. Note that the arsR promoter responds specifically and monotonically to increasing concentrations of arsenic alone and in combination with other heavy metals (rightmost conditions) without exhibiting crosstalk. Plots represent the mean fold change, the normalized counts (taking into account both the library depth and the gene length), and the "% CDF expression level." This measure represents the position of the gene in the Cumulative Distribution Function (CDF) obtained from the normalized counts for a given experimental condition; that is, a large CDF indicates a high expression level for the gene compared to the other genes in the same experiment. Replicate samples for each toxin are shown in the same color. Control samples for each batch of experiments are shown in white. As shown in the two panels below, the numbers at the x-axis correspond to the four corresponding bars above the numbers. For example the first 4 bars correspond to the number 1, the second set of 4 bars correspond to the number 2 and so forth.

DEFINITIONS

Figure 1A:
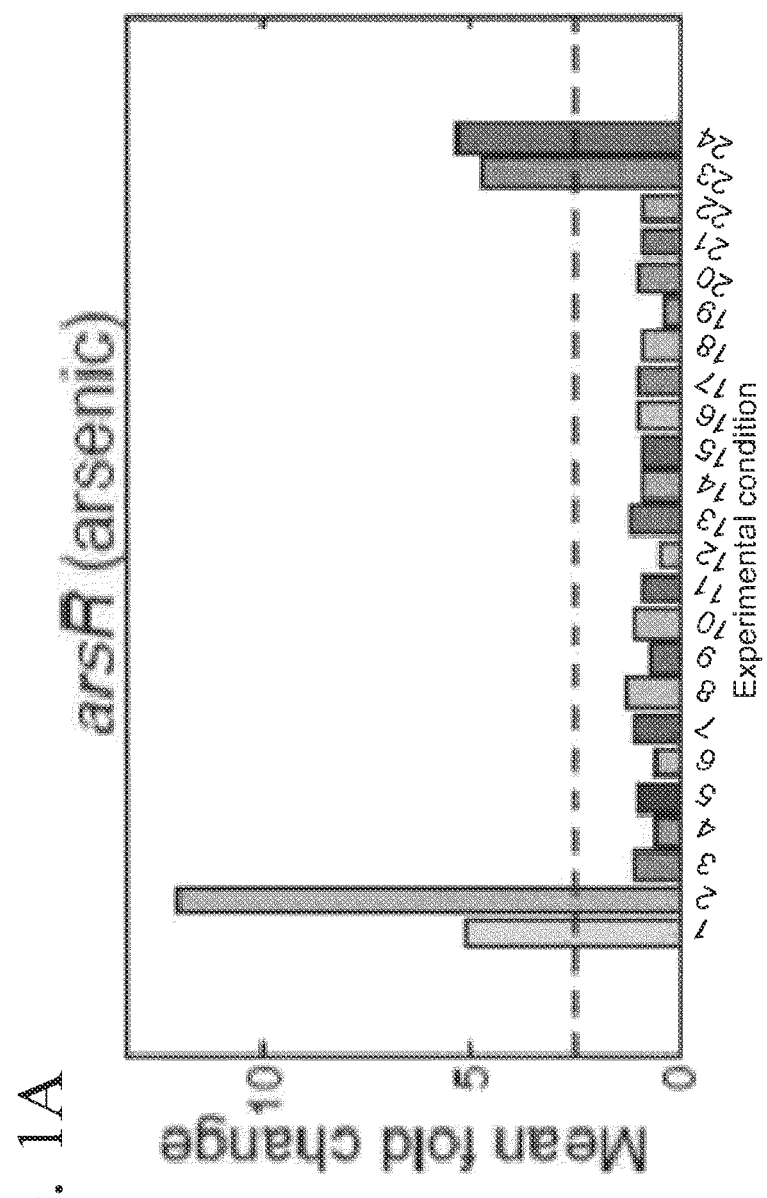
FIG. 1, (FIGS. 1A, 1B, 1C, 1D, 1E, 1F, 1G, 1H, and 1I) illustrates sensitive and specific gene candidates for eight toxins identified by RNA-Seq analysis in *E. coli* MG1655, where the mean fold change threshold to indicate DE has been set to 2.5. The eight toxins are arsenic (arsR), cadmium (zntA), chromium (VI) (recN), chromium (VI) (*sulA*), cobalt (ygbA), copper (curR), lead (ybiI), malathion (nemR) and zinc (araP).
Figure 1B:
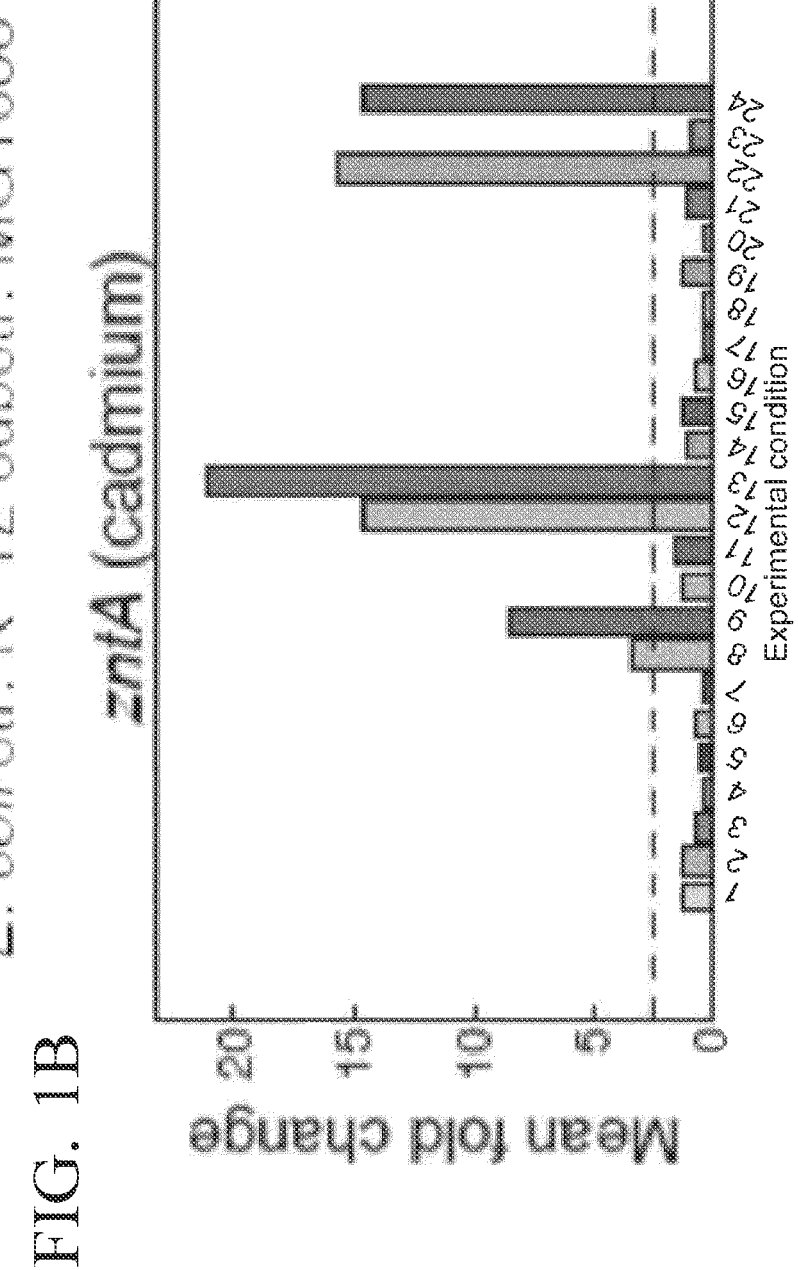
Figure 1C:
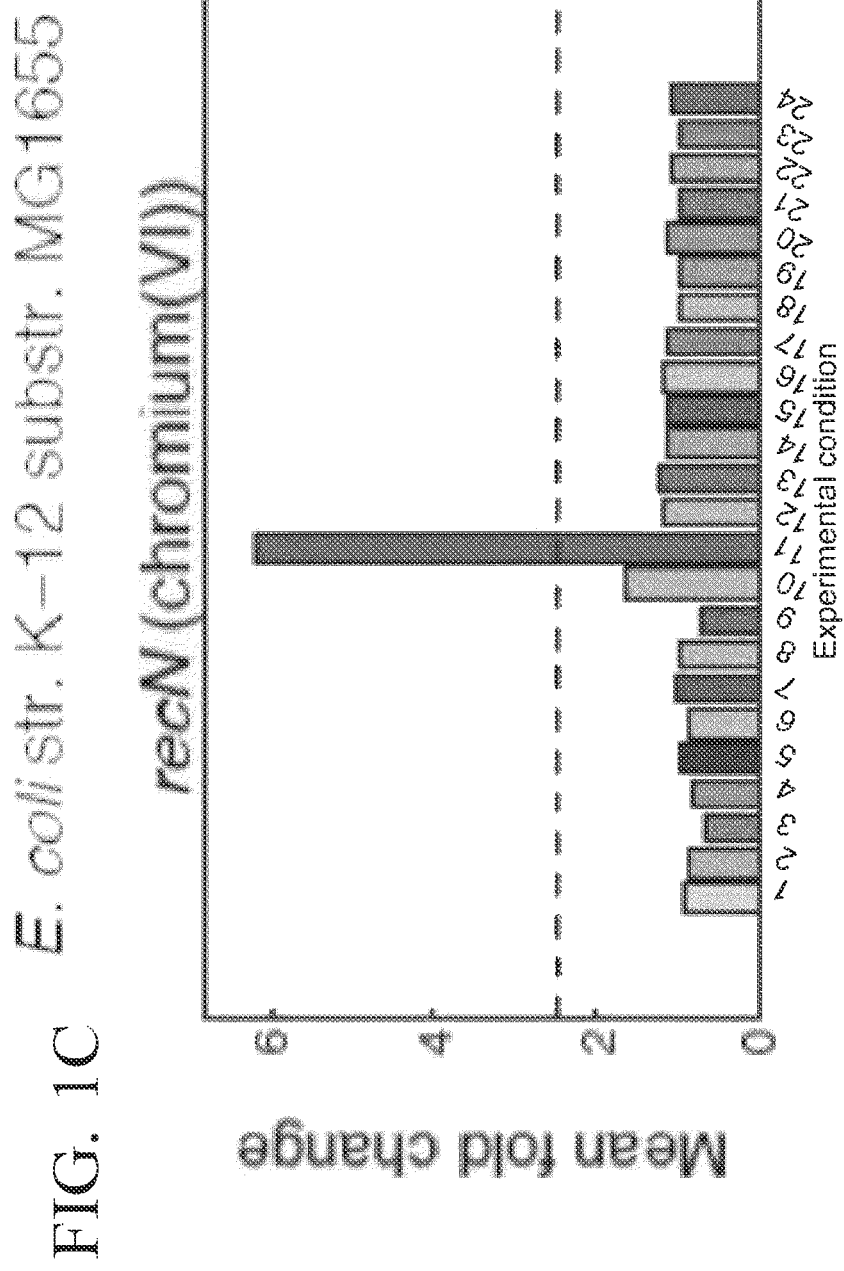
Figure 1D:
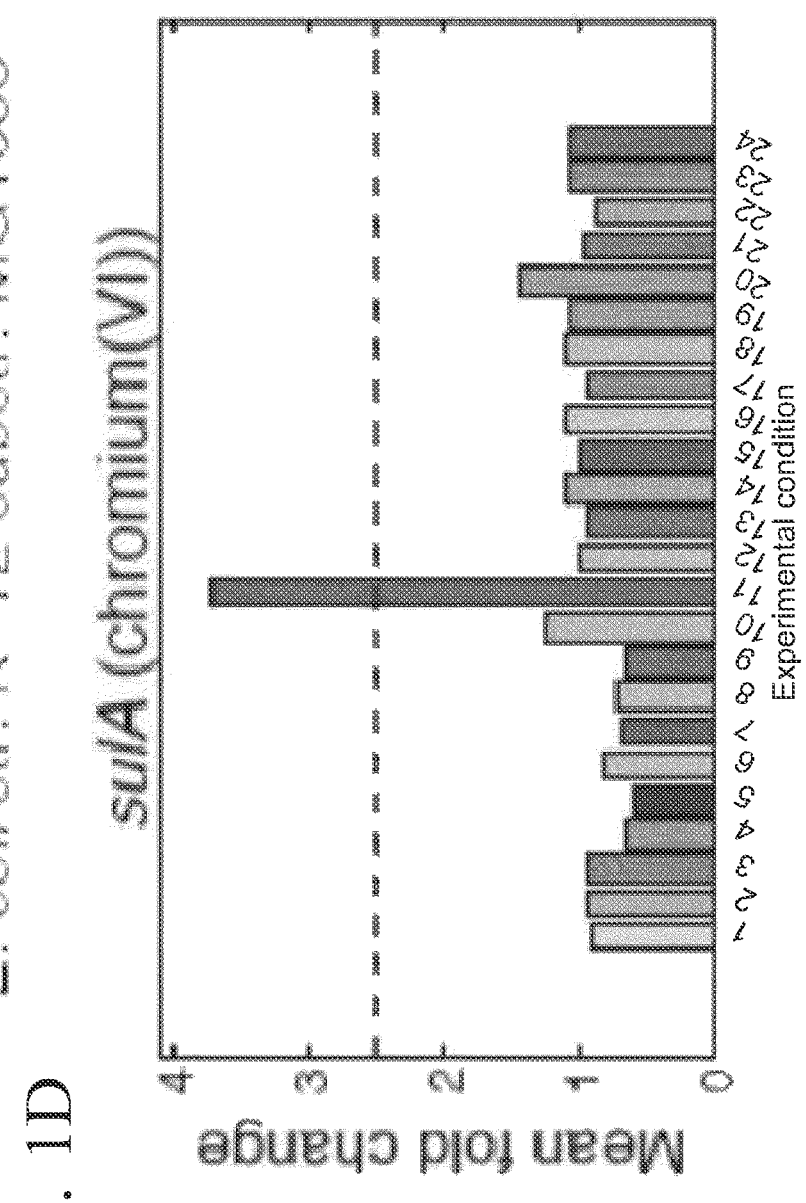
Figure 1E:
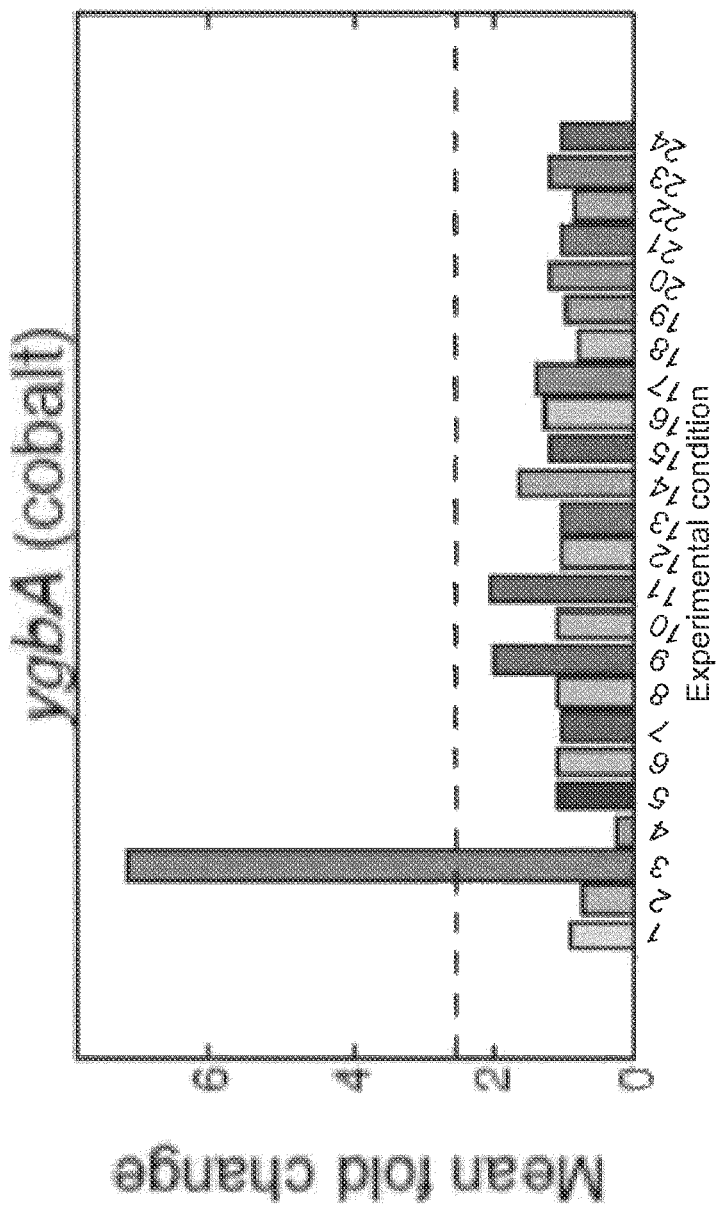
Figure 1F:
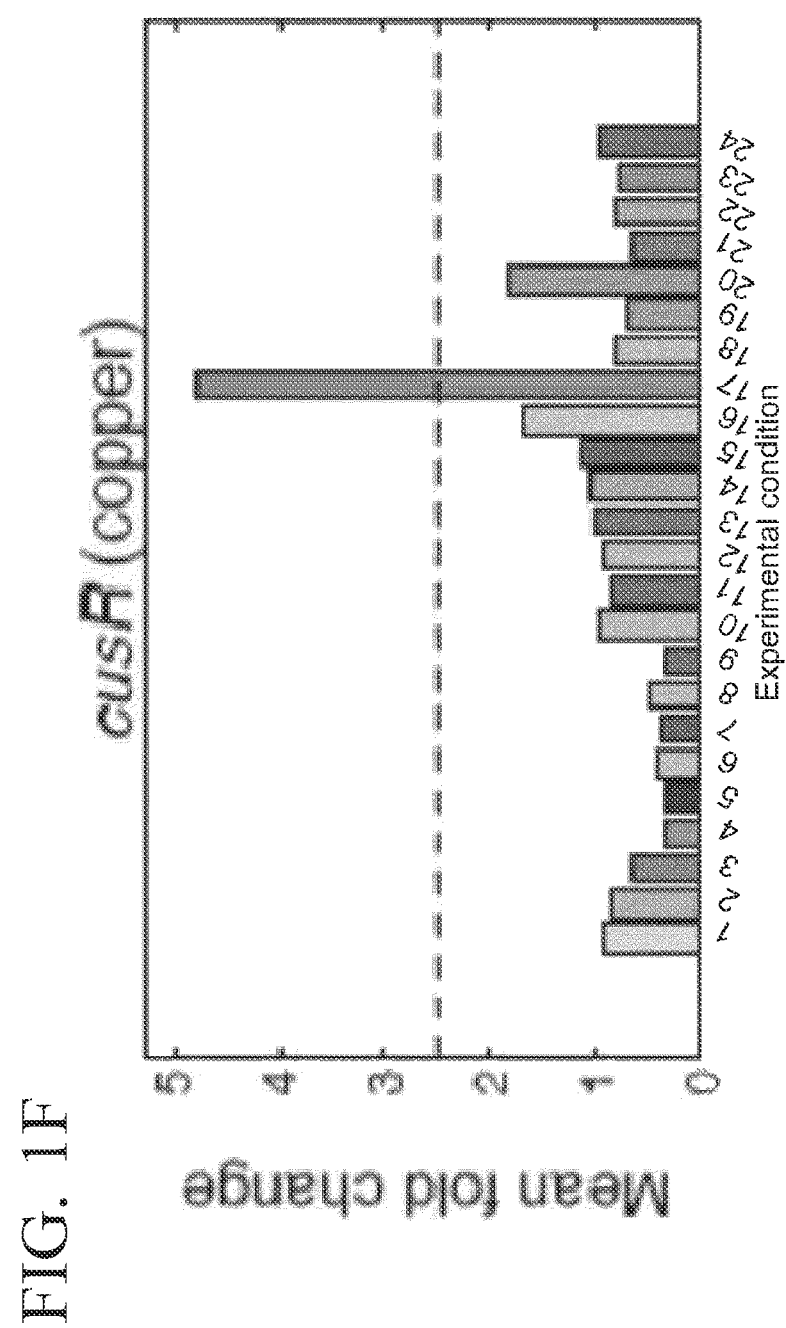
Figure 1G:
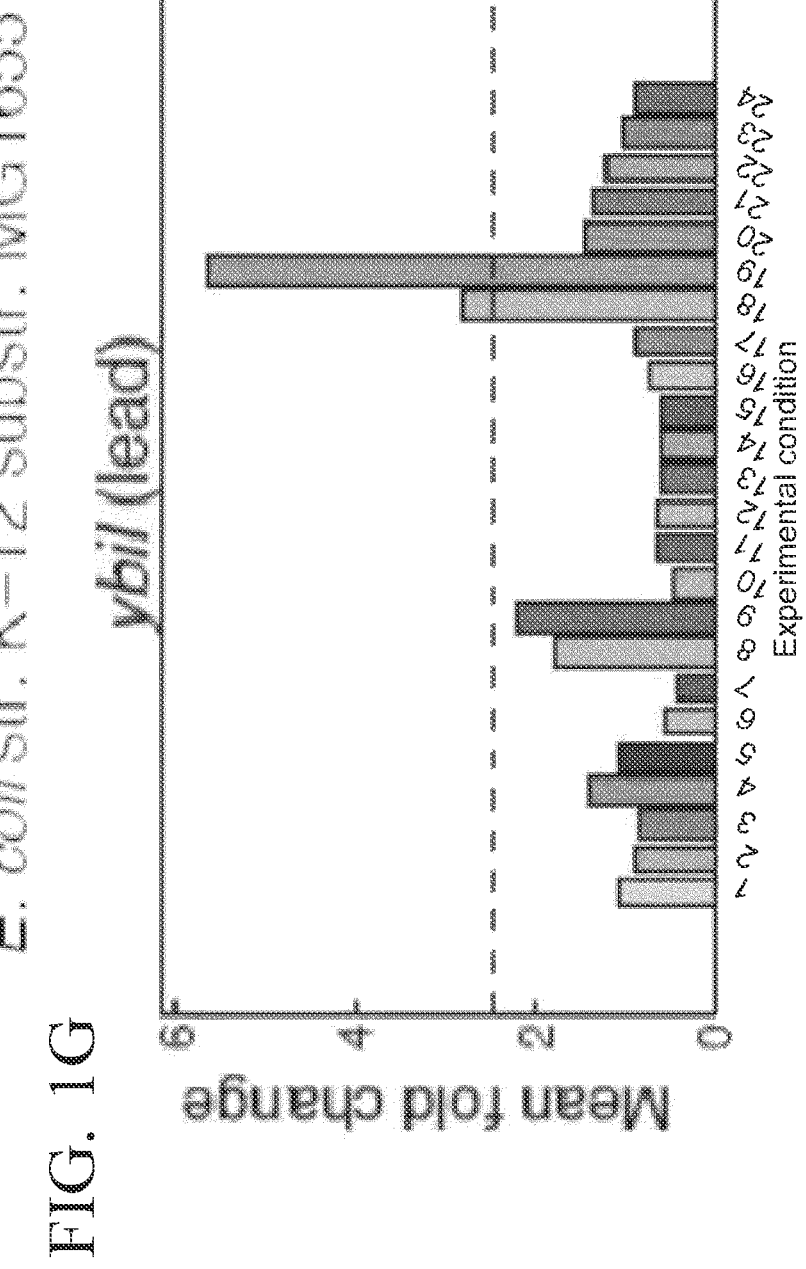
Figure 1H:
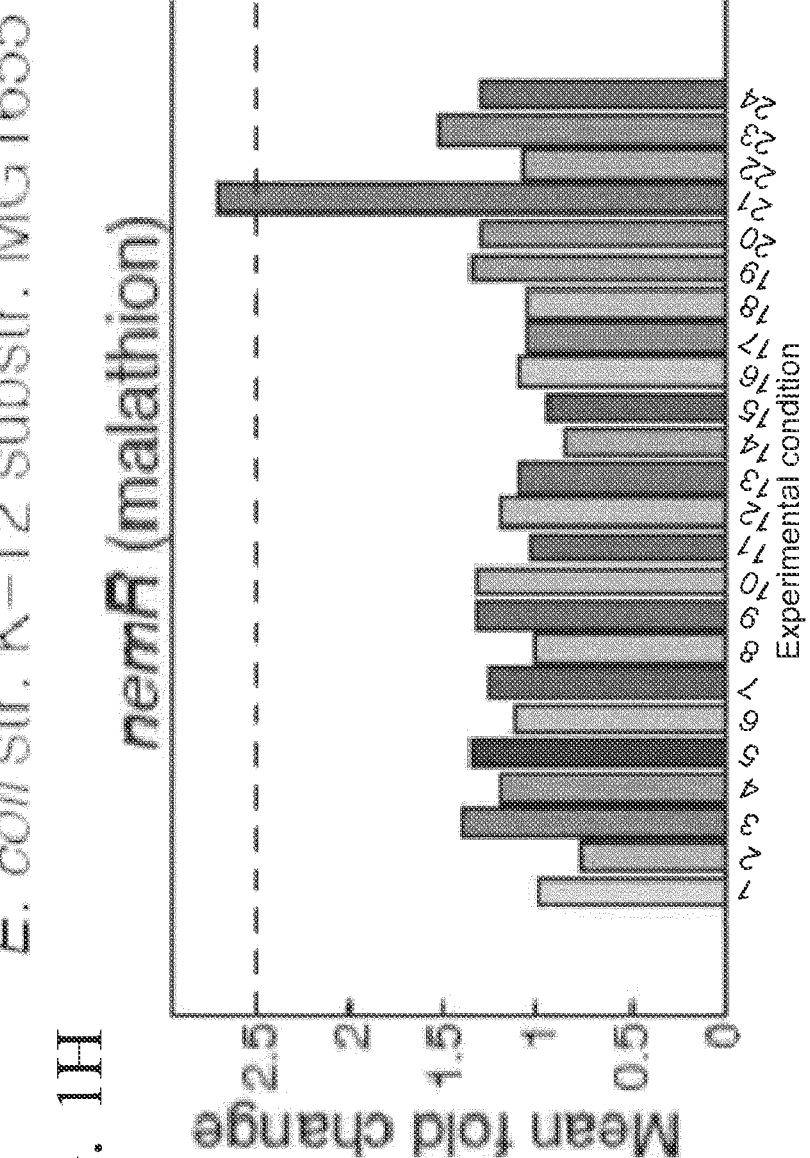

The term "response element" refers to sequences of DNA that are able to bind specific transcription factors or analytes and regulate transcription of genes. Specific response elements are described herein and in Intl. Appl. No. PCT/US2012/069914, hereby incorporated herein in its entirety for all purposes.

The term "analyte" refers to any compound o5 agent of interest for detection. As appropriate, the analyte can be an element, a nucleic acid, a protein, a carbohydrate, a lipid or a small organic compound. The analyte can be organic or inorganic.

The terms "identical" or percent "identity," and variants thereof in the context of two or more polynucleotide sequences, refers to two or more sequences or subsequences that are the same. Sequences are "substantially identical" if they have a specified percentage of nucleic acid residues or nucleotides that are the same (e.g., at least 60% identity, optionally at least 65%, 70%, 75%, 80%, 85%, 91%, 92%, 93%, 94%, 95%, 96%, 97%, 98%, or 99% identity over a specified region (or the whole reference sequence when not specified)), when compared to a reference sequence (e.g., SEQ ID NOs: 1-43) and aligned for maximum correspondence over a comparison window, or designated region as measured using one of the following sequence comparison algorithms or by manual alignment and visual inspection. The present invention includes polynucleotides improved for expression in host cells that are substantially identical to the polynucleotides described herein. Optionally, the identity exists over a region that is at least about 50 nucleic acid bases or residues in length, or more preferably over a region that is 100, 200, 300, 400, 500, 600, 800, 1000, 1500, 2000, 2500, 3000, or more, nucleic acids in length, or over the full-length of the sequence. In some alternatives described herein, the identity exists over a region that is at least about 50 nucleic acid bases or residues in length, or more preferably over a region that is 100, 200, 300, 400, 500, 600, 800, 1000, 1500, 2000, 2500, 3000, or more, nucleic acid bases in length, or over the full-length of the sequence, or any number of bases defined by a range in between any two aforementioned values.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Without being limiting, the percent sequence identities for the test sequences relative to the reference sequence can be calculated by a program such as BLAST using the default parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)). Examples of an algorithm that is suitable for determining percent sequence identity and sequence similarity include the BLAST suite using default parameters, available on the internet at blast.ncbi.nlm.nih.gov/, and known to those of skill in the art. In some alternatives, a "comparison window" is made, and comprises variants thereof, and can include reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned or any number defined by a range within any to aforementioned values.

The term "substantial identity" of polynucleotide sequences means that a polynucleotide comprises a sequence that has at least 80% sequence identity, e.g., at least about 85%, 90%, 91%, 92%, 93%, 94%, 95%, 96%, 97%, 98%, 99%, or higher, compared to a reference sequence (e.g., SEQ ID NOs: 1-45), using sequence alignment/comparison algorithms set to standard parameters. One of skill will recognize that these values can be appropriately adjusted to determine corresponding identity of proteins encoded by two nucleotide sequences by taking into account codon degeneracy, amino acid similarity, reading frame positioning and the like.

"Substantial identity" of amino acid sequences for these purposes means sequence identity of at least 80% sequence identity, e.g., at least about 85%, 90%, 91%, 92%, 93%, 94%, 95%, 96%, 97%, 98%, 99%, or higher, using sequence alignment/comparison algorithms set to standard parameters. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, asp artic acid-glutamic acid, and asparagine-glutamine. Determination of "substantial identity" can be focused over defined subsequences, such as known structural domains.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 1 molar at pH 7 and the temperature is at least about 60° C.

An "expression cassette" refers to a nucleic acid construct, which when introduced into a host cell, results in transcription and/or translation of a RNA or polypeptide, respectively.

The term "promoter" or "regulatory element" refers to a region or sequence determinants located upstream or downstream from the start of transcription that direct transcription. As used herein, a promoter includes necessary nucleic acid sequences near the start site of transcription, such as, in the case of a polymerase II type promoter, a TATA element. A promoter also optionally includes distal elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter) and a second nucleic acid sequence, such as a nucleic acid encoding an antigen, wherein the expression control sequence directs transcription of the nucleic acid corresponding to the second sequence. The promoters used in the present expression cassettes are active in the host cells, but need not originate from that organism. It is understood that limited modifications can be made without destroying the biological function of a regulatory element and that such limited modifications can result in regulatory elements that have substantially equivalent or enhanced function as compared to a wild type regulatory element. These modifications can be deliberate, as through site-directed mutagenesis, or can be accidental such as through mutation in hosts harboring the regulatory element. All such modified nucleotide sequences are included in the definition of a regulatory element as long as the ability to confer expression in the host cell is substantially retained. Without being limiting, some examples of promoters are listed in Table 1. As shown in Table 2 are more examples of toxin responsive promoter constructs identified from the literature, synthesized by Transcriptic, cloned into *E. coli*, and demonstrating high sensitivity in the microfluidic device, ordered by toxin. The promoter source and RBS used in the synthetic construct are shown alongside the toxin concentration sensed and SNR after 6 h. (Refer to FIG. 36 for on-chip time-lapse induction responses).

A detectable agent can be a nucleic acid, detectable protein, antibody-linked reporter protein, enzymatic assay product, or electrochemical reaction product. A detectable agent can also be a reporter protein that can be detected by an antibody. A detectable agent can be a nucleic acid or a protein that can be assayed to determine a concentration or a signal in response to a detectable analyte such as a toxin. The nucleic acid can be an RNA or a DNA that is transcribed following a promoter being modulated by a signal.

A "reporter protein" as described herein, refers to a protein that is detected which is indicative of transcription or translation from a regulatory sequence of interest in a bacteria, cell culture or animal. A reporter gene is a gene that is attached to a regulatory sequence of another gene. These can be used to indicate whether a certain gene is expressed in the presence of an analyte. Without being limiting common reporter genes to express a reporter proteins can be green fluorescent protein, luciferase (which can catalyze a reaction with luciferin to produce light, and red fluorescent protein. Without being limiting a common reporter in bacteria is *E. coli* lacZ gene, which encodes beta-galactosidase which can cause bacteria to appear in a blue color when grown in a medium that contains the substrate X-gal.

In regards to an "electrochemical reaction product" detection method, in some embodiments there has been success in detecting hydrogen peroxide ($H_2O_2$) produced by reactive oxygen species formed when green fluorescent protein molecules are illuminated within their excitation spectrum. This $H_2O_2$ is detected at microelectrodes integrated into the microfluidic device. The microelectrodes may be functionalized by coating them with a thin film (for example, Prussian blue) to increase sensitivity and selectivity. They may also be coated with a protectant (for example, Nafion) to prevent fouling. Microelectrodes may be positioned in the same fluidic channel as the cells or in an adjacent fluidic channel, separated by a thin barrier of PDMS. The latter sensing methodology may limit chemical fouling of the microelectrode surface over long measurement durations and is feasible due to the ability of $H_2O_2$ to diffuse through PDMS. In some embodiments, an electrochemical reaction product is product that can produce a detectable electric current. These types of reactions can involve electric charges that can move between the electrode and the electrolyte. In some embodiments, of the microfluidic devices described herein, the microfluidic devices comprise microelectrodes integrated into the microfluidic device. In some embodiments, the microelectrodes may be functionalized by coating them with a thin film (e.g. Prussian blue) to increase sensitivity and selectivity. In some embodiments, the microelectrodes are coated with a protectant (e.g. Nafion) to prevent fouling. In some embodiments, the microelectrodes are positioned in the same fluidic channel as the cells or in an adjacent fluidic channel, separated by a thin barrier of PDMS.

"Enzymatic assay product" as described herein, can be a product or a protein that is usually detected from an enzymatic reaction. Without being limiting, one example would be to engineer the cells to produce the beta-galactosidase enzyme (e.g. lacZ for bacteria). The medium can then be supplemented with the organic compound X-gal (BCIG, for 5-bromo-4-chloro-3-indolyl-β-D-galactopyranoside), and the beta-galactosidase enzyme would hydrolyze this to an insoluble blue compound that is detectable by an imaging system. Alternatively, another way to assay for the enzymatic assay product is to engineer the cells to produce the beta-galactosidase enzyme. The medium would then be supplemented with LuGal, a soluble conjugate of luciferin and galactose, and the beta-galactosidase enzyme would hydrolyze this to luciferin. Effluent from each strain would be collected from the microfluidic device and subjected to a luciferase assay for the sensitive detection of luciferin. In some embodiments, a microfluidic device is provided, wherein the microfluidic device comprises one or more colonies or cultures of microorganism cells at one or more predetermined addressable locations, wherein each of the cells within the one or more colonies or cultures comprises an expression cassette comprising a biosensor or promoter operably linked to a polynucleotide encoding a detectable agent, wherein transcription of the biosensor or promoter is modulated by the presence of an analyte. In some embodiments, the detectable agent is a nucleic acid, detectable protein, antibody-linked reporter protein, enzymatic assay product, or electrochemical reaction product. In some embodiments, the detectable agent is an enzymatic assay product. In some embodiments, the enzymatic assay product is beta-galactosidase enzyme. In some embodiments, the detectable agent is detected by addition of X-gal or LuGal.

TABLE 1

Identified promoters from literature

| Toxin | Source Organism | Gene/Promoter |
|---|---|---|
| Arsenic | *E. coli* plasmid | arsR/$p_{arsR}$ |
| | *E. coli* genome | arsR/$p_{arsR}$ |
| | *S. aureus* plasmid | arsR/$p_{arsR}$ |
| | *B. subtilis* genome | arsR/$p_{arsR}$ |
| Cadmium | *S. aureus* plasmid | cadC/$p_{cadC}$ |
| | *P. putida* genome | cadR/$p_{cadR}$ |
| | *S. salivarius* genome | cadX/$p_{cadX}$ |
| | *S. lugdunensis* genome | cadX/$p_{cadX}$ |
| Chromium(VI) | *C. metallidurans* plasmid | chrB/$p_{chrB}$ |
| | *O. tritici* transposon | chrB/$p_{chrB}$ |
| | *B. subtilis* genome | chrS/$p_{chrS}$ |
| Copper | *E. coli* genome | cueR/$p_{copA}$ |
| | *E. coli* genome | (cusS/R)/$p_{cusC}$ |
| Lead | *C. metallidurans* plasmid | pbrR/$p_{pbrR}$ |
| Mercury | *E. coli* plasmid | merR/$p_{merR}$ |
| | *S. aureus* plasmid | merR/$p_{merR}$ |
| | *S. marcescens* plasmid | merR/$p_{merR}$ |
| | *S. lividans* genome | merR/$p_{merR}$ |
| Ammonia | *B. subtilis* genome | $P_{nasA}$ |
| | *B. subtilis* genome | $P_{nasB}$ |
| | *B. subtilis* genome | $P_{spo1-mrA}$ |

TABLE 2

| Toxin | Gene/Promoter | Source | RBS | Host Strain/Plasmid | Concentration Sensed in Microfluidic Device (µM) | SNR after 6 h | Refer to Figure Panel |
|---|---|---|---|---|---|---|---|
| Arsenic | arsR/$p_{arsR}$ | E. coli plasmid | native | E. coli MG1655/As1 | 0.13 | 20 | 37a |
| Arsenic | arsR/$p_{arsR}$ | E. coli genome | synthetic | E. coli MG1655/As3 | 0.13 | 33 | 37a |
| Cadmium | cadC/$p_{cadC}$ | S. aureus plasmid | native | E. coli MG1655/Cd1 | 0.04 | 17 | 37b |
| Chromium(VI) | chrB/$p_{chrB}$ | O. tritici transposon | native | E. coli LABEC01/Cr5 | 5 | 5 | 37c |
| Copper | cueR/$p_{cueA}$ | E. coli genome | native | E. coli MG1655/Cu1 | 25 | 65 | 37d |
| Lead | pbrR/$p_{pbrR}$ | C. metallidurans plasmid | synthetic | E. coli LABEC01/Pb2 | 7 | 18 | 37e |
| Mercury | merR/$p_{merR}$ | E. coli plasmid | synthetic | E. coli MG1655/Hg3 | 0.1 | 20 | 37f |

DETAILED DESCRIPTION

Introduction

Disclosed are methods, materials and devices that pertain to a robust microfluidic biosensor that is suitable for continuously monitoring toxin levels in sources such as water supplies, and runs freely for 30 days without intervention. In some embodiments, the device and/or microfluidic biosensor can run for 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days or any number of days defined by a range between any two aforementioned values, without intervention. The invention is inexpensive, able to detect more toxins than conventional means, and can be deployed with minimal or no infrastructure. A functional working embodiment is described. Applications include general water supply monitoring and defense against terrorist water supply attacks.

Also provided are methodologies to pre-load and freeze-dry an array of bacterial sensor strains within a microfluidic chip to increase survival rates during long-term storage. Upon device deployment, strains are revived on-chip using a mixture of sampled water and concentrated growth medium for time-lapse fluorescence imaging. An on-board computer analyzes the acquired images in real time before generating and wirelessly transmitting a toxin signature to a secure database. In some embodiments, the device successfully detects the presence of heavy metals and ammonia at levels relevant to drinking water safety and can be easily adapted to sense other chemicals of interest.

In some embodiments, methods are provided for preloading and freeze drying bacterial sensor strains within a microfluidic chip to increase their survival rates for long term storage. In some embodiments, the chips can be stored for 1 month, 2 months, 3 months, 6 months, 12 months, or any amount of time defined by a range set forth in any of the aforementioned values. In some embodiments, the bacterial sensor strains are preloaded as a liquid culture. In some embodiments, the liquid culture comprises 0.1%, 0.2%, 0.3%, 0.4% 0.5%, 1%, 5%, 10%, 20%, 30%, 40%, 50%, 60%, 70% or 80% glycerol or any percent amount of glycerol within a range in between any aforementioned values. Alternatively, any viscous solution for the storage of bacteria at low temperature can be used in order to cryopreserve the bacteria. Such solvents are known to those skilled in the art.

In varying embodiments, the devices can comprise an enclosure which houses a microscope, computer, heating element, peristaltic pump, and microfluidic chip. The microfluidic chip can be pre-loaded with multiple distinct strains of bacteria, each of which has been genetically engineered to produce a detectable agent such as fluorescent protein (FP) (e.g., GFP) or derivative thereof in response to toxin. In some embodiments, the bacteria can be loaded within a liquid culture, in which the bacteria has an $OD_{600}$ (i.e. concentration) of between 1 and 2. In some embodiments, the bacteria are loaded into the chip as a small volume of culture, in which the culture contains the bacteria to be loaded. In some embodiments, the culture comprises glycerol. Glycerol can be used as a cryoprotectant for the cells. Without being limiting, examples of fluorescent proteins can include cyan fluorescent protein, green fluorescent protein, yellow fluorescent protein, red fluorescent protein, and far-red fluorescent protein. In some alternatives described herein, the fluorescent protein can be cyan fluorescent protein, green fluorescent protein, yellow fluorescent protein, red fluorescent protein, and far-red fluorescent protein.

The pump can draw water from the water supply and feed it into the microfluidic chip, where it is mixed with a concentrated M9 minimal bacterial growth medium and flows past the bacterial traps. The fluorescence microscope is used to image the bacteria at 5-minutes intervals to determine the FP expression level of each strain. In some embodiments, the bacteria are imaged at 1, 2, 3, 4, 5, 6 7, 8, 9, or 10 minute intervals, or any amount of time between a range between any two aforementioned values. This can give a real-time readout of toxin levels as they enter the water supply. Each strain has been engineered with a DNA construct comprising the operably linked elements of an antibiotic resistance gene, a promoter that either increases or decreases transcription levels specifically in response to one or more toxins, and a gene encoding an FP. For Escherichia coli strains, these constructs can be integrated on a plasmid, e.g., with the p15A origin of replication. For Bacillus subtilis strains these constructs can be integrated into the genome.

There are several aspects to the development of the biosensor such as the application of synthetic biology to develop novel microbial sensor strains that will have sensitive and specific responses to analytes such as critical water toxins, and the use of state-of-the-art microfluidic techniques and optical technology along with computational biology to detect and interpret the signals from these analyte-sensing organisms.

Some embodiments focus on biological aspects, with the goal of identifying combinations of cellular signals that can be harnessed to provide specific responses to the presence of a range of analytes such as potential water toxins. The literature was searched to identify known cellular signaling pathways responsive to toxins of interest and selected several candidate promoters from a variety of microbial organisms. In an exemplary embodiment, the plasmids were designed with each of these promoters driving GFP and these sequences were constructed. As proof of principle, microfluidics were used to test two such plasmids that were built in-house. These preliminary sensor strains were subjected to various toxin levels within a novel microfluidic chip, and bright response signals were observed in some alternatives described herein. In addition to taking advantage of known toxin-sensitive pathways, a program of Next Generation Sequencing was conducted to greatly expand the number of known response promoters for each toxin. Novel RNA-Seq analysis algorithms were also developed to identify specific differentially expressed genes in our large data set. The promoter regions were located for the most promising differentially expressed genes and sensor circuits based on them were designed. The construction of plasmid-based microbial sensor strains was also completed for all toxins, based on promoters identified via literature searches and RNA-Seq. In some embodiments, microfluidics were also used to demonstrate the proper induction of each strain by various levels of the relevant toxin.

Another exemplary embodiment focused primarily on mechanical sensor development, including the microfluidic device design, optical technology, and computational tools required to translate a series of optical signals from multiple sensor strains into a meaningful toxin level determination. In an exemplary embodiment, a microfluidic device was also developed to culture and sequentially expose an array of sensing strains to various levels of toxins of interest over a period of several weeks. This "gill" chip contains tall cell traps that provide a bright fluorescent signal from a large population of cells. In some embodiments described herein, complimentary technologies were also developed that allowed one to mix concentrated media with a natural water source and to dispose of the microbial species safely upon exiting the device. A partnership with the Ziva Corporation was also developed to make a low cost, field capable optical system to image our microfluidic devices. The capabilities of this optical system demonstrated that it was comparable to a research grade microscope at low optical power. To enable viable long-term storage of biosensor chips, an embodiment is described in which a method was developed to deposit and freeze-dry strains in a defined array within our microfluidic device. The successful revival of our strains were demonstrated after four weeks of room temperature storage with little loss of viability. In some embodiments, herein, the strains can be revived at room temperature for use in a test for metals. Lastly, replacing the GFP reporter with bacterial luciferase toward the goal of increasing SNR by eliminating background autofluorescence was investigated. In an exemplary embodiment, an arsenic sensor modified in this manner shows much greater sensitivity, even compared to analytical methods approved by the EPA for detecting arsenic in drinking water. Strain response data was also used to train the classifier to identify the presence of each toxin of interest in a water source of unknown composition in real time. Furthermore, classifier performance was strengthened by acquiring long data sets (up to 50 days) of both on- and off-target toxin exposures within the microfluidic devices. In some embodiments, the data sets are acquired for 1, 2, 3, 4, 5, 6, 7, 8, 9, 10, 20, 30, 40 or 50 days or any number of days between a ranges defined between any two aforementioned values.

In another exemplary embodiment, technologies were developed to make an inexpensive and robust sensor prototype that can be deployed in real bodies of water to continuously monitor for toxin contamination. In some embodiments, a peristaltic pumping system is developed to mix water and growth media on-chip and a filter utilized to prevent clogs in the microfluidic device. In another embodiment, a comprehensive software package is developed to control fluid flow, image acquisition, and wireless data transfer. A solar energy harvesting system was also constructed for powering the device in an off-grid field environment. The development of a functional prototype of our biosensor for use in comprehensively testing our sensor strains was also completed. The biological, fluidic, and computational components were integrated into a temperature-controlled enclosure containing all optics and electronics necessary to draw a water sample, acquire images of the biosensor strains within the microfluidic device, analyze this data using the embedded classifier algorithm, and transmit the results via encrypted Wi-Fi.

In an exemplary embodiment, the final deliverable is a self-contained water sensor prototype. Below, are several alternatives described herein which have results that demonstrate the ability to acquire and analyze data in real time to provide an accurate and continuous determination of water quality.

These results mark some conclusions of an exemplary embodiment that combined Next Generation Sequencing, genetic engineering, and microfluidic technology to precisely engineer a highly sensitive and specific biosensor platform that can continuously monitor water supplies for the presence of chemical toxins. In the following alternatives, the update section describes several milestones along with related data and results demonstrating their achievement.

An overview of the sensor can be seen in FIG. 39. In order to acquire the large amount of data required to successfully train the classifier, five replicates of the fully self-contained device prototype were built, in which the microfluidic devices are mounted and imaged using custom-designed optics as shown in some embodiments herein (Milestone 6.9). The majority of the data for this project was acquired using a novel microfluidic device capable of housing eight different bacterial strains that receive media from a shared source. This enables the simultaneous testing of the responses of eight different strains to each toxin concentration, providing information on specific and non-specific responses, which can be used to strengthen the classifier (FIG. 39D). The design was expanded to house 18 strains and we have begun taking data with this new chip to provide larger datasets to the classifier. A detailed CAD drawing of this device can be seen in FIG. 56. The 18 cell trapping regions are vacuum-loaded from 18 downstream fluidic ports. Long, serpentine channels upstream of the trapping regions serve as fluidic buffer zones to prevent the cross-contamination of strains while loading. The toxin concentration is controlled dynamically by a peristaltic pump that mixes a water/toxin combination (representing the source water stream) with a concentrated medium stock.

Figure 40A:
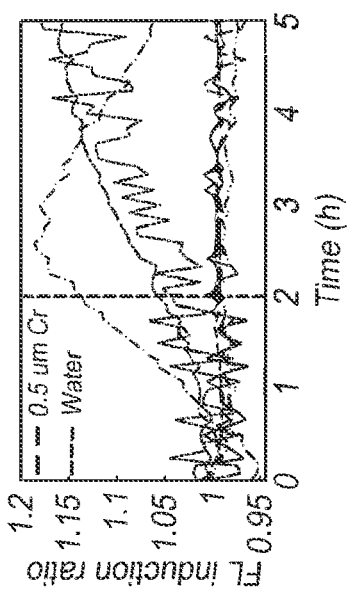
FIGS. 40 (40A, 40B, 40C, 40D, 40E and 40F) shows 8-strain chip induction data for six toxins, demonstrating the sensor-specific induction of the expected strains as well as any response from non-specific strains.
Figure 40B:
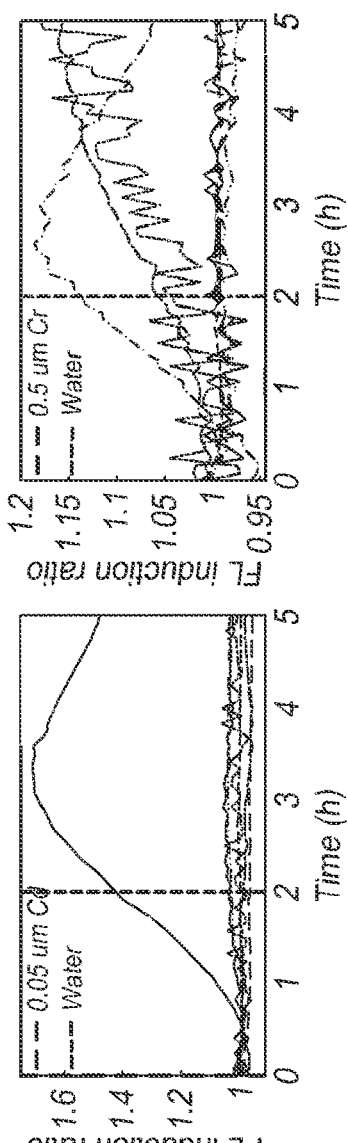
Figure 40C:
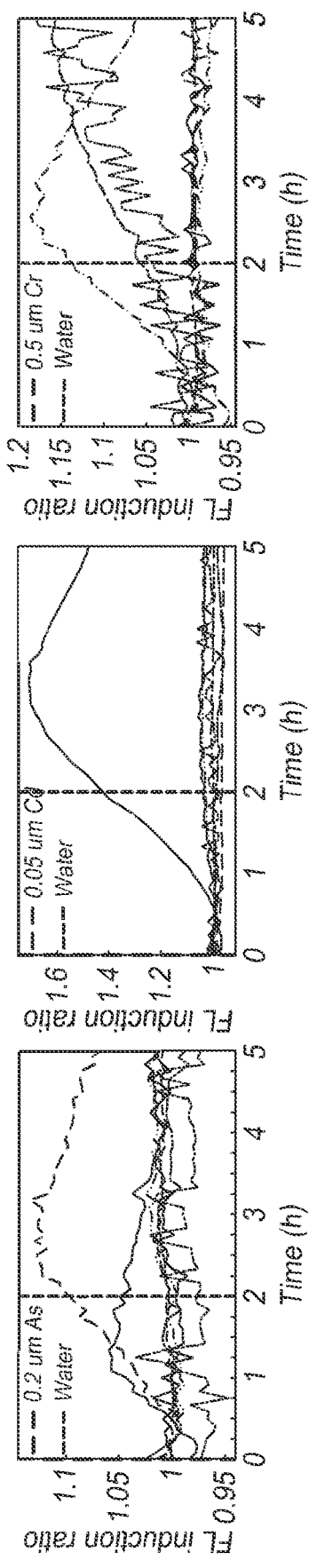
Figure 40D:
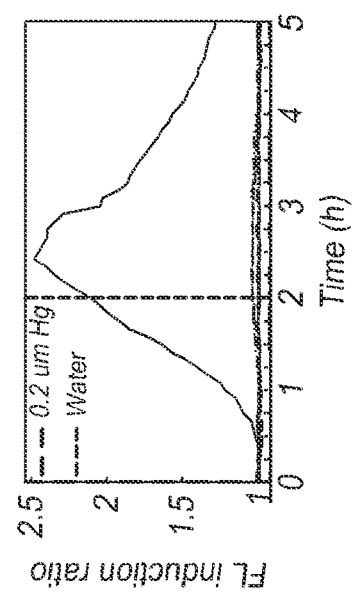
Figure 40E:
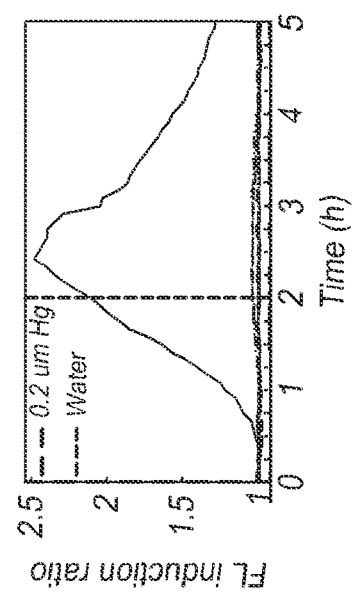
Figure 40F:
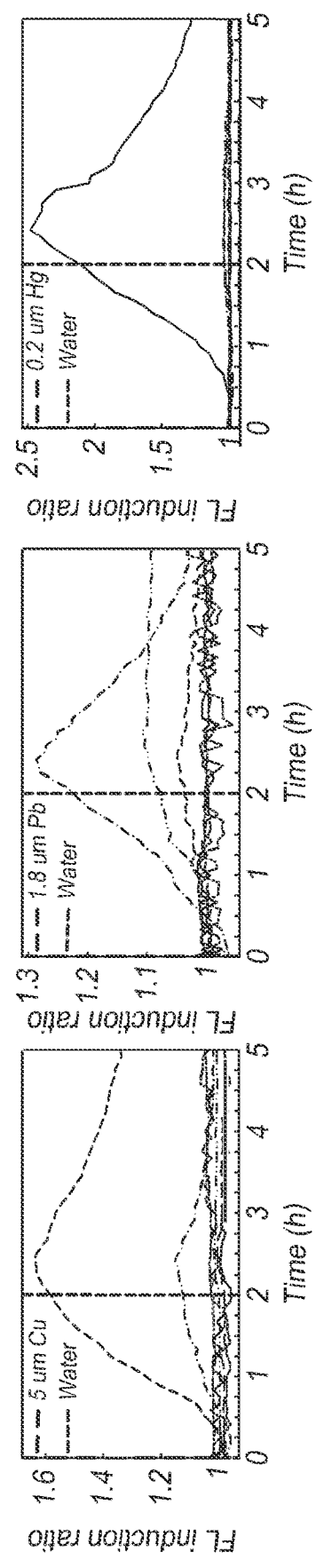

Importantly, the ability to house many strains on the same chip and subject them to the same toxin inductions enables one to look not only at toxin-specific induction but at crosstalk as well. In FIG. 40, a single induction time series plot for each of the following six toxins is shown: arsenic, cadmium, chromium (VI), copper, lead, and mercury. Each induction plot shows the fluorescence induction ratio (calculated as (mean fluorescence following induction)/(mean fluorescence prior to induction)) for multiple strains being cultured in the chip, where the toxin is introduced at t=0 and replaced by pure water at t=2 hours. In each panel, the time series data for the "on-target" responding strain is plotted in bold. As expected, the GFP fluorescence traces for the "on target" responding strains increase with induction and decrease with un-induction, with some delay due to the cellular response machinery. FIG. 40A shows strain *E. coli* MG1655/As7 sensitively responding to 0.2 μM arsenic, with *E. coli* MG1655/Pb7 exhibiting a smaller response. It was discovered in several experiments that strain *E. coli* MG1655/Pb7 is a less specific responder that aids in toxin identification mainly through combinatorics. FIG. 40B shows strain *E. coli* MG1655/Cd1 and *E. coli* MG1655/Hg3 responding to 0.05 µM cadmium, with *E. coli* MG1655/Pb7 exhibiting a much larger response. FIG. 40C shows strain *E. coli* MG1655/Cr11 and *E. coli* MG1655/Co7 responding to 0.5 µM chromium (VI), with *E. coli* MG1655/Pb7 exhibiting an equal magnitude but more rapid response. FIG. 40D shows strain *E. coli* MG1655/Cu1 sensitively responding to 5 µM copper, with *E. coli* MG1655/Pb7 exhibiting a smaller response. FIG. 40E shows strain *E. coli* MG1655/Pb7 responding to 1.8 µM lead, with *E. coli* MG1655/Cd1 and *E. coli* MG1655/Cu1 responding at lesser magnitudes. Finally, FIG. 40F shows strain *E. coli* MG1655/Hg3 sensitively responding to 0.2 µM mercury.

In an embodiment herein, the toxin response data across 18 unique sensing strains were also collected using a new chip design that houses 16 *E. coli* strains and 2 *B. subtilis* strains. This chip was initially used to test the ammonium sensor, with a representative induction shown in FIGS. 41A and 41B. The *B. subtilis* NCIB 3610/Amm3 construct is a "lights-off" sensor, meaning that GFP production drops when ammonium is introduced, following a slight increase due to faster growth on this preferred nitrogen source. This behavior was observed in response to 5 ppm $NH_4$-N in FIG. 41C. The two *B. subtilis* "gill" regions harboring the Amm3 strain respond sensitively to ammonium, whereas various strains in the *E. coli* "gill" regions shown in FIG. 41A do not. Additional toxin exposures of previously untested strains in this 18-strain chip demonstrated the ability to sense cobalt, an additional toxin not included in our primary list of eight. It was discovered that strain *E. coli* MG1655/Pb7 responds sensitively to cobalt, whereas no other *E. coli* or *B. subtilis* strain does (see FIG. 41C, 41D). It was found that strains *E. coli* MG1655/Zn6, *E. coli* MG1655/Pb7, and *E. coli* MG1655/Pb8 respond sensitively to lead in descending magnitude, whereas no other strains do (see FIGS. 41E, 41F). By combining these sensor responses, we can identify cobalt by the unique response of Pb7 alone and lead by the unique combination of Zn6, Pb7, and Pb8 responses.

Figure 42:
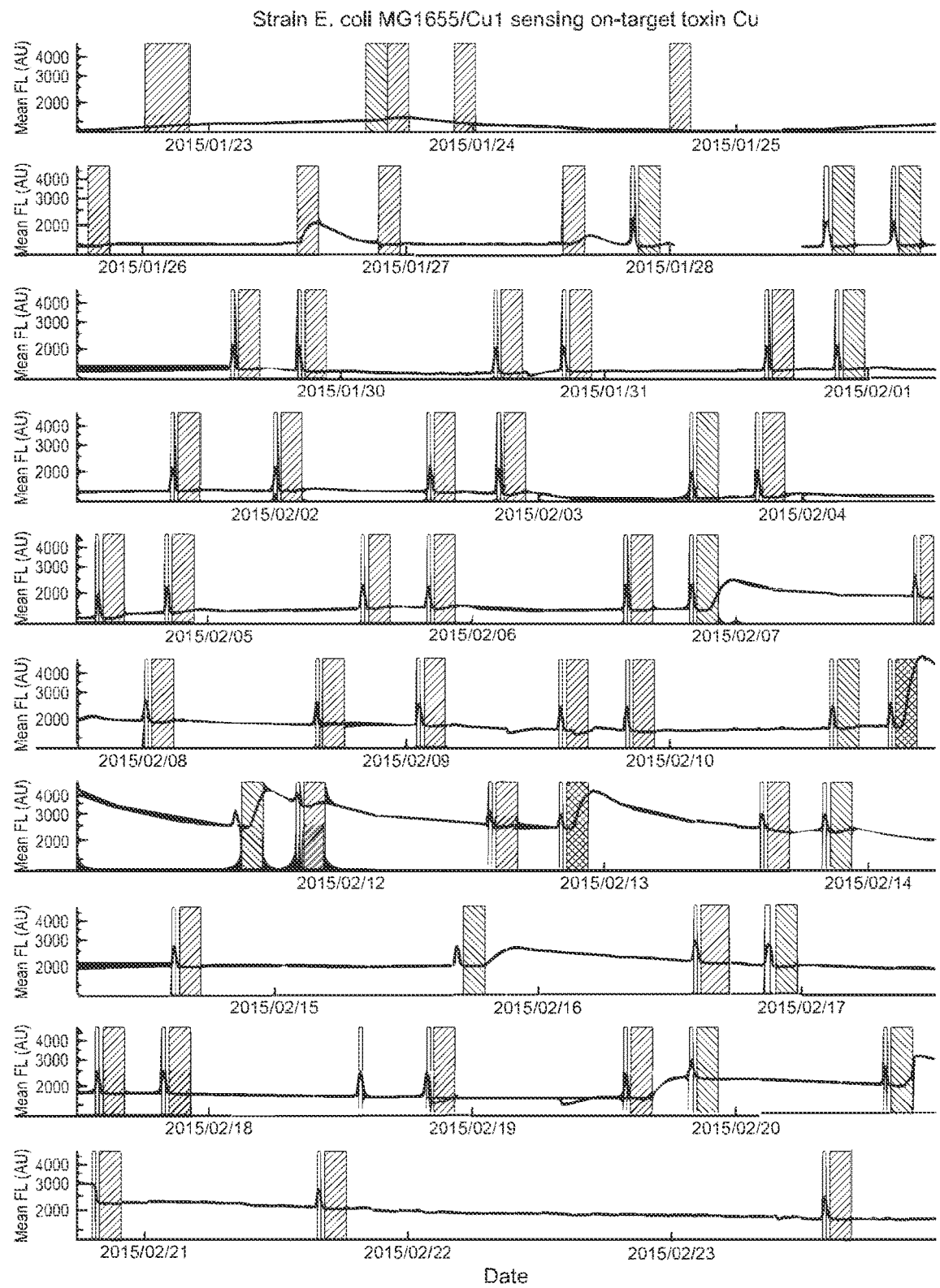
FIG. 42 shows 34 days of continuous fluorescence data from the *E. coli* MG1655/Cu1 strain as it responds to two inductions per day of various toxins and concentrations. Exposures to "on-target" toxins are shown in the top (first) panel as the second bar, the fifth panel as the twelfth bar, the seventh panel as the second bar, the eighth panel as the fourth bar, and the ninth panel as the ninth and twelfth bar. Exposures to "off-target" toxins are the thick bars on all the panels that are hatched (excluding the described on-target toxins). Double-toxin exposures that include the "on-target" toxin are cross-hatched and are shown in the sixth panel as the fourteenth bar and in the seventh panel as the eighth bar. These green fluorescent pulses are shown as the thin bars with no hatching and appear as thin white bars.

To date, 247 on-chip toxin exposures with these five prototype sensors were performed, capturing a total of 109,000 transmitted light and fluorescence images. A single microfluidic chip was run for up to 50 days, which includes inducing and un-inducing the strains with various toxins twice each day. FIG. 42 shows the response of a single copper-sensitive strain periodically exposed to toxins and imaged over a period of 34 days, where each row contains approximately three days of data. Mean fluorescence of cells within the trapping region is plotted over time, and toxin exposure events are color coded. Exposures to "on-target" toxins are shown in the top (first) panel as the second bar, the fifth panel as the twelfth bar, the seventh panel as the second bar, the eighth panel as the fourth bar, and the ninth panel as the ninth and twelfth bar. Exposures to "off-target" toxins are the thick bars on all the panels that are hatched (excluding the described on-target toxins). Double-toxin exposures that include the "on-target" toxin are cross-hatched and are shown in the sixth panel as the fourteenth bar and in the seventh panel as the eighth bar. Toxin-spiked water samples were drawn through peristaltic pump tubing to the cells with delays ranging from 1-9 hours, depending on the pump speed and length of tubing. In some embodiments, the delays can be for 1, 2, 3, 4, 5, 6, 7, 8, 9 or 10 hours or any amount of time in between a range defined by any two aforementioned values. Current long delays are due solely to slow pump rates and long tubing lengths in our initial prototype and not to any fundamental characteristic of the genetic circuits or microfluidic devices. As such, in some embodiments, they are minimized in design iterations. To visualize and accurately determine the moment of cellular exposure to toxin, a 20-minute pulse of green fluorescent tracer dye was provided, followed by a 20-minute pulse of pure water before flowing in the toxin. These green fluorescent pulses are shown as the thin bars with no hatching and appear as white bars.

Figure 43:
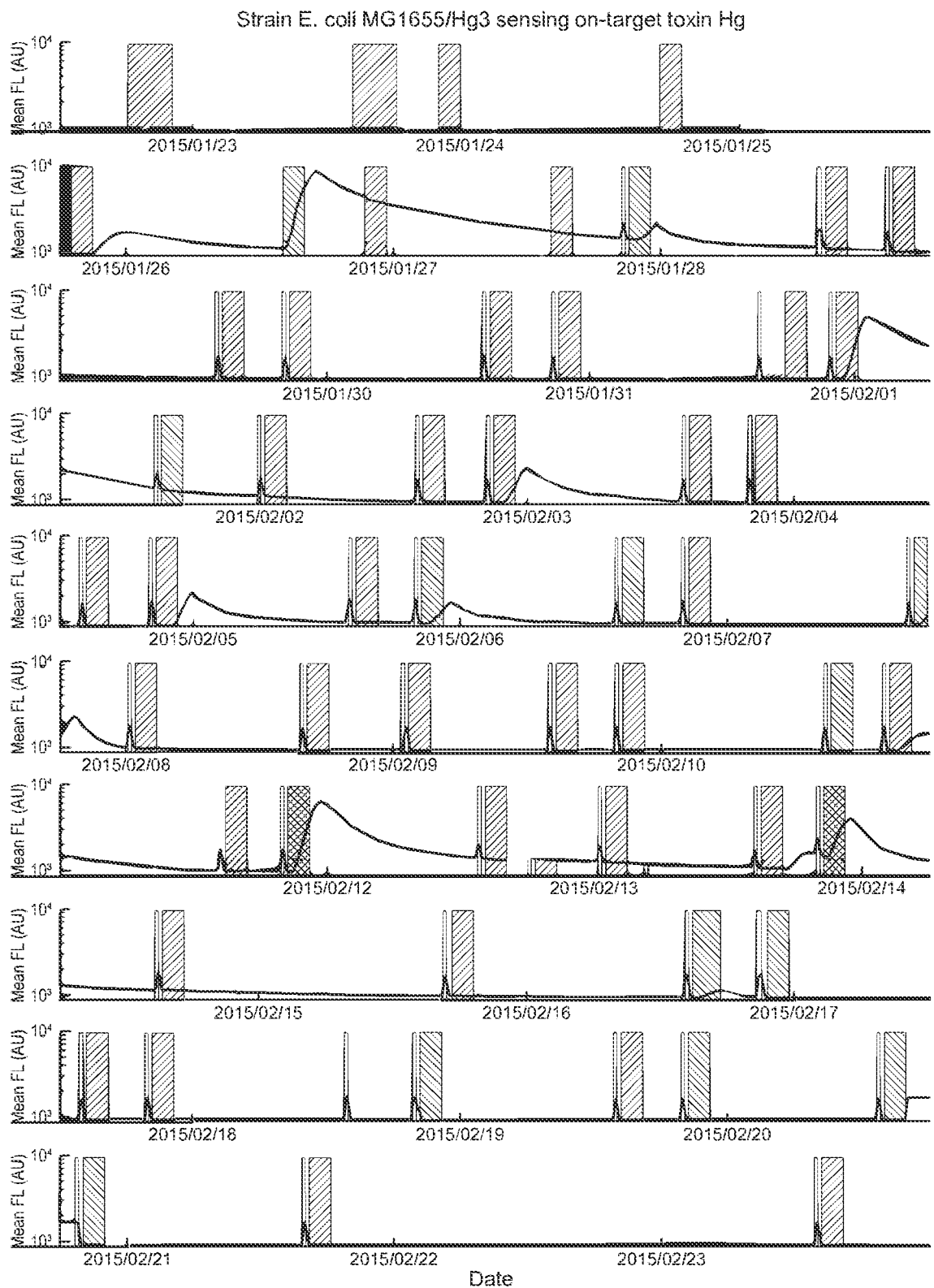
FIG. 43 shows 34 days of continuous fluorescence data from the *E. coli* MG1655/Hg3 strain as it responds to two inductions per day of various toxins and concentrations. the exposures to "on-target" toxins are shown in the second panel as the second and sixth bar, the fourth panel as the second bar, the fifth panel as the eight, tenth and fourteenth bar, the sixth panel as the first and thirteenth bar, eighth panel as the sixth and eighth bar, the ninth panel as the seventh and eleventh bar, and the tenth panel as the second bar. Exposures to "off-target" toxins are the thick bars on all the panels that are hatched (excluding the described on-target toxins). Double-toxin exposures that include the "on-target" toxin are cross-hatched and are shown in the seventh panel as the fourth and twelfth bar. These green fluorescent pulses are shown as the thin bars with no hatching and appear as thin white bars.

In FIG. 42, all the "on-target" copper exposures are followed by a rise in mean cellular fluorescence. This indicates that the *E. coli* MG1655/Cu1 strain responds sensitively to copper. Conversely, the majority of "off-target" toxin exposures are not followed by a rise in mean fluorescence. This indicates that the *E. coli* MG1655/Cu1 strain responds quite specifically to copper. For comparison, FIG. 43 shows the response of the *E. coli* MG1655/Hg3 strain to various toxin exposures over the same 34-day period. The initial "on-target" mercury exposures through 2/16 were intended to establish our sensing ability. The detection limit of this strain was subsequently probed by flowing in low concentrations of mercury, which did not elicit a response. Strain *E. coli* MG1655/Hg3 also exhibits less specificity than strain *E. coli* MG1655/Cu1, as indicated by rises in mean fluorescence following "off-target" inductions. This has not been problematic, as a unique combination of strain responses that is specific for mercury were identified. Movies of the 8-strain single-chip experiment analyzed in FIGS. 42 and 43 can be found at http://biodynamics.ucsd.edu/DARPA movies/index DARPA.html. As shown in FIG. 43, the exposures to "on-target" toxins are shown in the second panel as the second and sixth bar, the fourth panel as the second bar, the fifth panel as the eight, tenth and fourteenth bar, the sixth panel as the first and thirteenth bar, eighth panel as the sixth and eighth bar, the ninth panel as the seventh and eleventh bar, and the tenth panel as the second bar. Exposures to "off-target" toxins are the thick bars on all the panels that are hatched (excluding the described on-target toxins). Double-toxin exposures that include the "on-target" toxin are cross-hatched and are shown in the seventh panel as the fourth and twelfth bar. These green fluorescent pulses are shown as the thin bars with no hatching and appear as white bars.

Figure 44:
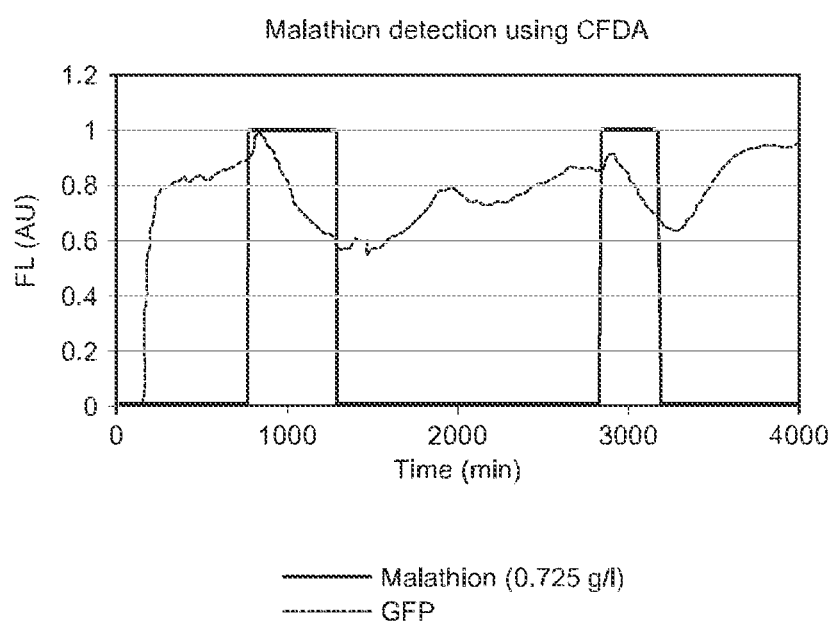
FIG. 44 shows inhibition of cellular esterase activity in *S. cerevisiae* during malathion exposure.

Transitioning at least one candidate toxin-sensitive promoter for each toxin from RNA-Seq analysis to microscope experiments to prototype sensor experiments with the exception of our initial construct based on the single promoter candidate for malathion (Ma11), which did not produce a discernable response upon loading into the sensor device, was successful. Additional constructs based on this promoter were generated while collecting on-chip response data for all other sensing strains using the sensor prototypes was performed. After some investigation, a more robust malathion detection scheme was discovered that leverages its esterase inhibition effect in yeast. *S. cerevisiae* was loaded into a gill chip and CFDA (carboxyfluorescein diacetate) was added to the growth medium. Because CFDA permeates the cell membrane and is cleaved by cellular esterases into a fluorescent product, it was expected that the inhibition of esterase activity by malathion would decrease cell fluorescence. This is what was observed during two sequential exposures to malathion in FIG. 44. GFP signal significantly drops in the presence of 0.725 g/l malathion, both at around 1,000 and 3,000 min, and subsequently recovers. Because CFDA breaks down in the medium over time thereby increasing the background signal, fresh medium+CFDA was introduced at 1,500 and 2,000 min. This explains the drift in baseline GFP during this period, which can be eliminated in subsequent experiments by mixing dye and medium on-chip.

The successful measurement of esterase inhibition by malathion in wildtype yeast illustrates the power of our forthcoming whole-genome detection scheme, which will be continually measured for the responses of 2,000 to 4,000 *E. coli* and *S. cerevisiae* promoters arrayed in a microfluidic chip. It is expected that the observed esterase inhibition will to be significantly represented in the genomic response of this multi-strain library during malathion exposure.

Additional Alternatives

The following alternatives are offered to illustrate, but not to limit the claimed invention.

Alternative 1

Microfluidic Aqueous Biosensor Device

Methods

Clone the Promoters into an Expression Plasmid Driving the Production of GFP:

Synthetic constructs were transformed into both standard *E. coli* MG1655 (ATCC 700926) and optimized *E. coli* LABEC01 cells for expression analysis. By serially passing MG1655 in M9 medium through several generations, we evolved the common MG1655 lab strain, which has been adapted for growth in rich lysogeny broth (LB) medium, into a strain well-suited to growth in M9 minimal medium within our microfluidic devices. The M9-adapted strain, which we named LABEC01, exhibited multiple phenotypic changes. The growth rate in minimal medium increased by approximately 10%, colonies on minimal medium plates were observed to be smoother as compared to the parent MG1655, and the bacteria aggregated less when grown in microfluidic devices. To investigate how these adaptations affect the cellular response to toxins and the activity of sensitive promoters, we also exposed strain LABEC01 to the full set of toxins for RNA-Seq analysis. Table 3 shows a list of promoters. In some embodiments, the promoters used for the detection of the toxin are provided in Table 3 and can be turned on by ammonia, arsenic, cadmium, chromium (VI), cobalt, copper, lead, malathion, mercury, and zinc.

In some embodiments a method of making an expression vector for the detection of a toxin is provided. The method can comprise insertion of a promoter into an expression vector, wherein the promoter is operably linked to a sequence encoding a reporter protein. Transcription from the promoter can be increased or decreased by the presence of an analyte, such as a toxin. In some embodiments the toxin is ammonia, arsenic, cadmium, chromium (VI), cobalt, copper, lead, malathion, mercury or zinc.

Table 3 lists all candidate toxin-responsive promoters identified in this work, ordered by the toxin of expected sensitivity. In the case of promoters identified by RNA-Seq, the gene is unknown. For promoters that have been expressed in a synthetic construct, the selected RBS and host strain are shown. This synthetic construct has been used to sense the toxin within a microfluidic device, the concentration sensed and SNR after 6 hours are shown.

TABLE 3

| Toxin | Gene/Promoter | Source | RBS | Host Strain/Plasmid | Concentration Sensed in Microfluidic Device (µM) | SNR after 6 h |
|---|---|---|---|---|---|---|
| Ammonia | $P_{nasA}$ | *B. subtilis* genome | native | | | |
| Ammonia | $P_{nasA}$ | *B. subtilis* genome | synthetic | | | |
| Ammonia | $P_{nasB}$ | *B. subtilis* genome | native | | | |
| Ammonia | $P_{nasB}$ | *B. subtilis* genome | synthetic | | | |
| Ammonia | $P_{spo1-mrA1}$ | *B. subtilis* genome | synthetic | | | |
| Ammonia | $P_{spo1-mrA2}$ | *B. subtilis* genome | synthetic | | | |
| Arsenic | arsR/$p_{arsR}$ | *E. coli* plasmid | native | *E. coli* MG1655/As1 | 0.13 | 20 |
| Arsenic | arsR/$p_{arsR}$ | *E. coli* genome | synthetic | *E. coli* LABEC01/As3 | | |
| Arsenic | arsR/$p_{arsR}$ | *E. coli* genome | synthetic | *E. coli* MG1655/As3 | 0.13 | 33 |
| Arsenic | arsR/$p_{arsR}$ | *S. aureus* plasmid | native | *E. coli* MG1655/As5 | | |
| Arsenic | $p_{arsR}$ | *E. coli* RNA-Seq | | | | |
| Cadmium | cadC/$p_{cadC}$ | *S. aureus* plasmid | native | *E. coli* MG1655/Cd1 | 0.04 | 17 |
| Cadmium | cadC/$p_{cadC}$ | *S. aureus* plasmid | synthetic | *E. coli* MG1655/Cd2 | | |
| Cadmium | cadR/$p_{cadR}$ | *P. putida* genome | native | *E. coli* MG1655/Cd4 | | |
| Cadmium | cadR/$p_{cadR}$ | *P. putida* genome | synthetic | *E. coli* MG1655/Cd3 | | |
| Cadmium | $P_{antA}$ | *E. coli* RNA-Seq | | | | |
| Chromium(VI) | chrB/$p_{chrB}$ | *C. metallidurans* plasmid | native | *E. coli* MG1655/Cr3 | | |
| Chromium(VI) | chrB/$p_{chrB}$ | *C. metallidurans* plasmid | synthetic | *E. coli* MG1655/Cr2 | | |
| Chromium(VI) | chrB/$p_{chrB}$ | *O. tritici* transposon | native | *E. coli* LABEC01/Cr5 | 5 | 5 |
| Chromium(VI) | chrB/$p_{chrB}$ | *O. tritici* transposon | native | *E. coli* MG1655/Cr5 | | |
| Chromium(VI) | chrB/$p_{chrB}$ | *O. tritici* transposon | synthetic | *E. coli* LABEC01/Cr4 | | |
| Chromium(VI) | chrB/$p_{chrB}$ | *O. tritici* transposon | synthetic | *E. coli* MG1655/Cr4 | | |
| Chromium(VI) | chrS/$p_{chrS}$ | *B. subtilis* genome | synthetic | *E. coli* MG1655/Cr1 | | |
| Chromium(VI) | $p_{recN}$ | *E. coli* RNA-Seq | | | | |
| Chromium(VI) | $p_{sulA}$ | *E. coli* RNA-Seq | | | | |
| Chromium(VI) | $p_{umuD}$ | *E. coli* RNA-Seq | | | | |
| Cobalt | $p_{dadA}$ | *E. coli* RNA-Seq | | | | |
| Cobalt | $p_{hmp}$ | *E. coli* RNA-Seq | | | | |
| Cobalt | $p_{ilvB}$ | *E. coli* RNA-Seq | | | | |
| Cobalt | $p_{lipA}$ | *E. coli* RNA-Seq | | | | |
| Cobalt | $p_{mmuP}$ | *E. coli* RNA-Seq | native | *E. coli* MG1655/Co7 | | |
| Cobalt | $p_{mmuP}$ | *E. coli* RNA-Seq | synthetic | *E. coli* MG1655/Co8 | | |
| Cobalt | nmtR/$p_{nmtR}$ | *M. tuberculosis* genome | native | *E. coli* MG1655/Co1 | | |
| Cobalt | nmtR/$p_{nmtR}$ | *M. tuberculosis* genome | synthetic | *E. coli* MG1655/Co2 | | |

TABLE 3-continued

| Toxin | Gene/Promoter | Source | RBS | Host Strain/Plasmid | Concentration Sensed in Microfluidic Device (µM) | SNR after 6 h |
|---|---|---|---|---|---|---|
| Cobalt | $p_{soxR}$ | E. coli RNA-Seq | | | | |
| Cobalt | $p_{tehA}$ | E. coli RNA-Seq | | | | |
| Cobalt | $p_{ygbA}$ | E. coli RNA-Seq | native | E. coli MG1655/Co3 | | |
| Cobalt | $p_{ygbA}$ | E. coli RNA-Seq | synthetic | E. coli MG1655/Co4 | | |
| Cobalt | $p_{yjbJ}$ | E. coli RNA-Seq | native | E. coli MG1655/Co5 | | |
| Cobalt | $p_{yjbJ}$ | E. coli RNA-Seq | synthetic | E. coli MG1655/Co6 | | |
| Cobalt | $p_{yqfA}$ | E. coli RNA-Seq | | | | |
| Copper | cueR/$p_{copA}$ | E. coli genome | native | E. coli MG1655/Cu1 | 25 | 65 |
| Copper | (cusS/R)$p_{cusC}$ | E. coli genome | native | E. coli MG1655/Cu2 | | |
| Copper | $p_{cusC}$ | E. coli RNA-Seq | | | | |
| Copper | $p_{cusR}$ | E. coli RNA-Seq | | | | |
| Lead | pbrR/$p_{pbrR}$ | C. metallidurans plasmid | native | E. coli LABEC01/Pb1 | | |
| Lead | pbrR/$p_{pbrR}$ | C. metallidurans plasmid | native | E. coli MG1655/Pb1 | | |
| Lead | pbrR/$p_{pbrR}$ | C. metallidurans plasmid | synthetic | E. coli LABEC01/Pb2 | 7 | 18 |
| Lead | pbrR/$p_{pbrR}$ | C. metallidurans plasmid | synthetic | E. coli MG1655/Pb2 | | |
| Lead | $p_{mntH}$ | E. coli RNA-Seq | | | | |
| Lead | $p_{shtA}$ | E. coli RNA-Seq | | | | |
| Lead | $p_{ybtI}$ | E. coli RNA-Seq | | | | |
| Lead | $p_{yjjz}$ | E. coli RNA-Seq | | | | |
| Malathion | $p_{cusC}$ | E. coli RNA-Seq | | | | |
| Malathion | $p_{nemR}$ | E. coli RNA-Seq | | | | |
| Mercury | merR/$p_{merR}$ | E. coli plasmid | native | E. coli MG1655/Hg4 | | |
| Mercury | merR/$p_{merR}$ | E. coli plasmid | synthetic | E. coli MG1655/Hg3 | 0.1 | 20 |
| Mercury | merR/$p_{merR}$ | S. aureus plasmid | native | E. coli MG1655/Hg2 | | |
| Mercury | merR/$p_{merR}$ | S. aureus plasmid | synthetic | E. coli MG1655/Hg1 | | |
| Mercury | merR/$p_{merR}$ | S. marcescens plasmid | native | E. coli MG1655/Hg6 | | |
| Mercury | merR/$p_{merR}$ | S. marcescens plasmid | synthetic | E. coli MG1655/Hg5 | | |
| Zinc | $p_{mntH}$ | E. coli RNA-Seq | | | | |
| Zinc | $p_{shtA}$ | E. coli RNA-Seq | | | | |
| Zinc | $p_{yjjz}$ | E. coli RNA-Seq | | | | |
| Zinc | $p_{zntA}$ | E. coli RNA-Seq | | | | |
| Zinc | $p_{zraP}$ | E. coli RNA-Seq | | | | |

RNA-Seq Results for Promoter Activation in E. coli MG1655 in Response to Single and Multiple Toxin Exposures at Low and High Concentrations:

Our analysis of the sequencing data from RNA-Seq experiments to determine candidate genes that are induced upon toxin exposure consisted of three main tasks: sequence alignment, quantification of gene expression, and identification of differentially expressed genes. Sequence alignment: Reads were aligned to the reference E. coli K-12 substr. MG1655 genome using a tolerance of at most two mismatches per alignment to protect against sequencing errors. The alignment was performed using Bowtie software, 5 which is known to be very efficient in aligning reads to a reference genome. Without being limiting, Bowtie software 5 can be used for the alignment. Those skilled in the art will appreciate that there are many such software programs for performing alignments.

Quantification of Gene Expression:

The expression level of each gene was determined as a function of the number of aligned reads mapping to the gene. After analyzing several approaches adopted in the literature to tabulate the number of reads mapping to each gene, we implemented our own software capable of reproducing the counting algorithms behind some of the standard toolboxes such as Bedtools6 and HTSeq.7 In particular, we counted the number of reads mapping to each gene regardless of whether the read mapped to several genes, taking into account the strand-specificity of each read. Additionally, we implemented our own algorithms for sequence alignment and quantification of gene expression in order to crosscheck all results.

Identification of Differentially Expressed Genes:

Finally, a set of statistical and information theory algorithms were applied in order to extract not only differentially expressed (DE) genes for each toxin with respect to the control samples (pure water) but also toxin-specific genes. DESeq is a standard tool for identifying DE genes that allowed us to select sensitive genes with differential expression between the control samples (pure water) and the cells exposed to toxin. It assumes that the number of counts for each gene across experimental replicates follows a negative binomial distribution (8, 9). We considered genes with a False Discovery Rate (FDR) lower than 1% as DE in order to ensure statistically robust DE genes. We note that some genes showed high variability in the control samples across different batches of RNA-Seq experiments, indicating that these genes are very sensitive to environmental conditions. We identified 846 of these genes by performing a DESeq differential analysis (FDR<1%) between the control samples in different batches and subsequently removed them from the candidate pool. The number of DE genes (FDR<1%) identified for each condition when compared to the negative samples in the same batch and after removing genes that are DE between control samples is given in Table 6 (below). Ideally, good candidate specific genes are those with a significant fold-change with respect to the control samples but with a negligible fold-change with respect to the other toxins. Additionally, genes with the largest number of counts and expression levels are preferable in order to maximize the signal-to-noise ratio. When it is not possible to find toxin-specific genes, the next generation of good candidates is formed by those genes satisfying the above properties for a small subset of toxins (multiple-toxin response). It is desirable to have single-toxin-specific genes for several of the toxins in the combination in order to determine toxin-specific multi-gene-responses by means of logical operations. In rare cases there are shared genes differentially expressed. Therefore, we have developed information theoretic measures to improve the toxin separability. The core idea of the approach is that low entropies (or highly informative genes) correspond to toxin-specific genes, while large entropies (low information) are associated with scenarios in which DE fold-changes across different toxins are similar and should be discarded. The result of the analysis shows that toxins can very easily discriminated by using simple boolean rules.

Results

We have analyzed our sequencing data and were able to identify significant numbers of candidate genes for each toxin of interest at false discovery rates below 1% (see FIG. 1). Note that unlike for other toxins the gene identified for ammonia is down-regulated in response to the toxin, allowing construction of a "lights-off" sensor. See, FIG. 2. This is desirable because unlike the other water toxins of interest, ammonia is expected to increase the growth rate of biosensor cells. In this situation, a "lights-on" sensor could be triggered by any substance that increases the growth rate and resulting GFP production ability of cells, whereas a "lights-off" sensor remains immune to this effect.

We have cloned all identified promoters into a standardized plasmid expression system (see FIG. 3). The malathion sensor strain in was observed to accumulate high levels of GFP in some cells even before induction, likely due to leaky expression of the sensor construct. We have designed constructs where the responsive promoter has been placed on a lower copy plasmid as well as a version with a weaker promoter which we expect will alleviate the metabolic burden on the cells. In addition, we have identified the likely transcription factor responsible for regulating this promoter (NemR) and designed constructs over expressing this protein. The set of validated constructs shown in FIG. 3 contains one construct that is sensitive to each toxin of interest.

Method to Freeze-Dry Cells Allowing them to be Rehydrated with Little Loss of Viability:

We have successfully developed a method for in-chip lyophilization and revival after long-term storage. A range of cryoprotectants suitable for engineered biosensor strains and for microfluidic geometries was formulated from a combination of literature-based protocols, current industrial practices, and experimentation. The investigated cryoprotectants include:
  1. 2.5% Luria-Bertrani Broth (LB) (w/v)+spectinomycin
  2. 2.5% LB+0.4% glucose (w/v)+spectinomycin
  3. 2.5% LB+0.4% sucrose (w/v)+spectinomycin
  4. 2.5% LB+0.4% trehalose (w/v)+spectinomycin
  5. M9+0.4% glucose+spectinomycin E. coli biosensor strains E. coli MG1655 (ATCC 700926) and LABEC31 and B. subtilis biosensor strain LABBS31 were grown overnight to stationary phase and sporulation phase, respectively. The strains were then double washed in cryoprotectant and concentrated to 50→ their batch culture concentration. After lyophilization in a commercial freeze dryer for 12 h, the strains were stored in anaerobic, nitrogen-flushed, desiccated, and opaque packaging at room temperature to protect from oxidation.

In some embodiments, a method for making a cell for determination of a toxin provided. The method can comprise delivering a nucleic acid to a cell, wherein the nucleic acid comprises a sequence set forth in any one of sequences comprising the sequences set forth in SEQ ID NO:'s 1-43. In some embodiments, the cells are grown in a minimal media culture. In some embodiments, the minimal media comprises glycerol. In some embodiments, the cells are frozen at −80 C.

Relative cryoprotectant efficacy was determined via plate reader revival experiments performed 24 h, 1 wk, 2 wk, 4 wk, and 8 wk after lyophilization. Cells were revived via rehydration and resuspension in 200 µl of revival medium within microplate wells. The plates were then immediately placed into a Tecan Infinite M200 Pro plate reader, where growth rates were monitored over the next 48 h.

Revival media included:
  1. M9+0.4% glucose+spectinomycin
  2. Trace Select M9+0.4% glucose+spectinomycin
  3. Trace Select M9+0.4% glucose
  4. HM9 (nitrate)+0.4% glucose
  and were selected to be representative of the growth media used in the final device.

Strains protected with optimal cryoprotectants showed little difference in viability between cryoprotectants after two months of preservation. Both E. coli and B. subtilis strains responded similarly to lyophilization in the cryoprotectants listed above (see FIG. 4). The best cryoprotectants, including LB+0.4% glucose and LB+0.4% sucrose, were used to perform on-chip lyophilization and have successfully demonstrated shelf-lives of at least two weeks. Microfluidic revivals are ongoing at the time of writing and a maximum shelf-life has yet to be determined.

Revival occurred in Trace Select M9+0.4% glucose+spectinomycin, HM9 (ammonia)+0.4% glucose, and HM9 (nitrate)+0.4% glucose via de-gas driven chip wetting and subsequent gravity- or pump-driven flow. Initial signs of revival occur on time scales equivalent to those in the plate reader.

In order to independently load cryoprotected strains, 16- and 18-strain chips were designed and constructed with independent loading ports and cell reservoirs. After each strain is injected into its unique, fluidically-isolated reservoir, the entire device is lyophilized. The loading ports are then sealed with a fast-curing silicone elastomer (Sylgard 170, Dow Corning). The chips are preserved and packaged using the same method as described above.

A biosensor chip loaded with pLBAmm3 (LABBS31), lyophilized with optimal cryoprotectants, and protectively packaged according to the protocol above was transported and exposed to rough conditions in the high Mojave Desert for 48 h, followed by storage indoors at room temperature for an additional 72 h. Temperatures to which the chip was exposed ranged from near-freezing up to 35° C. All reservoirs containing this lyophilized ammonia sensing strain revived following the introduction of medium.

Additionally, the ammonia-sensing B. subtilis LABBS31 strain has been successfully sporulated using standard sporulation medium, which offers an additional preservation method with extreme shelf-life.

Deposition technique to place cells into a region of a microfluidic device that is then bonded to a glass coverslip: We have successfully developed a deposition strategy whereby individual biosensor strains are injected into on-chip reservoirs, where they can then be lyophilized and revived after storage. These modifications originated from finite element modeling of variations of the original gill device.

Figure 5A:
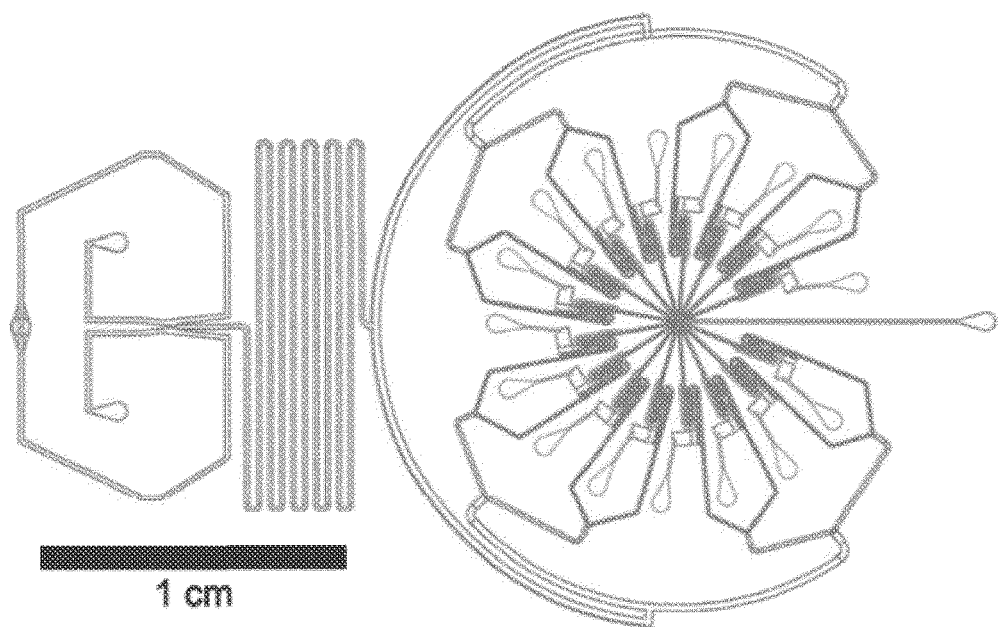
FIG. 5, (FIGS. 5A, 5B) 5A) Chip design with 16 loading ports (16 tear drop shaped constructions) and reservoirs. 5B) Resulting chip with independently cryoprotected, loaded, and lyophilized strains.
Figure 5B:
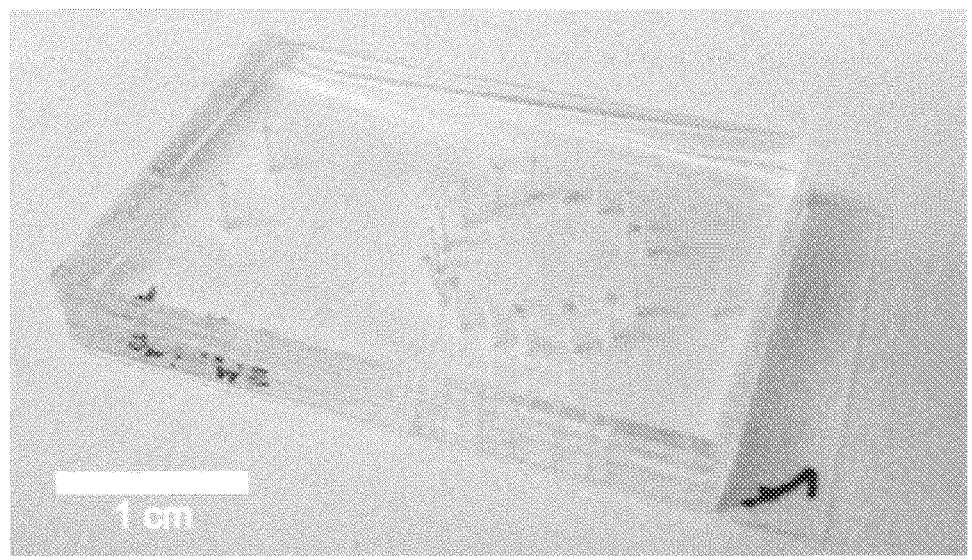

To independently culture multiple biosensor strains, 16-strain and 18-strain chips were designed, built, and successfully tested for multi-strain loading and freeze-drying (see FIG. 5A). The chip dimensions conform both to the demands of the biosensor's optical detection systems and strain requirements. The independent loading technique has been successfully tested with this device (see FIG. 5B).

An air-drying and chemical bonding-based method is currently being developed in parallel with the port-loading technique to reduce the number of required fluidic connections to the biosensor device.

Low Cost Optical Methods Development.

Figures 6A, 6B, 6C:
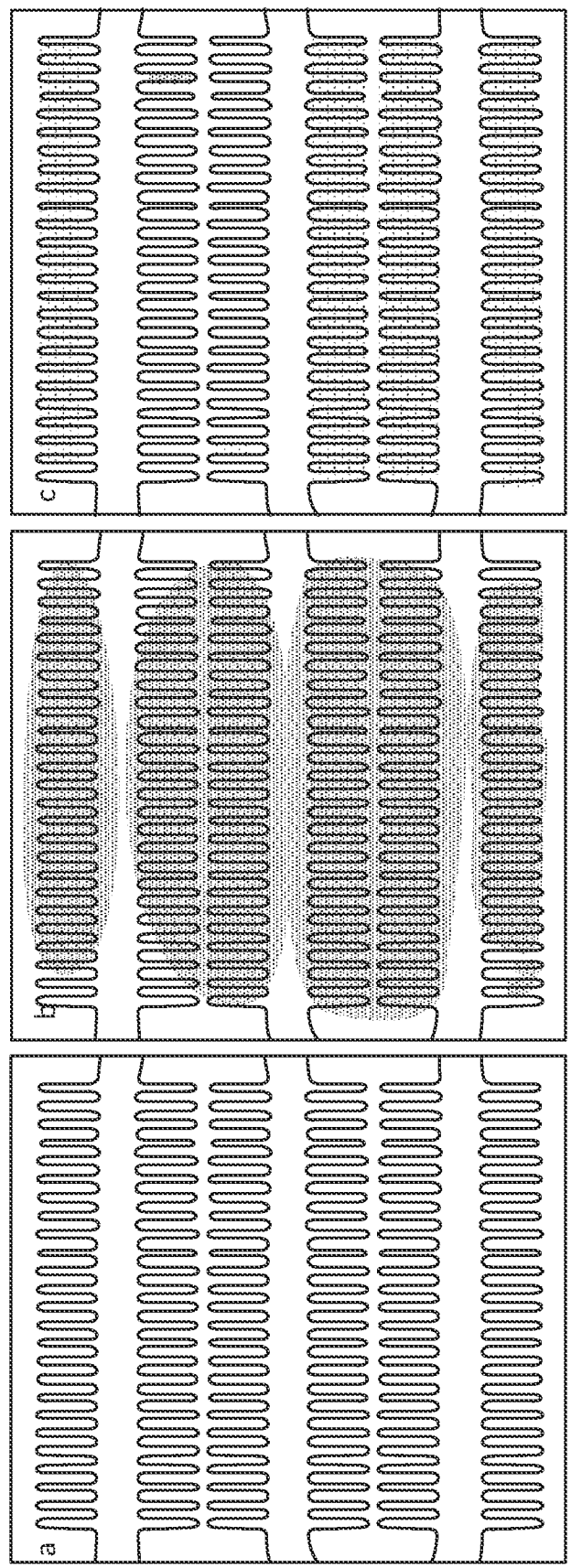
FIG. 6 (FIGS. 6A, 6B and 6C) illustrates a comparison of optical systems using the chromium Cr11 sensor strain induced with 1.25 uM of chromate. The same microfluidic device was imaged with a) and b) low cost biosensor optics developed by the Ziva Corporation and c) a research grade Olympus IX81 microscope. 6A) and 6B) show brightfield and GFP fluorescence images acquired by the Ziva optics, magnified to match the image field of view produced by the Olympus optics with 4× objective. (Note that this decreases the apparent resolution of the Ziva optics.) 6C) shows the same fluorescence image as in b), but acquired using the Olympus optics with 4× objective. The optical quality of the Ziva system is remarkable given the difference in cost ($2K for Ziva versus about $100K for Olympus).

We have successfully developed a low cost optical system. We further have determined that bioluminescent systems can be significantly more sensitive than fluorescence based systems. We have built an imaging system using the "Chameleon" camera (part #CMLN-12S2M-CS) from Point Grey Research Inc. with the design assistance of the Ziva Corporation. This is a 1.3 megapixel monochrome camera featuring a Sony ICX445 CCD imager. It contains a 12-bit analog-to-digital converter with a maximum gain of 24 dB. The camera package includes a software development kit (SDK), known as FlyCapture, which is compatible with the PandaBoard single board computer system that we have chosen for our electronics platform. The microfluidic "gill" chip was used to compare the optical system developed by the Ziva Corporation with our research grade microscope, an Olympus IX81. The Ziva optical system was designed with lower resolution optics compared to those of the 4× objective on the Olympus in order to lower cost while increasing the image field of view by 20× for imaging multiple "gill" trapping regions. Images acquired with the Ziva optics compare favorably with those acquired with the Olympus, as shown in FIG. 6. Notably, the Ziva optics are about 2× more sensitive at detecting GFP than the Olympus optics (SNRs are 23.8 and 11.6, respectively). Because our primary objective is to detect weak signals, the Ziva system outperforms the Olympus system at about 50× lower cost.

Figure 7A:
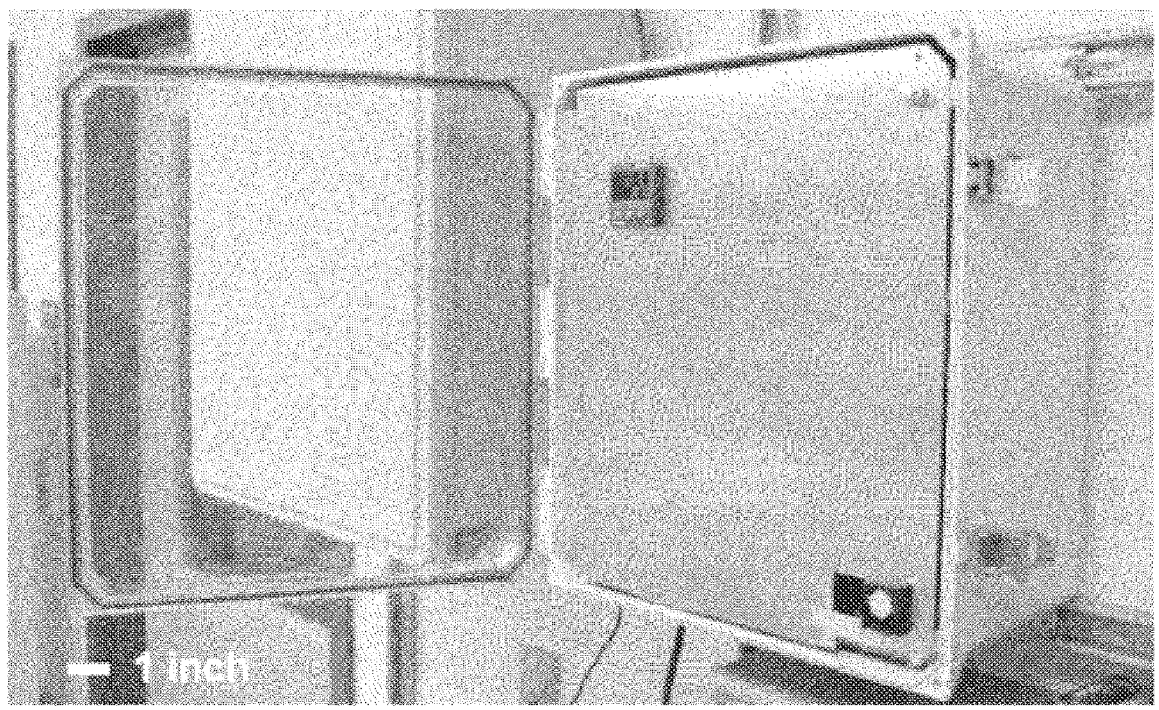
FIG. 7, (FIGS. 7A, 7B, 7C, 7D, 7E, 7F, 7G), illustrates biosensor self-contained prototype: 7A) Device enclosure, note temperature controller (upper left) and peristaltic pump (lower right) mounted to the aluminum front panel. 7B) Enclosure with front panel opened to expose internal components. b1: Electronics sub-enclosure, b2: temperature controller, b3: AC power distribution devices, b4: tri-output DC power supply, b5: Ziva optical assembly, b6: Fan/heater, b7: DC power distribution block, b8: peristaltic pump. 7C) Solidworks detail of the electronics sub-enclosure. c1: Arduino Uno, c2: BuckBlock LED drivers, c3: PandaBoard, c4: LED control relays. 7D) Ziva optical assembly. d1: transmitted light optics, d2: stage/temperature probe, d3: Focal adjustment knob, d4: dichroic mirror holder, d5: GFP excitation optics, d6: monochrome camera. 7E) Microfluidic device being illuminated with the GFP excitation LED. 7F). Representative images acquired with our device prototype—top: transmitted light, bottom: GFP excitation. 7G) image of the prototype running in an outdoor environment with solar power.
Figure 7B:
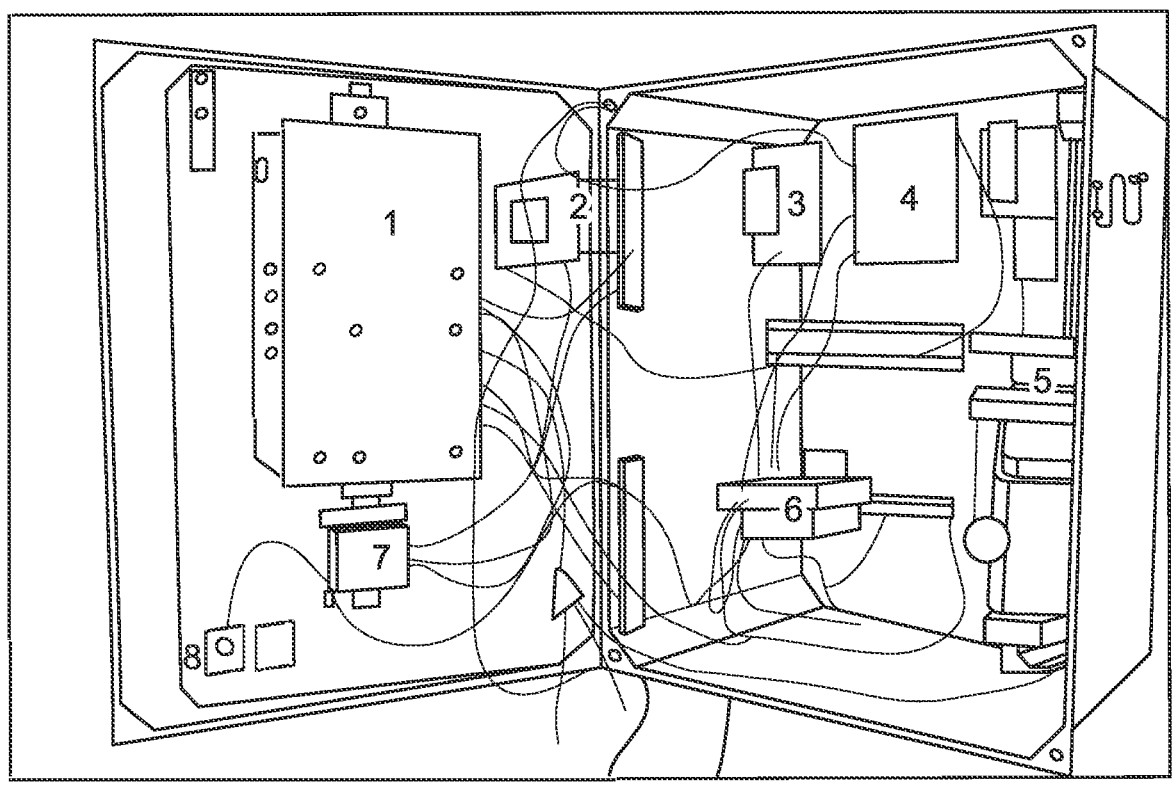

Completed Device Prototype:

We have assembled the individual components into a functional prototype that is capable of acquiring and processing data. Images of this prototype are shown in FIG. 7. The prototype is contained in a 16"×14" fiberglass enclosure (FIG. 7A) with an aluminum front panel designed to protect the interior components from the environment. A proportional-integral-derivative (PID) temperature controller is visible in the upper left hand corner of the front panel with the peristaltic water pump in the lower right corner. The interior of the prototype is shown in FIG. 7B with the electronics sub enclosure (FIG. 7B-1) and Ziva optical system clearly visible (FIG. 7B-5). The use of a PID controller rather than a simple thermostat is necessary for precise control of the enclosure's internal temperature to within 0.1° C. of the set point.

Figure 4:
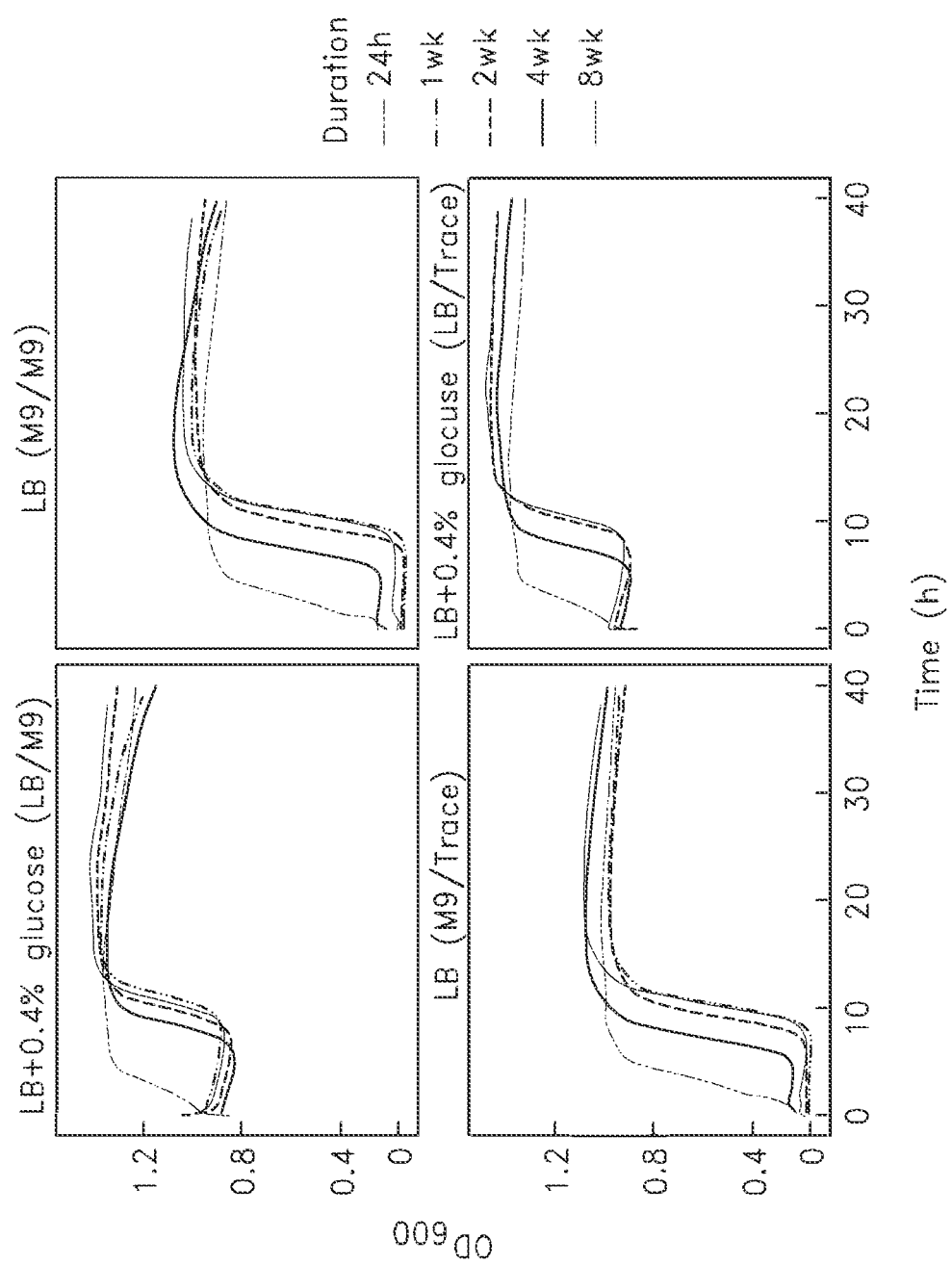
FIG. 4 illustrates Cryoprotectant revival rates for arsenic detecting *E. coli* plasmid/strain pLB-As3/MG1655. The cryoprotectant is listed over each plot, with the overnight and revival media listed in that order in parentheses; i.e., a strain cryoprotected in LB after being grown overnight in M9 and revived in Trace Select M9 media is denoted by LB (M9/Trace).
Figure 9:
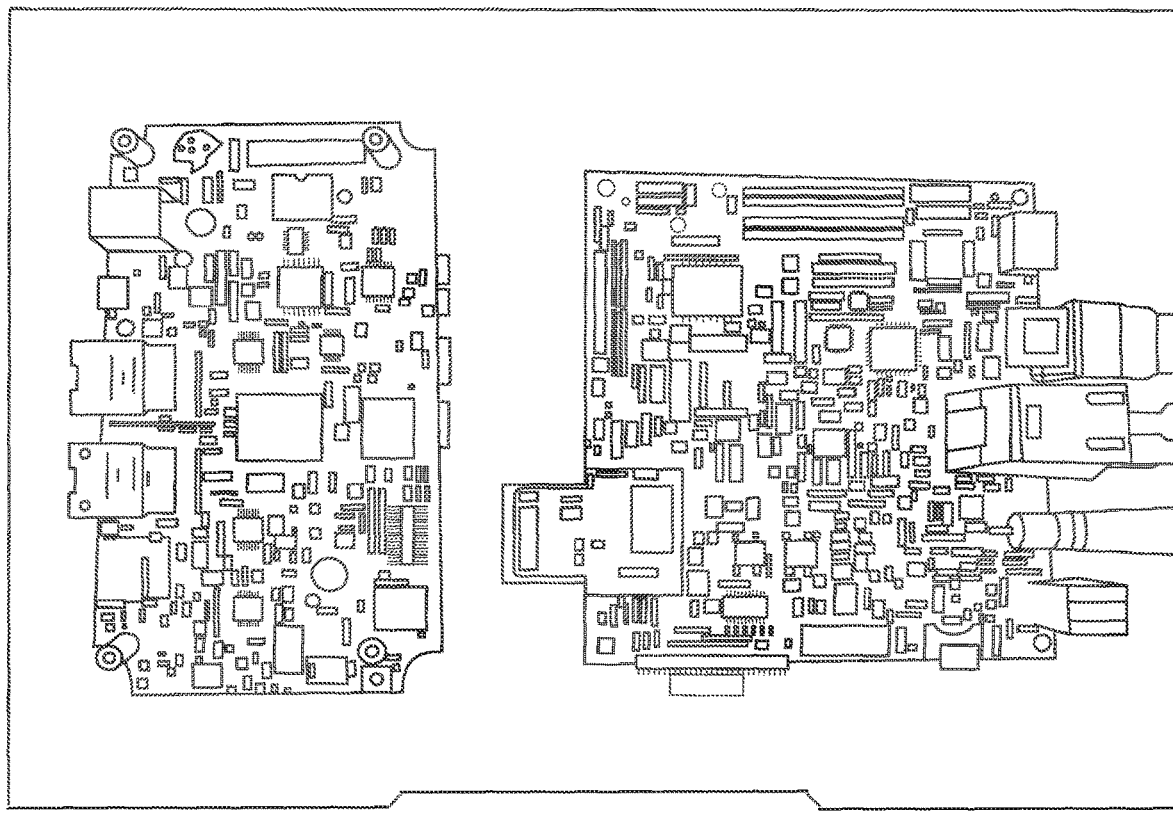
FIG. 9 illustrates two platforms with wireless capability: (Left) the Sitara-ARM (Texas Instruments AM335x), and (Right) the PandaBoard using the Cortex-A9 processor. The PandaBoard has allowed us to install a full Linux operating system.

Individual components are numbered 1-8. Briefly, the electronics enclosure (FIG. 7B-1) contains the hardware for controlling the Ziva optics, processing images and transmitting data. This system can also communicate with the temperature controller (FIG. 7B-2) to adjust the interior temperature of the enclosure (normally kept at 37° C.) using the Modbus protocol. This version of the prototype is designed to be powered from a 120 VAC source and the AC power distribution block, along with a supplemental protection circuit breaker and solid state relay for controlling the heater, is shown in FIG. 7B-3. A tri-voltage power supply, outputting 5, 12 and 24 VDC for the electronics and pumps is shown in FIG. 7B-4. The Ziva optical system for acquiring image data is shown in FIG. 7B-5. The heater is combined with a circulating fan to distribute warm air throughout the enclosure (FIG. 7B-6). Briefly, the user inputs the desired temperature through a custom software package designed by our group that runs on the PandaBoard system (FIG. 9B-1). The PandaBoard communicates with the PID controller (FIG. 7B-2) to set the desired temperature using the Modbus protocol. The PID controller modulates the heater's activity based on the set-point temperature and the current temperature of the enclosure. To regulate the heater's output, the PID controller generates a pulse wave signal that drives the activity of a solid state relay (FIG. 7B-3), which turns the heater's AC power source on and off (Note: the fan remains constantly on to circulate air). FIG. 7B-7 shows the DC power distribution system for the electronics and peristaltic water pump (FIG. 7B-8).

Figure 7F:
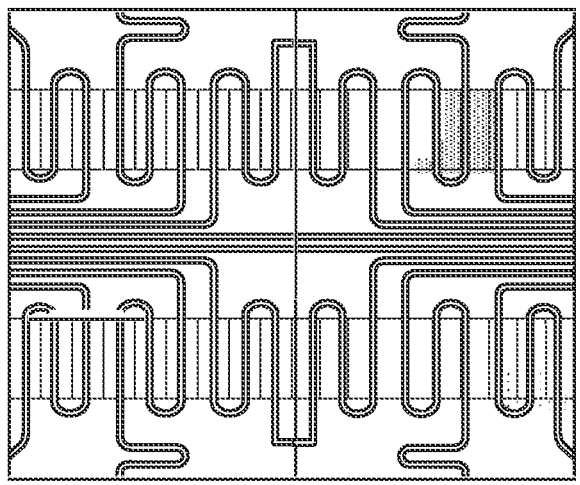
Figure 7E:
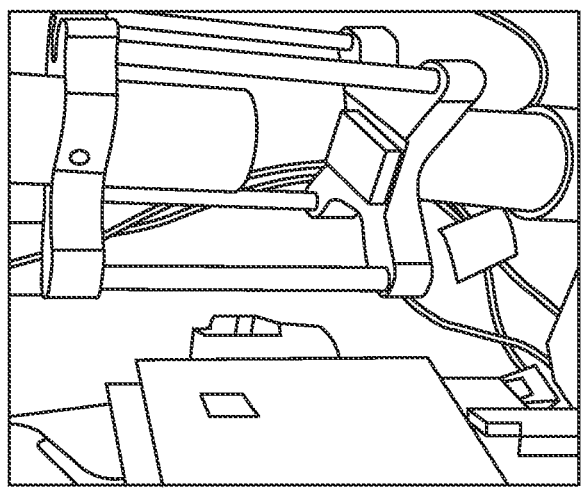
Figure 7D:
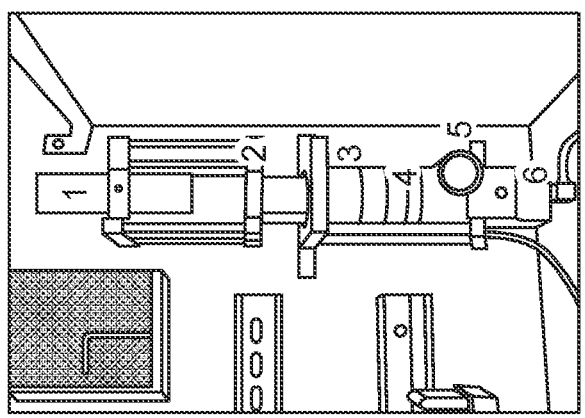
Figure 7C:
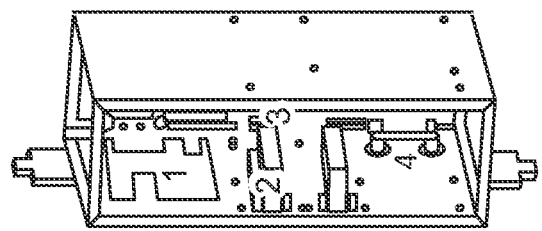
Figure 7G:
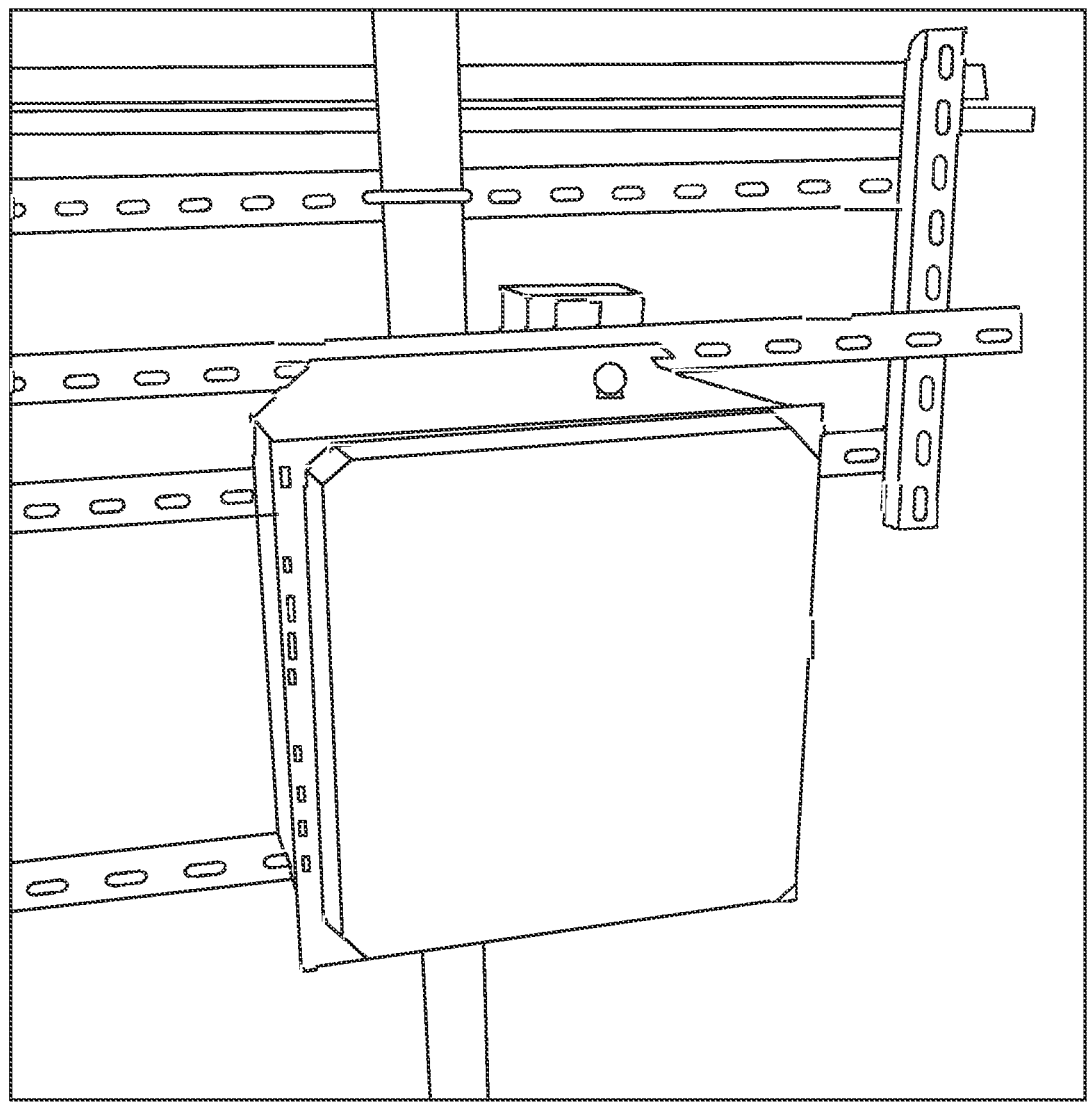
Figure 8D:
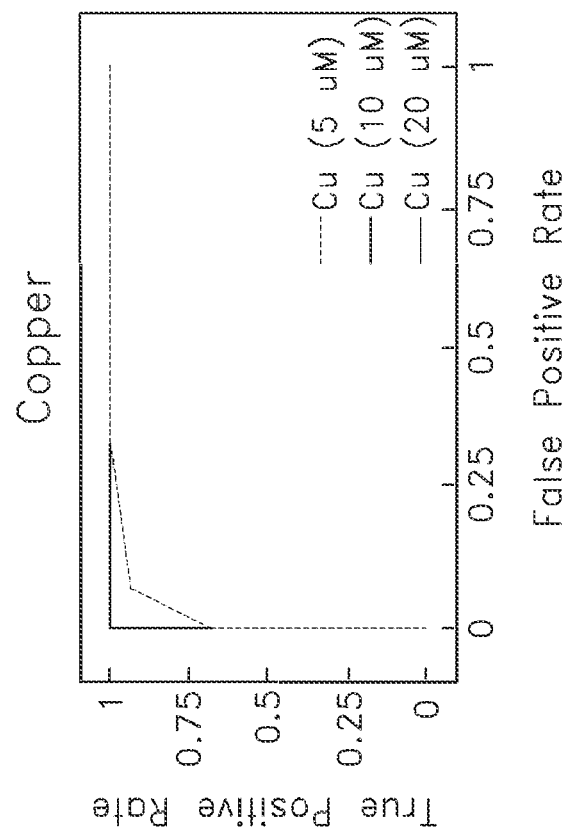
FIG. 8, (FIGS. 8A, 8B, 8C, 8D, 8E, 8F, 8G, 8H), illustrates Receiver Operating Characteristic (ROC) curves for the sensors. This parametrized curve quantifies the trade-off between the true positive rate and the false positive rate of a classifier. An optimal classifier is represented by a step function (e.g. Arsenic), since this point corresponds to correct identification of 100% of the positive cases (toxin present) with no false alarms. In the other limit, worst-case classifiers are characterized by a diagonal ROC curve. Note that the arsenic, chromium, copper, lead and malathion sensors are nearly perfect at all tested levels, while very low levels of cadmium, mercury, and ammonia lead to suboptimal classification due to the detection limit of the genetic circuitry.
Figure 8C:
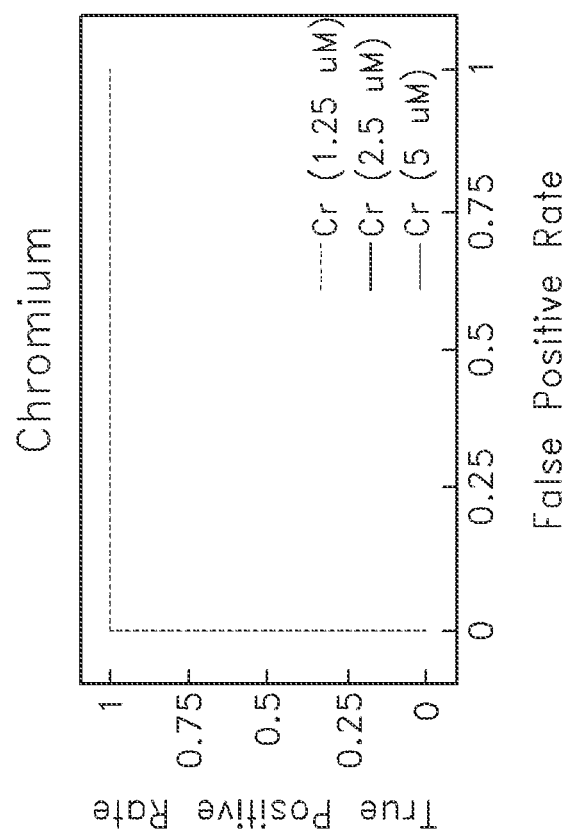
Figure 8E:
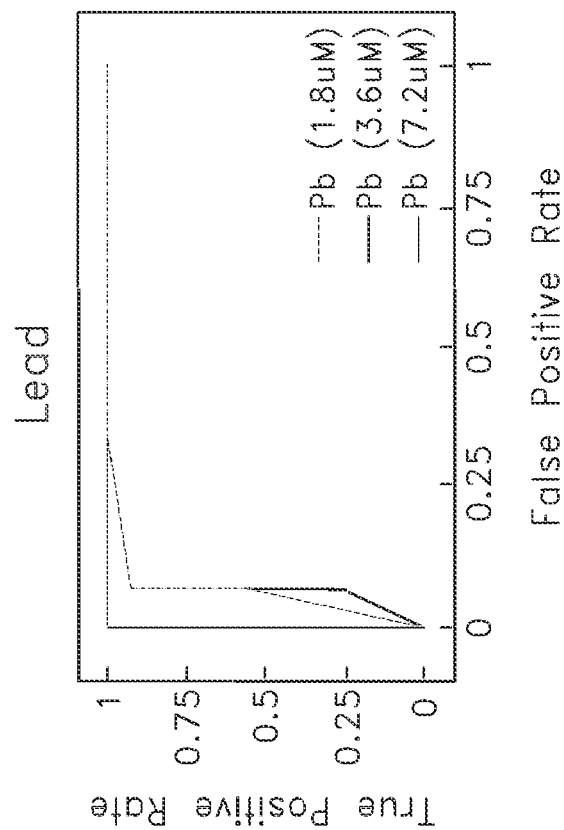
Figure 8F:
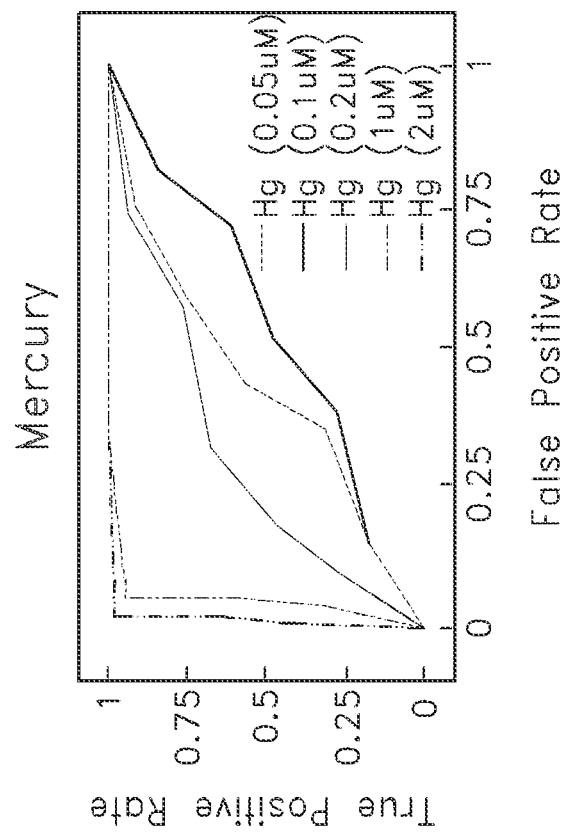
Figure 8H:
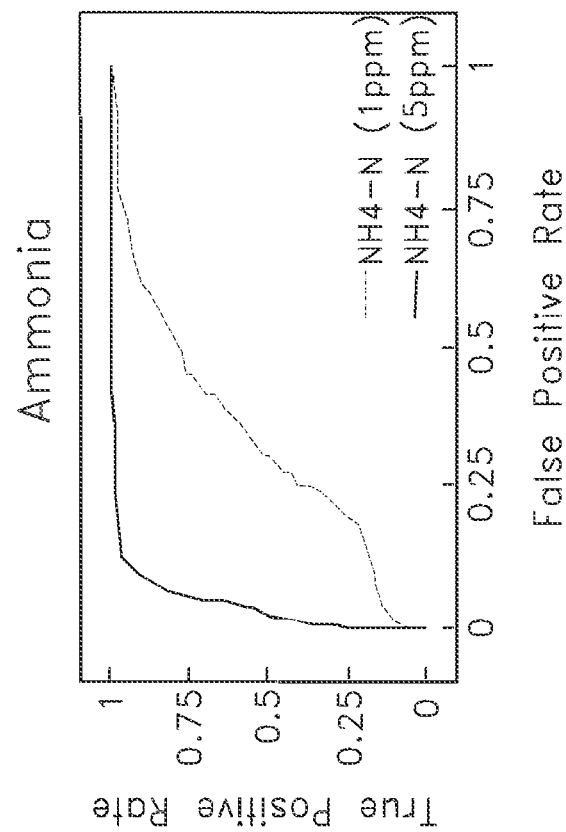
Figure 8G:
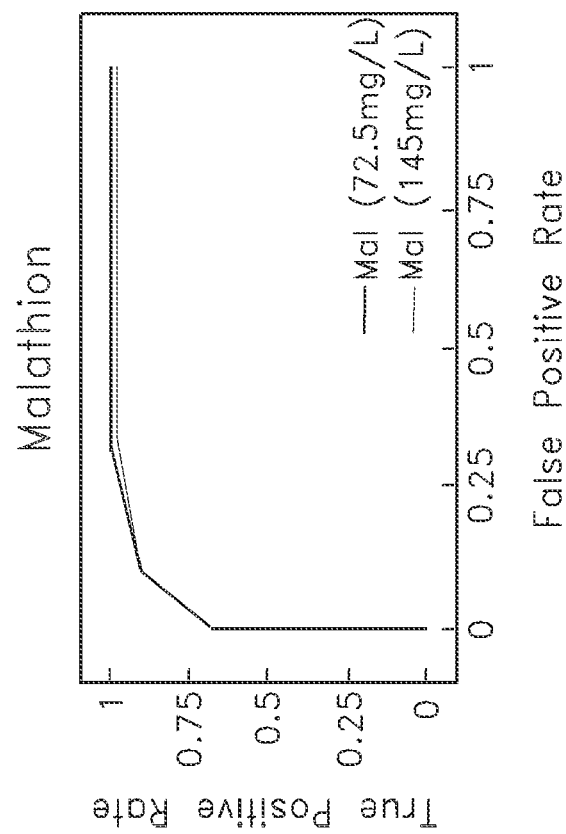

To mount the necessary electronics for acquiring and processing data and to protect them from water exposure, we designed a custom sub-enclosure using Solidworks (Dassault Systems) and had it fabricated using additive manufacturing (3D printing) by a local machine shop (FIG. 7C). A depiction of the Solidworks representation of this enclosure, showing an Arduino Uno (FIG. 7C-1), BuckBlock LED drivers (FIG. 7C-2), PandaBoard system on a chip (FIG. 7C-3) and LED control relays (FIG. 7C-4) is shown in this Figure. The PandaBoard communicates with the Arduino over a RS-232 (serial) link to modulate the LED control relays. The Arduino then generates a pulse wave modulated output signal which is interpreted by the BuckBlock LED drivers to control the brightness of the LEDs (one for both transmitted light and GFP excitation). The PandaBoard is then responsible for acquiring an image from the Ziva optical system (FIG. 7B-5) and finally signaling for the LEDs to be turned off. The acquired data is analyzed on the PandaBoard and the results are transmitted via a secure Wi-Fi link to our data repository server. The software to do this was custom programmed in Java and C using the Point Grey Fly-Capture SDK and implemented on a PandaBoard ES rev B.3 running Ubuntu Server. The various components of the Ziva optical system are shown in FIG. 7D, including: the transmitted light optics (FIG. 7D-1), the microfluidic device stage and thermistor temperature probe (FIG. 7D-2), the focus adjustment system (FIG. 7D-3), the dichroic mirror holder (FIG. 7D-4), the GFP excitation system (FIG. 7D-5) and the Point Grey Chameleon monochrome camera (FIG. 7D-6). An image of a microfluidic device, illuminated with the Ziva GFP excitation optics is shown in FIG. 7E with example images shown in FIG. 7F (top transmitted light, bottom GFP fluorescence).

Computational Models to Determine the Threshold of Detection for Specific Sensors Based on Models of Experimental GFP Responses.

We used machine learning techniques to determine the relationships between the GFP output signal and the presence of a toxin. We have created a database containing the collected sensor response data. We have quantified the GFP threshold of detection for each sensor construct. We have constructed Receiver Operating Characteristic (ROC) curves for each sensor to achieve robust sensing. We constructed machine learning models capable of inferring the relationships between the GFP sensor responses and the presence or absence of a toxin at a given concentration. The algorithm learns these relationships from a set of training samples (GFP sensor responses) defined by the set of experimental conditions from which they were generated. The aim of the algorithm is to provide a general method capable of determining the experimental conditions associated with GFP sensor responses through the use of historical data. Specifically, we have built classification models based on Support Vector Machines (SVMs), which is one of the most popular classifiers due to its excellent performance in many contexts and its solid mathematical basis (1). For each toxin and concentration, we solved a binary classification problem in which the positive class represents the presence of the toxin in water and the negative class is associated with clean environments. Patterns were constructed with features containing GFP sensor responses at various timestamps to capture the temporal dynamics of the GFP signal. The optimal meta-parameters of the SVM classifier were determined by applying a 5-crossvalidation during the training phase (2). In order to have a reliable estimate of the performance of the model when deployed in real environments, we measured its performance over a set of samples (test patterns) not seen during the training phase. The SVM's performance was determined by the percentage of test samples correctly labeled as toxin/no toxin (classification accuracy). 80% of samples were used for training the SVM models and the remaining 20% of samples was used to evaluate their effectiveness. We generated 20 random training/test partitions to have an estimate of performance independent of the data partition. Table 4 shows the average classification accuracy over the test set obtained across the 20 random partitions for each binary classification problem.

TABLE 4

Classification accuracy results (Acc) obtained from the GFP sensor responses for different toxins at different concentrations (Conc.).

| Toxin | Conc.(µM) | Acc (%) |
|---|---|---|
| As | 0.2 | 97.35 |
| (pRS18) | 0.55 | 100 |
| | 1 | 100 |
| As | 0.1 | 97.35 |
| (pZA47a) | 0.5 | 100 |
| | 1 | 100 |
| Cd | 0.022 | 65.00 |
| | 0.044 | 54.16 |
| | 0.44 | 90.00 |
| Cr | 1.25 | 96.67 |
| | 2.5 | 97.50 |
| | 5 | 94.17 |

| Toxin | Conc.(µM) | Acc.(%) |
|---|---|---|
| Cu | 5 | 95.00 |
| | 10 | 96.67 |
| | 20 | 95.00 |
| Hg | 0.2 | 63.33 |
| | 1 | 87.50 |
| | 2 | 99.17 |
| Pb | 1.8 | 95.83 |
| | 3.6 | 95.00 |
| | 7.2 | 95.00 |
| Malathion | 72.5 mg/L | 87.50 |
| | 145 mg/L | 89.17 |
| NH4+ | 1 ppm | 71.05 |
| | 5 ppm | 91.79 |

Based on the results presented in (Table 4) and the ROC curves (FIG. 8), the models establish the threshold of detection at 0.2 µM for Arsenic using the plasmid pRS18, 0.1 µM for Arsenic using pZA47a, 0.44 µM for Cadmium, 1.25 µM for Chromium, 5 µM for Copper, 1 µM for mercury, and 1.8 µM for lead. Malathion can be detected when diluted at 72.5 mg/L and ammonia can be detected at concentrations of one particle per million.

Construction of the Receiver Operating Characteristic curve (ROC) for the sensors to minimize false negatives and false positives): The results in were obtained by assuming that the penalties of misclassification are identical for positive and negative classes. In other words, the cost of classifying a GFP signal as "toxic" when it is not (or vice versa) is the same. However, it may be the case that the cost is not symmetric for positive and negative cases. A water sensor is a good example of this situation since it might be preferable to ensure high accuracy when toxins are actually in the water (true positive rate, TP) in exchange for increasing the number of cases that are classified as "toxin present" when there is not any toxin in the water (false positive rate, FP). The Receiver Operating Characteristic (ROC) curve is 2-D parametrized curve used to quantify and represent the tradeoff between the true positive rate and the false positive rate of a given classifier. The abscissa represents the False Positive rate, while the ordinate shows the True Positive rate. Therefore, the optimal classifier is represented by a point in the upper left corner of the ROC curve, since this point corresponds to the best possible case in which the classifier is able to correctly identify 100% of positive cases (toxin present) with no false alarms. The parameter that defines the ROC curve in our classification model is the decision threshold, which determines whether a pattern (GFP signal) is classified as positive (toxin present) or negative (toxin not present). The SVM model provides a value (decision function) for each pattern that represents the confidence of the model in its prediction, and the final classification is obtained by assigning to the negative class those points with decision functions that are below the decision threshold, and classifying as positive samples those patterns with decision functions above this threshold. Therefore, by sweeping a grid of possible values for the SVM decision threshold, we obtained the ROC curves for the different toxins shown in FIG. 8.

Design the Controller Board with Wireless Capability:

We have chosen to implement a single board computer that contains wireless Ethernet capability. We tested two low-power platforms based on the Texas Instruments ARM processor with wireless capability: one based on the Sitara ARM and the other based on the Cortex-A9 (see FIG. 9). We have opted for the more powerful Cortex-A9 due to the ease of use and low power consumption. We are currently using a PandaBoard, which is powered by a Texas Instruments OMAP4430 system on chip (SoC) device. The OMAP4430 chipset contains a dualcore 1 GHz ARM Cortex-A9 MPCore CPU with 1 GB of DDR2 SDRAM, wireless Ethernet capability, and an SD card slot offering up to 32 GB of storage. The electronics are similar to a modern smartphone in terms of processing power and power consumption. The PandaBoard solution allows us to install a Linux operating system so that we can use standard gnu compilers and run our software without any major modifications, which we demonstrate in the next two aims.

Reduce the Size of the Pattern Recognition Algorithms to be Able to be Embedded in the PandaBoard.

Figure 11:
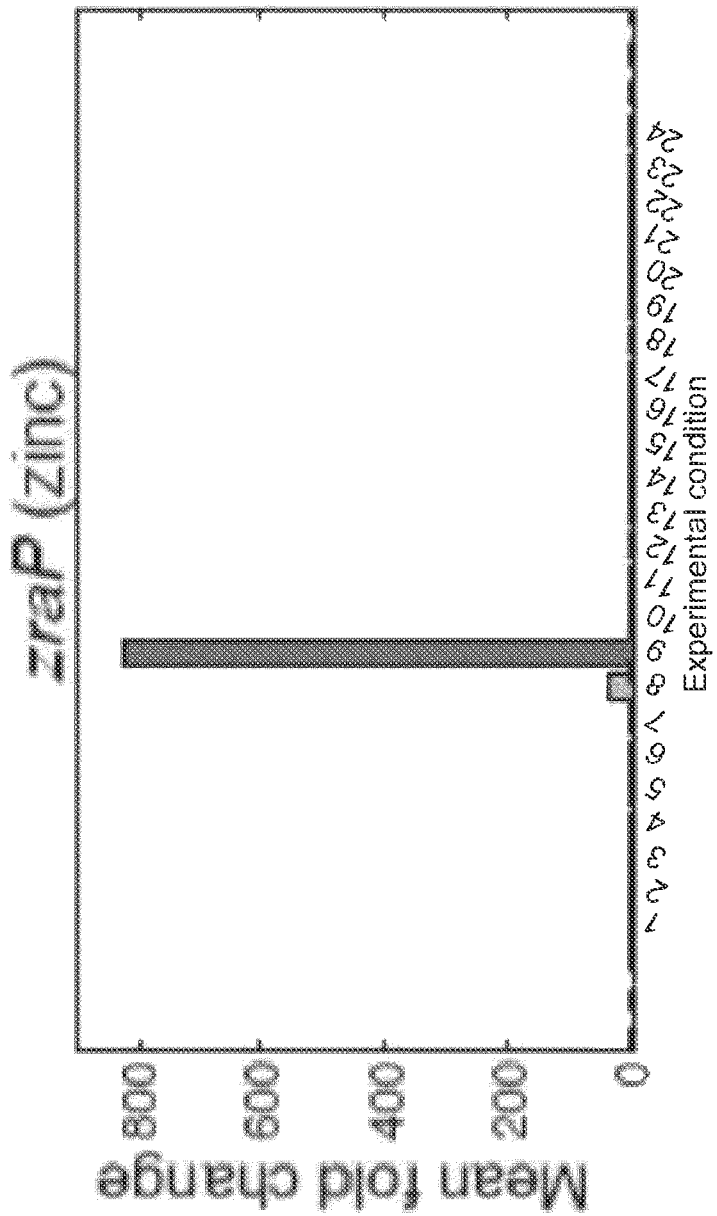
FIG. 11, (FIGS. 11A, 11B, 11C and 11D) illustrate Quadratic Programming Feature Selection weights representing the importance of each pixel for the discrimination task (0: least relevant pixels/1: most relevant pixels) a) Weights assigned to each pixel. Weights of the first b) 100, c) 200, and d) 500 features selected.
Figure 10A:
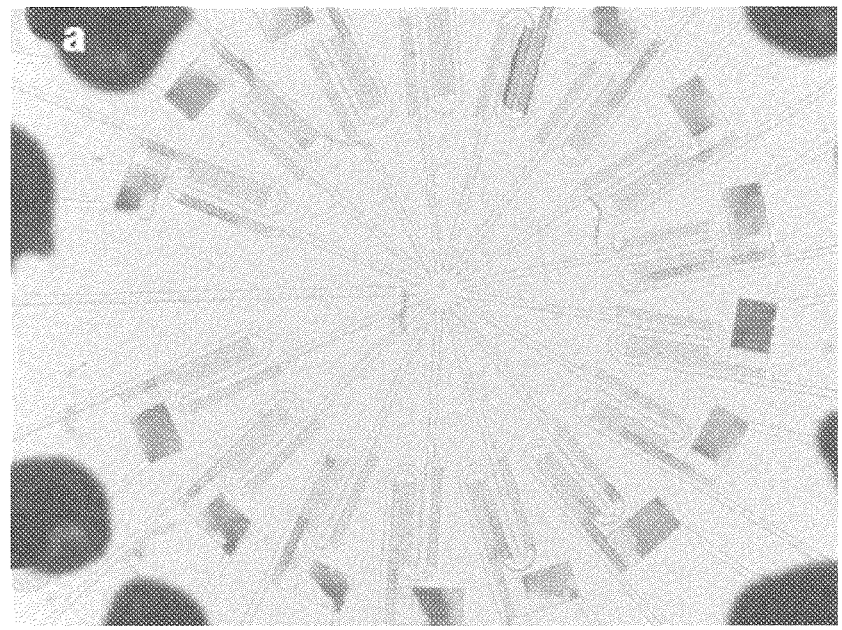
FIG. 10, (FIGS. 10A and 10B) illustrate 10A) Brightfield image of a microfluidic device comprising sixteen rotationally symmetric "gill" cell trapping regions for imaging sixteen biosensor strains. 10B) Fluorescence image of the same microfluidic device. Each cell strain trapped in a "gill" region is engineered to produce GFP upon exposure to a specific toxin in the mixed medium. The fluorescence image is analyzed to interpret the intensity of the GFP signal in each trapping region as a concentration of the relevant toxin in the natural water source.
Figure 10B:
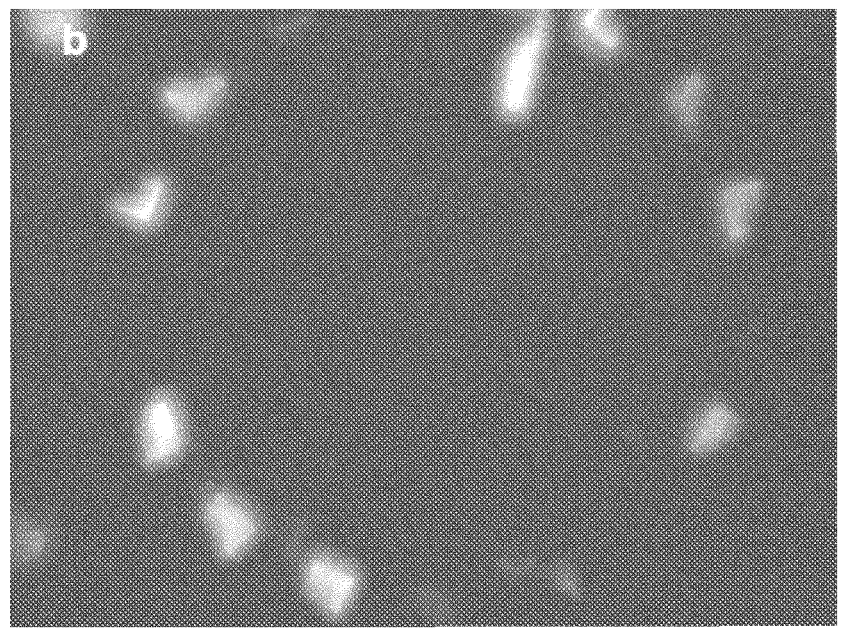
Figure 12:
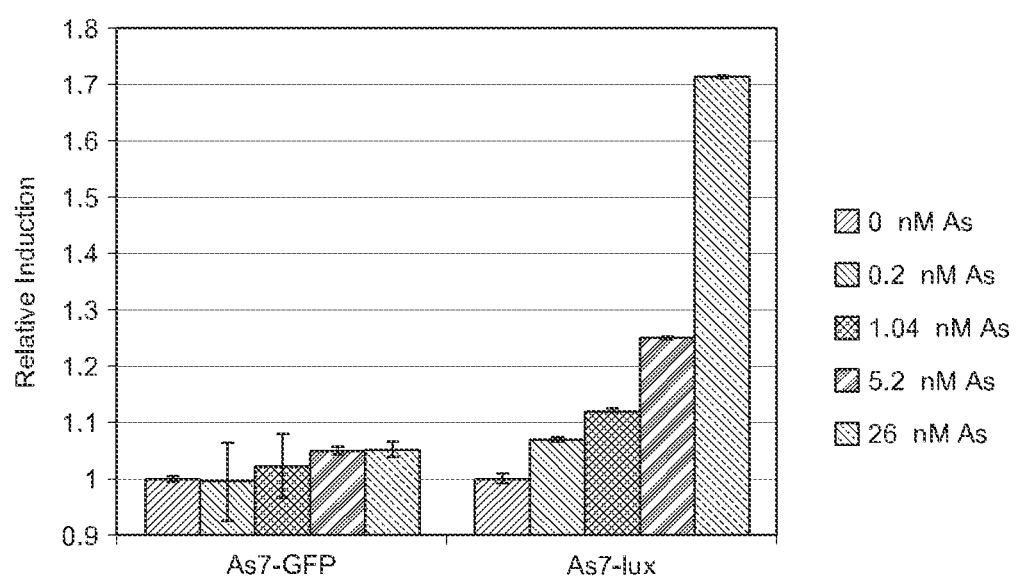
FIG. 12 illustrates a side-by-side comparison of reporter systems on otherwise identical plasmid backbones demonstrates the superior detection limit achieved by using luminescence.
Figure 13:
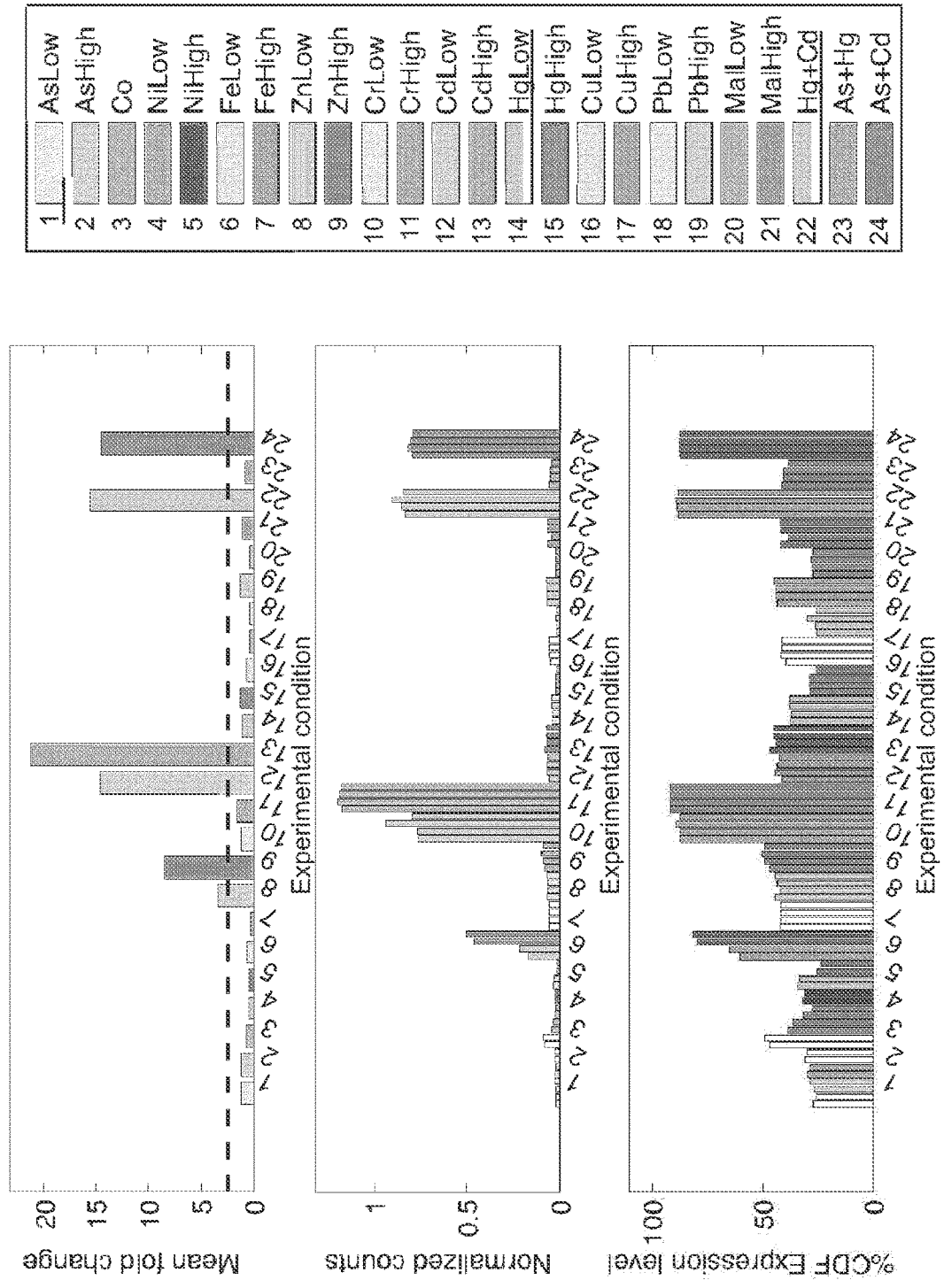
FIG. 13 shows the response of the zntA promoter in E. coli MG1655 for sensing cadmium and zinc. The zntA promoter responds monotonically to increasing concentrations of cadmium alone and in combination with other heavy metals (rightmost conditions) without exhibiting crosstalk. A cadmium-specific sensor can be implemented by combining this response with the zinc-specific response of zraP using the Boolean expression (zntA)^(¬zraP). As shown in the two panels below, the numbers at the x-axis correspond to the four corresponding bars above the numbers. For example the first 4 bars correspond to the number 1, the second set of 4 bars correspond to the number 2 and so forth.
Figure 14:
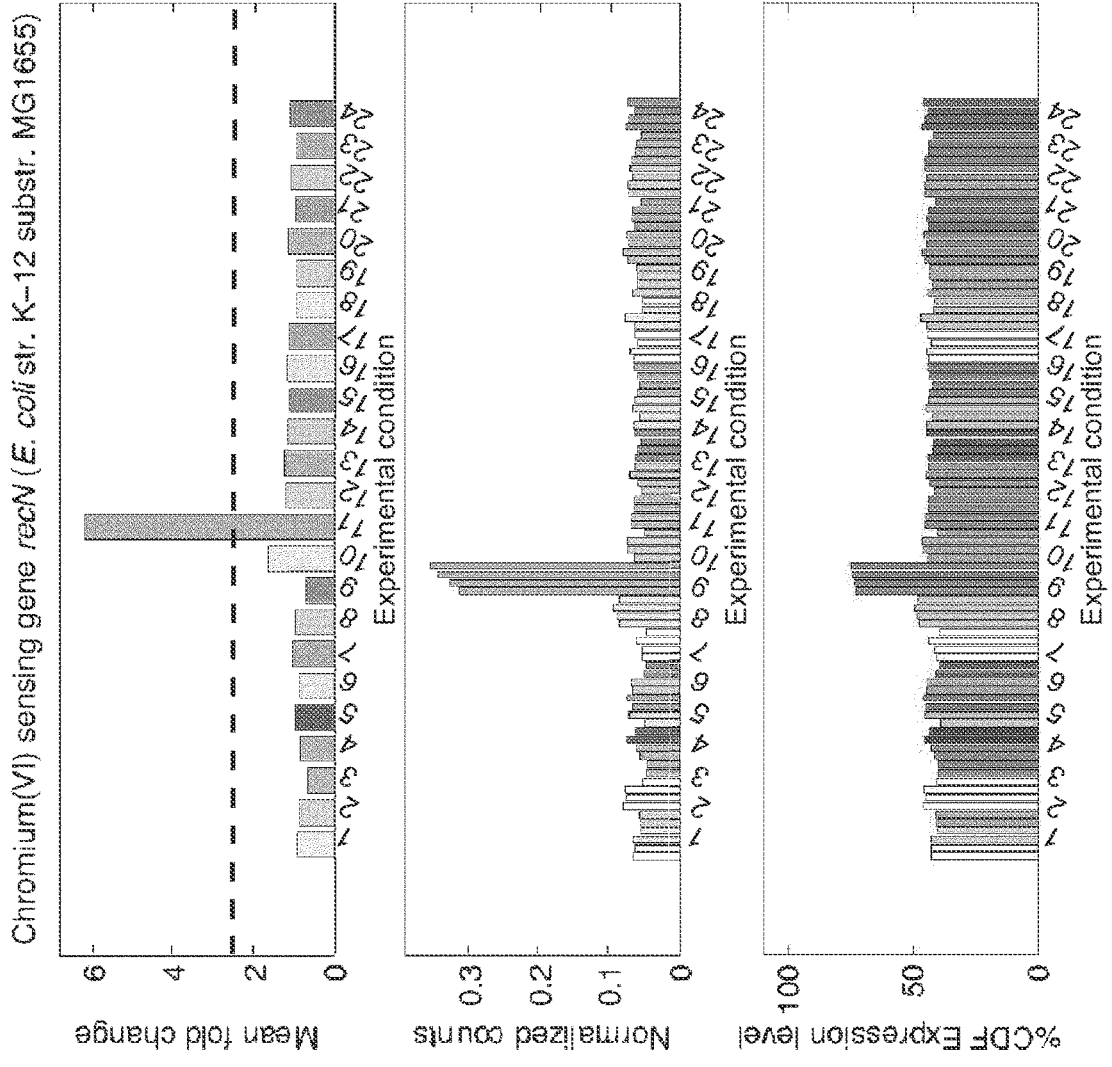
FIG. 14 shows the response of the recN promoter in E. coli MG1655 for specifically sensing chromium (VI). The response of the recN promoter is specific to chromium (VI) alone but only shows sensitivity to high concentrations of chromium (VI). As shown in the two panels below, the numbers at the x-axis correspond to the four corresponding bars above the numbers. For example the first 4 bars correspond to the number 1, the second set of 4 bars correspond to the number 2 and so forth.
Figure 15:
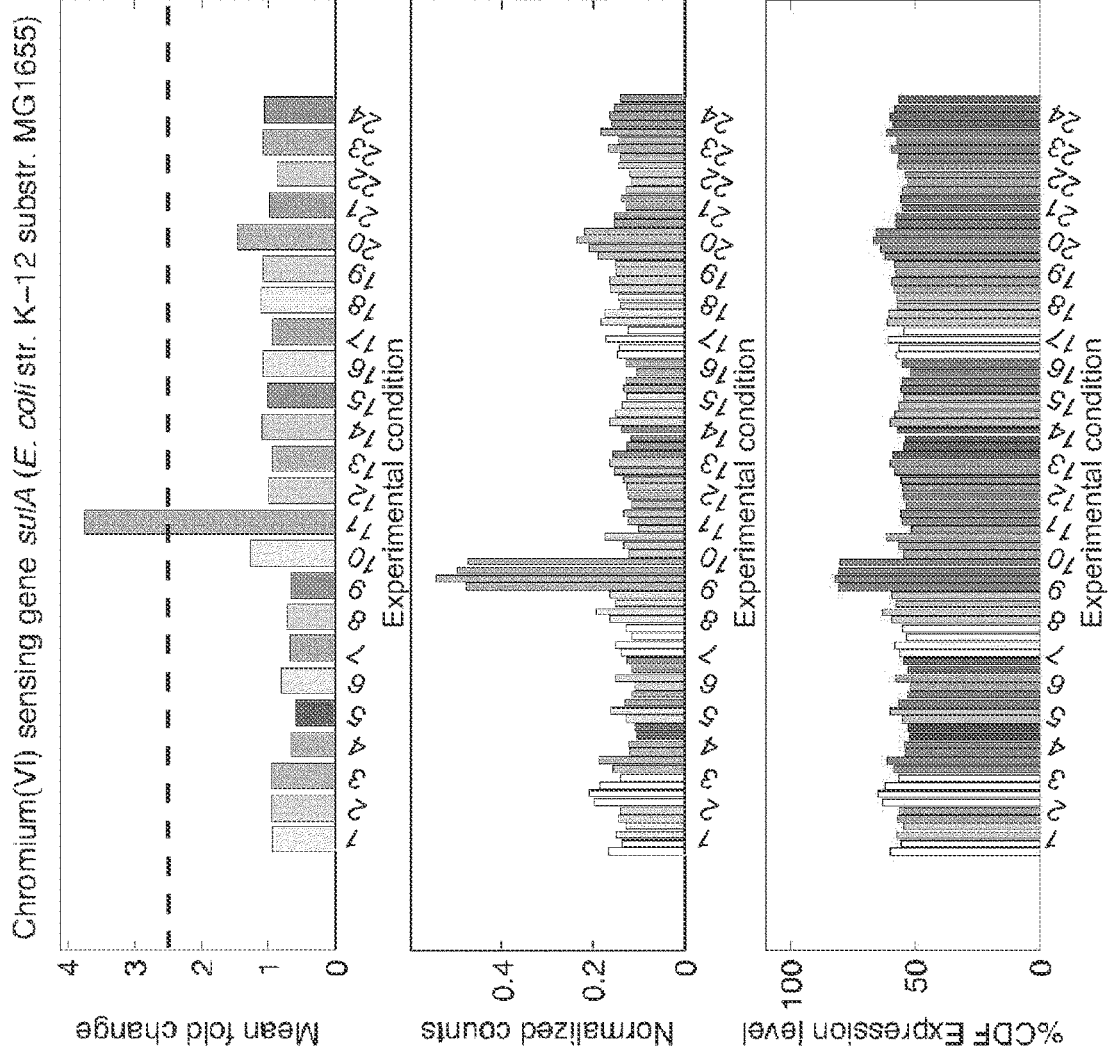
FIG. 15 shows the response of the sulA promoter in E. coli MG1655 for specifically sensing chromium (VI). The response of the sulA promoter is specific to chromium (VI) alone but only shows sensitivity to high concentrations of chromium (VI). As shown in the two panels below, the numbers at the x-axis correspond to the four corresponding bars above the numbers. For example the first 4 bars correspond to the number 1, the second set of 4 bars correspond to the number 2 and so forth.
Figure 16:
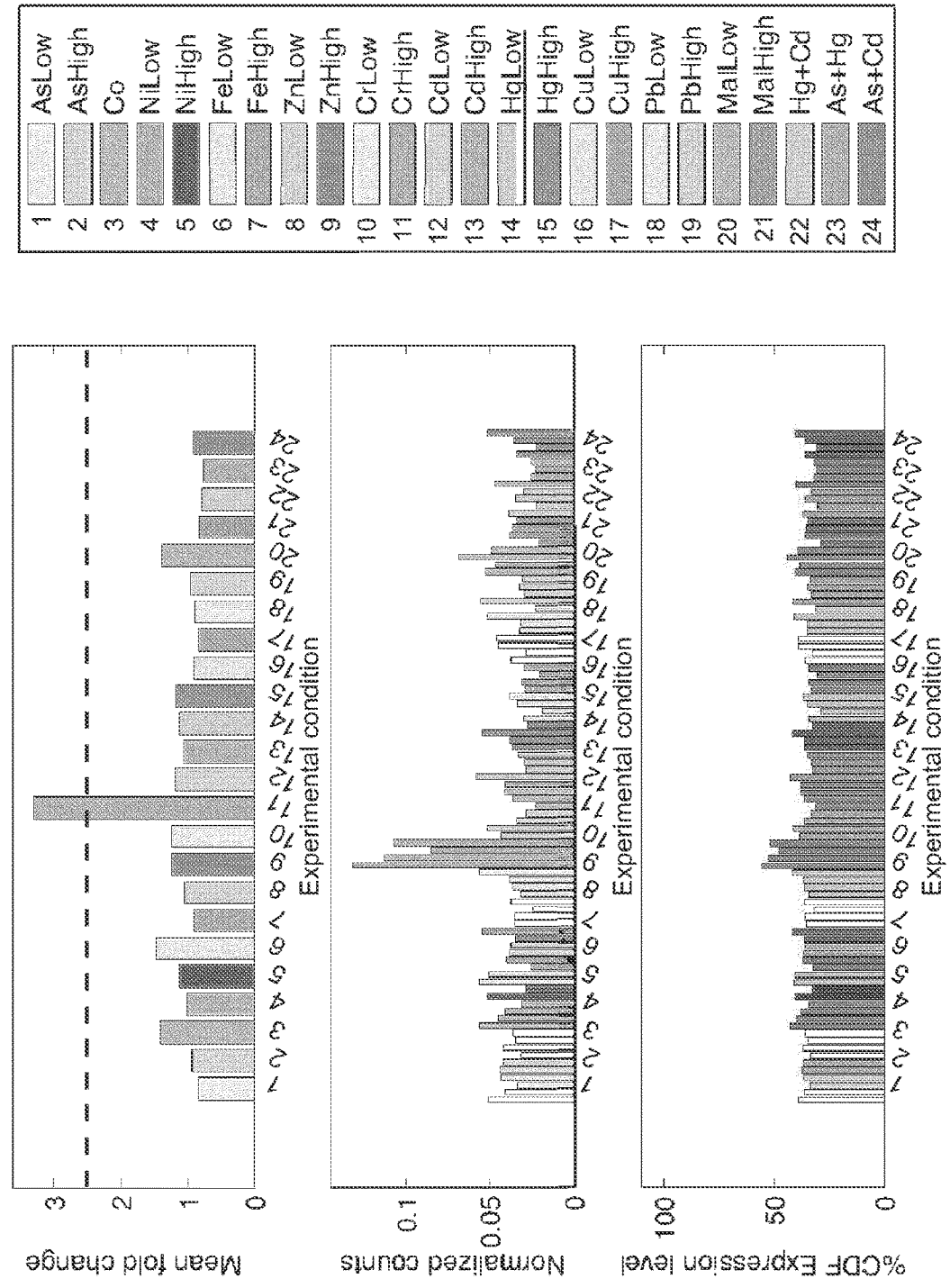
FIG. 16 shows the response of the umuD promoter in E. coli MG1655 for specifically sensing chromium (VI). The response of the umuD promoter is specific to chromium (VI) alone but only shows sensitivity to high concentrations of chromium (VI). As shown in the two panels below, the numbers at the x-axis correspond to the four corresponding bars above the numbers. For example the first 4 bars correspond to the number 1, the second set of 4 bars correspond to the number 2 and so forth.
Figure 18:
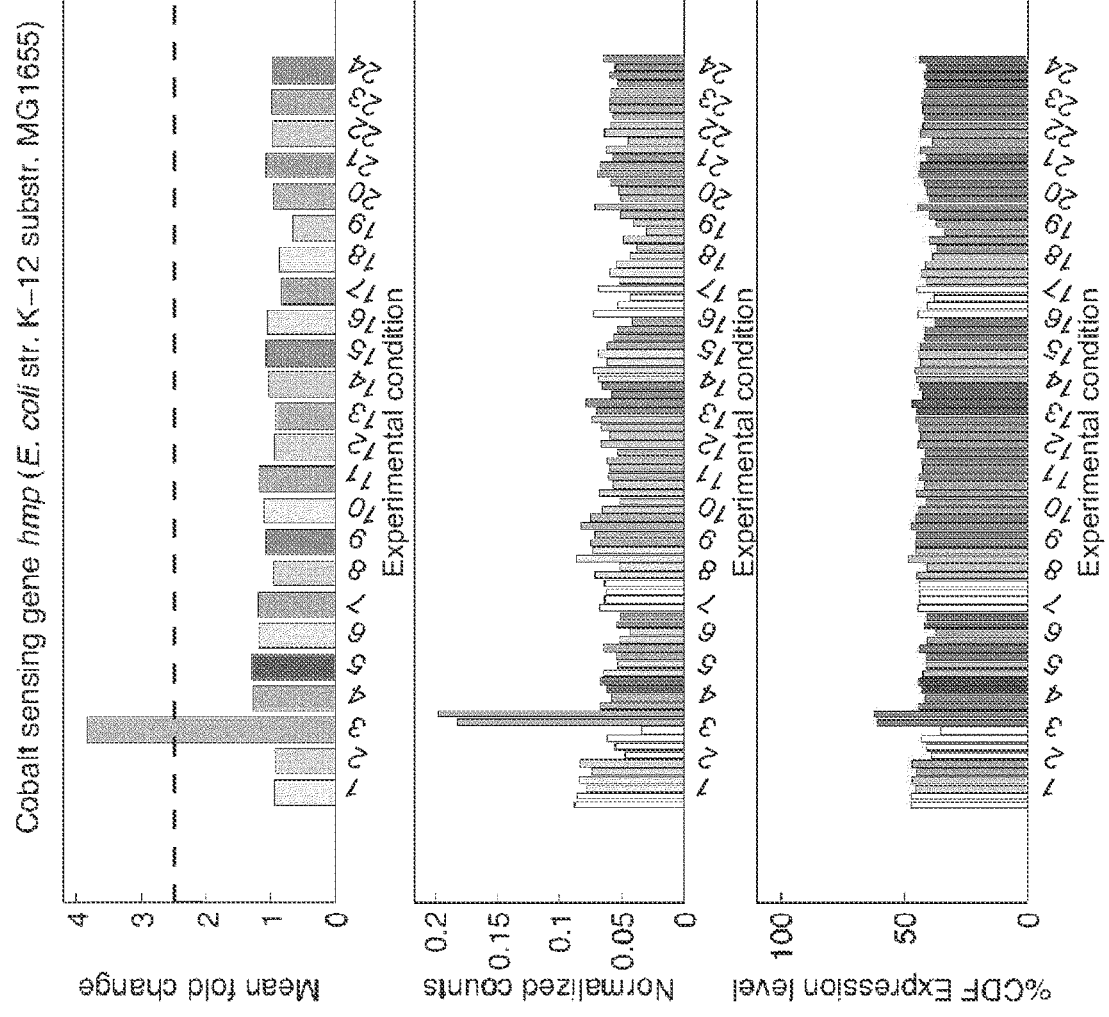
FIG. 18 shows the response of the hmp promoter in E. coli MG1655 for specifically sensing cobalt. The response of the hmp promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 19:
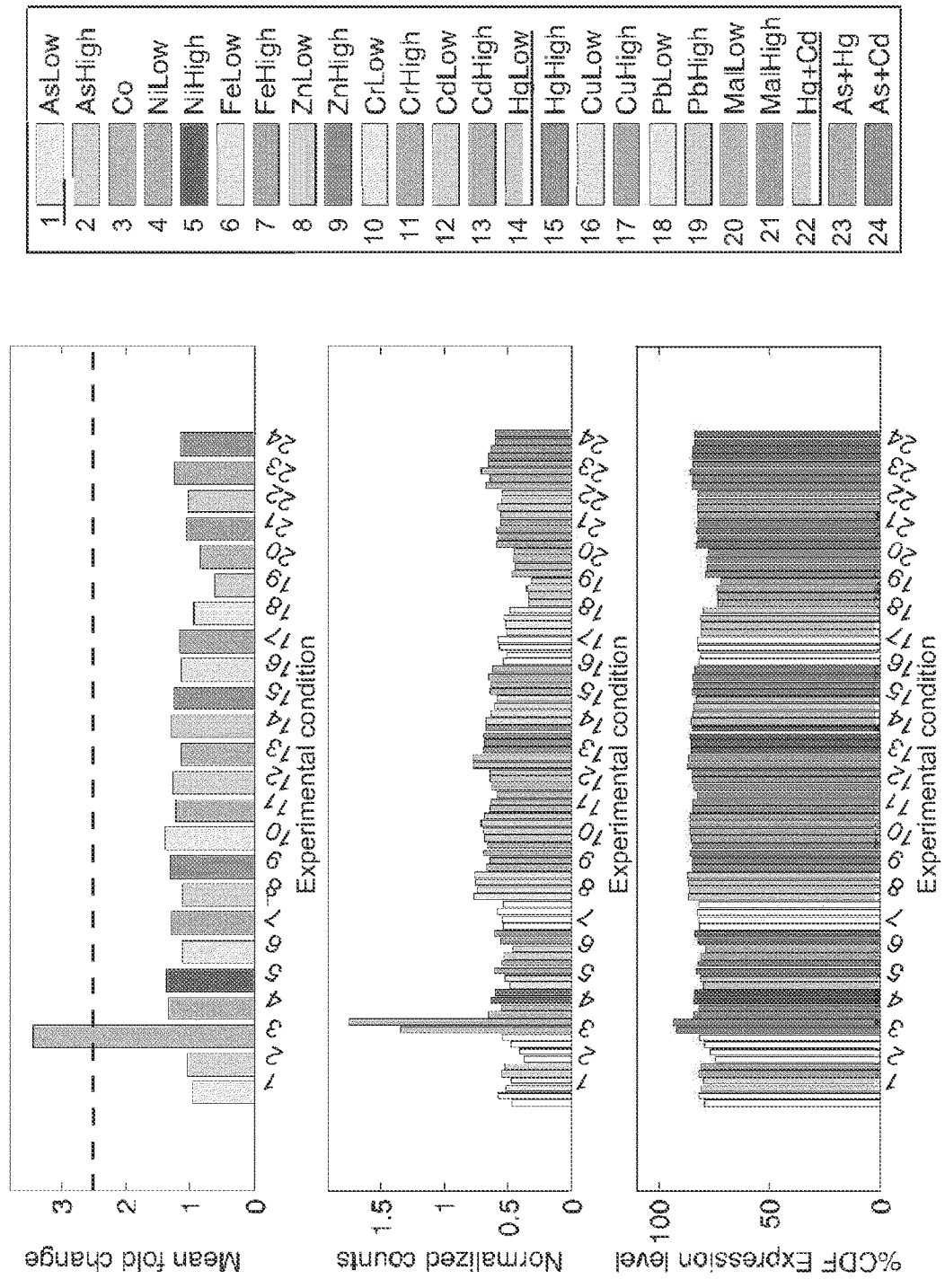
FIG. 19 shows the response of the ilvB promoter in E. coli MG1655 for specifically sensing cobalt. The response of the ilvB promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 20:
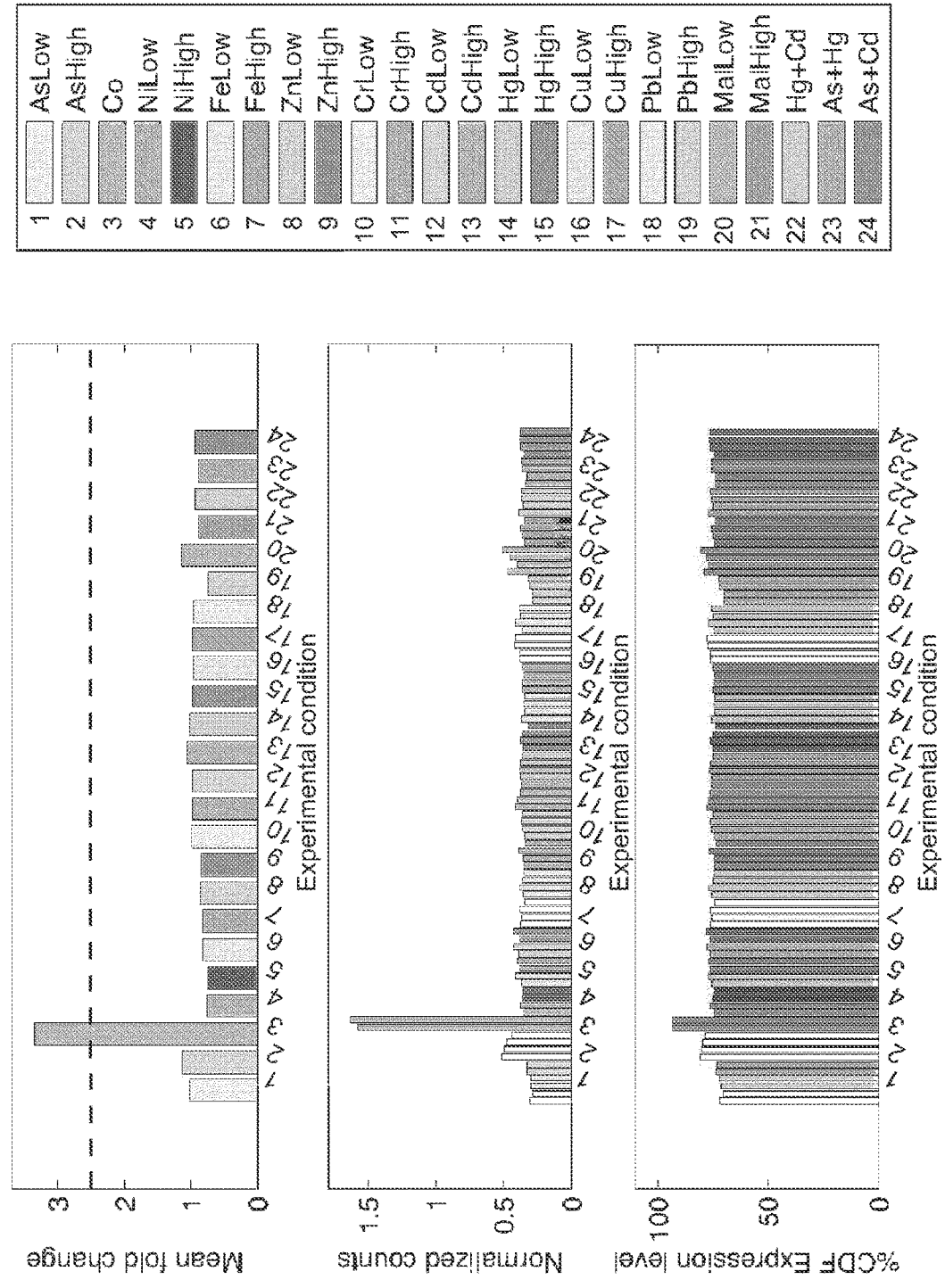
FIG. 20 shows the response of the lipA promoter in E. coli MG1655 for specifically sensing cobalt. The response of the lipA promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 21:
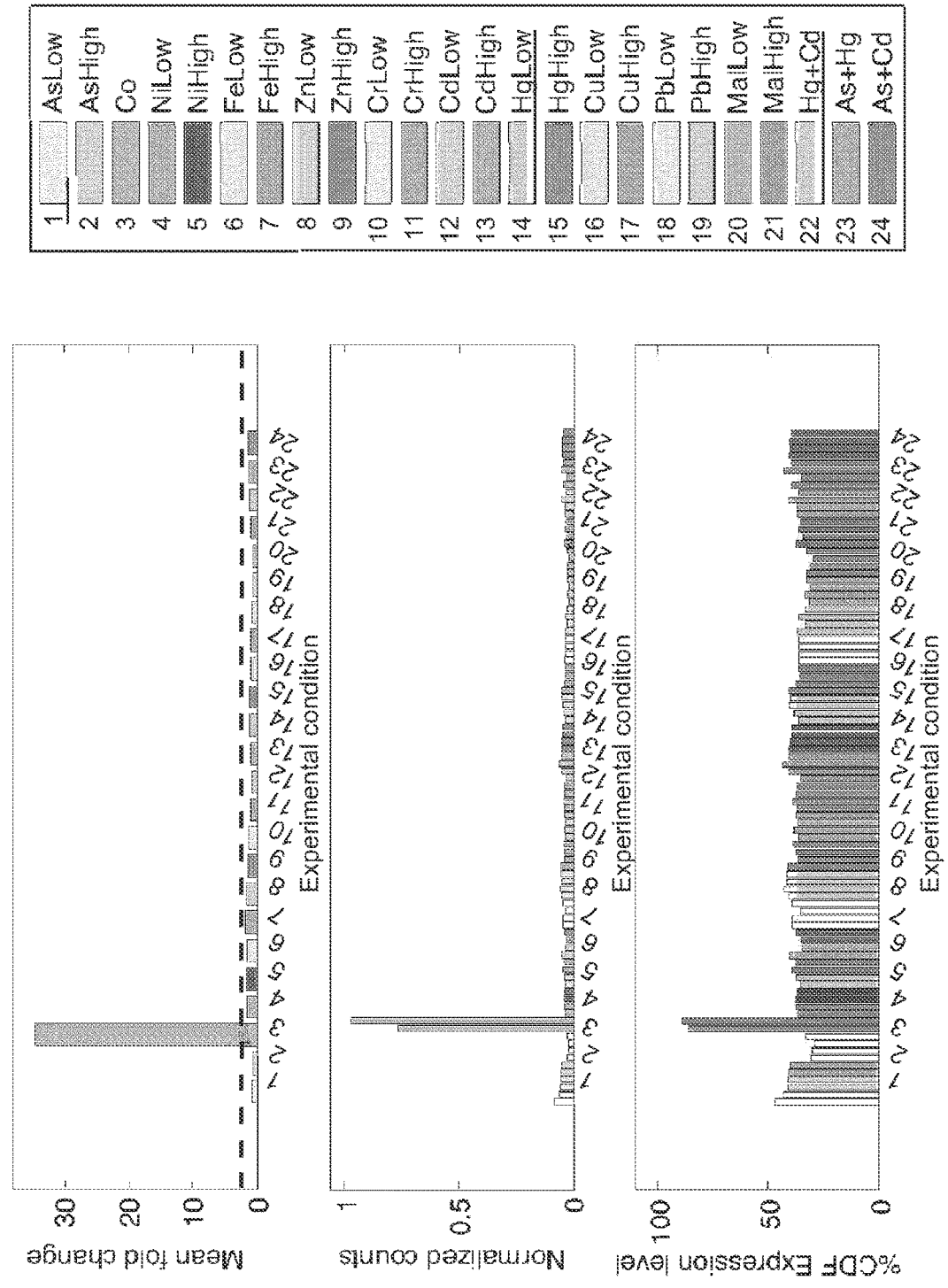
FIG. 21 shows the response of mmuP promoter in *E. coli* MG1655 for specifically sensing cobalt. The response of the mmuP promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 22:
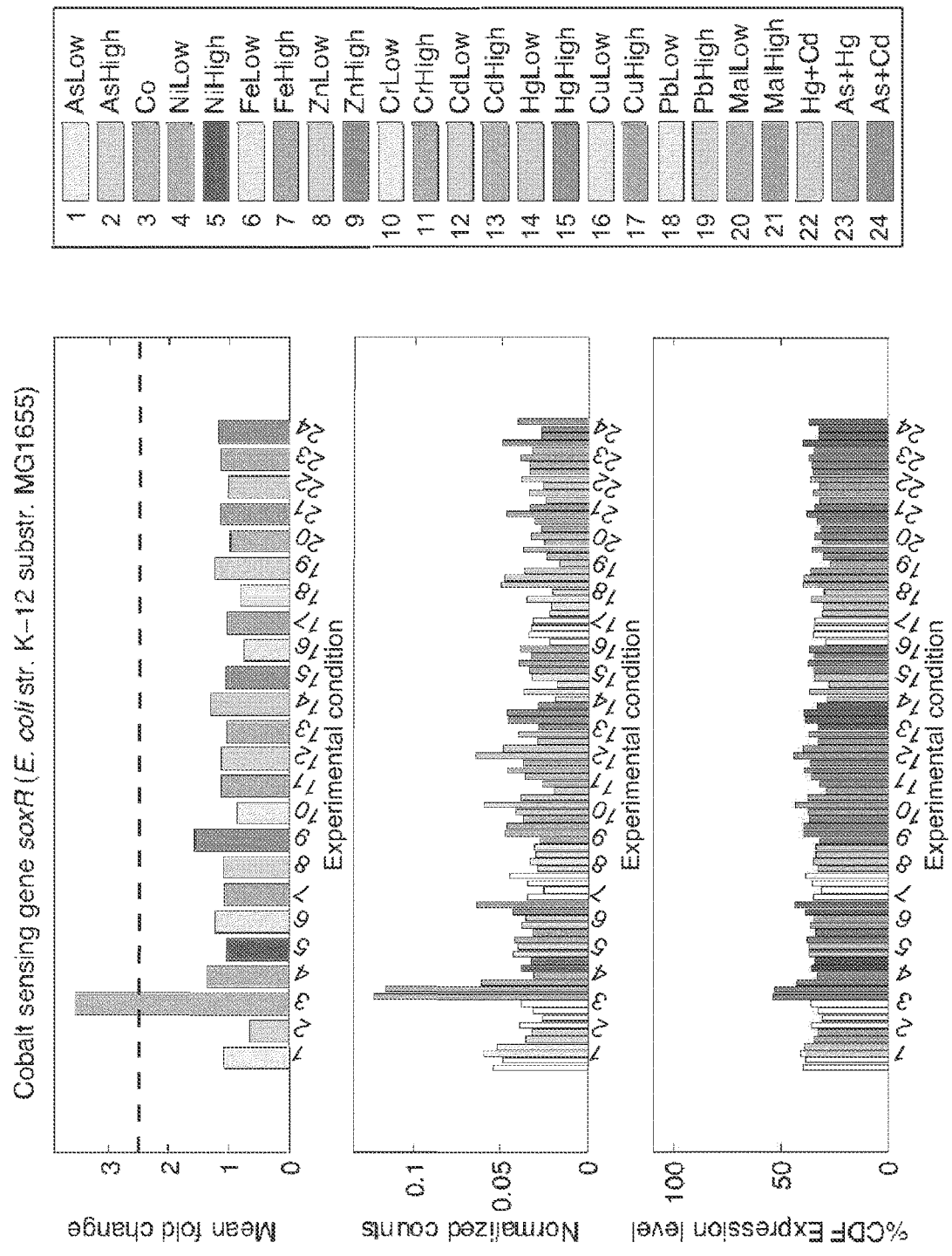
FIG. 22 shows the response of the soxR promoter in *E. coli* MG1655 for specifically sensing cobalt. The response of the soxR promoter is specific to cobalt alone. The response of the soxR promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 23:
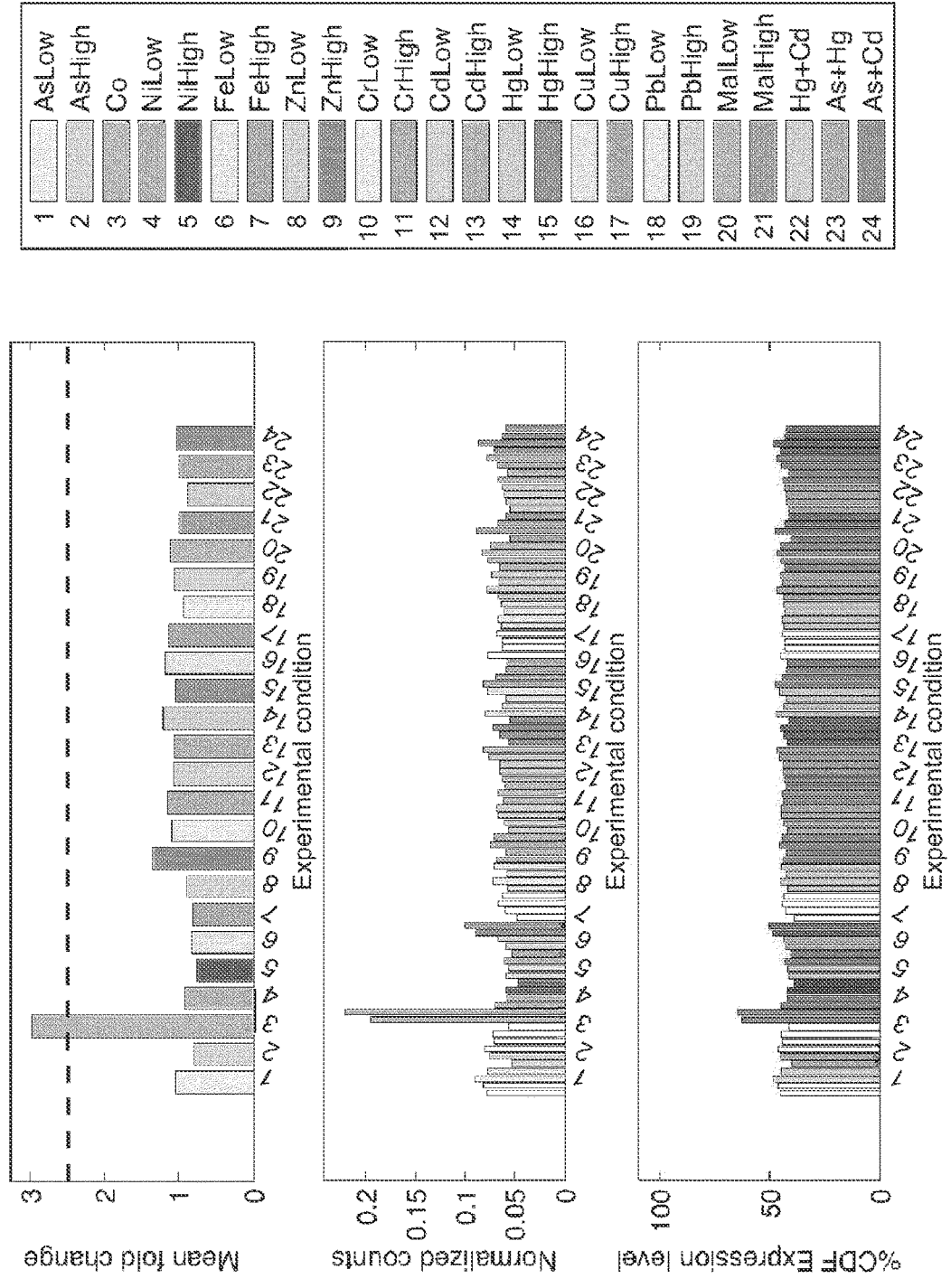
FIG. 23 shows the response of the tehA promoter in *E. coli* MG1655 for specifically sensing cobalt. The response of the tehA promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 24:
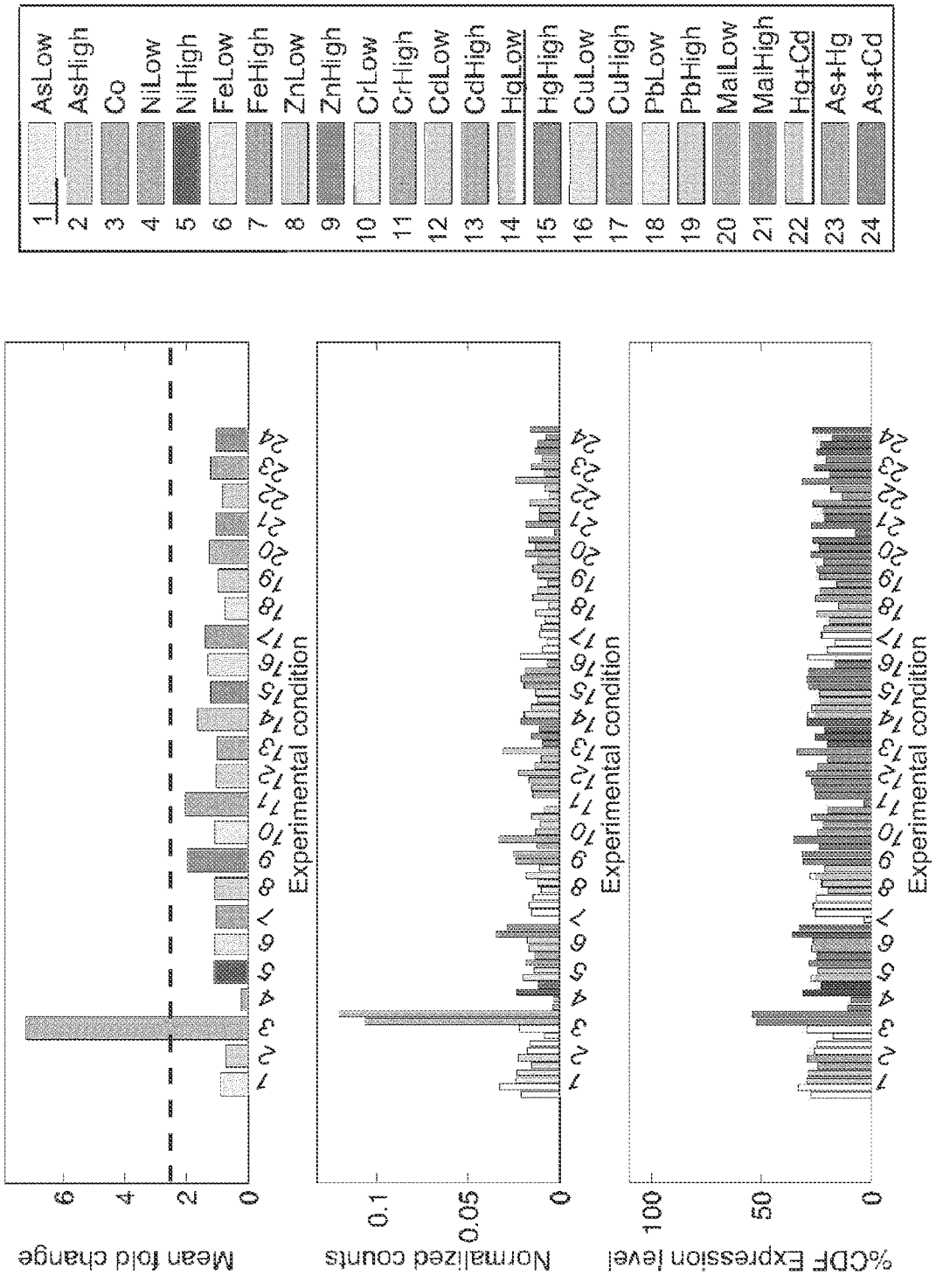
FIG. 24 shows the response of the ygbA promoter in *E. coli* MG1655 for specifically sensing cobalt. The response of the ygbA promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 25:
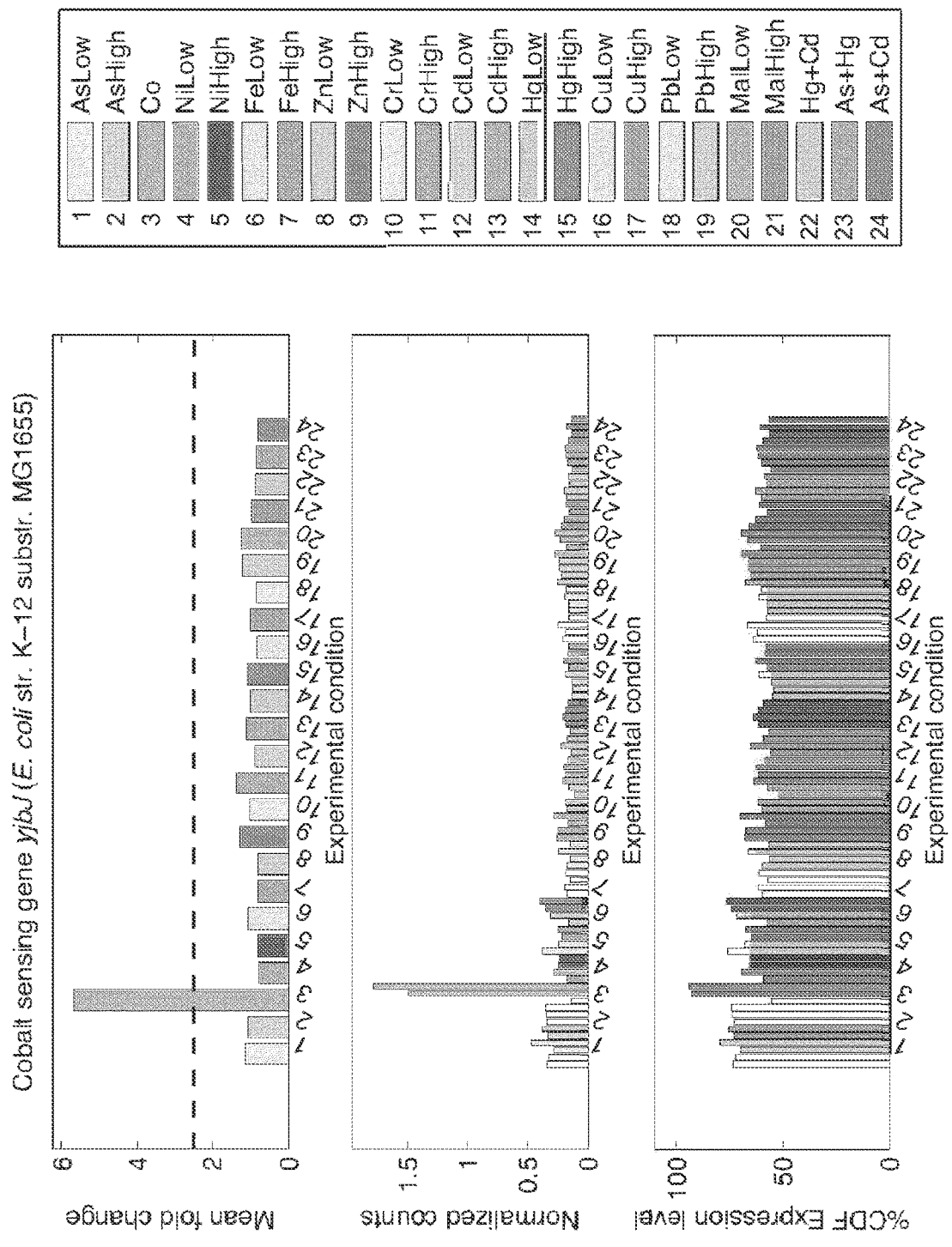
FIG. 25 shows the response of the yjbJ promoter in *E. coli* MG1655 for specifically sensing cobalt. The response of the yjbJ promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 26:
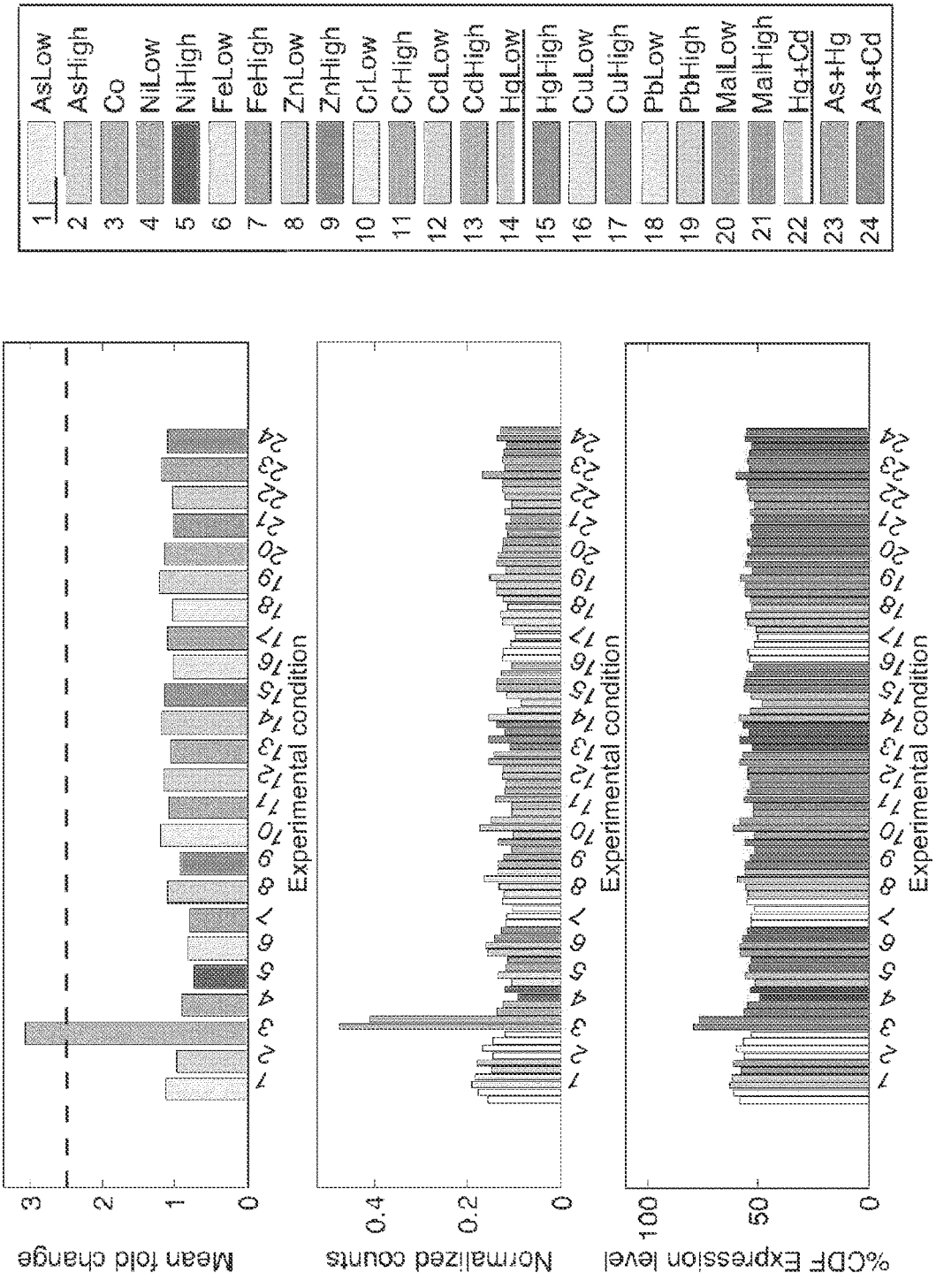
FIG. 26 shows the response of the yqfA promoter in *E. coli* MG1655 for specifically sensing cobalt. The response of the yqfA promoter is specific to cobalt alone. As shown in the two panels below, the numbers at the x-axis correspond to the four corresponding bars above the numbers. For example the first 4 bars correspond to the number 1, the second set of 4 bars correspond to the number 2 and so forth.
Figure 27:
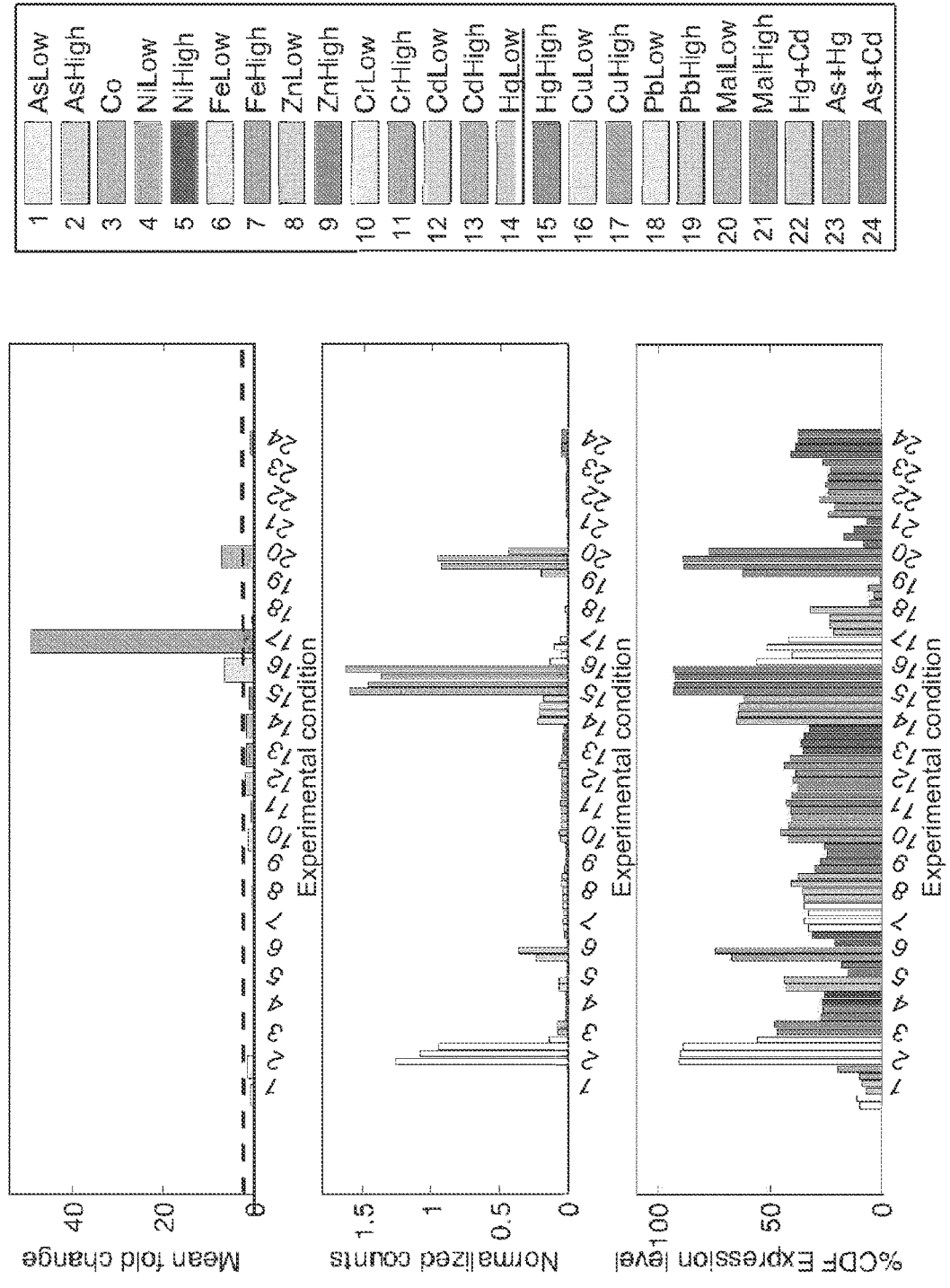
FIG. 27 shows the response of the cusC promoter in *E. coli* MG1655 for sensing copper and malathion. The cusC promoter responds monotonically to increasing concentrations of copper alone and to low concentrations of malathion alone. A copper-specific sensor can be implemented by combining this response with the malathion-specific response of nemR using the boolean expression (cusC)^(¬nemR). Alternatively, a malathion-specific sensor can be implemented by combining this response with the copper-specific response of cusR using the boolean expression (cusC)^(¬cusR). As shown in the two panels below, the numbers at the x-axis correspond to the four corresponding bars above the numbers. For example the first 4 bars correspond to the number 1, the second set of 4 bars correspond to the number 2 and so forth.
Figure 28:
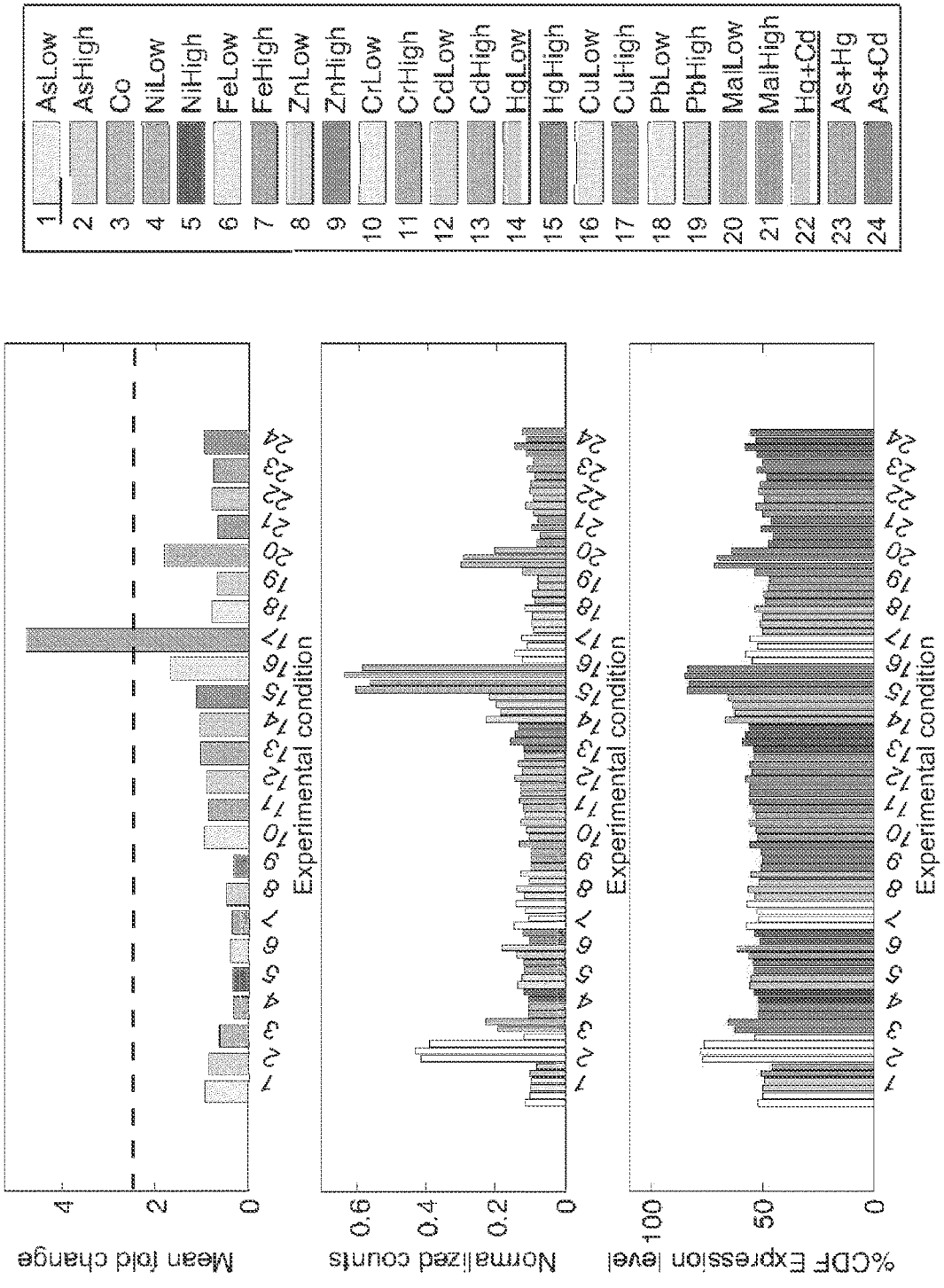
FIG. 28 shows the response of the cusR promoter in *E. coli* MG1655 for specifically sensing copper. The response of the cusR promoter is specific to copper alone but only shows sensitivity to high concentrations of copper. As shown in the two panels below, the numbers at the x-axis correspond to the four corresponding bars above the numbers. For example the first 4 bars correspond to the number 1, the second set of 4 bars correspond to the number 2 and so forth.
Figure 29:
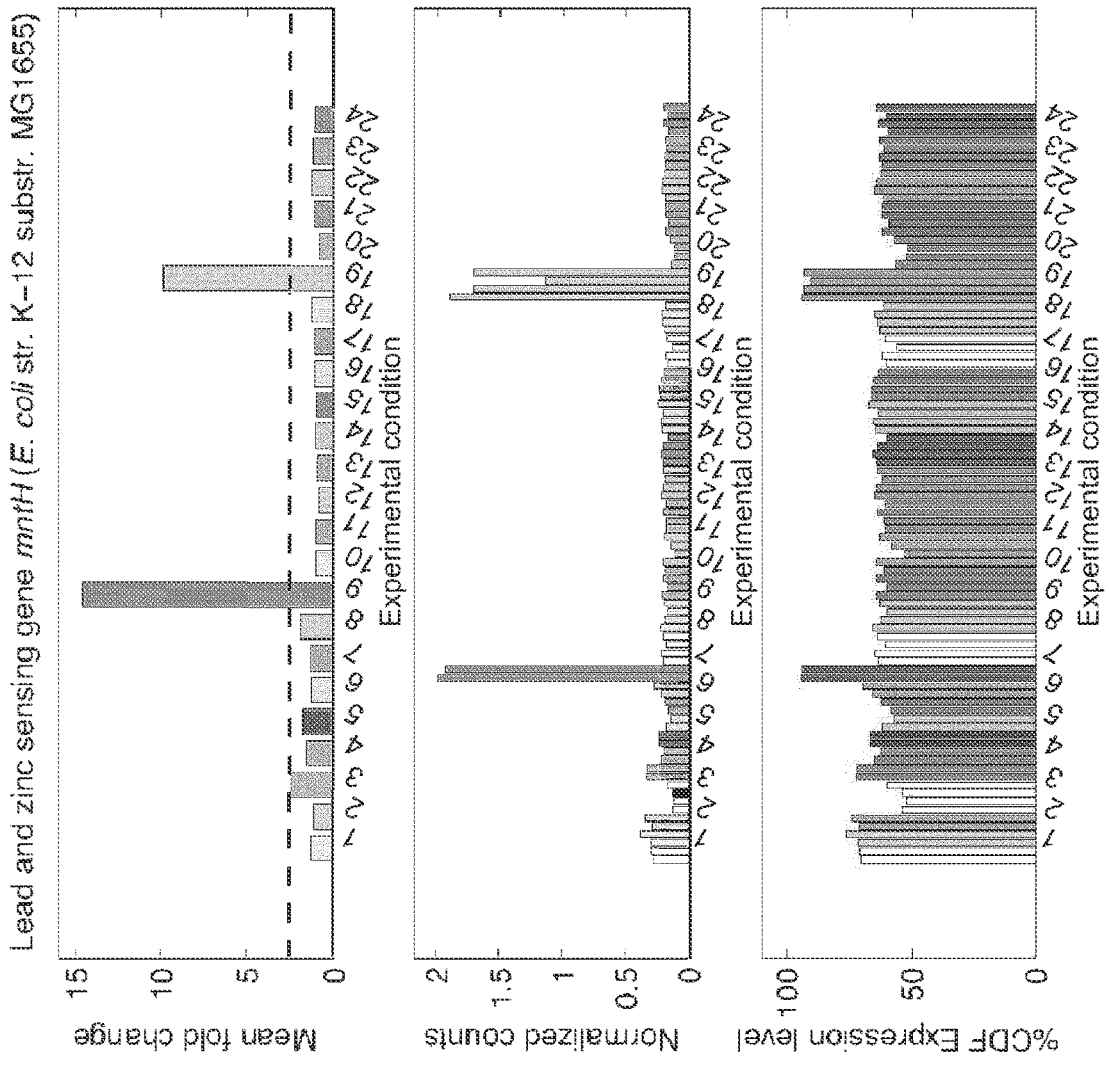
FIG. 29 shows the response of the mntH promoter in *E. coli* MG1655 for sensing lead and zinc. The mntH promoter responds to high concentrations of lead alone and high concentrations of zinc alone. A lead specific sensor can be implemented by combining this response with the zinc-specific response of zraP using the boolean expression (mntH)^(¬zraP). Alternatively, a zinc-specific sensor can be implemented by combining this response with the lead-specific response of ybiI using the boolean expression (mntH)^(¬ybiI). As shown in the two panels below, the numbers at the x-axis correspond to the four corresponding bars above the numbers. For example the first 4 bars correspond to the number 1, the second set of 4 bars correspond to the number 2 and so forth.
Figure 30:
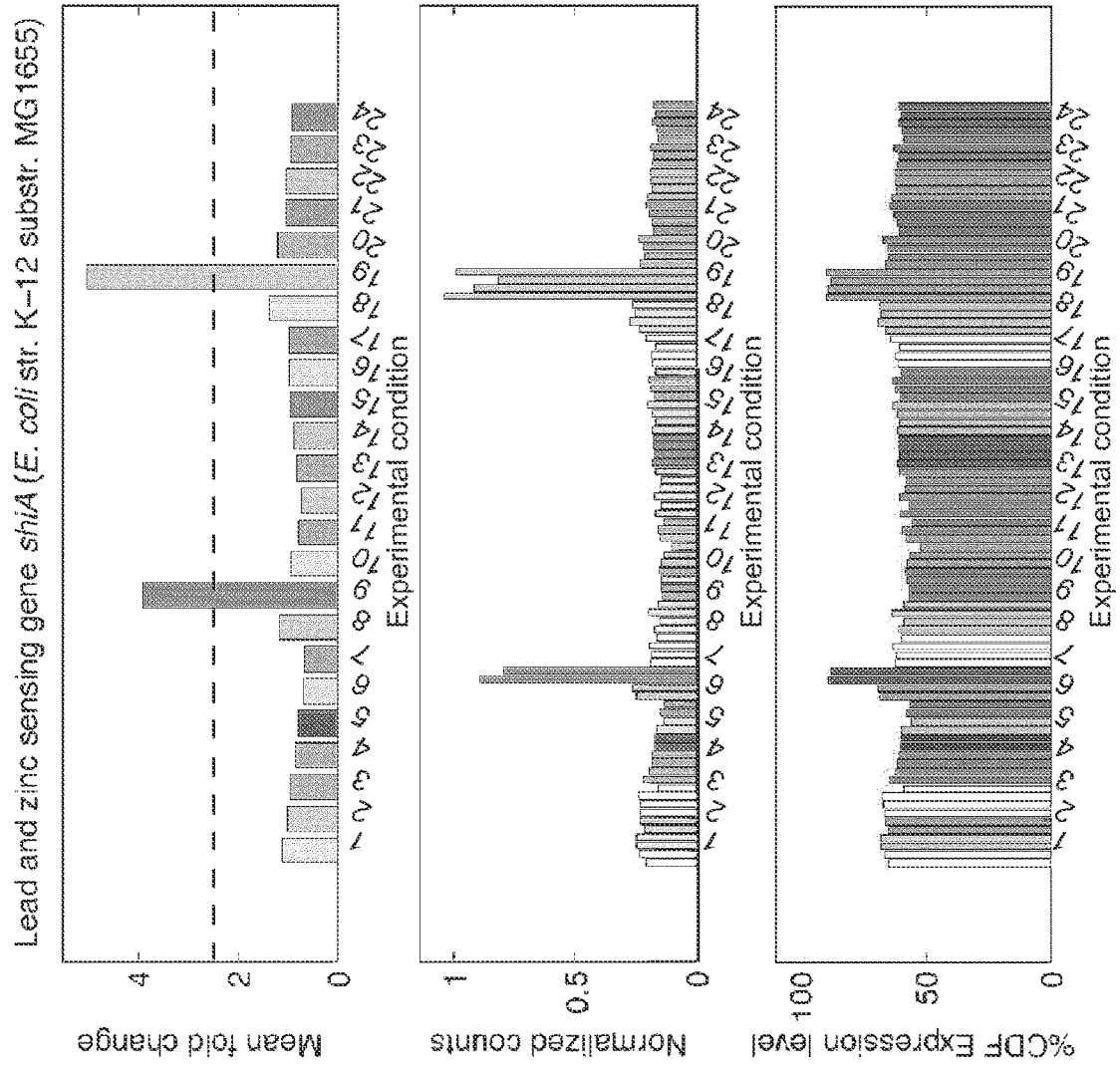
FIG. 30 shows the response of the shiA promoter in *E. coli* MG1655 for sensing lead and zinc. The shiA promoter responds to high concentrations of lead alone and high concentrations of zinc alone. A lead specific sensor can be implemented by combining this response with the zinc-specific response of zraP using the boolean expression (shiA)^(¬zraP). Alternatively, a zinc-specific sensor can be implemented by combining this response with the lead-specific response of ybiI using the boolean expression (shiA)^(¬ybiI). As shown in the two panels below, the numbers at the x-axis correspond to the four corresponding bars above the numbers. For example the first 4 bars correspond to the number 1, the second set of 4 bars correspond to the number 2 and so forth.
Figure 31:
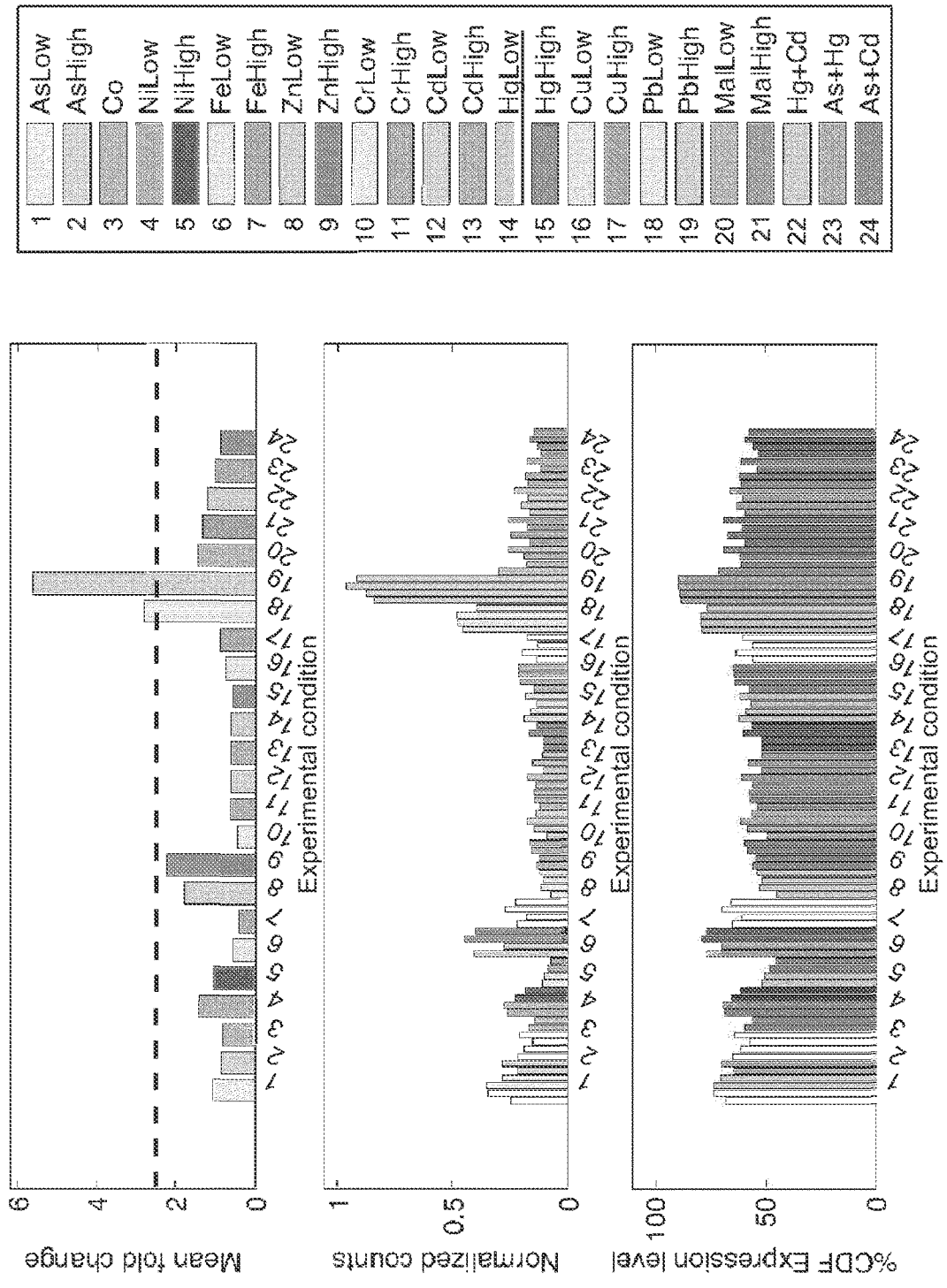
FIG. 31 shows the response of the ybiI promoter in *E. coli* MG1655 for specifically sensing lead. The ybiI promoter responds specifically and monotonically to increasing concentrations of lead alone. As shown in the two panels below, the numbers at the x-axis correspond to the four corresponding bars above the numbers. For example the first 4 bars correspond to the number 1, the second set of 4 bars correspond to the number 2 and so forth.
Figure 32:
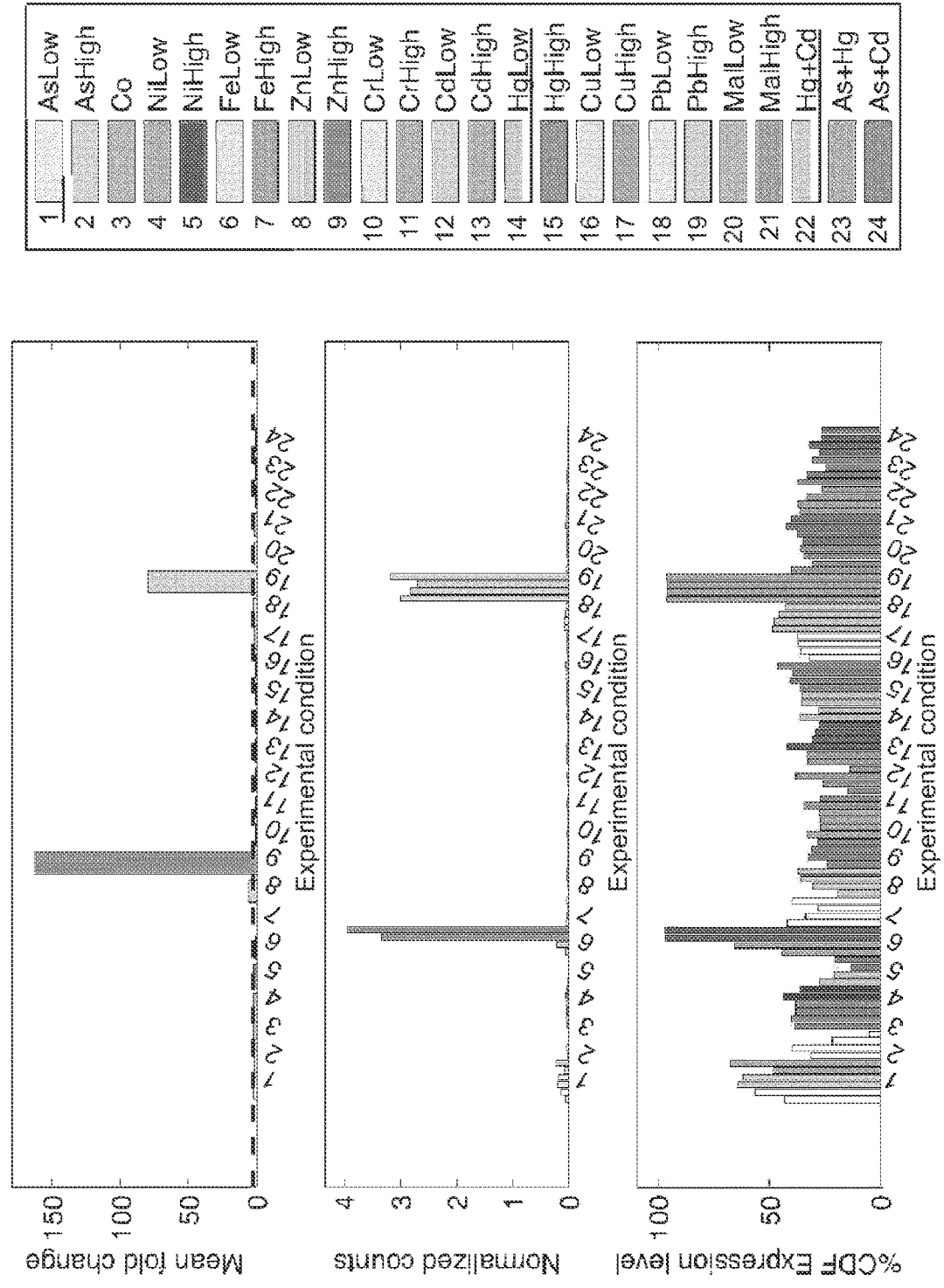
FIG. 32 shows the response of the yjjZ promoter in *E. coli* MG1655 for sensing lead and zinc. the yjjZ promoter responds monotonically to increasing concentrations of zinc alone and to high concentrations of lead alone. A lead-specific sensor can be implemented by combining this response with the zinc-specific response of zraP using the boolean expression (yjjZ)^(¬zraP). Alternatively, a zinc-specific sensor can be implemented by combining this response with the lead-specific response of ybiI using the boolean expression (yjjZ)^(¬ybiI). As shown in the two panels below, the numbers at the x-axis correspond to the four corresponding bars above the numbers. For example the first 4 bars correspond to the number 1, the second set of 4 bars correspond to the number 2 and so forth.
Figure 33:
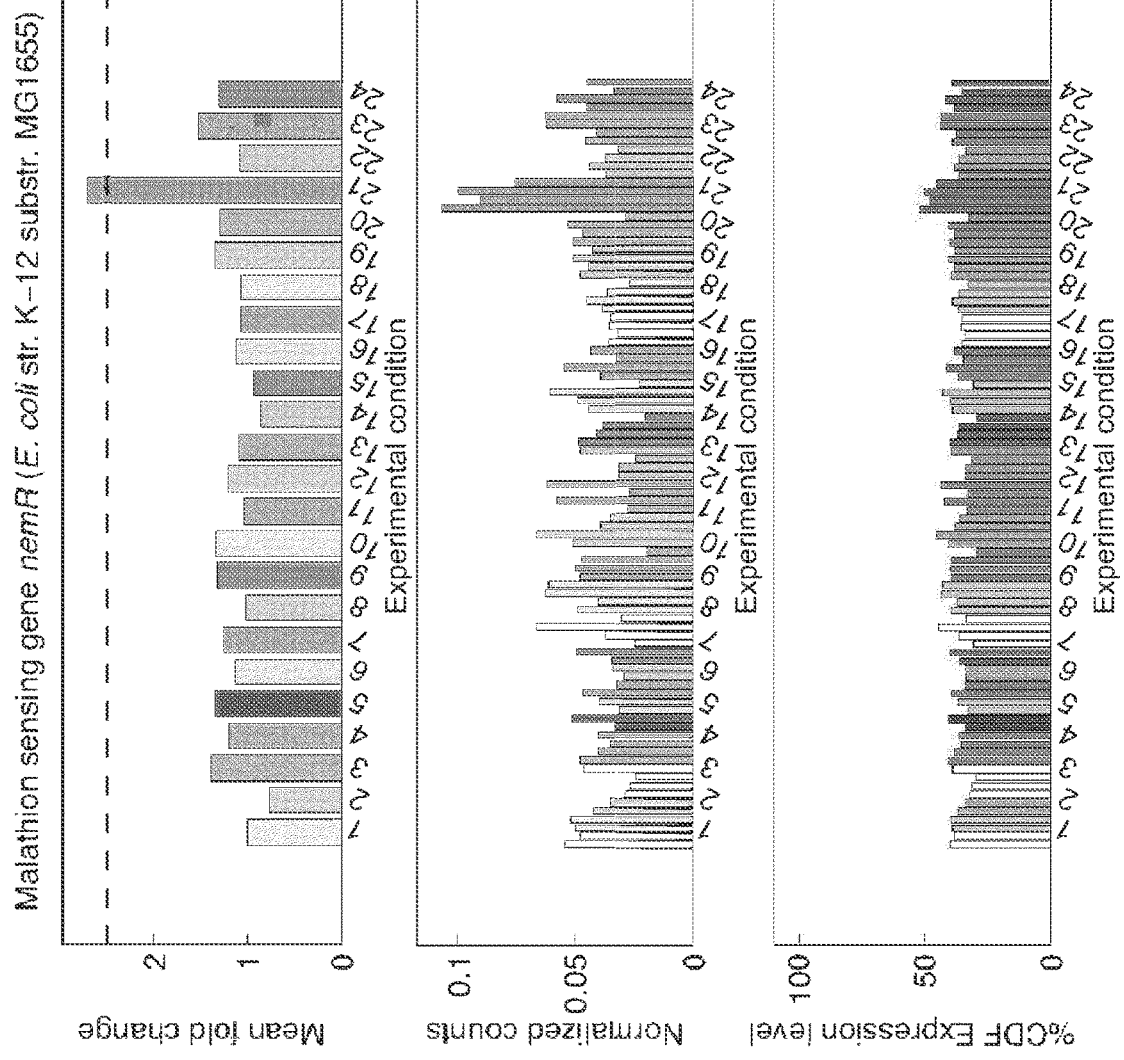
FIG. 33 shows the response of the nemR promoter in *E. coli* MG1655 for specifically sensing malathion. The nemR promoter responds to high concentrations of malathion alone. As shown in the two panels below, the numbers at the x-axis correspond to the four corresponding bars above the numbers. As shown in the two panels below, the numbers at the x-axis correspond to the four corresponding bars above the numbers. For example the first 4 bars correspond to the number 1, the second set of 4 bars correspond to the number 2 and so forth.
Figure 34:
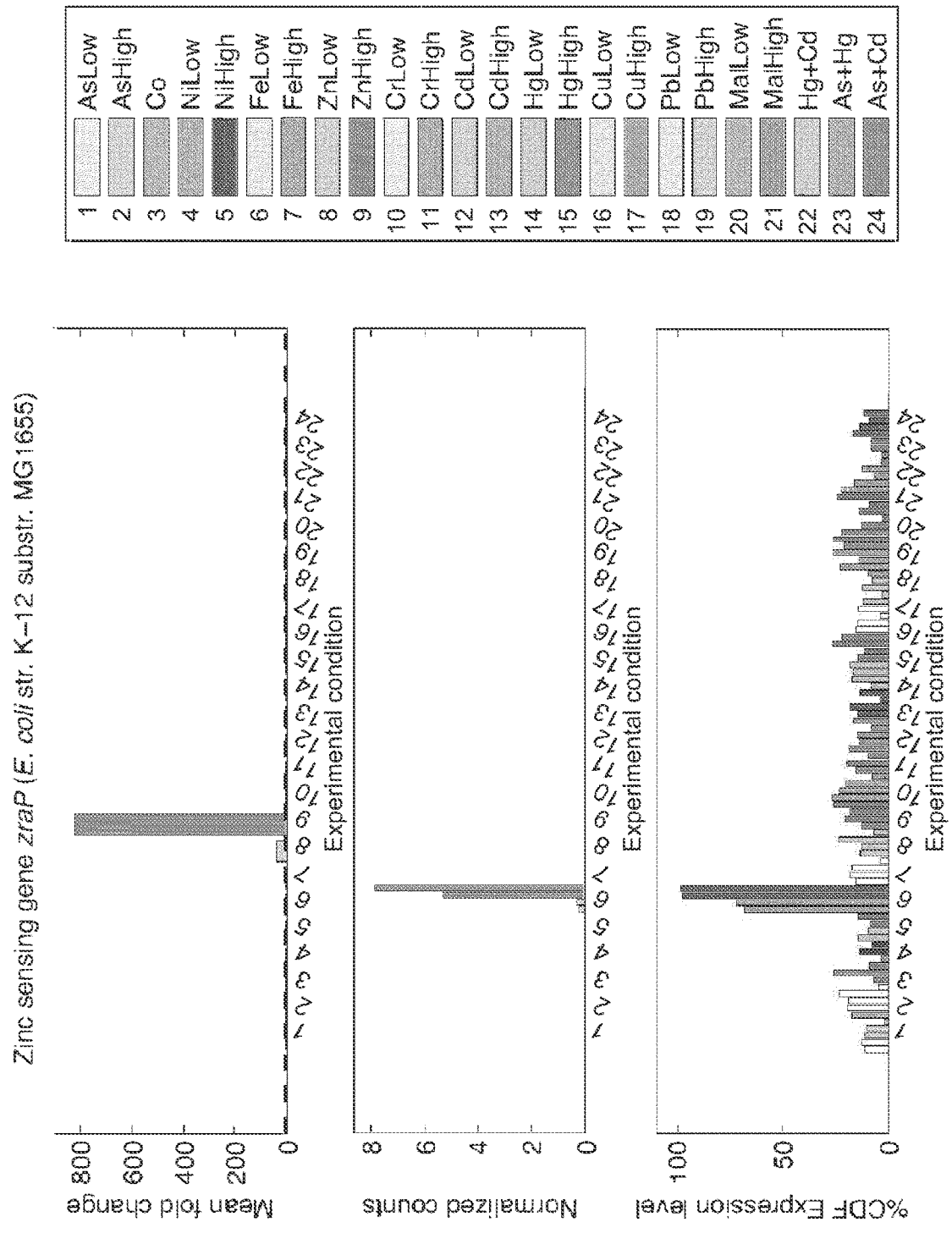
FIG. 34 shows the response of the zraP promoter in *E. coli* MG1655 for specifically sensing zinc. The zraP promoter responds specifically and monotonically to increasing concentrations of zinc alone. As shown in the two panels below, the numbers at the x-axis correspond to the four corresponding bars above the numbers. As shown in the two panels below, the numbers at the x-axis correspond to the four corresponding bars above the numbers. For example the first 4 bars correspond to the number 1, the second set of 4 bars correspond to the number 2 and so forth.
Figure 35:
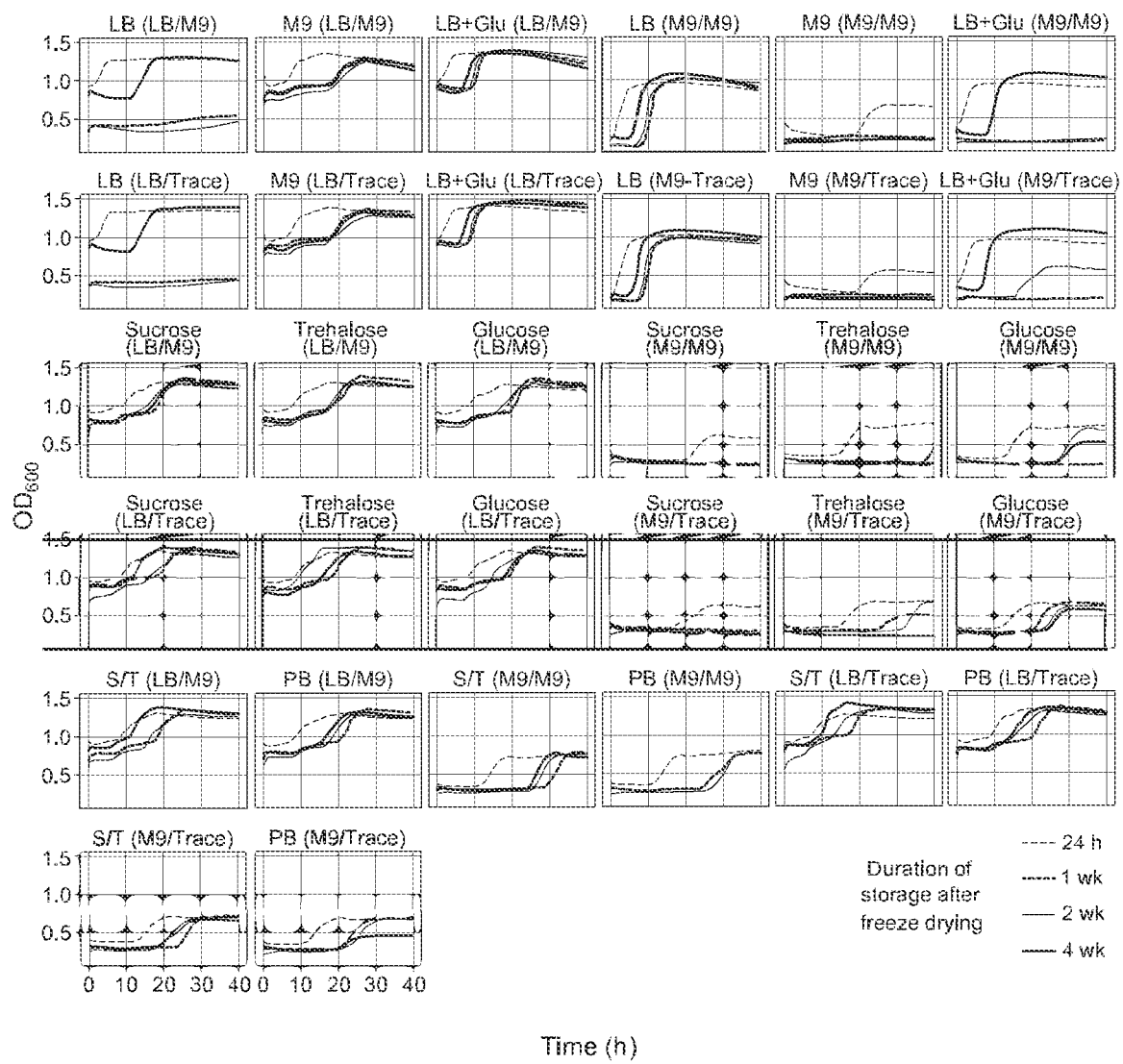
FIG. 35 shows the growth curves for the revival of engineered *E. coli* strains following freeze-drying with various cryoprotectants. Cryoprotectant experiments are annotated as follows: Cryoprotectant (Overnight Growth Medium/Revival Medium). Lyophilized (freeze-dried) cultures were stored for periods of 24 h, 1 wk, 2 wk, and 4 wk before revival in resuspension medium. All media contained the appropriate antibiotic for plasmid maintenance. S/T denotes a cryoprotectant mixture of both sucrose and trehalose. LB and LB+glucose media exhibited the best cryoprotective performance, as measured by lag time to exponential growth phase. Traditional cryoprotectants exhibited slower revival times.
Figure 36A:
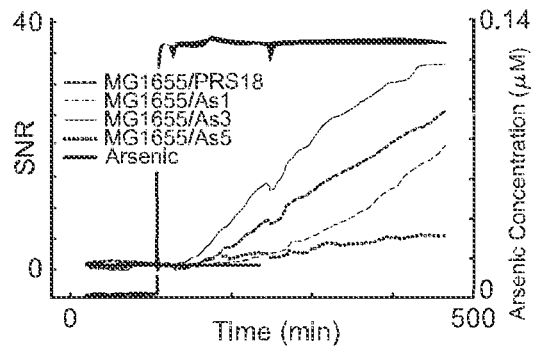
FIG. 36 (FIGS. 36A, 36B, 36C, 36D, 36E, 36F) shows on-chip time-lapse induction responses of promoter constructs identified from the literature, expressed in *E. coli*, and summarized in Table 2. 36A) MG1655/As3, MG1655/pRS18, and MG1655/As1 show high sensitivity to 0.13 µM arsenic. (Note that pRS18, a plasmid generated in our lab for previous work, shares the same promoter as Transcriptic plasmid As7.) 36B) MG1655/Cd1 shows high sensitivity to 0.04 µM cadmium. 36C) LABEC01/Cr5 shows high sensitivity to 5 µM chromium (VI). 36D) MG1655/Cu1 shows high sensitivity to 25 µM copper. 36E) LABEC01/Pb2 shows high sensitivity to 7 µM lead. 36F) MG1655/Hg3 shows high sensitivity to 0.1 µM mercury.
Figure 36B:
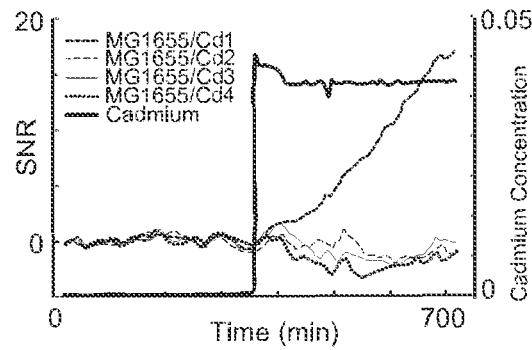
Figure 36C:
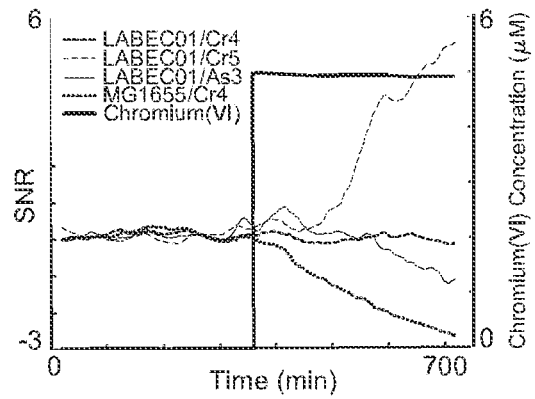
Figure 36D:
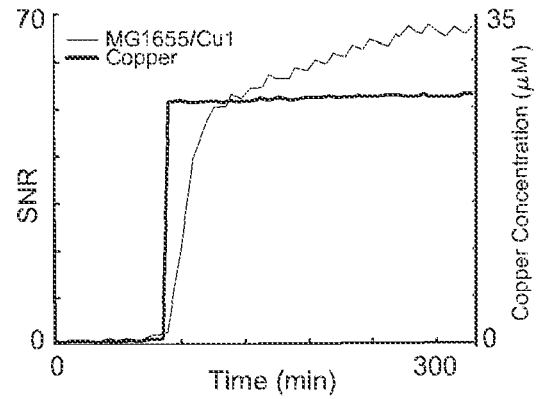
Figure 36E:
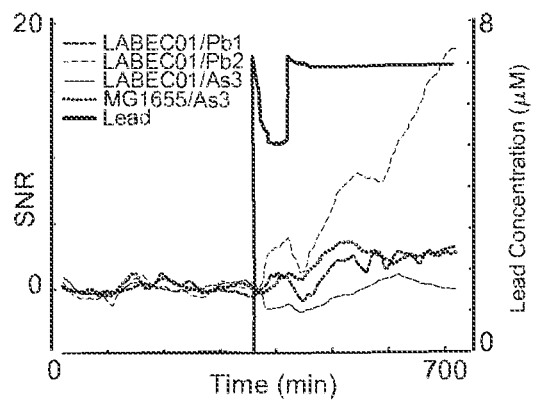
Figure 36F:
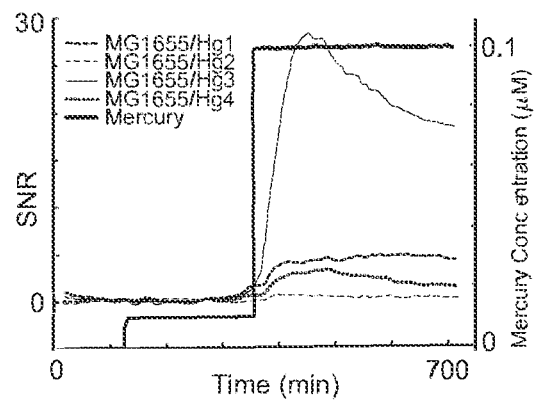
Figure 37:
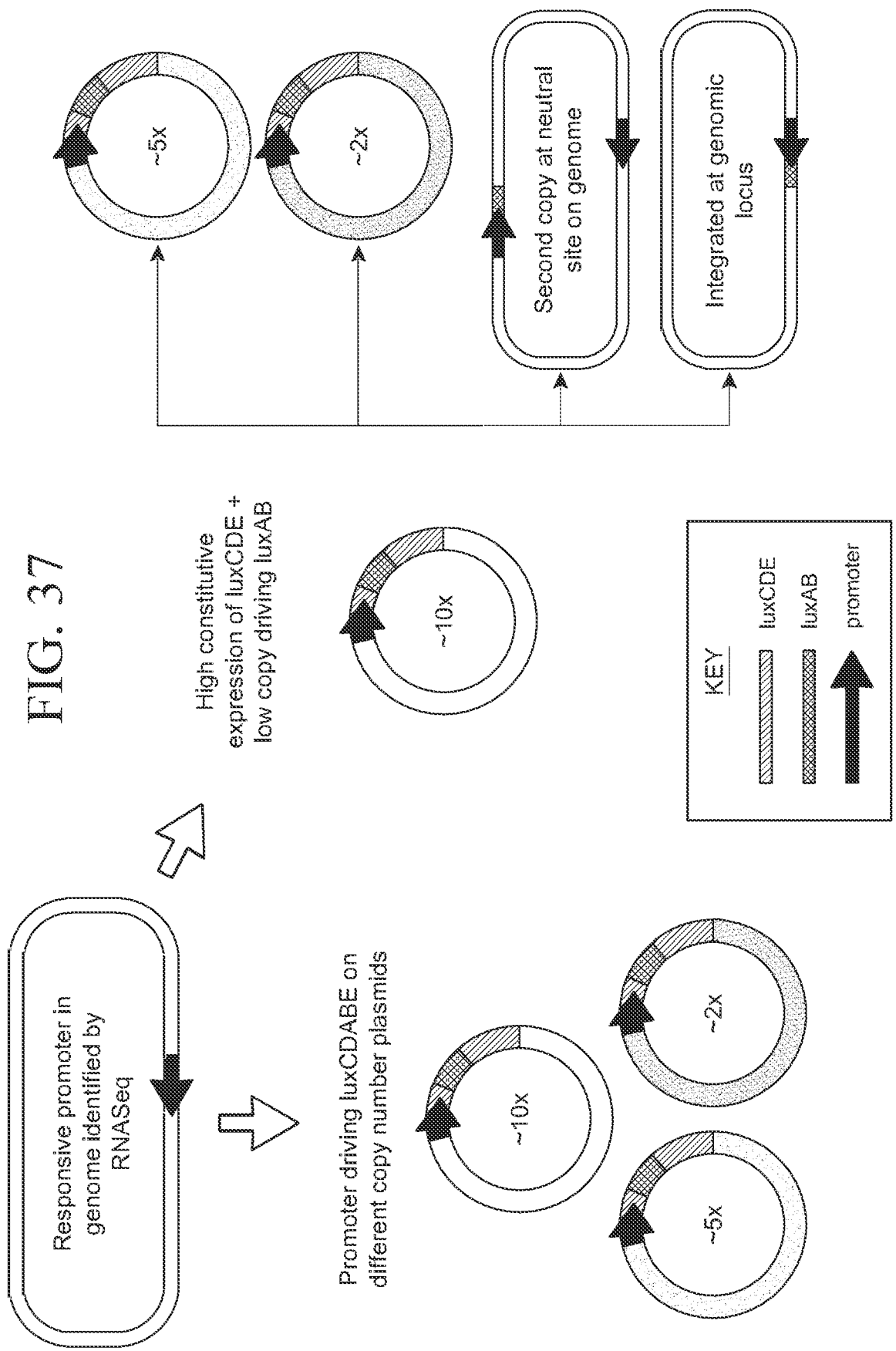
FIG. 37 shows multiple expression systems for promoters identified using RNA-Seq. For proper regulation of synthetic constructs, promoters will be cloned into various copy number plasmids to maintain appropriate ratios with low-copy native regulatory elements. In expression systems using Lux instead of GFP, the operon will be optionally split to remove substrate limitation. The light-producing luxAB element will be optionally integrated either downstream of a second copy of the candidate promoter at a neutral site on the genome or directly downstream of the gene regulated by the candidate promoter.

Fluorescence images are used to train our classifier to be able to detect and discriminate between different toxins. In order to speed up the operation of the classifier we must reduce its computational cost, which is directly linked to the number of images and the number of features in each image. Each image consists of a set of numerical features, each containing the intensity of a pixel in the image. In FIG. 10, we show examples of images captured by sensor prototype. Each image has a resolution of 1280×960 pixels, which means that each pattern is defined by 1, 228, 800 features. This is a large size for a pattern recognition algorithm, especially if it is intended to run in the PandaBoard. Fortunately, the images contain several irrelevant features both near the edges and center of the image (see FIG. 10A), and they are also likely to have a large number of redundant features in neighboring pixels. Therefore, it is extremely useful to apply a feature selection algorithm to find the most informative features and to reduce the computational cost of the classifier. To this end, we implemented a Quadratic Programming Feature Selection (QPFS) algorithm that takes into account both the relevance and redundancy of features and has been shown to be an effective approach for selecting features in images. We generated a dataset formed by 288 images captured with GFP signal in one of the chambers in the presence of Arsenic (FIG. 10B), and we rotated these images at 16 different angles to simulate different responses of the chambers to multiple chemical inputs. The images were compressed by a factor of 16, and images were padded with black pixels in order to create square images after rotation. The resolution of the resulting images was 114× 114, yielding a final dataset formed by 288×16=4, 608 images in a 114×114=12, 996 dimensional space. QPFS was applied to this data using the Pearson's correlation between each pixel as a measure of redundancy and the toxin signature as a measure of relevance. The QPFS assigned a weight to each pixel between 0 and 1, and features with larger weights were considered better variables to use for classifier training. The result of the QPFS algorithm is presented in FIG. 11A, which shows how the feature selection process is able to detect the underlying structure of the images. Additionally, FIGS. 11B-D show the first 100, 200, and 500 features selected by QPFS, respectively. According to these preliminary results, 500 features is enough to recover the discriminative information in the images. This represents a reduction in the dimensionality of the problem by a factor >2, 400 (1, 228, 800/500), which enables the integration of the pattern recognition algorithm in the PandaBoard.

We successfully compiled the software, trained the model, and ran the trained model. The PandaBoard can classify an image in real time in an average of 0.05 seconds. The algorithms were developed using the open MP software and compiled using gnu g++. Both are well established and stable options that run perfectly fine on the PandaBoards. We implemented aggressive compiler optimizations that produce fast native code on the ARMs. The multicore Cortex-A9 processors proved to be extremely fast and sufficient to run all of the algorithms.

Luminescent Reporters.

We have investigated replacing the standard GFP reporter with one based on bacterial luciferase (Lux), and we have demonstrated that an arsenic sensor plasmid modified in this way shows increased sensitivity, likely due to eliminated autofluorescence. In fact, data provided herein shows that a bioluminescent sensor is more sensitive than many analytical methods approved by the EPA for testing arsenic in drinking water, demonstrating the power of our techniques. In FIG. 8, we compare these reporters driven by an arsenic-responsive promoter, where the induction response was measured side-by-side using a Tecan plate reader.

The background noise was significantly lower for the Lux construct, allowing detection of arsenic at a concentration of 0.2 nM; the GFP construct appears to be sensitive to arsenic only above the 5.2 nM level. For comparison, the arsenic concentration used for testing the GFP construct in a microfluidic device was 130 nM, or 0.13 µM. Thus, replacing GFP with Lux promises to greatly increase the sensitivity of the biosensor.

Table 5 shows specificity results for toxin-sensing plasmids identified from the literature and cloned into synthetic constructs expressed in E. coli. Here, strains representing the most sensitive promoters from our microfluidic induction experiments were grown in the wells of a microplate in the presence of on- and off target heavy metals. Each column represents the fluorescence response of a strain to the on-target metal (normalized to "1") and all off-target metals, where "0" represents the unchanged response for the no-toxin control. Although these promoters are generally specific to the on-target toxin, some crosstalk is evident (i.e. Cr5 is sensitive to iron; Hg3 is sensitive to chromium (VI) and zinc; Pb2 is sensitive to several off-target toxins). Fortunately, in cases of significant crosstalk, nonspecific promoter responses can be combinatorially combined with other promoter responses to generate specific multi-promoter responses (see FIG. 2 and Appendix B).

TABLE 5

| | | Strain/On-Target Toxin | | | | | |
|---|---|---|---|---|---|---|---|
| Toxin | Conc (µM) | As3/ Arsenic | Cd1/ Cadmium | Cr5/ Chromium(VI) | Cu1/ Copper | Pb2/ Lead | Hg3/ Mercury |
| Arsenic | 1.3 | 1.00 | −0.18 | 0.24 | −0.05 | 0.33 | 0.25 |
| Cadmium | 0.44 | −0.13 | 1.00 | −0.02 | −0.08 | 0.46 | −0.26 |
| Chromium(VI) | 2 | −0.22 | 0.62 | 1.00 | −0.06 | 1.69 | −0.96 |
| Copper | 20 | | −0.09 | −0.08 | 1.00 | −0.17 | 0.16 |
| Lead | 1 | −0.05 | 0.06 | 0.01 | −0.05 | 1.00 | 0.12 |
| Mercury | 0.1 | −0.18 | −0.09 | 0.58 | −0.05 | 1.44 | 1.00 |
| Cobalt | 20 | 0.30 | 0.67 | −0.11 | −0.01 | 0.80 | |
| Iron | 500 | −0.06 | −0.31 | 0.86 | 0.17 | 0.96 | −0.38 |
| Nickel | 1.7 | −0.08 | −0.08 | −0.35 | −0.05 | 0.16 | |
| Zinc | 7.6 | −0.04 | −0.09 | 0.35 | −0.08 | 1.06 | 0.78 |

Table 6 shows differentially expressed (DE) genes at a false discovery rate below 1% for each condition of interest.

TABLE 6

| Condition | Number DE |
|---|---|
| Arsenic low | 3 |
| Cachnium low | 132 |
| Cliromium(VI) low | 270 |
| Cobalt low | 609 |
| Copper low | 110 |
| Iron low | 32 |
| Lead low | 99 |
| Malathion low | 370 |
| Mercury low | 165 |
| Nickel low | 43 |
| Zinc low | 24 |
| Arsenic high | 14 |
| Cadmium high | 38 |
| chromium(VI) high | 377 |
| Cobalt high | 1274 |
| Copper high | 77 |

TABLE 6-continued

| Condition | Number DE |
|---|---|
| Iron high | 70 |
| Lead high | 489 |
| Malathion high | 41 |
| Mercury high | 218 |
| Nickel high | 95 |
| Zinc high | 596 |

Alternative 2 (Task A

Milestone 1: Create an Initial Library of Transcription Based Sensors.

A major goal is to identify a combination of cellular signals that will indicate the detection of specific targeted chemical agents. In order to accomplish this goal, an initial library of transcription based sensors is created and then the library of the transcription based sensors is expanded using Next Generation Sequencing (NGS) techniques. What is deliverable is a comprehensive list of list of candidate genes in E. coli that respond to target compounds. We obviated the need to intermediately test the response of the expression constructs in batch culture using a plate reader in Milestone 1.3 by directly validating within custom microfluidic devices in Milestone 1.4.

Create an Initial Library of Transcription Based Sensors.

A list of toxin responsive promoters based on literature research was constructed in milestone 1.1. Promoters were assembled from multiple bacterial species along with necessary regulatory genes into synthetic expression constructs. The need to intermediately test the response of the expression constructs in batch culture using a plate reader was obviated by directly validating within custom microfluidic devices.

Milestone 1.1. Identify 3 Promoters for Each Toxin of Interest Based on Literature Searches:

3 or more promoters from literature for each toxin, when available, were identified. The exceptions are copper (2), lead (1), and malathion (0), for which less than three promoters are known.

Bacteria that grow in environments with high toxin levels, occurring either naturally or as a result of pollution, have evolved pathways to mitigate their effects on cellular metabolism. These resistance pathways are often activated by a specific transcription factor that is sensitive to the intracellular concentration of the toxin. The scientific literature was searched to identify well-characterized transcription factor/promoter pairs. Where divergent pathways responding to the same toxin have been characterized, at least one representative pathway from each major evolutionary clade was chosen. Identified candidate regulatory mechanisms for specific toxins, including the native organism and naturally-occurring DNA construct, are provided below.

Arsenic:

The arsR family of transcription factors contains many arsenic-sensing members, including one found on the E. coli genome and another encoded on the E. coli R773 plasmid. These two candidates were selected for synthesis because they are native to E. coli and have been used previously to construct a biosensor. We also synthesized an arsR construct from S. aureus.

Cadmium:

Cadmium-responsive transcription factors have been identified from both the arsR family and the merR family of transcriptional regulators. A representative member from each group: cadC from S. aureus and cadR from P. putida was selected.

Chromium (VI):

The chromate-responsive element from O. tritici was selected, which has been characterized and used to construct a highly specific biosensor, a related system from C. metallidurans, and an unrelated chromate-responsive transcription factor from the genome of B. subtilis NCIB 3610.

Copper: Two well-studied functionally-unique copper-responsive elements native to E. coli were selected. CueR functions as an activator/repressor of the merR family, while cusS/R is a two-component sensor system including a histidine kinase, which may aid in signal amplification.

Lead:

The only lead-specific system identified in the literature is pbrR, found on a mega plasmid in C. metallidurans.

Mercury:

Mercury-inducible merR systems have previously been used to construct biosensors with low detection limits, where merR functions as a repressor in the absence of mercury and an activator in the presence of mercury. The same strategy for our biosensor plasmids was adapted, selecting three well-studied members of the merR family. Another more evolutionarily divergent merR protein from S. lividans was not pursued because it was shown to function only as a repressor.

Ammonium:

Sensing ammonium requires culturing cells in a background nitrogen source that is less-preferred than ammonium. While nitrate is the most suitable background nitrogen source for this purpose due to its long-term stability in solution, E. coli MG1655 is unable to assimilate it under aerobic conditions. Therefore, it was decided to sense ammonium using the bacterium B. subtilis NCIB 3610, which can utilize both nitrate and ammonium as a nitrogen source. The native ammonium-sensitive promoters $p_{nasA}$ and $p_{nasB}$ and the synthetic promoter $n_{spo1-tnrA}$ were incorporated into plasmids for integration into a neutral site on the B. subtilis NCIB 3610 genome, where they act as a second copy of the promoter to drive GFP expression in the presence of ammonium.

For completeness, in Table 1 the full list of identified candidate constructs is presented. Sensor plasmids containing the most promising regulatory candidates (shown in boldface in Table 1) for arsenic, cadmium, chromium (VI), copper, lead, and mercury were synthesized by the cloning vendor and ported into E. coli to drive GFP expression in the presence of the toxin. Synthesized sensing constructs for ammonium were integrated into a modified version of the B. subtilis NCIB 3610 host strain, where a motility gene (hag) and a biofilm pathway gene (epsH) were knocked out for improved growth within microfluidic devices.

In some embodiments, a method of making a nucleic acid for detection for the presence or levels of an analyte in an aqueous sample is provided. The method can comprise attaching a promoter to a reporter protein, wherein the promoter is specifically turned on by ammonia, arsenic, cadmium, chromium (VI), cobalt, copper, lead, malathion, mercury, and zinc. In some embodiments, the reporter protein is a fluorescent protein, such as GFP.

Milestone 1.2: Clone the Promoters into an Expression Plasmid Driving the Production of GFP:

All promoters identified from the literature were cloned into a standardized plasmid expression system. Two standardized plasmid backbones for testing the candidate toxin-responsive elements identified in the literature in E. coli were synthesized. Both vectors include the p15A medium-copy origin of replication, a spectinomycin resistance cassette for selection of positive transformants, and a promoter-less GFP insulated by flanking terminators. One of the vectors replaces the native ribosome binding site (RBS) in front of GFP with a version known to produce high levels of expression in *E. coli* MG1655.

Both synthesis of the plasmid backbones and insertion of the sequences for candidate toxin-responsive elements into each version were carried out by Transcriptic. The sequence of interest was inserted such that the transcriptional regulator remains under the control of its native promoter, with the inducible promoter driving expression of GFP. Because all DNA constructs were completely synthesized, we were able to codon optimize sequences for improved heterologous expression in *E. coli* MG1655.

Those skilled in the art will appreciate that gene expression levels are dependent on many factors, such as promoter sequences and regulatory elements. Another factor for maximal protein selection is adaptation of codons of the transcript gene to the typical codon usage of a host. As noted for most bacteria, small subsets of codons are recognized by tRNA species leading to translational selection, which can be an important limit on protein expression. In this aspect, many synthetic genes can be designed to increase their protein expression level. The design process of codon optimization can be used to alter rare codons to codons known to increase maximum protein expression efficiency. In some alternatives, codon selection is described, wherein codon selection is performed by using algorithms that are known to those skilled in the art to create synthetic genetic transcripts optimized for higher levels of transcription and protein yield. Programs containing algorithms for codon optimization are known to those skilled in the art. Programs can include, for example, OptimumGene™, GeneGPS® algorithms, etc. Additionally synthetic codon optimized sequences can be obtained commercially for example from Integrated DNA Technologies and other commercially available DNA sequencing services.

Milestone 1.3: Validate the Response of the Promoters Using Traditional Batch Experiments (Note Validation Indicates a Ratio of Induced Fluorescence Signal to Uninduced of at Least 3:1):

Instead of performing preliminary testing in batch, we validated the response of the promoters directly in our microfluidic devices.

It was expected that the development of the microfluidic devices would lag the construction of our toxin-sensing plasmids, thereby requiring that initial induction experiments be performed using a fluorescent plate reader. However, rapid development of the microfluidics allowed running of initial induction experiments of the sensing strains on chip, and, upon successfully inducing sensing strains on-chip, as such there was no need to replicate experiments in batch culture for several reasons. First, since cellular measurements are highly dependent upon growth phase, and batch culture cannot provide a constant growth environment, it is expected to have more reproducible results from the microfluidic chemostats. Second, inducing on-chip can allow one to dynamically control the inducer concentration and thereby more efficiently scan the induction range for each sensing strain. Finally, the deployable biosensor device will incorporate microscopic culturing and optical imaging; therefore, microscope imaging on-chip is more relevant than reading fluorescence values within the batch culture wells of a plate reader.

Milestone 1.4: Validate the Response of the Promoters Using Microfluidic Devices. Quantitatively Measure GFP Signal in Response to Various Relevant Levels of Toxins of Interest:

The response of the promoters in microfluidic devices for all toxins of interest have been validated.

Figure 45:
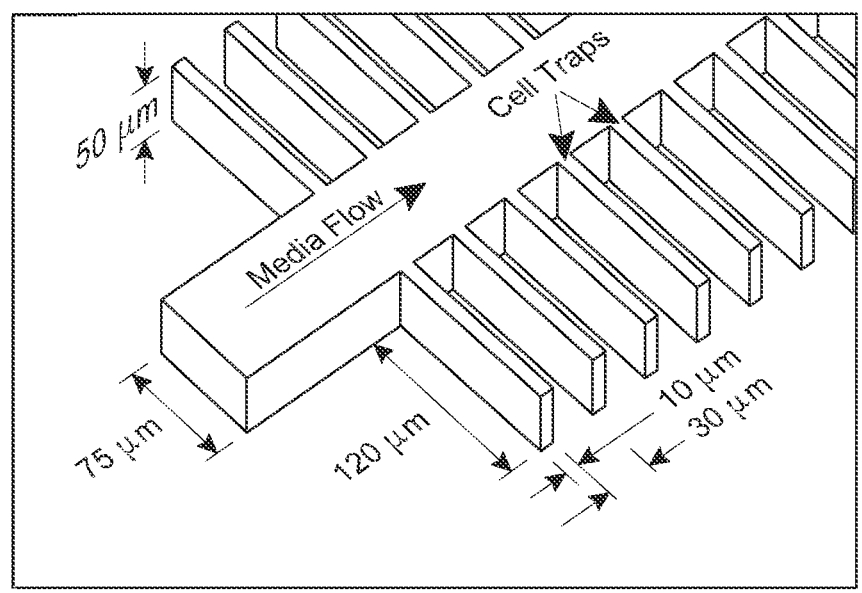
FIG. 45 shows the functional unit of the microfluidic "gill chip." Medium is delivered via the main channel, and cells are cultured in the branched channels.

A microfluidic device to culture and induce each sensing strain with varying levels of toxins of interest was developed. Termed the "gill chip," this device is a variation on the "biopixel" device previously developed in the lab. Structurally, this microfluidic device consists of a polydimethylsiloxane (PDMS) elastomer block with recessed channels that are sealed upon bonding to a glass cover slip. Fluidically, the core functional unit of the device is a microfluidic channel with long, narrow branches along the sides that serve to retain cultures of cells (FIG. 45). The precise geometry of the "cell trap" creates high-resistance, low-flow regions where cells grow in a defined area with continuous perfusion of fresh medium. Previous studies of synthetic gene circuits required microfluidic devices which grow cells in a monolayer in order to perform single-cell tracking. The gill chip uses a similar side trap geometry, but the trap width is decreased from 100 mm to 10 mm, and the trap height is increased from 1.65 mm to 50 mm. By using thin, tall traps, the optical signal is increased while maintaining the ability to selectively grow cells in a low-flow trap region. The overall device consists of an array of trapping units connected in parallel, each supporting the long-term culturing of a cell strain. The central channels of the trapping regions are fed by a single switchable medium source.

Figure 46:
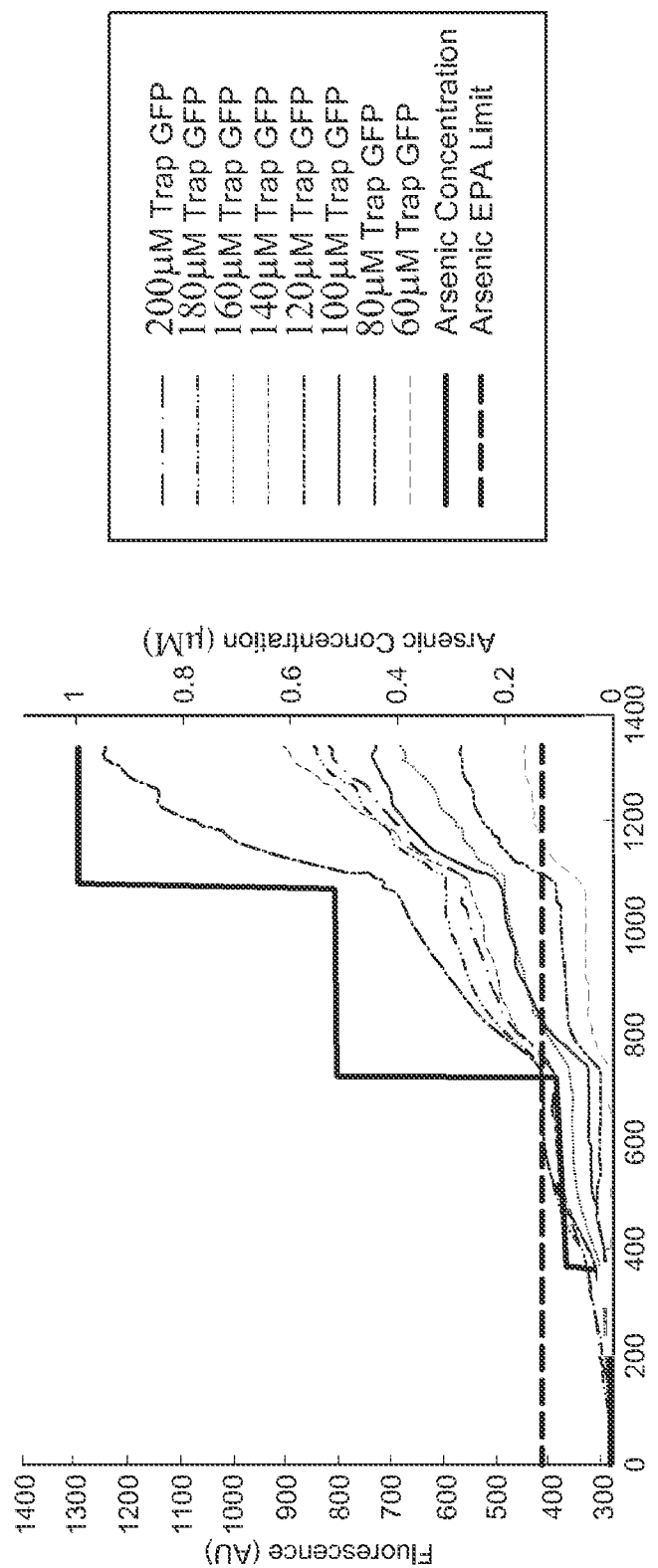
FIG. 46 shows the optimization of cell trap length based on GFP expression level. 120-mm-long traps provide the greatest fluorescent signal for all arsenic concentrations.

The length of the cell trapping channels of the gill chip was optimized to maximize fluorescent signal while ensuring adequate medium delivery for healthy cell growth. Medium delivery to the packed cells in the trapping channels is limited by diffusion, and it was observed that excessively long channels slowed cell growth and GFP production. The optimal trap length was determined by fabricating multiple versions in parallel and measuring expressed fluorescence from a preliminary arsenic-sensing strain. In FIG. 46, it was seen that a 120 μm channel length produces the largest fluorescent signal for arsenic levels ranging from below 1× to 10× the EPA limit. Therefore, our trap length will be standardized in future experiments at 120 μm. It was confirmed that representative gram-negative (*E. coli* MG1655, *S. Typhimurium*) and gram-positive (*B. subtilis* NCIB 3610) bacterial strains as well as yeast (*S. cerevisiae* MFSC120) form stable cultures in the gill chip with 120-μm-long trapping channels. Initial experiments continuously growing *E. coli* MG1655 in LB medium in the gill chip demonstrated a device lifetime of 27 days before flow stopped due to channel clogging. This lifetime was later extended to 50 days by slowing the cellular growth rate by replacing LB medium with M9 minimal medium.

While waiting for Transcriptic to synthesize the initial library of toxin-sensitive plasmids based on our literature search, the microfluidic device was used to measure the response of two toxin-sensing promoters in *E. coli* MG1655 generated in the lab for previous work.

Figure 47C:
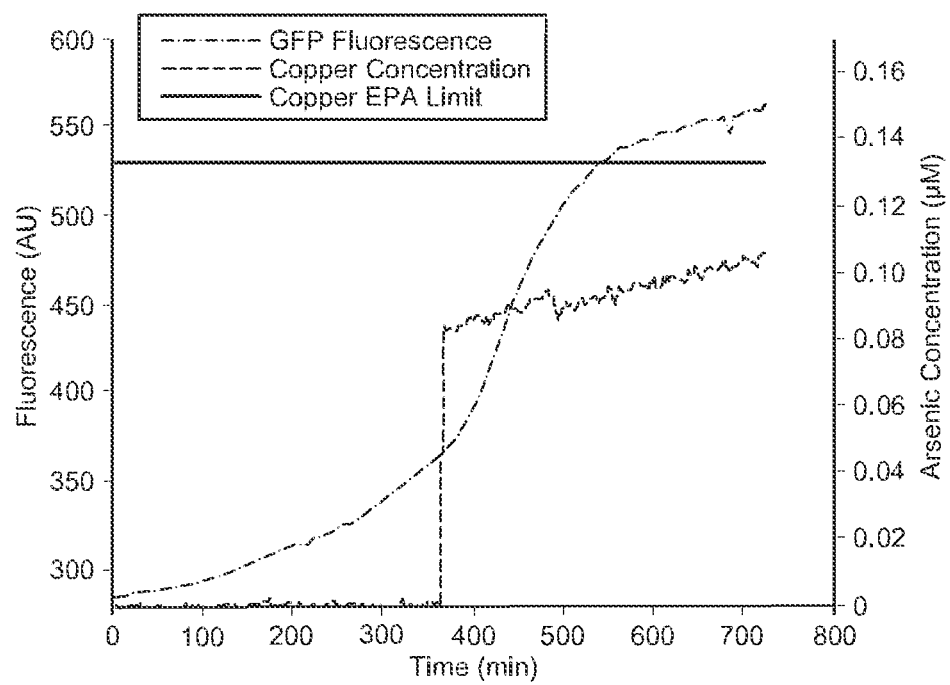
FIGS. 47 (47A, 47B, 47C) shows the response of arsenic-sensing plasmid pRS18 (from previous work) to step-induction with arsenic. Images before (47A) and after (47B) induction with 0.1 µM arsenic. 47C) Measured GFP expression over time for induction with 0.1 µM arsenic.

Induction of pRS18, an arsenic-sensing plasmid, was first tested in the microfluidic device. A recombinant strain of *E. coli* MG1655 containing pRS18 was vacuum loaded into the microfluidic device, grown to confluence, and step-induced with sodium ortho-arsenite (Na3AsO3) in M9 minimal medium supplemented with 0.4% glucose. Images were collected using a Nikon Ti microscope with 4× objective magnification. Step induction was executed using the gravity-driven "Dial-A Wave" automated flow control system to mix two medium sources in a defined ratio. The cells were sequentially exposed to arsenic concentrations of 0 µM, 0.1 µM, 0.5 µM, and 1 µM in 6-h windows, allowing time for the cells to respond to each concentration increase. The data shows a significant detection of 0.1 µM arsenic, which is below the EPA limit of 0.13 µM. FIG. 47 shows the trapped cells prior to (panel a) and following (panel b) 6 h of induction at 0.1 µM arsenic. We believe that the rise in GFP expression prior to the induction step is due to a small leak of inducer into the medium stream. Average fluorescence within the trapping regions of the images as well as arsenic concentration is plotted over time in FIG. 47C.

Figure 48:
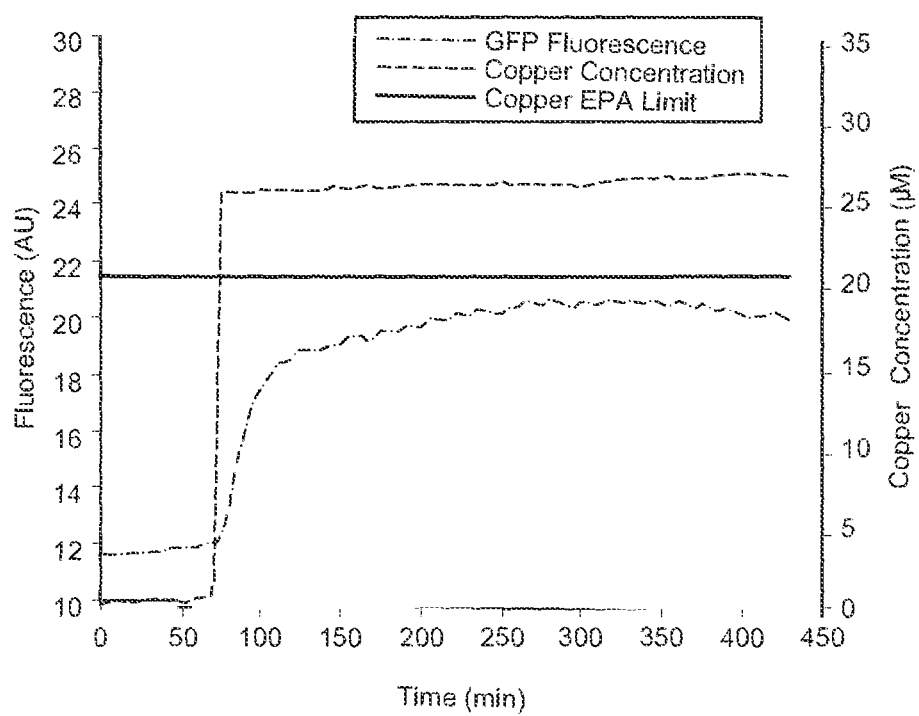
FIG. 48 shows the response of copper-sensing plasmid pCueCopA (from previous work) to step-induction with copper. Measured GFP expression over time for induction with 25 µM copper demonstrates that we can detect copper concentrations near the EPA limit

Second, induction of pCue-CopA, a copper-sensing plasmid, was tested in the microfluidic device. A recombinant strain of *E. coli* MG1655 containing pCueCopA was vacuum-loaded into a microfluidic device, grown to confluence, and step-induced with copper sulfate (CuSO4) in LB medium. Images were collected using an Etaluma LumaScope microscope with 20× objective magnification. Step induction was again performed using the "Dial-A-Wave" automated flow control system. The cells were sequentially exposed to copper concentrations of 0 µM, 25 µM, 52 µM, 77 µM, and 99 µM in 6-h windows. FIG. 48 shows a significant detection of 25 µM copper, which is slightly above the EPA limit of 20.5 µM.

Figure 49:
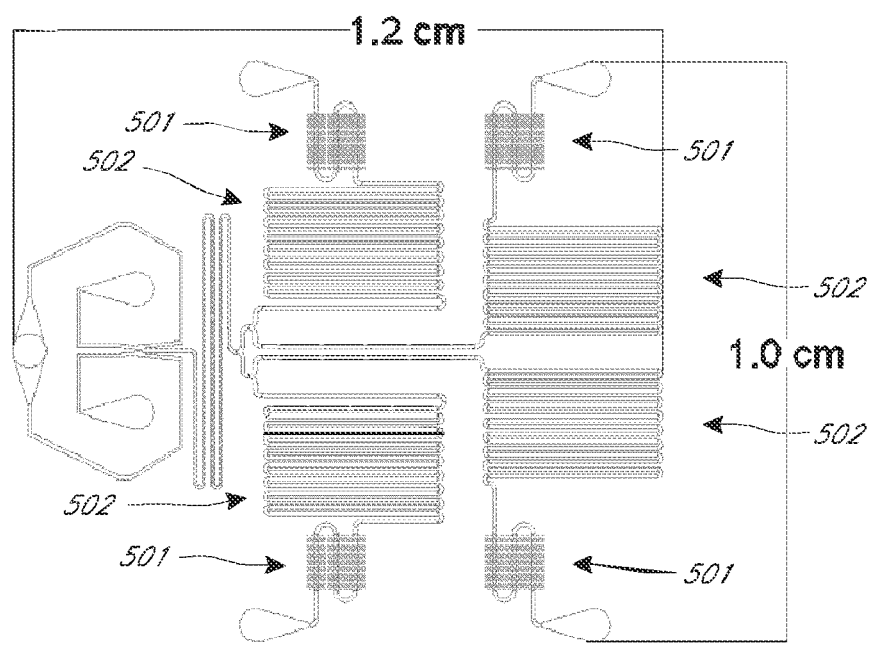
FIG. 49 shows the gill chip v9-C for parallelizing the on chip testing of toxin-responsive promoters. Four cell trapping regions (501) are vacuum loaded from four downstream fluidic ports. Long, serpentine channels upstream of the trapping regions (502) serve as fluidic "buffer zones" to prevent the cross-contamination of strains. The three-port "Dial-A-Wave" module at the left serves to mix two medium streams to precisely and dynamically define the toxin concentration in the cell trapping regions.

A literature-based library of synthesized sensor plasmids from Transcriptic was received and transformed into both *E. coli* MG1655 and *E. coli* LABEC01 (See Detailed Methods for strain details) for on-chip testing. To increase the throughput of the microfluidic experiments, a version of the gill chip with four independently loadable cell growth areas for culturing four sensing strains in parallel was developed (see FIG. 49). These growth areas are fed from the output of an on-chip "Dial-A-Wave" system to dynamically control the local toxin concentration.

For on-chip induction experiments, strains were loaded into the device and grown in M9 minimal medium with 0.4% glucose and 50 µg/ml spectinomycin (for plasmid maintenance) for 2 days in the absence of toxin. Cells were imaged under 4× brightfield and GFP fluorescence filters on an Olympus IX-81 microscope every 2 min for 6 h under these non-inducing conditions to generate a fluorescence baseline. The toxin was then introduced to induce GFP expression and the cells were imaged every 2 min for 6 h.

To determine the response to toxin induction, the raw fluorescence images before and after induction were compared. The image stacks were analyzed using a custom ImageJ script to measure the average GFP signal over time for each cell trap. Any linear trend in the uninduced fluorescence data due to cell growth was subtracted from the data. In this manner, the dynamic signal-to-noise ratio (SNR) was calculated as: (current fluorescence−mean uninduced fluorescence)/(standard deviation of uninduced fluorescence).

This microfluidic platform was then used to measure the response of several toxin responsive promoter constructs identified from the literature and synthesized by Transcriptic. Table 2 summarizes the results of these experiments, listing the most sensitive promoter constructs exposed to each toxin and the calculated SNR values after 6 h of induction. Note that SNR values greater than ≈2 indicate a significant response.

The on-chip time-lapse induction response of each promoter construct in this table can be seen in FIG. 36. In each figure panel, the moment of toxin introduction is represented as a step in the red trace. While some promoter constructs exhibit a sensitive response by highly expressing GFP immediately following induction, others do not. Note that the arsenic sensor plasmid As3 was used as a negative control for experiments with non-arsenic-sensing strains, and it showed no induction in the presence of other heavy metals.

To investigate the specificity of the most sensitive promoter construct for each toxin identified from the literature, cloned into synthetic constructs expressed in *E. coli*, and measured on-chip (see Table 2), these strains were grown in the wells of a microplate in the presence of on- and off-target heavy metals. Although the ability to sense cobalt, iron, nickel, and zinc is of secondary importance, these heavy metals were included as potential off-target inducers because they may be present in the natural water supply under test. Each column of Table 5 shows the fluorescence response of a strain to the on-target metal (normalized to "1") and all off-target metals, where "0" represents the unchanged response for the no toxin control. Although these promoters are generally specific to the on-target toxin, some crosstalk is evident. Fortunately, in cases of significant crosstalk (e.g. Pb2 lead sensing strain), nonspecific promoter responses can be combinatorially combined with other promoter responses to generate specific multi-promoter responses (see FIG. 1 and Appendix B). This combinatorial logic was implemented in algorithms. Additionally, the literature-identified promoters were supplemented with highly specific promoters via RNA-Seq analysis (e.g. ybiI lead responsive promoter).

Milestone 2: Massively Expand the Library of Transcription Based Sensors Using Next Generation Sequencing (NGS) Techniques.

The proposed work was expanded by exposing multiple strains of bacteria (in addition to *E. coli*) to relevant levels of all toxins and extracting RNA (Milestone 2.1). To ensure that the biosensor will have high selectivity for the toxins of interest, the sensing bacteria were exposed to multiple toxins at once and RNA was extracted (Milestone 2.2). The need for testing at multiple temperatures was obviated by ensuring tight temperature control in our prototype enclosure as described heron (Milestone 2.3). The microfluidic devices were optimized to achieve growth rates similar to a batch culture as described herein (Milestone 2.4). Isolated RNA was prepared and sequence data was generated as described herein (Milestone 2.5). The sequencing data for all toxins and discovered numerous differentially expressed genes as described in the embodiments herein (Milestone 2.6).

Milestone 2.1: Expose Target Cells to Toxins of Interest Over Four Orders of Magnitude of Concentration and Extract RNA:

Three strains of bacteria were exposed to relevant levels of all toxins and extracted RNA. The toxin exposure protocol involves first growing a culture of bacterial cells to mid-log phase (OD≤0.2). Second, it was diluted with fresh media, then the toxin of interest was add, and it was cultured at 37° C. for 3 h, ensuring that the cells do not exit exponential growth phase before harvesting (OD_0.25). Finally, cellular RNA was stabilized using Qiagen RNA Protect reagent, the cells were centrifuged, and the pellet was frozen at −80° C. To investigate the cellular RNA response to toxin insult, we exposed *E. coli* MG1655, *E. coli* LABEC01, and *B. subtilis* 168 cells to the toxins and concentrations shown in Table 7 and extracted RNA.

TABLE 7

Concentrations used for single-toxin exposures of bacterial strains to investigate the cellular RNA response for sensitivity. Most water toxins to be sensed by our device (boldfaced) are identified by the EPA as being of primary (P) importance. Sensing is expected to occur in the presence of interfering substances of secondary (S) importance (not boldfaced)

| Toxin | P/S | Exposure Conc. (µM) | | |
|---|---|---|---|---|
| | | E. coli MG1655 | E. coli LA BEC01 | B. Subtilis 168 |
| Ammonium | n/a | | | 71.4, 714 |
| Arsenic | P | 0.25, 1 | 0.1, 1 | |
| Cadmium | P | 0.4, 1.2 | 0.04, 0.4 | |
| Chromium(VI) | P | 0.2, 2 | 0.2, 2 | |
| Cobalt | S | 20, 200 | | |
| Copper | P | 0.2, 2, 20 | 0.2, 2 | |
| Iron | S | 5.4, 54 | | |
| Lead | P | 0.1, 3 | 0.1, 3 | |
| Malathion | n/a | 21.9, 219 | 21.9, 219 | |
| Mercury | P | 0.01, 0.1 | 0.01, 0.1 | |
| Nickel | n/a | 0.77, 7.7 | | |
| Zinc | S | 76, 760 | | |

Figures 50A, 50B:
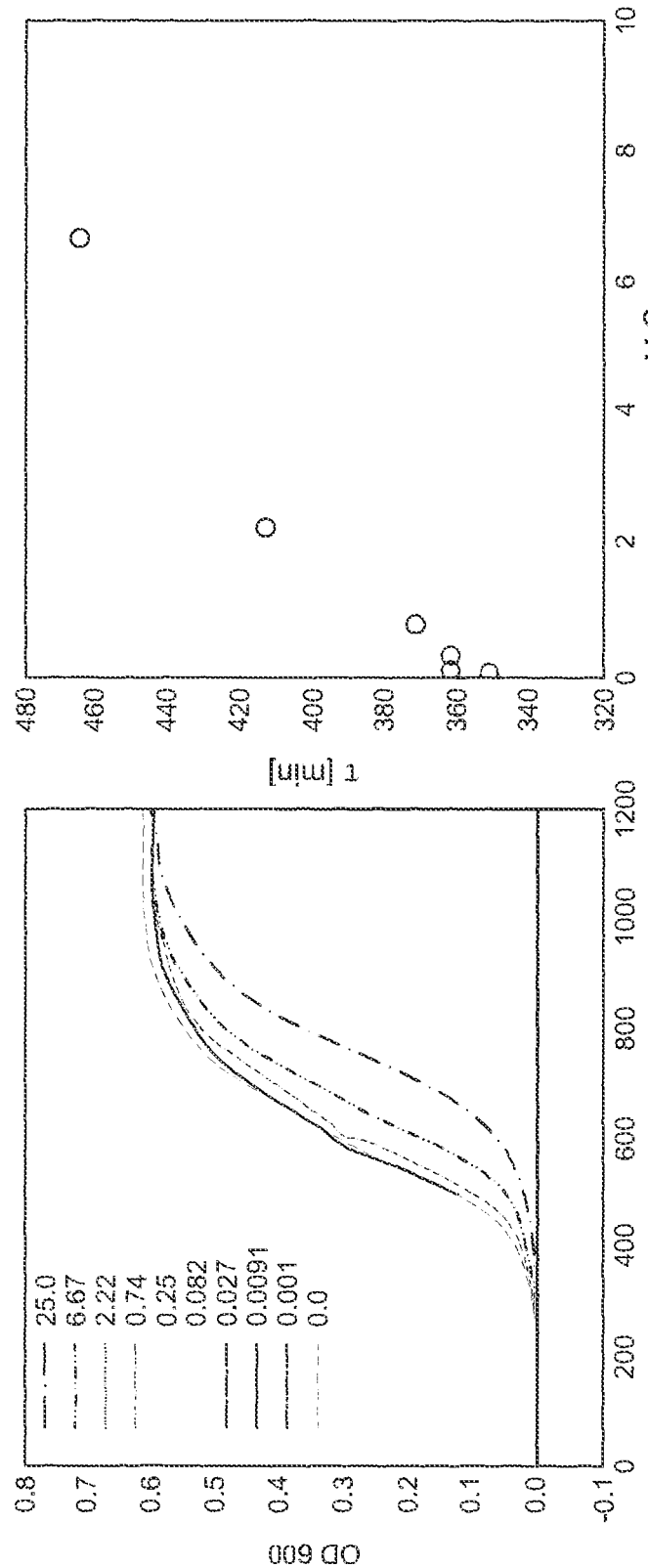
FIGS. 50 (50A, 50B, 50C and 50D) shows batch growth rate data for *E. coli* MG1655 cells exposed to 50B) copper, 50C) mercury, and 50D) chromium (VI). Panel 50B) shows the approximately linear scaling of lag prior to exponential growth phase with copper concentration.
Figures 50C, 50D:
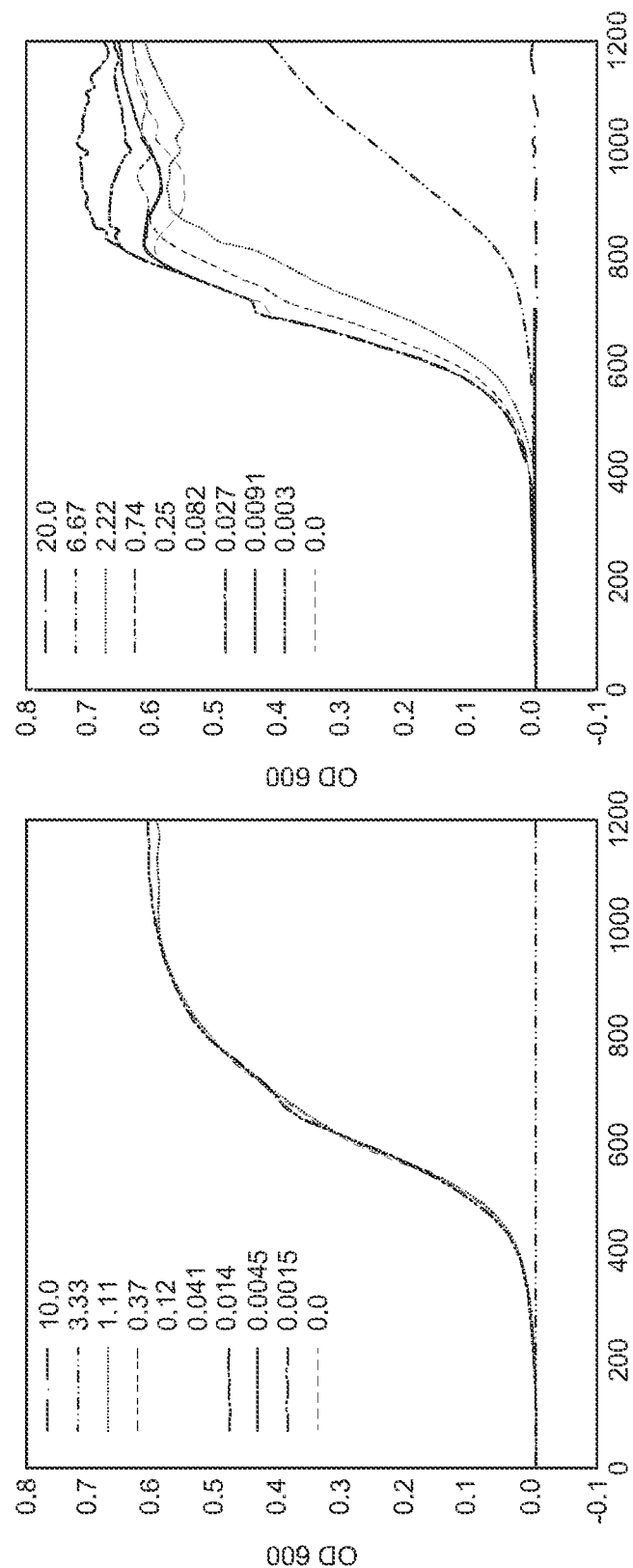

In determining the toxin concentrations for exposure, EPA limit was explored. A growth curve data for *E. coli* MG1655 cells exposed to each toxin at levels around the EPA limit was generated (FIG. 50) and, combined with our induction data, found that the concentration range of interest between the detection limit and cell death is generally less than 4 orders of magnitude. Surprisingly, toxin levels in this range tend not to slow down growth rate but instead delay the onset of the exponential growth phase, as illustrated by copper exposure in FIG. 50A. FIG. 50B shows that the dependence of growth phase lag on copper concentration is approximately linear. If cells exposed to a toxin at the EPA limit did not exhibit this growth phase lag (see growth rates for mercury exposure in FIG. 50C), it was assumed that they were not at risk of death and we probed additional toxin concentrations that were higher. If cells exposed to a toxin at the EPA limit exhibited this growth phase lag (see growth rates for chromium (VI) exposure in FIG. 50D), it would be assumed that they were at risk of death and we probed additional toxin concentrations that were lower. The general strategy was to examine the cellular RNA response at toxin levels where the cells are responding specifically to the presence of the toxin without triggering a universal (and unspecific) cellular stress response.

Milestone 2.2: Expose Target Cells to Multiple Toxins at Once and Extract RNA to Determine Selectivity Sensor Response and Use Computational Algorithms to Determine a Highly Accurate Relationship Between Cellular Signals and Sensor Response:

Cells were exposed to multiple toxins at once and we determined that the promoters we identified respond as expected, even in the presence of an additional toxin.

Six RNA-Seq experiments were performed with As+Cd, As+Hg, and Cd+Hg in *E. coli* MG1655 and LABEC01 to investigate the specificity of the expression responses. Concentrations used for each multiple-toxin exposure are shown in Table 8.

TABLE 8

Concentrations used for multiple-toxin exposures of *E. coli* strains to investigate the specificity of the cellular RNA response.

| | Exposure conc. (µM) | |
|---|---|---|
| Toxin Combination | E. coli MG1655 | E. coli LA BEC01 |
| Arsenic/Cadmium | 0.25/0.4 | 0.1/0.04 |
| Arsenic/Mercury | 0.25/0.1 | 0.1/0.01 |
| Cadmium/Mercury | 0.4/0.1 | 0.04/0.01 |

For this subset of toxin combinations, only those RNA-Seq promoter candidates responding to each individual toxin also respond to the same toxin in combination with others (See the rightmost three conditions in FIG. 51 and additional figures in Appendix B). To avoid the complexity of using this RNA-Seq approach combinatorically to investigate specificity across all toxin combinations, it was concluded that the most efficient approach is to develop sensor strains based on RNA data extracted following single-toxin exposures and then expose these strains to other toxins to look for non-specific responses. Because there were several strains that respond to each toxin, even for some overlap in response between certain promoters and multiple toxins, computational analysis can be used to determine a disjoint set of genes, and therefore a unique response signature, for each toxin of interest. The prototype device containing an array of sensing strains was exposed to each toxin and used the GFP "fingerprint" (i.e. which strains are responding at what intensities) to train a robust computational algorithm to decode this fingerprint into the toxin and concentration present in the sample.

Milestone 2.3: The Above Discussed Experiments were Repeated at 25° C., 30° C., and 37° C.:

All biosensing organisms grow optimally at 37° C. Upon investigating the ability to maintain a constant on-chip temperature, the sensor was designed with temperature control, as this implementation will be simple and will eliminate the risk of any temperature-related sensitivity or specificity issues.

Milestone 2.4: Determine how Growth System Affects Gene Expression—Compare Batch Grown Cells to Microfluidic Grown and Ensure Proper Growth and Response of Cells to Toxins in Device Environment:

The microfluidic device was developed and confirmed that the cells in the chambers are healthy, expressing normally, and their growth rates are comparable to those observed in batch conditions. A simple method to indicate healthy cell growth on-chip is to compare estimated microfluidic growth rate with calculated batch growth rate. E. coli MG1655 cells were grown in M9 minimal medium supplemented with 0.4% glucose in the plate reader and extracted a doubling time of 0.93 h from measurements of OD600 over time. The cells were grown in the microfluidic device with the same medium and the growth rate was estimated by collecting the effluent exiting the device, serially diluting it, and plating it on LB medium in agar to determine the viable cell count. Using this data, it was determined that the on-chip doubling time is about 0.94 h, which is in excellent agreement with batch data. Certainly, the batch and on-chip growth rates are comparable, and from our extensive microfluidics experience we observed with confidence that the on-chip cells are healthy and expressing normally.

Milestone 2.5: Prepare Isolated RNA for Illumina Sequencing Using Vendor Provided Reagents and Carry Out Sequencing:

We have prepared libraries and carried out sequencing for all toxins of interest. After exposing bacterial cultures to various levels of toxins, we extracted the cellular RNA and prepared it for sequencing. First, we thawed the cell pellet, homogenized the pellet using bead beating with RNase-free zirconium oxide, and extracted the RNA using Qiagen RNeasy Kits. Second, we removed any contaminating genomic DNA with DNase and performed a final purification step using a Zymo Clean and Concentrator column. Third, we prepared the RNA library for sequencing by enriching for mRNA using Epicentre Ribo-Zero rRNA removal kits. Fourth, we generated cDNA and prepared an indexed Illumina library using NEBNext Ultra Directional RNA Library Prep Kits, which retain strand-specific orientation information. Finally, we prepared and loaded these libraries on our Illumina MiSeq instrument for 2×75 bp paired-end sequencing.

Milestone 2.6: Analyze Data to Determine Candidate Genes which are Induced Upon Toxin Exposure:

We analyzed our sequencing data and identified significant numbers of candidate genes for each toxin of interest at false discovery rates below 1%. As we explain in Milestone 3.3, we experimentally validated selected candidate genes for cobalt detection.

Our analysis of the sequencing data from RNA-Seq experiments to determine candidate genes that are induced upon toxin exposure consisted of three main tasks: sequence alignment, quantification of gene expression, and identification of differentially expressed (DE) genes. The established software was rigorously tested and development of the software was performed to corroborate and verify all the candidate DE genes (see Table 9). We took into account the stranding of the MiSeq reads to achieve greater than 95% alignment with the MG1655 genome. Details of our quantification of the DE genes are provided in Appendix B.

TABLE 9

Number of differentially expressed (DE) genes at a false discovery rate below 1% for each toxin exposure condition of interest.

| Toxin | Number DE Genes | |
|---|---|---|
| | Low Conc. | High Conc. |
| Arsenic | 3 | 14 |
| Cadmium | 132 | 38 |
| Chromium(VI) | 270 | 377 |

TABLE 9-continued

Number of differentially expressed (DE) genes at a false discovery rate below 1% for each toxin exposure condition of interest.

| Toxin | Number DE Genes | |
|---|---|---|
| | Low Conc. | High Conc. |
| Cobalt | 609 | 1274 |
| Copper | 110 | 77 |
| Iron | 32 | 70 |
| Lead | 99 | 489 |
| Malathion | 370 | 41 |
| Mercury | 165 | 218 |
| Nickel | 43 | 95 |
| Zinc | 24 | 596 |

The resulting genes were cross inspected using different methods to confirm that the most specific genes were selected. In order to simultaneously analyze mean fold change with respect to the negative conditions, the normalized counts, and the expression level with respect to other genes, we implemented a toolbox that depicts a summary figure for a gene candidate as shown in FIG. 51 (see the full set of gene candidates in Appendix B).

From an analysis of all gene candidates, we set our mean fold change threshold to indicate DE to 2.5. Our most sensitive and specific gene candidates for eight toxins identified via. RNA-Seq analysis in E. coli MG1655 are shown in FIG. 1. The arsR promoter in FIG. 1A responds specifically and monotonically to increasing concentrations of arsenic alone and in combination with other heavy metals without exhibiting crosstalk. This gene serves as an excellent positive control for our analysis methods, as our literature search revealed it to be the most widely studied gene for sensing arsenic in E. coli. The zntA promoter in FIG. 1B responds monotonically to increasing concentrations of cadmium alone and in combination with other heavy metals without exhibiting crosstalk, but it also shows sensitivity to low and high concentrations of zinc. However, since the zraP promoter is specific for zinc, the boolean logic expression (zntA)^(:zraP) represents a unique combined promoter response that is specific for cadmium. The recN and sulA promoters in FIG. 1C-D respond specifically to high concentrations of chromium (VI) alone. These promoters are known to activate during multiple double-strand DNA breaks and the cell SOS response, respectively. Their differential expression here corroborates recent reports of chromium (VI) acting as a carcinogen in water supplies and may provide information on its mode of action. The ygbA promoter in FIG. 1E responds specifically to cobalt alone. The cusR promoter in FIG. 1F responds specifically to high concentrations of copper alone. This gene serves as another excellent positive control, as our literature search showed it to be among the most widely studied genes for sensing copper in E. coli. The ybiI promoter in FIG. 1G responds specifically and monotonically to increasing concentrations of lead alone and shows higher specificity than the pbrR promoter identified from the literature. The nemR promoter in FIG. 1H responds specifically to high concentrations of malathion alone. The identification of a sensitive and specific gene for detecting malathion in E. coli is entirely unexpected, as the mechanism of toxicity for organophosphate pesticides is known to only operate in eukaryotes, as organophosphate pesticides are neurotoxins. Lastly, the zraP promoter in FIG. 1I responds specifically and monotonically to increasing concentrations of zinc alone. The sensitivity of zraP to zinc is extremely high, making this promoter an excellent candidate for logical combination with promoters exhibiting zinc interference to generate toxin-specific multi-promoter responses.

Figure 2:
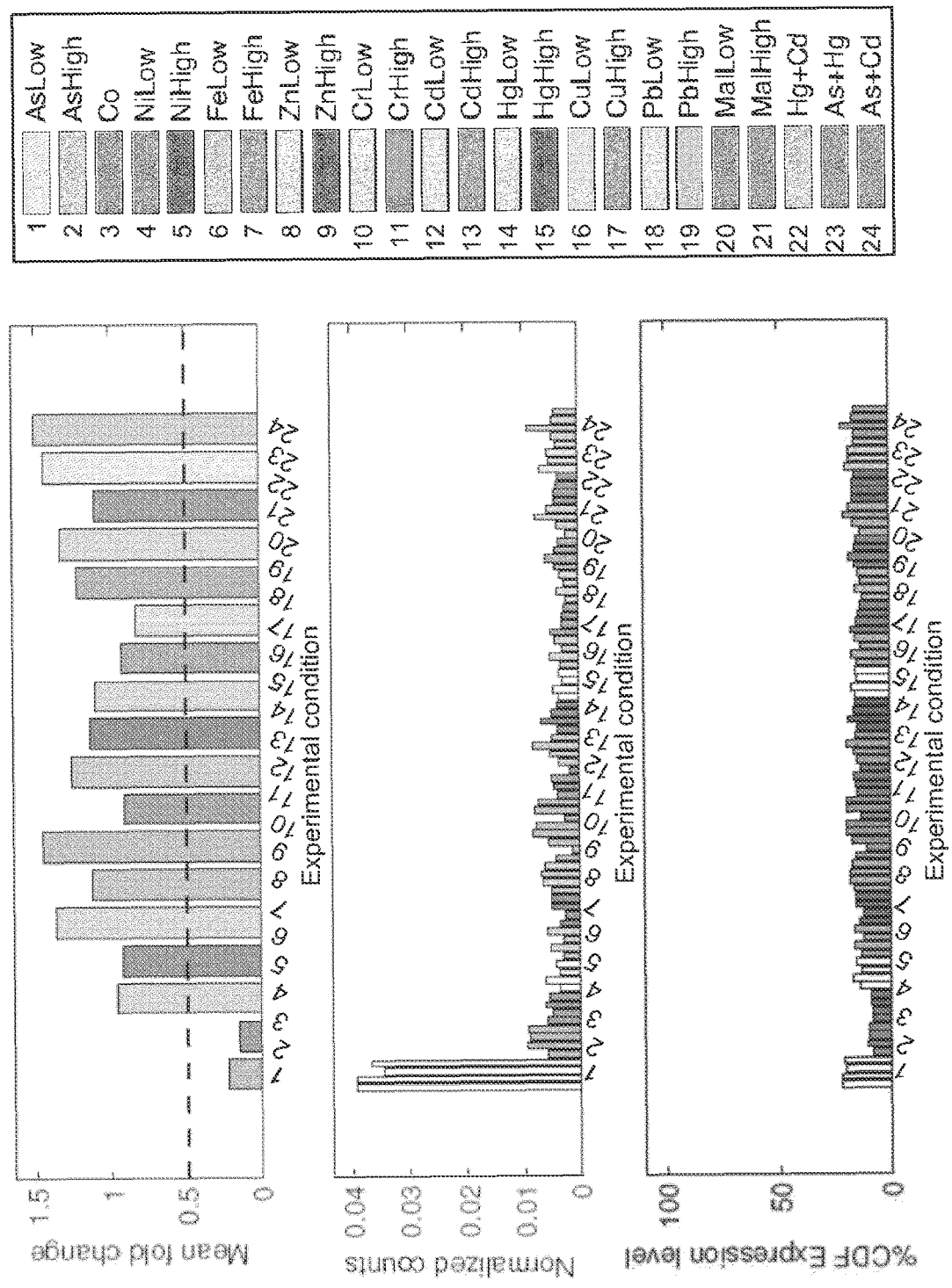
FIG. 2 illustrates that the nasB promoter in *Bacillus subtilis* 168 was found to be sensitive and specifically downregulated in response to ammonia. As shown in the two panels below, the numbers at the x-axis correspond to the four corresponding bars above the numbers. For example the first 4 bars correspond to the number 1, the second set of 4 bars correspond to the number 2 and so forth.
Figures 3A, 3B:
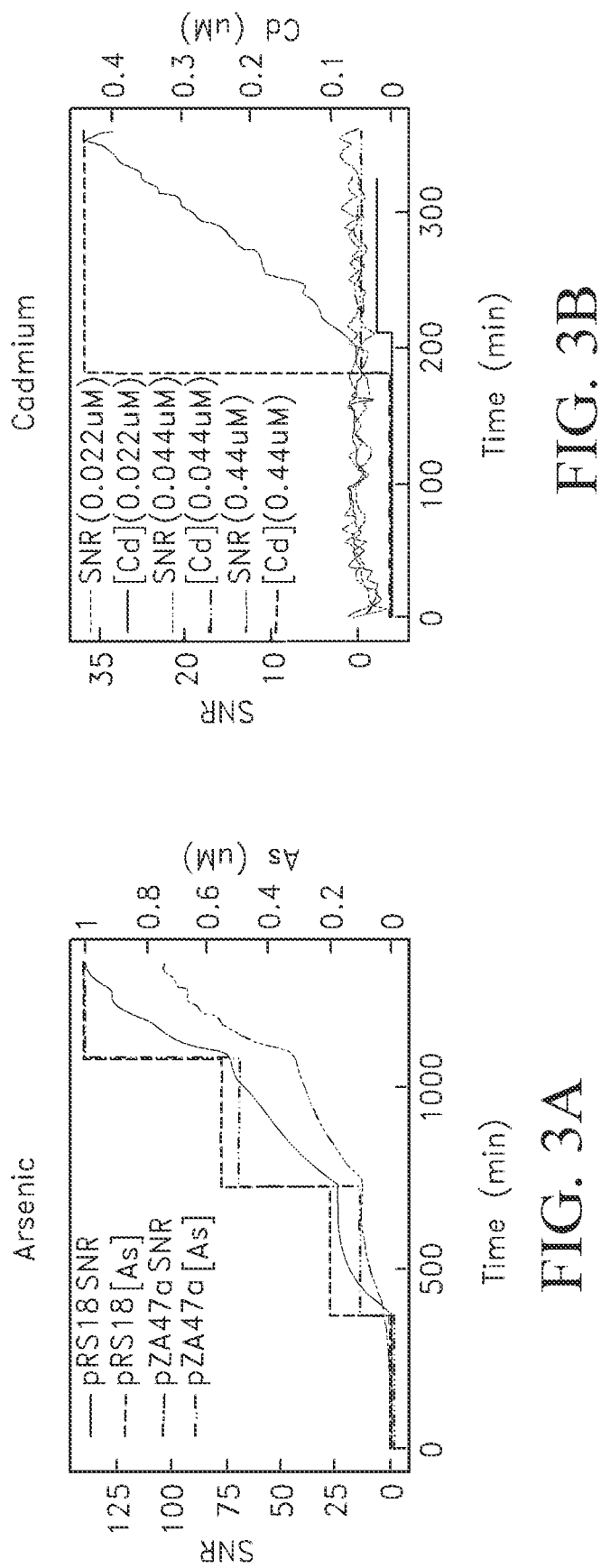
FIG. 3, (FIGS. 3A, 3B, 3C, 3D, 3E, 3F, 3G, and 3H), illustrate on-chip time-lapse induction responses of promoter constructs. All sensor constructs are on plasmids transformed into *E. coli* MG1655, except for the ammonia construct which is integrated into the genome of *B. subtilis* 168. 3A) pRS18 and pZA47a show induction by arsenic. 3B) Cd1 shows induction by cadmium. 3C) Cr11 shows induction by chromium (VI). 3D) Cu1 shows induction by copper. 3E) Hg3 shows induction by mercury. 3F) Pb7 shows induction by lead. 3G) Ma11 shows induction by malathion. 3H) Amm3 shows induction by ammonia.
Figure 3D:
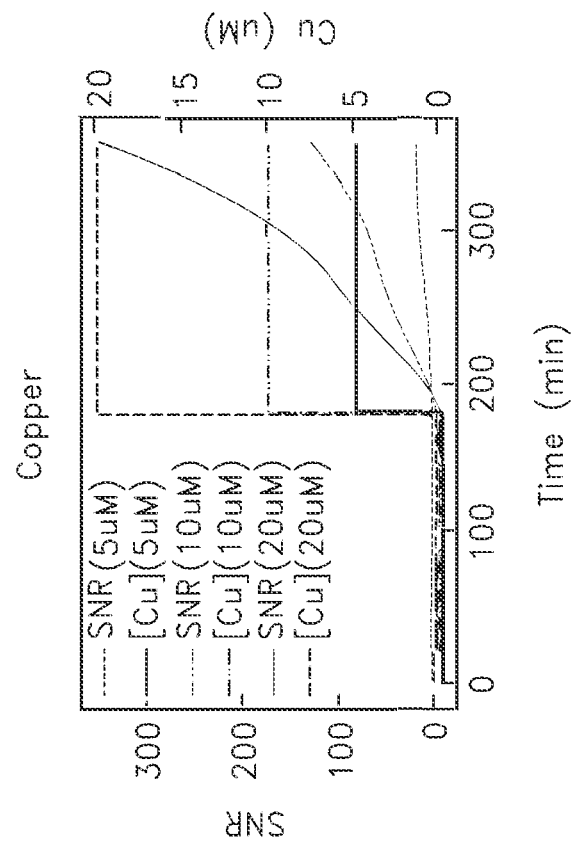
Figure 3C:
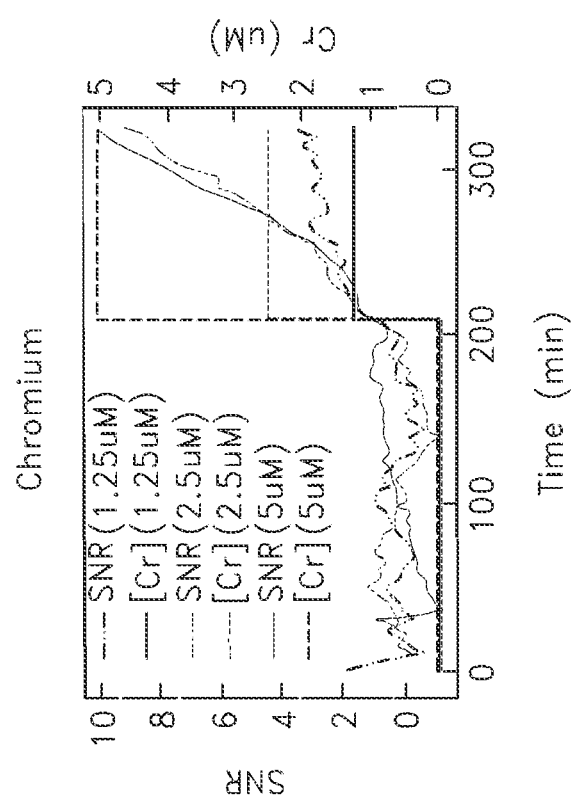
Figures 3E, 3F:
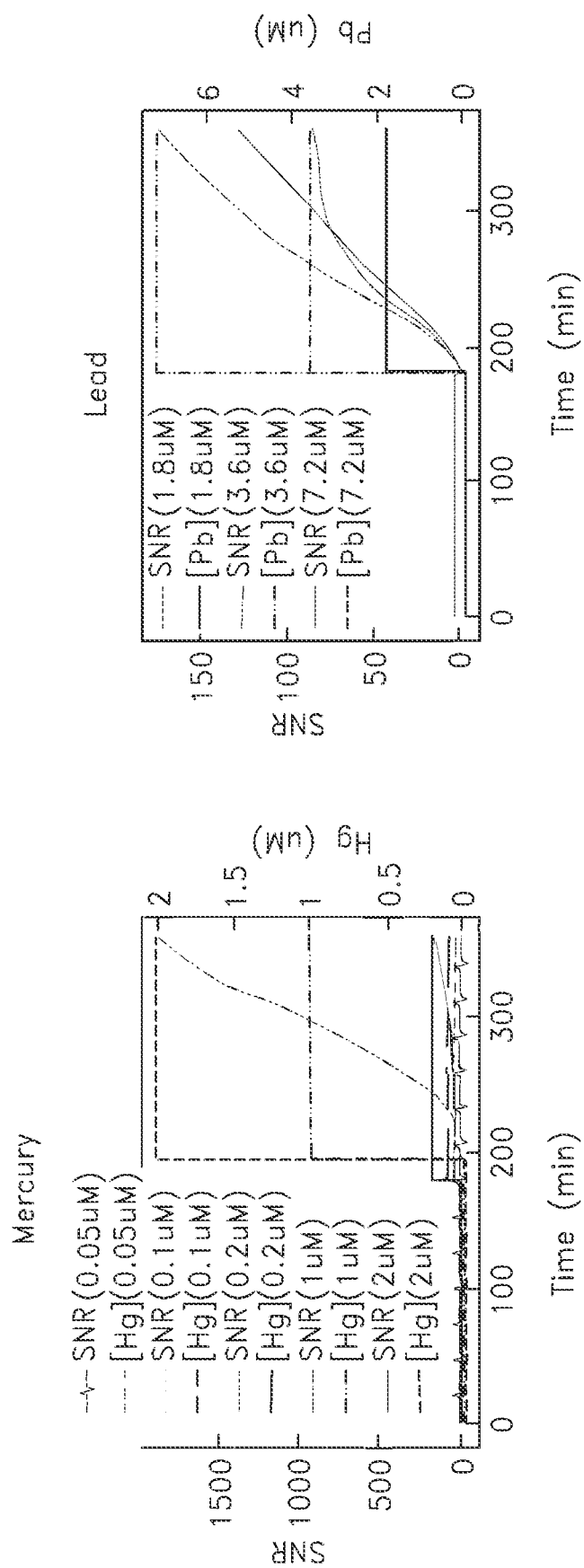
Figure 3H:
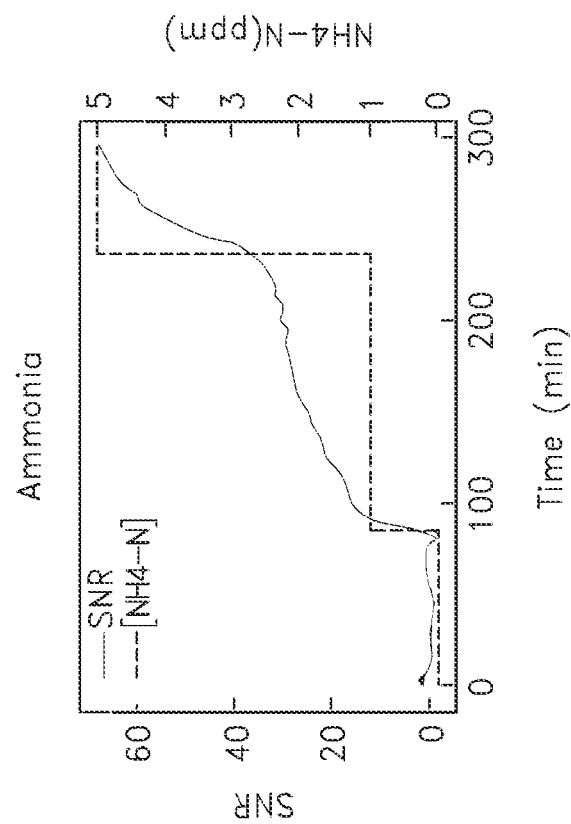
Figure 3G:
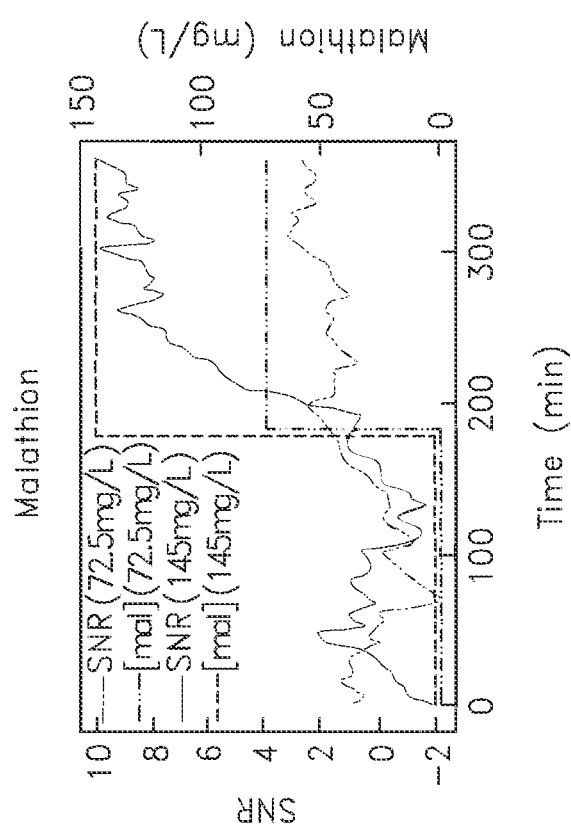

We used RNA-Seq to verify the nasB promoter in *B. subtilis* 168 as a sensitive and specific promoter for the last remaining toxin, ammonium (see FIG. 2). As opposed to other response circuitry, nasB is down-regulated in response to the toxin, allowing the construction of a "lights-off" sensor. This is desirable because, unlike the other water toxins of interest, ammonium is expected to increase the growth rate of biosensor cells. In this situation, a "lights-on" sensor could be triggered by any substance that increases the growth rate and resulting GFP production ability of cells, whereas a "lights-off" sensor remains immune to this effect.

In summary, through constructing strains based on literature searches and performing RNA-Seq analysis, we discovered sensitive promoters for all toxins of interest. See Appendix A for a full list of candidate toxin-responsive promoters.

Alternative 3

Milestone 3: Develop a Preliminary Microfluidic Device that can Culture Many Independent *E. coli* Sensor Strains Simultaneously Library Expansion of Transcription Based Sensors Microfluidic Device Development to Support Environmental Sensing Low Cost Optical Methods Development Library of *E. coli* clones with target promoters producing GFP; preliminary microfluidic device capable of culturing many different clonal populations in a defined array.

Library Expansion of Transcription Based Sensors.

We have completed this milestone. The promoter regions for the differentially expressed genes identified in Milestone 2 were located using computational tools (Milestone 3.1). We have cloned these promoters into the Milestone 1 expression systems (Milestone 3.2). We validated the functionality of these new promoter constructs using microfluidics (Milestone 3.3). This validation of our RNA-Seq identified promoters provides strong evidence of the power and utility of our approach to developing novel transcription based biosensors.

Milestone 3.1: Perform Sequence Analysis to Determine the Promoters of Candidate Genes Identified in Milestone 2:

We have identified the promoter regions for all candidate genes. The promoters of interest are located on the genome directly upstream of the genes identified by RNASeq. For uncharacterized promoters, we used 200 bp upstream of the gene's transcription start site to construct the sensor plasmid. Including this entire region ensures that even cryptic regulatory sites acting on the promoter are included in the sensor construct.

Milestone 3.2: Clone the Promoters into the Expression System Validated in Milestone 1:

We have cloned all identified promoters into the standardized plasmid expression system validated in Milestone 1.

Figure 52:
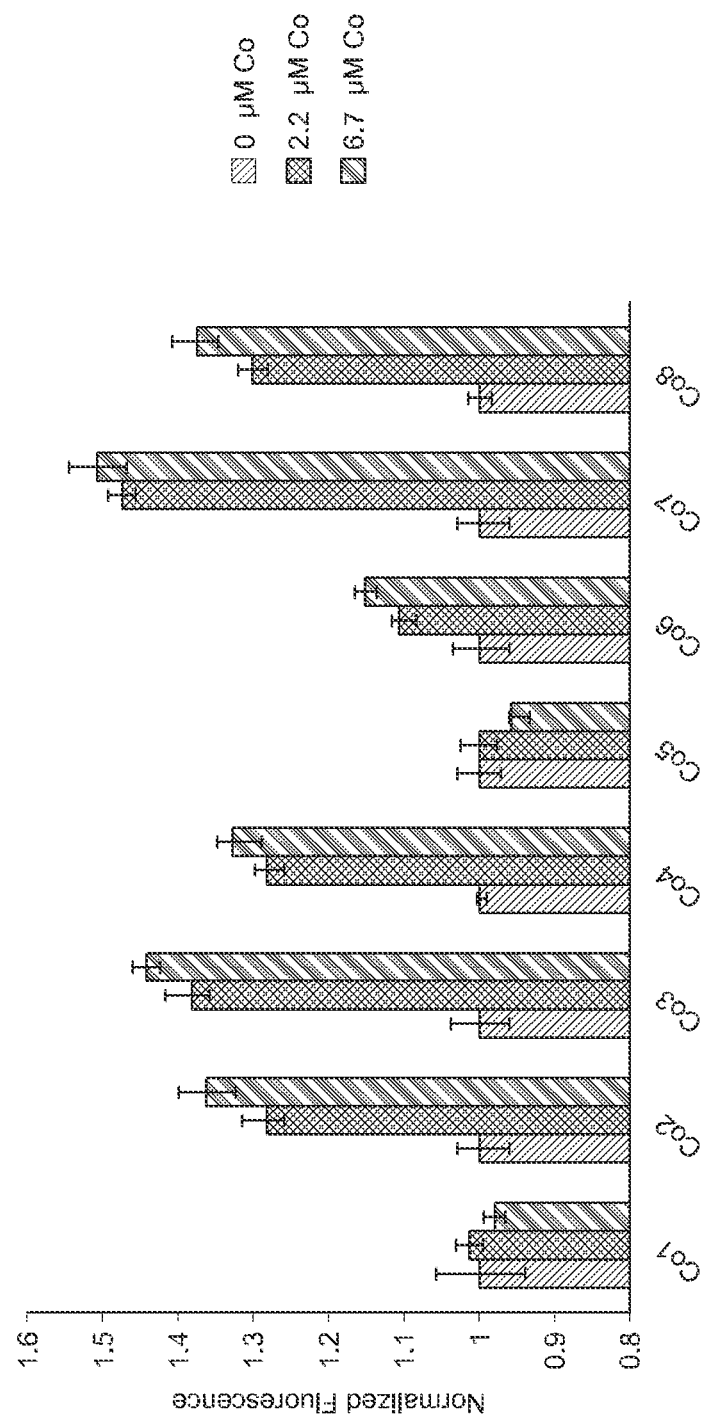
FIG. 52 shows the validation of five cobalt-sensing promoters (Co3, Co4, Co6, Co7, Co8) identified via RNASeq analysis with *E. coli* and one (Co2) identified from literature.

Milestone 3.3: Validate the Response of the Promoters Using the Methods Developed in Milestone 1:

We validated our RNA-Seq approach to identifying toxin-responsive promoters using plate reader data from five cobalt-sensing promoters identified via RNA-Seq analysis (see FIG. 52). We grew strains in microplate wells in the presence of various concentrations of cobalt and measured GFP fluorescence. *E. coli* MG1655 strains Co1 and Co2 incorporate the nmtR promoter from the *M. tuberculosis* genome as the cobalt-sensing element, whereas *E. coli* MG1655 strains Co3-Co8 incorporate cobalt-responsive promoters identified through RNA-Seq. Odd numbered strains express GFP using the native RBS, whereas even-numbered strains use the optimized Lutz RBS. We concluded that strains Co2-Co4 and Co6-Co8 significantly respond to the presence of cobalt in the growth medium. Therefore, we have demonstrated that our exhaustive methodology for RNA-Seq analysis supported by multiple techniques and algorithms works.

The set of validated constructs shown in FIG. 3 contains one construct that has been demonstrated sensitive to each toxin of interest within our sensor prototype, with the exception of malathion for which the positive results that we observed in our original microscopy runs (shown in this plot) have not yet translated to our sensor boxes. During investigation, we discovered a more robust malathion detection scheme that leverages its esterase inhibition effect in yeast (see FIG. 44). Our successful testing of this method on our microscope illustrates the power of our forthcoming whole-genome detection scheme, whereby we will continually measure the responses of 2,000 to 4,000 *E. coli* and *S. cerevisiae* promoters arrayed in a microfluidic chip. We expect the observed esterase inhibition to be significantly represented in the genomic response of this multi-strain library during malathion exposure.

Milestone 4: Microfluidic Device Development to Support Environmental Sensing

We developed a concentrated media additive to enable robust growth of *E. coli* in natural water sources (Milestone 4.1). We cultured *E. coli* in our microfluidic devices for up to 50 days, demonstrating long-term reliability (Milestone 4.2). We developed and optimized a microfluidics-capable peristaltic pump for extracting natural water (Milestone 4.3). We greatly expanded our microfluidic device, allowing the culture of multiple strains (Milestone 4.4). We significantly increased the fluorescence signal from our microfluidically cultured cells by optimizing the trap geometry (Milestone 4.5). We developed techniques to prevent the release of our genetically modified organisms (Milestone 4.6). We developed a reliable method to freeze-dry and store cells at room temperature (Milestone 4.7). We modified our "gill" microfluidic device to allow freeze-drying of cells on-chip (Milestone 4.8). We successfully tested our microfluidic devices using our low-cost optical system (Milestone 4.9).

Milestone 4.1:

Develop a concentrated media additive that can be mixed with natural waters to support *E. coli* growth: We have developed and tested medium formulations that successfully culture *E. coli* and *B. subtilis* in batch and on-chip. For all batch culture experiments, M9 minimal medium supplemented with 0.4% w/v glucose, 0.1 mM CaCl2, and 2 mM MgSO4 was used. For *B. subtilis*, the medium was additionally supplemented with 0.075% v/v TWEEN 20, 50 μM FeCl3, 50 μM MnCl2, and 1 μM ZnCl2. For *B. subtilis* ammonium exposure experiments, the NH4Cl in M9 minimal medium was replaced with NaNO3, keeping the concentration of nitrogen constant.

For microfluidic experiments, we developed a minimal medium optimal for growth of bacteria and heavy metal sensing, adapted from HMM. This medium replaces the inorganic phosphate in M9 minimal medium with glycerol-2-phosphate, MOPS (pH=7.2), and KCl. Inorganic phosphate is undesirable because of its metal chelation properties and its propensity to form calcium phosphate deposits within microfluidic channels. To minimize contaminating metals, all microfluidic experiments were carried out with media made with extra high purity salts where available. We found that when using these pure salts robust *E. coli* growth required supplementing the medium with iron, and robust *B. subtilis* growth required iron, zinc, and manganese.

The final composition of our *E. coli* medium, following on-chip mixing with source water, was:
1. 40 mM PharmaGrade MOPS [Sigma #PHG0007-1KG] (from 1 M stock at pH 7.2)
2. 4 mM glycerol-2-phosphate [Sigma #G6501-25G]
3. 0.4% w/v dextrose (glucose) [Sigma #D9434-1KG]
4. 1 g/l (19 mM or 262 ppm NH4-N) TraceSelect NH4Cl [Sigma #09725-100G]
5. 3.7 g/l (50 mM) TraceSelect KCl [Sigma #05257-100G]
6. 0.075% v/v TWEEN 20 [Acros Organics #23336-0010]
7. 50 mg/mL spectinomycin (from spectinomycin dihydrochloride pentahydrate) [Sigma #S4014-5G]
8. 1 µM FeCl3 [Alfa Aesar #A16231-500G]
9. 0.01 mM CaCl2 [Macron Fine Chemicals #4160-12]
10. 0.2 mM MgSO4 [Macron Fine Chemicals #6066-04]

The final composition of our *B. subtilis* medium, following on-chip mixing with source water, was the same as for *E. coli* with the following modifications:
1. Replace NH4Cl with 1.6 g/NaNO3
2. Use 50 µM FeCl3 instead of 1 µM
3. Add 50 µM MnCl2 [Baker #2540-01]
4. Add 1 µM ZnCl2 [Macron #8780-04]

Note that TraceSelect formulations of reagents were used when available to minimize the potential for heavy metal contamination of the media.

Milestone 4.2: Perform Testing to Demonstrate the Long Term Culture Stability of Such Cells. Quantify Growth Rate of Cells and Lifespan of Cultures:

We have successfully grown cells in microfluidic devices with a stable growth rate comparable to batch culture.

We have continuously grown *E. coli* MG1655 in the gill chip for 23 days using growth medium concentrate mixed with natural water from Lake Miramar. In the most recent experiment, 10×M9 medium concentrate was mixed with Milli-Q water in a 1:9 ratio at a total flow rate of 1 ml/h using a dual-channel Instech P625 peristaltic pump. Cells were observed to grow and express GFP in the traps after 50 days in the device, proving that the sensor strain is stable over this time period.

Milestone 4.3:

Develop a metering and mixing system to combine the concentrated media stock with natural water at a fixed ratio and mix it well before cell exposure: We used an Instech P625 peristaltic pump to mix concentrated media with natural water at a fixed ratio and calibrated the pump to achieve the desired flow rate. Since our media additive stocks are concentrated 10-20×, we dilute them with natural water before delivery to the cells by using a peristaltic pump to drive each liquid at a defined volumetric flow rate through silicone tubing into the chip. Our pumping scheme uses a custom-made dual-channel tubing set with different tubing inner diameters, which results in a constant flow ratio. In laboratory tests, we have used tubing sets with 1:20 and 1:9 flow ratios to successfully combine and completely mix the two liquid streams on-chip using staggered herringbone mixers to support healthy cell growth.

Figure 53:
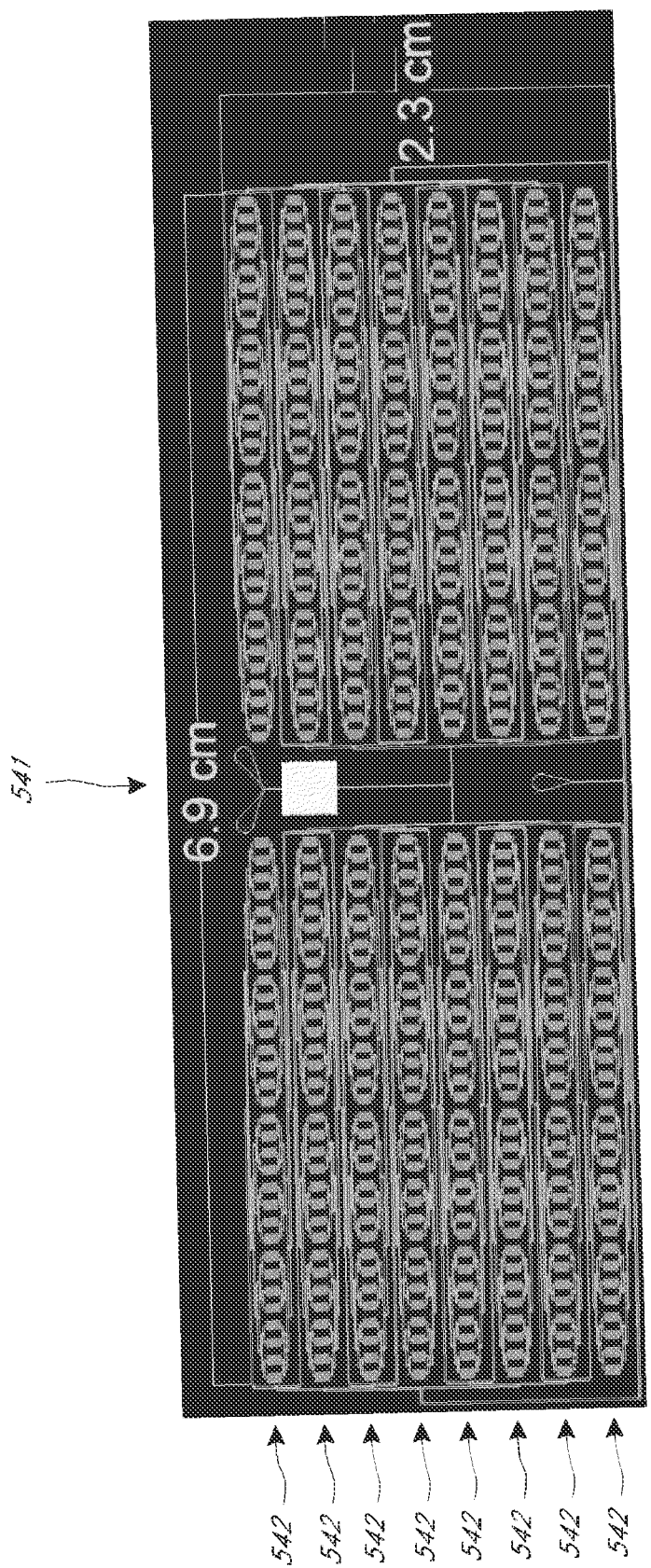
FIG. 53 shows the CAD design for a highly parallel microfluidic device capable of culturing 512 unique toxin-sensing promoter strains in individually addressable "gill" cell-trapping regions. Two inlet ports at the top are combined and mixed during passage through staggered herringbone mixers (541) before branching into 512 "gill" trapping regions (542) and recombining at the outlet port. The footprint of the entire device is small enough to fit on a 1"₁ 3" glass slide.

Milestone 4.4:

Expand the current *E. coli* large scale culture device (biopixel device) to have 500 individually addressable chambers: We have designed a large-scale gill chip using nested symmetrically-split parallel channels to produce balanced flow (see FIG. 53). However, our analysis of RNASeq data determined that the incidence of specific toxin-sensing promoters in *E. coli* is greater than expected. Therefore, we do not require hundreds of cell-trapping regions in the microfluidic device, and we decided to pursue a cell patterning strategy whereby cells are micropipetted into shallow but relatively large reservoirs upstream of the cell trapping regions.

Milestone 4.5:

Increase the height of the Biopixel device's chambers to increase the output optical signal. Ensure the cell growth dynamics are unchanged: We constructed and tested an optimized gill chip design that raises the height of the cell trapping regions to 50 µm, thereby increasing the fluorescent signal.

Notably, we have observed synthetic strains of *E. coli* MG1655 produce levels of GFP within the device that are visible to the naked eye using the appropriate filters. Over the course of dozens of experiments, we have verified that cell growth rate is unaffected by these minor modifications to the "biopixel" cell trap design.

Milestone 4.6:

Develop a UV LED system that kills the cells as they emerge from the trapping region and enter waste collection. Perform viability test on media exiting the waste trap: We concluded that UV LEDs are an inefficient method for sanitizing the chip effluent Short-wave UV LEDs consume power, emit heat, and have short lifetimes, which unnecessarily reduces the operational lifetime of our biosensor device. Instead, we decided to route cell waste to a reservoir containing bleach, which has been used as an effective sanitizer for hundreds of years.

We tested this strategy by depositing effluent from the pump mixing experiments into a 1-1 glass bottle pre-filled with 100 ml of bleach. The waste bottle was used to collect cell waste throughout four experiments over a period of two months and filled to around 500 ml. To test for cell viability, the waste bottle was stirred, and 20 nil of the contents was plated on LB agar. As a positive control, 45 ml of waste was removed, bleached again, and plated using the same method. Neither the prebleached waste nor the post-bleached waste showed any bacterial growth after 1 day on LB agar without antibiotics, suggesting the pre-bleaching method is sufficient to eliminate viable cells in the waste bottle.

Milestone 4.7:

Develop a method to freeze-dry cells allowing them to be rehydrated with little loss of viability: We have successfully developed a method for in chip lyophilization and revival after long term storage. Several cryoprotectants suitable for engineered biosensor strains were formulated from a combination of literature-based protocols, current industrial practices, and experimentation. The investigated cryoprotectants include:
1. 2.5% Luria-Bertrani Broth (LB) (w/v)+spectinomycin
2. 2.5% LB+0.4% glucose (w/v)+spectinomycin
3. 2.5% LB+0.4% sucrose (w/v)+spectinomycin
4. 2.5% LB+0.4% trehalose (w/v)+spectinomycin
5. M9+0.4% glucose+spectinomycin Relative cryoprotectant efficacy was determined via plate reader revival experiments performed 24 h, 1 wk, 2 wk, 4 wk, and 8 wk after lyophilization. Cells were revived via rehydration and resuspension in 200 µl of revival medium within microplate wells. The plates were then immediately placed into a Tecan Infinite M200 Pro plate reader, where growth rates were monitored over the next 48 h.

Revival media included:
1. M9+0.4% glucose+spectinomycin
2. Trace Select M9+0.4% glucose+spectinomycin 3. Trace Select M9+0.4% glucose 4. HM9 (nitrate)+0.4% glucose and were selected to be representative of the growth medium used in the final device.

Strains protected with optimal cryoprotectants showed little difference in viability between cryoprotectants after two months of preservation. Both *E. coli* and *B. subtilis* strains responded similarly to lyophilization in the cryoprotectants listed above (see FIG. 4).

The best cryoprotectant was found to be LB+0.4% sucrose and was used to test batch and on-chip lyophilization and revival in biosensor host strains *E. coli* MG1655 and LABEC31 and *B. subtilis* NCIB 3610. In batch, revival efficacy experiments were performed at 24 h, 1 wk, 2 wk, 4 wk, and 8 wk after lyophilization, with no observed reduction in viability. For on-chip testing, strains were cultured overnight to stationary and sporulation phases, respectively. Strains were then double-washed in cryoprotectant and concentrated to 50× their batch culture concentration before being injected into an 18-strain chip through independent loading ports. Loading ports were sealed with a fast-curing silicone elastomer (Sylgard 170, Dow Corning), then the device was lyophilized in a commercial freeze-dryer for 17 h before being nitrogen-flushed, desiccated, and sealed within opaque packaging.

Figures 54A, 54B:
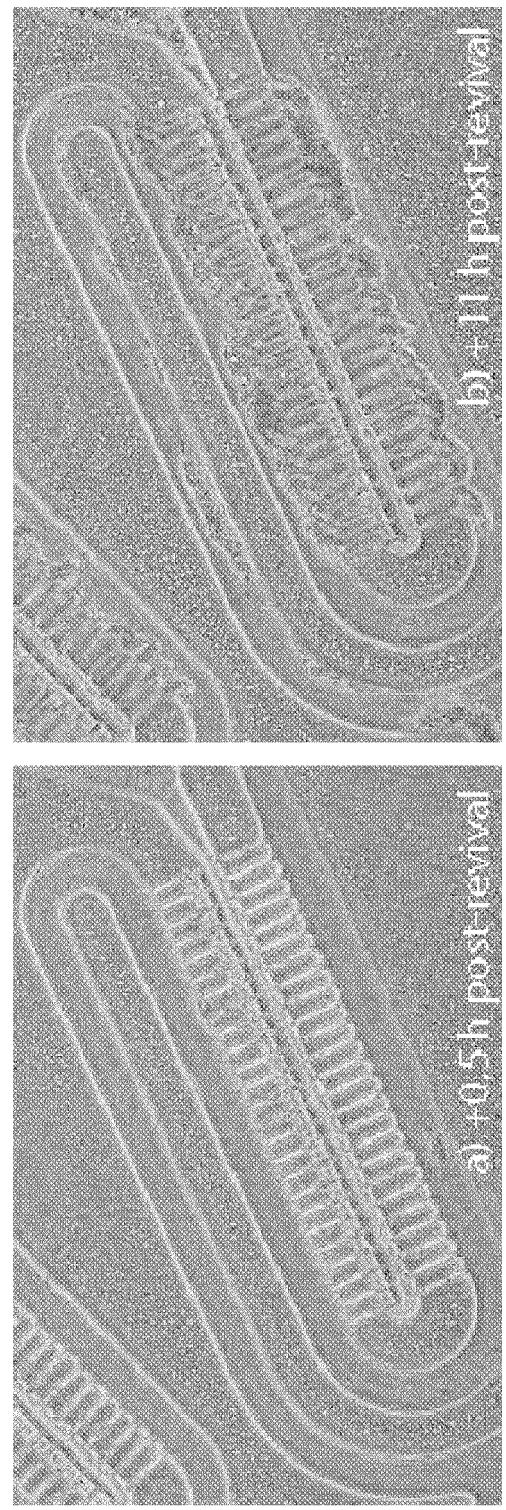
FIG. 54 (FIGS. 54A, and 54B) shows images showing the on-chip revival of lyophilized sensor strain pLB-As7 (MG1655). Device image 54A) 0.5 h after chip wetting and 54B) after 11 hours of robust post-revival growth. The strain was loaded, grown to confluence, lyophilized in LB+0.4% sucrose+spectinomycin for 17 h (9 h freeze, 8 h dry), stored for 24 h, and revived in LB+spectinomycin.

Following room-temperature storage for up to two months, strains were revived via de-gas driven chip wetting and pump driven flow. Upon introducing fresh medium, strains revived on time scales equivalent to those in batch (see FIG. 54). In addition, the ammonium sensing *B. subtilis* NCIB 3610 strain was successfully sporulated using standard sporulation medium, which offers an additional preservation method with extreme shelf life.

Milestone 4.8:

Develop a deposition technique to place cells into a region of a microfluidic device that is then bonded to a glass coverslip: We have successfully developed a deposition strategy whereby individual biosensor strains are injected into on-chip reservoirs, where they are lyophilized, stored, and revived.

To independently culture multiple biosensor strains, an 18-strain chip was designed, built, and successfully tested for multi-strain loading and freeze-drying. The chip dimensions conform to the requirements of both the strains and the biosensor's optical detection system.

Milestone 4.9:

Develop and test the microfluidic device in a laboratory environment: We have conducted extensive testing of our microfluidic devices in a laboratory environment, using both research grade and low cost optical systems.

Figure 55B:
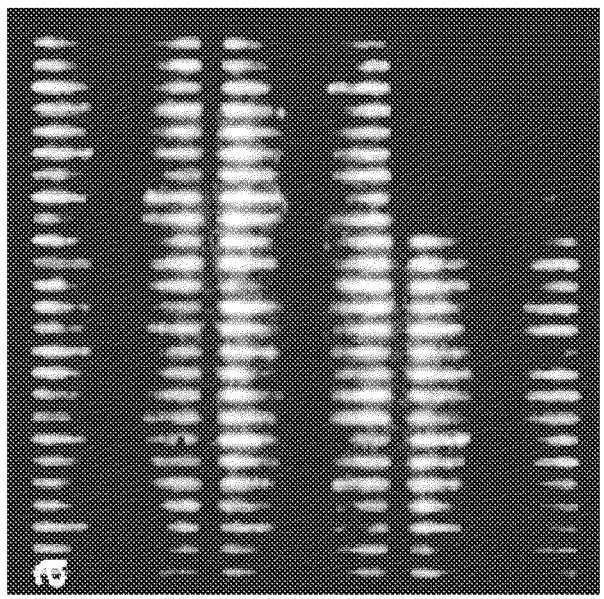
FIG. 55 (55A and 55B) shows a comparison of optical systems. The same microfluidic device was imaged with a) low cost biosensor optics developed by the Ziva Corporation and b) a research grade Olympus IX81 microscope. While the Ziva image may appear inferior, this is an artifact due to zooming of the image for comparison (the Ziva system is designed with a wide field of view compared to the Olympus). We have verified that the Ziva system yields images that equal the quality of the Olympus system, which is remarkable given the difference in cost ($2K for Ziva versus $125K for Olympus).
Figure 55A:
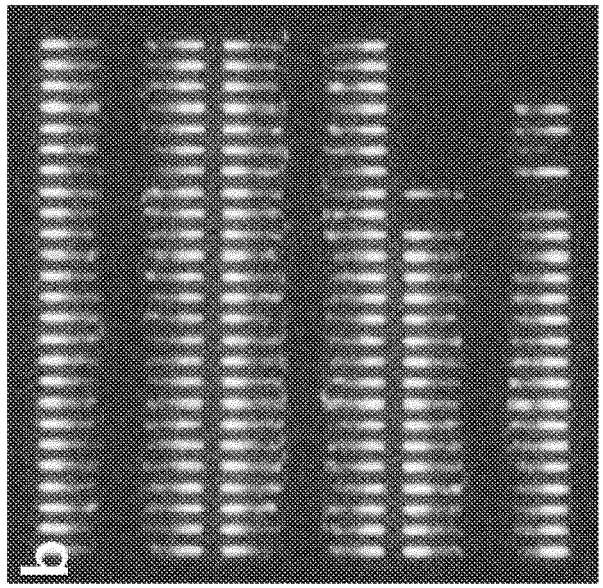

The microfluidic "gill" chip described in Milestone 1.4 was used to test the optical system developed by the Ziva Corporation. We compared the optical system to that of our research grade microscope, an Olympus IX81. The Ziva optical system was designed with lower resolution optics compared to those of the 4× objective on the IX81 in order to lower cost while increasing the imaged field of view. Although the Ziva optics are lower resolution, the produced images compare favorably with the IX81 as shown in FIG. 55.

Milestone 5: Low Cost Optical Methods Development Summary:

We have successfully completed this milestone. We have developed a low cost optical system by partnering with the Ziva Corporation, thereby completing sub-milestones 5.1, 5.2, and 5.3. We have also determined that bioluminescent systems can be significantly more sensitive than fluorescence based systems, thus completing Milestone 5.4.

Milestone 5.1: Design and Construct an LED Array for the GFP Excitation of the Cells in the Microfluidic Device:

The excitation LED system has been designed and delivered.

The optical setup was designed in partnership with the Ziva Corporation. We chose a CREE XTE Indus Star 1 Royal Blue High Power LED (manufacturer part #CRE-EXTE-ROY-1) with an emission wavelength maximum of 465 nm, which is well suited for GFP excitation. The LED is paired with a 1400 mA BuckBlock constant current LED driver (manufacturer part #0A009-DV-1400) and a LED light housing with a 15 W heat sink (manufacturer part #ALK-LH-15 W).

Milestone 5.2: Design and Construct Optical Filters for GFP Excitation and Emission which Cover the Entire Area of the Microfluidic Device:

The optical filters for GFP excitation and emission have been designed and delivered.

The optical setup was designed in partnership with the Ziva Corporation. The necessary filters were purchased from Semrock, Inc. The part numbers are FF495-Di03-25x36, FF01-520/35-23.3, and FF01-457/50-25 for the dichroic, emission, and excitation filters, respectively.

Milestone 5.3: Obtain and Characterize the Performance of a Low Cost Camera System to Image the Fluorescence Signal of the Device:

We have built an imaging system using the "Chameleon" camera (part #CMLN-12S2M-CS) from Point Grey Research, Inc. with the design assistance of the Ziva Corporation. This is a 1.3 megapixel monochrome camera featuring a Sony ICX445 CCD imager. It contains a 12-bit analog-to-digital converter with a maximum gain of 24 dB. The camera package includes a software development kit (SDK), known as FlyCapture, which is compatible with the PandaBoard single board computer system that we have chosen for our electronics platform.

The microfluidic "gill" chip developed in Milestone 1.4 was used to compare the optical system developed by the Ziva Corporation with our research grade microscope, an Olympus IX81. The Ziva optical system was designed with lower resolution optics compared to those of the 4× objective on the Olympus in order to lower cost while increasing the image field of view by 20× for imaging multiple "gill" trapping regions. Images acquired with the Ziva optics compare favorably with those acquired with the Olympus, as shown in FIG. 55. Notably, the Ziva optics are ~2× more sensitive at detecting GFP than the Olympus optics (SNRs are 23.8 and 11.6, respectively). Because our primary objective is to detect weak signals, the Ziva system outperforms the Olympus system at –50× lower cost.

Milestone 5.4: Replace the GFP Fluorescence System with a Luminescent System Based on the Lux Operon of *A. Fischeri*:

We have replaced the GFP fluorescence system with a Lux system for our best-performing arsenic sensor plasmid.

Figure 38:
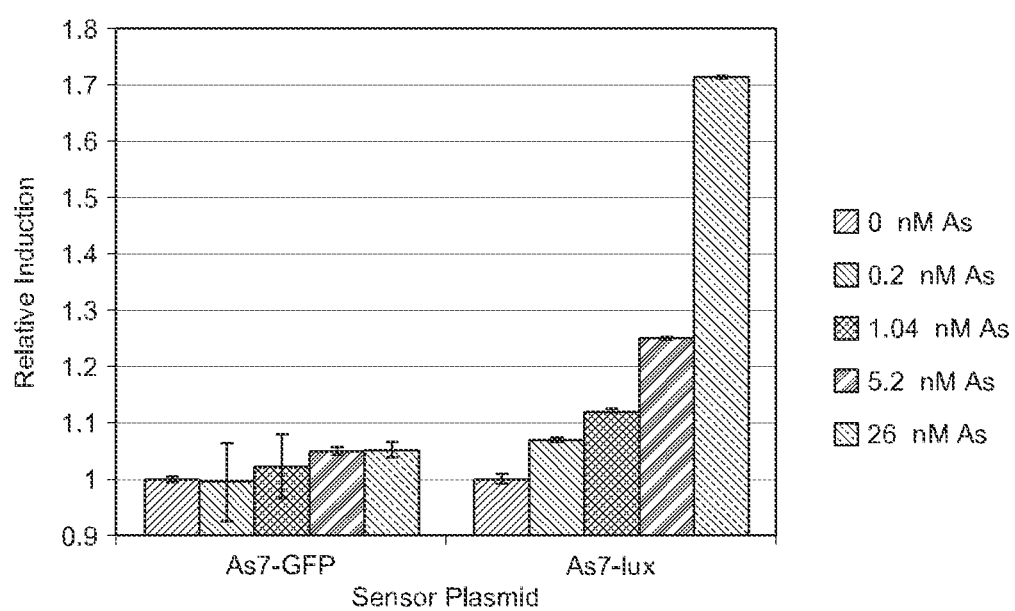
FIG. 38 shows side-by-side comparison of reporter systems on otherwise identical plasmid backbones demonstrates the superior detection limits achieved by using luminescence.
Figure 39A:
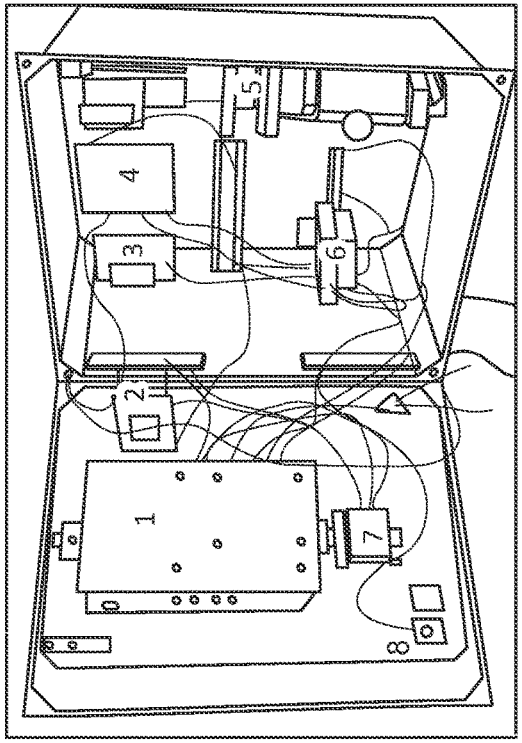
FIGS. 39 (FIGS. 39A, 39B, 39C, 39D, and 39E) shows an overview of our sensor prototype. 39A) We currently have five replicates of the sensor prototype running continuously in the lab. 39B) Sensor enclosure with front panel opened to expose internal components. b1: Electronics sub-enclosure, b2: temperature controller, b3: AC power distribution devices, b4: tri-output DC power supply, b5: Ziva optical assembly, b6: fan/heater, b7: DC power distribution block, b8: peristaltic pump. 39C) Microfluidic device being illuminated with the GFP excitation LED. 39D) Image taken using Ziva optics of eight strains growing inside our microfluidic device and responding to induction. 39E) Representative time series of data taken from one of the sensors. The green bar represents the introduction of tracer dye, and the red bar represents the introduction of the inducer, in this case mercury. Fluorescence of the mercury-specific strain rises and then falls as mercury is introduced and removed.
Figure 39B:
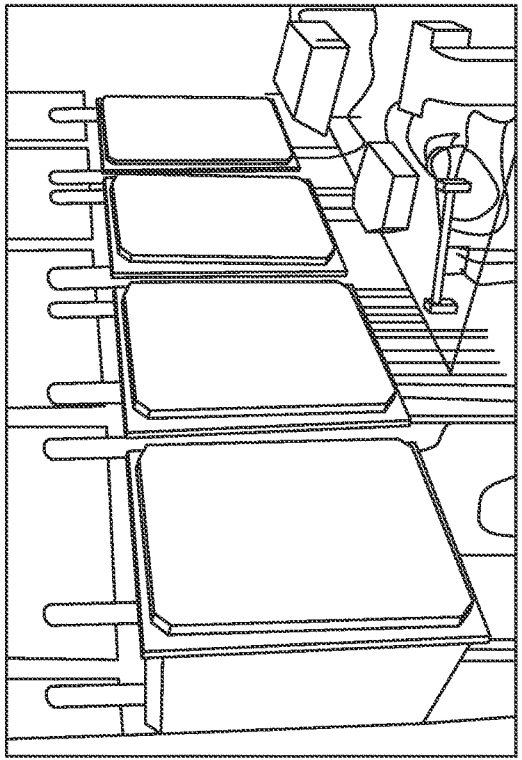
Figure 39C:
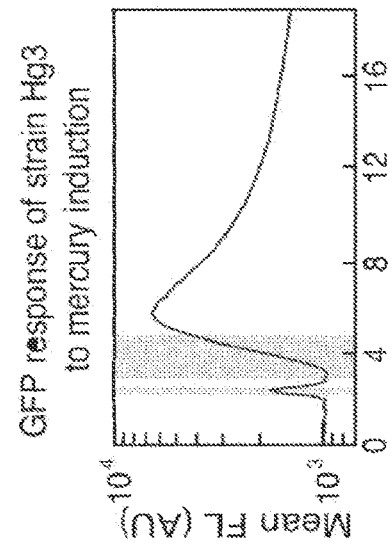
Figure 39D:
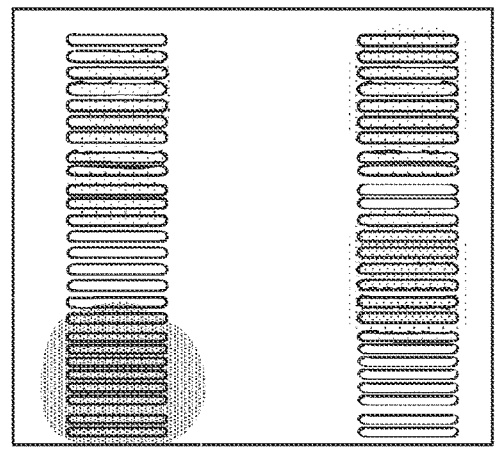
Figure 39E:
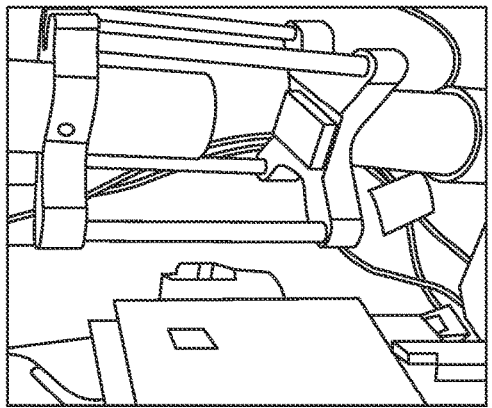

The arsenic sensor construct As7 was modified to replace the gfp gene with the luxCDABE operon, and relative induction (fluorescence or luminescence) of the two constructs was tested side-by-side using a Tecan Infinite M200 Pro plate reader (see FIG. 38). The background noise was significantly lower for the Lux construct, allowing the detection of arsenic at a concentration of 0.2 nM. In contrast, the GFP construct was sensitive to arsenic only above a concentration of 26 nM. For comparison, we were able to detect an arsenic concentration of 130 nM using the GFP construct in a microfluidic device. Thus, replacing GFP with Lux promises to greatly increase the sensitivity of the biosensor.

Task C

Task Objective: Develop a prototype of a deployable device for cheap and continuous monitoring of water contamination by specific target compounds Metrics/Completion Criteria:

Milestone 6: Device prototype development

Milestone 7: Build computational models to determine the threshold of detection for specific sensors based on models of experimental GFP responses Milestone 8: Use the models obtained in Milestone 7 to investigate whether the combination of nonspecific sensor responses to some toxins can be utilized to improve specificity Milestone 9: Develop the controller board to carry out sophisticated analysis of complex data Deliverable: Finalized device prototype and computational algorithm for continuous water quality monitoring Reporting Updates Milestone 6: Device Prototype Development We have successfully completed this milestone. We obtained and characterized a low power peristaltic pump (Milestone 6.1). We have obtained a filter to prevent device clogging (Milestone 6.2). We have demonstrated that flow reversal to prevent clogging is not necessary based on our filtration design (Milestone 6.3). We have obtained an environmental enclosure and heater (Milestones 6.4 and 6.5). We have obtained and developed the software components necessary for device control and data transmission (Milestone 6.6). We have developed a positive control stock for sensor testing purposes (Milestone 6.7). We have developed a solar cell based charging system (Milestone 6.8). We have assembled a fully functional prototype and have tested it in an outdoor environment (Milestone 6.9).

Milestone 6.1: Find and Characterize a Low Power Pumping System that can Pump Natural Water Through the Microfluidic Device at a Rate of 1 ml/h:

We have purchased and tested a low power peristaltic pump compatible with microfluidics.

Milestone 6.2: Develop a Filter System to Prevent Clogging of the Microfluidic Device:

We have successfully implemented filtering to prevent clogging when pumping natural water sources.

Milestone 6.3: Develop a Flow Reversal Pumping Regime to Help Clear the Filter of Contaminants. Test and Revise the De-Clogging Method to Ensure a Runtime of at Least One Month Per Sensor:

Due to the success of our filter system developed in Milestone 6.2, we determined that flow reversal was not necessary.

Milestone 6.4: Develop a Waterproof Enclosure that can be Used to House the Device and the Electronics:

We have purchased and tested an all-weather enclosure suitable for outdoor use.

Milestone 6.5: Develop a Heating System to Ensure the Microfluidic Device Maintains the Appropriate Growth Temperature:

We have tested a heating system for our device.

Milestone 6.6:

Develop the electronics/software to coordinate the pumping regimes, image capture, data transmission and device power management: We have obtained the necessary hardware and software for controlling the electronic components of our biosensor. We assembled components to support the time-lapse fluorescence imaging and analysis of cells within microfluidic devices. We also implemented a low cost, low power, all-solid-state PandaBoard single board computer to control image acquisition and peripherals. We implemented a fluorescence imaging assembly designed by the Ziva Corporation (FIG. 7D) to mount in our prototype imaging scaffold. Light from a blue excitation LED reflects off a dichroic mirror and illuminates the sample. The optics collect fluorescent light emitted by the sample and pass it though the dichroic mirror and emission filter while focusing it to an image at the CCD camera. We developed a custom software package to control data acquisition, regulate pump speed, and maintain appropriate environmental conditions for the biosensor.

Milestone 6.7: Develop a Chemical Control Stock to Test the Proper Operation of the Biosensor (i.e. Add Low Doses of Toxins for Positive Control):

We developed concentrated chemical stocks of the eight toxins that are easily mixed to form a solution containing low doses of toxins to serve as a positive control in testing proper biosensor operation.

Milestone 6.8: Develop a Solar Powered Version of the Prototype, Including Battery Panels and Charge Controller):

We have developed an independent solar charging station that can easily interface with our biosensor device. To ensure compatibility with solar or battery power, we selected all components of our device (including the heater) to be DC powered. We then located and purchased an isolated DC/DC converter (Mean Well part #SD-50A-12) that is capable of generating a regulated 12 VDC output from an unregulated 9.2-18 VDC input. The regulated 12 VDC supply is used to power our pump, heater, and electronics. The unregulated 9.2-18 VDC input is within the voltage range of a standard lead acid battery; therefore, we purchased a deep cycle, lead acid battery (Interstate battery part #DCM0035) with sufficient energy storage (35 Ah) to power our device for approximately two days. To charge the battery, we purchased a 100 W monocrystalline solar panel and a 30 A pulse wave modulation (PWM) charge controller from Renology Solar. The solar panel components were assembled and mounted onto a galvanized steel pole at our field test facility.

Milestone 6.9: Develop a Completed Device Prototype and Test in an Outdoor Environment):

We have assembled the individual components listed in sub-milestones 6.1-6.8 into a functional prototype that is capable of acquiring and processing data. Images of this prototype are shown in FIG. 7.

Figure 56:
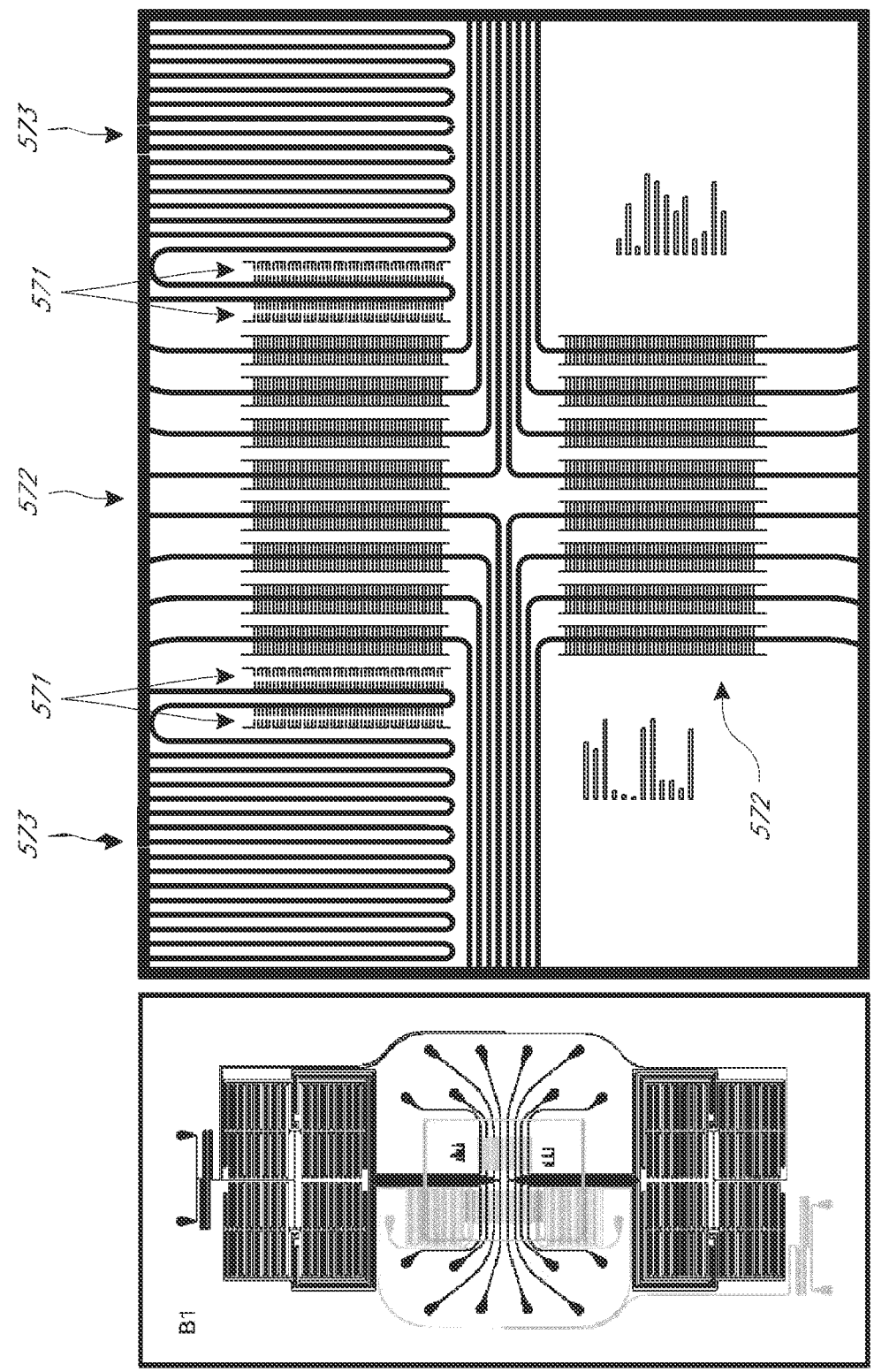
FIG. 56 shows a CAD drawing of the 18-strain microfluidic chip used to collect toxin response data from 18 different toxin-specific strains simultaneously. Left) View of the entire microfluidic device. The resistance to each cell trapping region is identical, ensuring equivalent flow to all areas of the device. Black channels: *E. coli* analyte distribution channels. channels 1: *B. subtilis* analyte distribution channels (573). rectangle (571): magnified area shown in the right panel. Right) The field of view captured by our imaging system. Red channels—(571): *B. subtilis* "gill" trapping regions. channels (572): *E. coli* "gill" trapping regions. The collections of rectangles flanking the lower *E. coli* trapping region are present to assist in automatic image registration.

We have finalized the design of our 18-strain microfluidic device that can collect toxin response data from 18 different toxin specific strains simultaneously (FIG. 56). This is housed inside our sensor prototype and imaged using our custom optics. The prototype is contained in a 16"_14" fiberglass enclosure (FIG. 7A) with an aluminum front panel designed to protect the interior components from the environment. A proportional-integral-derivative (PID) temperature controller is visible in the upper left hand corner of the front panel with the peristaltic water pump in the lower right corner. The interior of the prototype is shown in FIG. 7B with the electronics sub enclosure (FIG. 7B-1) and Ziva optical system clearly visible (FIG. 7B-5). The use of a PID controller rather than a simple thermostat is necessary for precise control of the enclosure's internal temperature to within 0.1_C of the set point. Individual components are numbered 1-8. Briefly, the electronics enclosure (FIG. 7B-1) contains the hardware for controlling the Ziva optics, processing images, and transmitting data. This system can also communicate with the temperature controller (FIG. 7B-2) to adjust the interior temperature of the enclosure (normally kept at 37° C.) using the Modbus protocol.

This version of the prototype is designed to be powered from a 120 VAC source, and the AC power distribution block, along with a supplemental protection circuit breaker and solid state relay for controlling the heater, is shown in FIG. 7B-3. A tri-voltage power supply, outputting 5, 12, and 24 VDC for the electronics and pumps, is shown in FIG. 7B-4. The Ziva optical system for acquiring image data is shown in FIG. 7B-5. The heater is combined with a circulating fan to distribute warm air throughout the enclosure (FIG. 7B-6). Briefly, the user inputs the desired temperature through a custom software package designed by our group that runs on the PandaBoard system (FIG. 7B-1). The PandaBoard communicates with the PID controller (FIG. 7B-2) to set the desired temperature using the Modbus protocol. The PID controller modulates the heater's activity based on the set point temperature and the current temperature of the enclosure. To regulate the heater's output, the PID controller generates a pulse wave signal that drives the activity of a solid state relay (FIG. 7B-3), which turns the heater's AC power source on and off (Note: the fan remains constantly on to circulate air). FIG. 7B-7 shows the DC power distribution system for the electronics and peristaltic water pump (FIG. 7B-8).

To mount the necessary electronics for acquiring and processing data and to protect them from water exposure, we designed a custom sub-enclosure using SolidWorks (Dassault Systems) and contracted its fabrication using additive manufacturing (3-D printing) by a local machine shop (FIG. 7C). A depiction of the SolidWorks representation of this enclosure, showing an Arduino Uno (FIG. 7C-1), BuckBlock LED drivers (FIG. 7C-2), PandaBoard system on a chip (FIG. 7C-3) and LED control relays (FIG. 7C-4) is shown in this Figure. The PandaBoard communicates with the Arduino over a RS-232 (serial) link to modulate the LED control relays. The Arduino then generates a pulse wave modulated output signal that is interpreted by the BuckBlock LED drivers to control the brightness of the LEDs (one each for transmitted light and GFP excitation). The PandaBoard is then responsible for acquiring an image from the Ziva optical system (FIG. 7B-5) and finally signaling for the LEDs to be turned off. The acquired data is analyzed on the PandaBoard, and the results are transmitted via a secure Wi-Fi link to our data repository server. The software to accomplish this was custom programmed in Java and C using the Point Grey FlyCapture SDK and implemented on a PandaBoard ES rev B.3 running Ubuntu Server. The various components of the Ziva optical system are shown in FIG. 7D, including the transmitted light optics (FIG. 7D-1), the microfluidic device stage and thermistor temperature probe (FIG. 7D-2), the focus adjustment system (FIG. 7D-3), the dichroic mirror holder (FIG. 7D-4), the GFP excitation system (FIG. 7D-5), and the Point Grey Chameleon monochrome camera (FIG. 7D-6). An image of a microfluidic device, illuminated with the Ziva GFP excitation optics is shown in FIG. 7E. We built five replicates of this completed prototype to run in our laboratory to collect data for the classifier. As proof of principle, we have also demonstrated that the biosensor can run in an outdoor environment and draw a sample of raw water from a public water source (FIG. 7F).

Milestone 7: Build Computational Models to Determine the Threshold of Detection for Specific Sensors Based on Models of Experimental GFP Responses Summary: We have successfully completed this milestone. We used machine learning techniques to determine the relationships between the GFP output signal and the presence of a toxin (Milestone 7.1). We have created a database containing the collected sensor response data and have incorporated all of the collected data (Milestone 7.2). We have quantified the GFP threshold of detection for each sensor construct (Milestone 7.3). We have constructed Receiver Operating Characteristic (ROC) curves for each sensor to achieve robust sensing (Milestone 7.4).

Milestone 7.1: Characterization of the Family of GFP Sensor Responses to the Set of Chemicals of Interest Via Computational Models):

We constructed machine learning models capable of inferring the relationships between the GFP sensor responses and the presence or absence of a toxin at a given concentration. The algorithm learns these relationships from a set of training samples (GFP sensor responses) defined by the set of experimental conditions from which they were generated. The aim of the algorithm is to provide a general method capable of determining the experimental conditions associated with GFP sensor responses through the use of historical data.

Specifically, we have built classification models based on Support Vector Machines (SVMs), which is one of the most popular classifiers due to its excellent performance in many contexts and its solid mathematical basis. For each toxin and concentration, we solved a binary classification problem in which the positive class represents the presence of the toxin in water and the negative class is associated with clean environments. Patterns were constructed with features containing GFP sensor responses at various timestamps to capture the temporal dynamics of the GFP signal. The optimal meta-parameters of the SVM classifier were determined by applying a 5-crossvalidation during the training phase.

In order to have a reliable estimate of the performance of the model when deployed in real environments, we measured its performance over a set of samples (test patterns) not seen during the training phase. The SVM's performance was determined by the percentage of test samples correctly labeled as toxin/no toxin (classification accuracy). 80% of samples were used for training the SVM models and the remaining 20% of samples was used to evaluate their effectiveness. We generated 20 random training/test partitions based on data collected in single-strain chips (no crosstalk data) to have an estimate of performance. Table 10 shows the average classification accuracy over the test set obtained across the 20 random partitions for each binary classification problem.

TABLE 10

Classification accuracy results obtained from the GFP sensor responses for multiple toxins at different concentrations

| Toxin | Conc. (µM) | Accuracy (%) |
| --- | --- | --- |
| Arsenic (pRS18) | 0.2 | 97.35 |
| | 0.55 | 100 |
| | 1 | 100 |
| Arsenic (pZA47a) | 0.1 | 97.35 |
| | 0.5 | 100 |
| | 1 | 100 |
| Cadmium | 0.022 | 65.00 |
| | 0.044 | 54.16 |
| | 0.44 | 90.00 |
| Chromium(VI) | 1.25 | 96.67 |
| | 2.5 | 97.50 |
| | 5 | 94.17 |

TABLE 10-continued

Classification accuracy results obtained from the GFP sensor responses for multiple toxins at different concentrations

| Toxin | Conc. (µM) | Accuracy (%) |
|---|---|---|
| Copper | 5 | 95.00 |
| | 10 | 96.67 |
| | 20 | 95.00 |
| Lead | 1.8 | 95.83 |
| | 3.6 | 95.00 |
| | 7.2 | 95.00 |
| Mercury | 0.2 | 63.33 |
| | 1 | 87.50 |
| | 2 | 99.17 |
| Ammonium | 1 ppm | 71.05 |
| | 5 ppm | 91.79 |

Milestone 7.2: Construction of a Database of Sensors' Responses to Chemicals of Interest and Null Chemicals to be Able to Establish the Statistical Significance in Detection:

We have constructed a database that is stored using MySQL in a Thecus NAS system capable of storing 22 TB of data. All of the image sequences gathered from the five device prototypes have been organized into a directory structure for each device and experiment. A master file containing the time stamp of each image and its file location has been compiled for quick image access via a Network File System (NFS). After being processed for rotation/translation and feature extraction, these images are the input variables to the machine learning algorithms. The training data is currently stored using the following columns of information:

1. Date time
2. Date time in milliseconds since Unix epoch
3. Experiment ID
4. Device number
5. Toxin concentration at the start point
6. Concentration units at the start point
7. Toxin at the start point
8. Toxin at the start point using machine learning label (see below)
9. Multiple toxin flag at the start point (are there multiple toxins? Y/N)
10. Toxin concentration at the end point
11. Concentration units at the end point
12. Toxin at the end point
13. Toxin at the end point using machine learning label
14. Multiple toxin flag at the end point
15. Responding strains
16. Additional notes
17. Delay time (time before the toxin(s) reach(es) the cells)
18. Success flag (did experiment complete successfully? Y/N)

The machine learning toxin labels are as follows: MilliQ ddH20=Code 1; Arsenic, As=2; Cadmium, Cd=3; Cobalt, Co=4; Chromium (VI), Cr=5; Copper, Cu=6; Mercury, Hg=7; Malathion, Mal=8; Lead, Pb=9; gfp tracer=10; and Ammonium, NH4-N=11.

Milestone 7.3: Quantification of the GFP Threshold of Detection with Respect to the Concentration Levels of the Toxins):

Based on the results of Milestone 7.1 (Table 10) and the ROC curves (FIG. 8), the models establish the limits of detection that are described in Table 11.

TABLE 11

Toxin detection results for each toxin at various concentrations using a two-sample T-test at a 0.05 significance level. The first column is the actual concentration, the second column is the average estimated concentration, the third column is the standard deviation of the estimation, and the fourth column is the result of the test.

| Toxin | Actual Conc. (µM) | Estimated Conc. (µM) | Std. Dev. Of Est. Conc. | T-Test Result |
|---|---|---|---|---|
| Arsenic | 0.000000 | 0.094873 | 0.054253 | FAIL |
| | 0.100000 | 0.166705 | 0.039146 | PASS |
| | 0.200000 | 0.121520 | 0.045036 | PASS |
| | 0.500000 | 0.269255 | 0.042667 | PASS |
| | 1.000000 | 0.290522 | 0.029472 | PASS |
| Cadmium | 0.000000 | 0.073605 | 0.039364 | FAIL |
| | 0.025000 | 0.084992 | 0.035848 | PASS |
| | 0.050000 | 0.061783 | 0.019154 | FAIL |
| | 0.100000 | 0.081460 | 0.028670 | PASS |
| | 0.440000 | 0.258721 | 0.054637 | PASS |
| Chromium(VI) | 0.000000 | 0.402180 | 0.211879 | FAIL |
| | 0.200000 | 0.458967 | 0.162400 | PASS |
| | 0.500000 | 0.558889 | 0.163777 | PASS |
| | 1.000000 | 0.816885 | 0.133032 | PASS |
| | 5.000000 | 1.215800 | 0.324680 | PASS |
| Copper | 0.000000 | 1.037426 | 0.628584 | FAIL |
| | 0.100000 | 0.138169 | 0.120940 | FAIL |
| | 0.500000 | 0.890369 | 0.184934 | FAIL |
| | 1.000000 | 1.428817 | 0.437622 | PASS |
| | 2.000000 | 2.332876 | 0.320600 | PASS |
| | 5.000000 | 1.875258 | 0.285088 | PASS |
| | 10.000000 | 2.931468 | 0.816670 | PASS |
| Lead | 0.000000 | 0.674518 | 0.526677 | FAIL |
| | 0.600000 | 0.917133 | 0.294116 | PASS |
| | 1.800000 | 1.636931 | 0.326718 | PASS |
| | 3.600000 | 2.284836 | 0.987410 | PASS |
| | 7.200000 | 3.417676 | 1.085822 | PASS |
| Mercury | 0.000000 | 0.247743 | 0.185409 | FAIL |
| | 0.100000 | 0.241039 | 0.102734 | FAIL |
| | 0.200000 | 0.245659 | 0.087578 | FAIL |
| | 0.500000 | 0.392381 | 0.067889 | PASS |

TABLE 11-continued

Toxin detection results for each toxin at various concentrations using a two-sample T-test at a 0.05 significance level. The first column is the actual concentration, the second column is the average estimated concentration, the third column is the standard deviation of the estimation, and the fourth column is the result of the test.

| Toxin | Actual Conc. (μM) | Estimated Conc. (μM) | Std. Dev. Of Est. Conc. | T-Test Result |
|---|---|---|---|---|
| | 2.000000 | 0.968285 | 0.084330 | PASS |
| | 6.000000 | 1.548434 | 0.286386 | PASS |

Toxin detection results at various concentrations were determined by using a two-sample T-test at a 0.05 significance level. A nonlinear support vector regressor was used with the metaparameters cross validated using 5-fold cross-validation.

Milestone 7.4: Construction of the Receiver Operating Characteristic Curve (ROC) for the Sensors to Minimize False Negatives and False Positives):

The results in Milestone 7.1 were obtained by assuming that the penalties of misclassification are identical for positive and negative classes. In other words, the cost of classifying a GFP signal as "toxic" when it is not (or vice versa) is the same. However, it may be the case that the cost is not symmetric for positive and negative cases. A water sensor is a good example of this situation, since it might be preferable to ensure high accuracy when toxins are actually in the water (true positive rate, TP) in exchange for increasing the number of cases that are classified as "toxin present" when there is not any toxin in the water (false positive rate, FP). The Receiver Operating Characteristic (ROC) curve is a 2-D parametrized curve used to quantify and represent the tradeoff between the true positive rate and the false positive rate of a given classifier. The abscissa represents the False Positive rate, while the ordinate shows the True Positive rate. Therefore, the optimal classifier is represented by a point in the upper left corner of the ROC curve, since this point corresponds to the best possible case in which the classifier is able to correctly identify 100% of positive cases (toxin present) with no false alarms.

The parameter that defines the ROC curve in our classification model is the decision threshold, which determines whether a pattern (GFP signal) is classified as positive (toxin present) or negative (toxin not present). The SVM model provides a value (decision function) for each pattern that represents the confidence of the model in its prediction, and the final classification is obtained by assigning to the negative class those points with decision functions that are below the decision threshold, and classifying as positive samples those patterns with decision functions above this threshold. Therefore, by sweeping a grid of possible values for the SVM decision threshold, we obtained the ROC curves for the various toxins shown in FIG. 8.

Milestone 8: Use the Models Obtained in Milestone 7 to Investigate Whether the Combination of Nonspecific Sensor Responses to Some Toxins can be Utilized to Improve Specificity Summary: We have successfully completed this milestone. We have demonstrated the high specificity of the strains we have developed (Milestone 8.1), and we have used state-of-the-art pattern recognition algorithms to improve the performance of the classifier (Milestone 8.2).

Milestone 8.1: Estimation of the Number of Nonspecific Sensors Required to Achieve Maximum Specificity in the Discrimination of the Target Chemicals:

Because we used RNA-Seq to find promoters that were highly chemically specific, we found there to be only a small amount of crosstalk. The combinatoric information provided by nonspecific responses was used to strengthen classification performance. To demonstrate this, we trained a classifier using a nonlinear support vector machine on the GFP images concatenated to the estimations of the pixel derivatives for two different time scales. In Table 9 we present the confusion matrix of the sensor-specific strains to six different chemicals at various concentrations.

TABLE 12

Confusion matrix solving a multiclass classification task for the following classes: baseline, Arsenic, Cadmiun, Chromium(VI), Copper, Lead, and Mercury. Cobalt also performs well, but there is not enough data to provide proper statistics. The machine learning algorithm used to calculate this table is a calibrated multiclass support vector machine using 10-fold cross validation on the data. This matrix should be read from left to right. For example, lead is confused with baseline activity 6.4% of the time at low concentrations, while it rarely gets confused with Mercury. The main diagonal indicates how often the algorithms provide the right answer (e.g. 81.3% of the time for lead).

| | None | Arsenic | Cadmium | Chromium(VI) | Copper | Lead | Mercury |
|---|---|---|---|---|---|---|---|
| None | 87.4% | 2.0% | 2.6% | 1.6% | 0.8% | 2.6% | 3.0% |
| Arsenic | 6.2% | 47.3% | 7.4% | 10.9% | 9.3% | 4.7% | 14.3% |
| Cadmium | 6.7% | 6.2% | 73.3% | 1.3% | 4.6% | 2.8% | 5.1% |
| Chromium(VI) | 4.8% | 10.6% | 1.5% | 74.9% | 3.4% | 3.4% | 1.3% |
| Copper | 2.1% | 7.7% | 4.5% | 2.9% | 76.5% | 2.4% | 3.9% |
| Lead | 6.4% | 2.9% | 2.6% | 2.7% | 2.3% | 81.3% | 1.8% |
| Mercuiy | 6.2% | 10.1% | 4.0% | 0.9% | 3.1% | 1.5% | 74.2% |

The derivation of this matrix includes all of the available concentrations in the experiments, taking into account any non-specific responses of the sensor-specific strains. Importantly, it demonstrates that the classifier can discriminate between the toxins. That is, in each row, there is one maximum number (i.e. the sensor responding to the correct toxin), and the rest of the numbers are uniformly low.

Generally, multi-class classification results nearing 80% represent a highly successful algorithm, particularly given the novelty of the devices and the data acquisition protocols. One issue contributing to negative results is the way in which we probed the sensors. We initially exposed the sensors to higher levels of toxins to verify that we could detect responses. However, once we established that we could sense these toxins well, we dropped down to much lower levels near the detection limit for the majority of the subsequent inductions. This weighted our data heavily toward the realm of low responses and low signal, skewing our results to contain more errors. As we have only begun to probe the parameter space, we expect to strengthen the confusion matrix significantly as we move forward.

We have performed a similar analysis of our recent data collected using the 18-strain chip. This chip contains the new ammonium strain, which provides for a new confusion matrix, as seen in Table 13,

TABLE 13

Confusion matrix obtained from the 18-strain data.

|  | None | Arsenic | Cadmium | Chromium(VI) | Cobalt | Copper | Lead | Ammonium |
| --- | --- | --- | --- | --- | --- | --- | --- | --- |
| None | 45.02% | 7.66% | 0.75% | 13.48% | 9.69% | 2.56% | 5.26% | 15.64% |
| Arsenic | 3.50% | 92.58% | 0.00% | 0.14% | 0.00% | 0.00% | 0.00% | 3.78% |
| Cadmium | 4.72% | 0.00% | 93.11% | 2.17% | 0.00% | 0.00% | 0.00% | 0.00% |
| Chromium(VI) | 8.05% | 0.18% | 0.25% | 90.43% | 0.11% | 0.11% | 0.52% | 0.35% |
| Cobalt | 9.75% | 0.00% | 0.00% | 0.21% | 89.32% | 0.49% | 0.00% | 0.22% |
| Copper | 15.73% | 0.00% | 0.00% | 1.12% | 2.75% | 78.27% | 0.00% | 2.14% |
| Lead | 7.71% | 0.00% | 0.00% | 1.22% | 0.00% | 0.00% | 90.76% | 0.31% |
| Ammonium | 10.94% | 4.99% | 0.00% | 0.35% | 0.12% | 0.19% | 0.12% | 83.30% |

This is a confusion matrix generated by taking the average of ten non-overlapping partitions of the training set (80% of the data) and the test set (20% of the data). Every training set of a partition was cross-validated to obtain the optimal metaparameters. After the cross-validation, the models were applied to the test set. We find that ammonium can be discriminated from the rest of the toxins 83% of the time.

Milestone 8.2: Apply State of the Art Pattern Recognition Algorithms Using the Database Built for Milestone 7 to Improve Performance of the Detection:

We have employed nonlinear support vector machine classification on images that have undergone two types of transformation: 1) rotation and translation of the image with respect to a template for each of the sensor device setups (FIG. 57), and 2) an exponential moving average on the derivatives of the images to filter the pixel noise.

Figure 57:
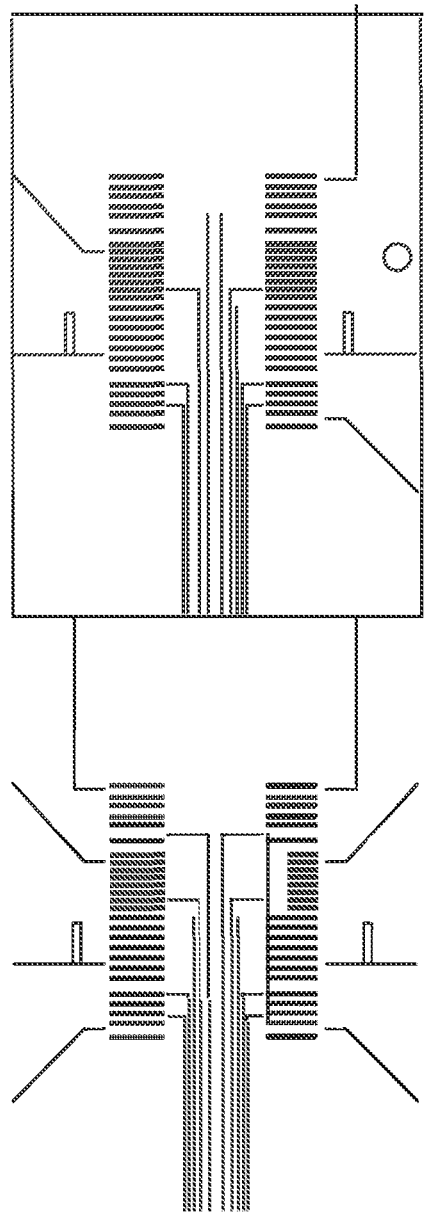
FIG. 57 shows on left panel: the template image used to align the images from all of the devices. The Right panel: the result of applying the algorithm to an image.

We tried two different algorithms for image rotation and translation: minimization of the scalar product of the image with the template reference image, and a normalized Euclidean distance from the bright field image to the template. We found the Euclidean distance to be the most effective method. The algorithm can run in real time to track the variations of the image's location in the device (FIG. 57). Once the images have been aligned, we can apply a feature extraction algorithm to zoom in on the traps where the strains are located.

The feature extraction algorithm involves two phases: image reduction and derivative calculation. The image reduction phase applies a smoothing algorithm on neighboring pixels according to a circular kernel using a radius of 41 pixels. The weights provided to the kernel have the maximum value in the center of the circle and decrease to a minimum value at the border of the circle. After the smoothing has been applied, the image is scaled from 720×640 pixels to 45×40 pixels. This operation reduces the size of the feature space significantly.

Figure 58:
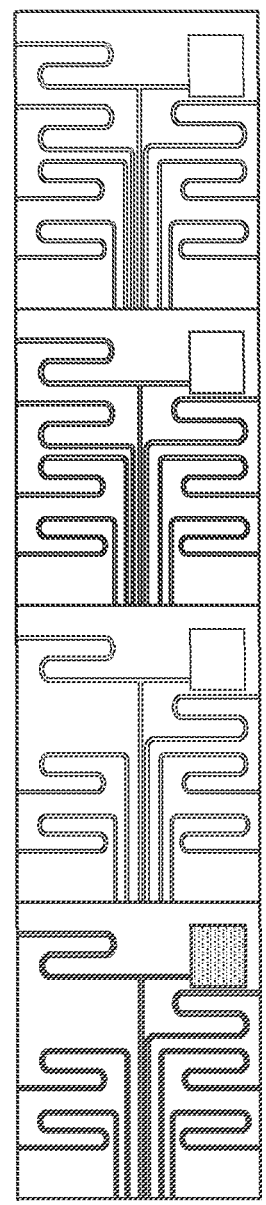
FIG. 58 shows an example of the results of the image transformation after applying the alignment, compression, and feature extraction on the GFP signal. This is the input signal that is provided to the classifier. The left square is the original image, and the other three squares show the changes made by the image processing techniques.

The feature extraction algorithm next calculates the derivatives of the images to enhance the dynamic changes in the chip. The formula is calculated as $\Delta p^\kappa_{ij}(t)=\alpha^\kappa \rho_{ij}(t)+(1-\alpha)(1-\rho^\kappa_{ij}(t-1))$, and the time scales used in the filter are $\alpha^1=1/11$, $\alpha^2=1/26$, and $\alpha^3=1/51$. In the end, the total number of features is (45×40)×4. In FIG. 58 we show the original GFP image and the result of the derivative estimation using three time scales ($\alpha^1$, $\alpha^2$, $\alpha^3$).

After the feature extraction algorithm has been applied, the classifier is trained using 80% of the data and tested using the remaining 20%. We apply a 10-fold cross validation on the 80% of the training data to determine the optimal model parameters before we test the model on the remaining 20%. The confusion matrices are then calculated by running an average on ten partitions of train and test. For the 8-strain chip data, the cross-validated classification accuracy obtained is 76% with a standard deviation of 2.57%. The results are summarized in the confusion matrix (Table 12). Arsenic is the toxin that has the highest likelihood of being confused with other toxins. This is due to collecting a majority of our data at very low arsenic levels to test the limits of the sensor, which skews the results. We have been continuously collecting data using five replicates of the sensor undergoing different alignment and feature extraction algorithms. Overall, we are extremely satisfied with the performance of this state-of-the-art classifier on this dataset, particularly given the limited amount of data collected thus far. Moreover, we have been intentionally probing the strains with concentration levels that are difficult to detect and classify. As we continue to collect data with all 18 strains, the classifier will improve further.

Milestone 9: Develop the Controller Board to Carry Out Sophisticated Analysis of Complex Data Summary: We have successfully completed this milestone. A PandaBoard system on a chip (SoC) was selected for the primary control system which contains integrated Wi-Fi (Milestone 9.1). We have developed advanced image processing algorithms and embedded them on the PandaBoard (Milestone 9.2). We have developed algorithms which can easily be stored and loaded on our PandaBoard SoC (Milestone 9.3).

Milestone 9.1: Design the Controller Board with Wireless Capability:

We tested two low-power platforms based on the Texas Instruments ARM processor with wireless capability: one based on the Sitara ARM and the other based on the Cortex-A9. We have opted for the more powerful Cortex-A9 due to the ease of use and low power consumption. We are currently using a PandaBoard, which is powered by a Texas Instruments OMAP4430 system on a chip (SoC) device. The OMAP4430 chipset contains a dual-core 1 GHz ARM Cortex-A9 MPCore CPU with 1 GB of DDR2 SDRAM, Wi-Fi capability, and an SD card slot offering up to 32 GB of storage. The electronics are similar to a modern smartphone in terms of processing power and power consumption. The PandaBoard solution allows us to install a Linux operating system so that we can use standard GNU compilers and run our software without any major modifications, which we demonstrate in the next two aims.

Milestone 9.2: Reduce the Size of the Pattern Recognition Algorithms to be Able to be Embedded in the PandaBoard.

Fluorescence images are used to train our classifier to be able to detect and discriminate between different toxins. In order to speed up the operation of the classifier, we must reduce its computational cost, which is directly linked to the number of images and the number of features in each image. Each image consists of a set of numerical features, each containing the intensity of a pixel in the image. Fortunately, the images contain many irrelevant features and regions as well as a large number of redundant features in neighboring pixels. Therefore, it is extremely useful to apply a feature selection algorithm to find the most informative features and to reduce the computational cost of the classifier. In Milestone 8.2, we describe the image processing and feature selection process that enabled us to reduce computational cost and embed our algorithms in the PandaBoard.

Milestone 9.3: Embed the Algorithms in the Microcontroller.

We have compiled and executed nonlinear support vector machines 24 on the images described in Milestone 9.2 after the feature selection process. We compiled the software, trained the model, and ran the trained model without any problems. The algorithms were developed using the openMP API and compiled using GNU g++. Both are well established and stable options that run well on the PandaBoards. We implemented aggressive compiler optimizations to produce native code that runs fast on the multicore Cortex-A9 processors. Resulting performance was more than sufficient to allow real-time operation, with our embedded algorithms proving capable of classifying each image within 0.05 seconds.

As shown in FIG. 59 (FIGS. 59A-D), a single strain bank within this device is shown in FIG. 59 panel A. Each strain is spotted within a reservoir (1), where it expands via growth through feeder channels (2) into ten vertical trapping chambers (3). The cells proliferate in exponential phase within the trapping chambers due to the delivery of fresh medium by convection through an adjacent channel (4) and diffusion into the trapping chambers. Excess proliferating cells extend out of the trapping chamber into the medium delivery channel, where they are cleared by convective flow. Trapping chambers remain densely packed due to cross-seeding by neighboring gills via a linker channel (5). The exponentially-growing culture in the trapping regions is imaged periodically to measure the reporter response to various agents introduced through the medium delivery channel.

Figure 59A:
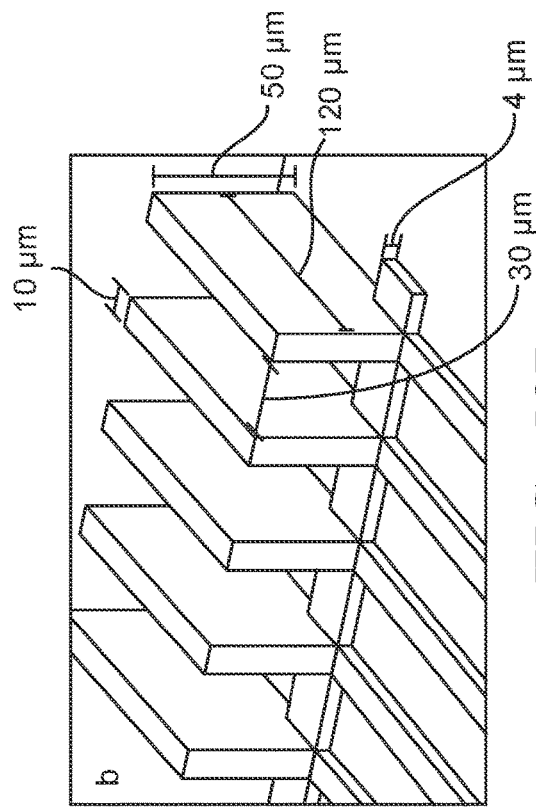
FIG. 59 (59A-59D) shows parallelized microfluidic device housing 2,048 unique engineered strains from two microbes in panels A, B, C and D. As shown a single strain bank within this device is shown in FIG. 1A. Each strain is spotted within a reservoir (1), where it expands via growth through feeder channels (2) into ten vertical trapping chambers (3). The cells proliferate in exponential phase within the trapping chambers due to the delivery of fresh medium by convection through an adjacent channel (4) and diffusion into the trapping chambers. Excess proliferating cells extend out of the trapping chamber into the medium delivery channel, where they are cleared by convective flow. Trapping chambers remain densely packed due to cross-seeding by neighboring gills via a linker channel (5). The exponentially-growing culture in the trapping regions is imaged periodically to measure the reporter response to various agents introduced through the medium delivery channel.
Figure 59B:
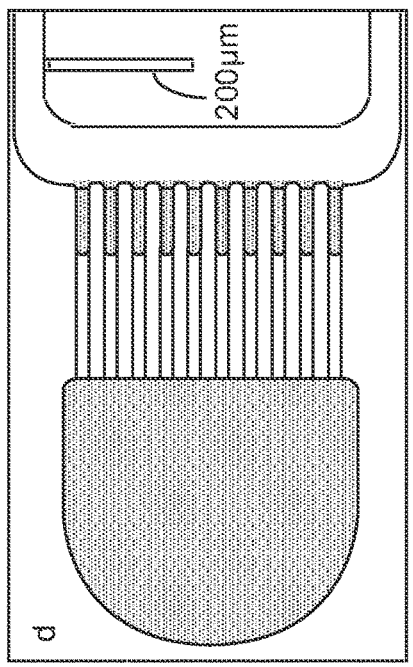

The cell trapping chambers are shown in detail in the FIG. 59B. The chamber width is restricted to 10 μm to retain cells by limiting convective flow. The maximum chamber length of 120 μm is restricted by the delivery of nutrients to the rear of the trap via diffusion. The chamber height of 50 μm was chosen to maximize photon collection along the vertical imaging axis while limiting the chamber aspect ratio to facilitate fabrication using standard methods. The cell chamber geometry and quantity per bank may be optimized for various reporter strengths and imaging sensitivities.

Figure 59C:
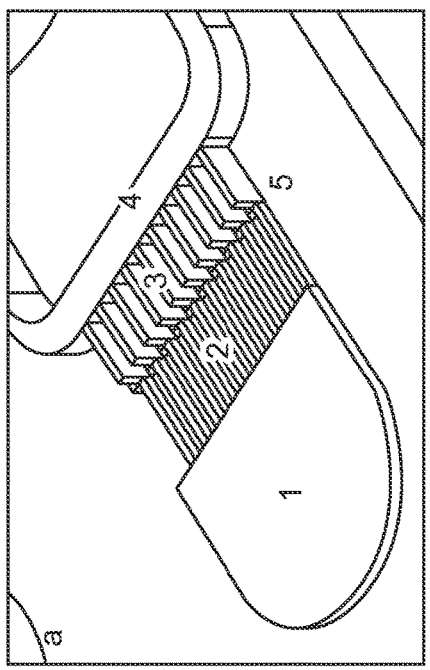

FIG. 59C shows a highly parallelized microfluidic device capable of housing 2,048 unique engineered strains. This embodiment of the device is divided into two strain arrays to allow simultaneous culturing and imaging of 1,024 reporter libraries of two microbial species. The pitch and format of the strain banks is compatible with spotting using a robotic pin tool or liquid handling instrument.

Figure 59D:
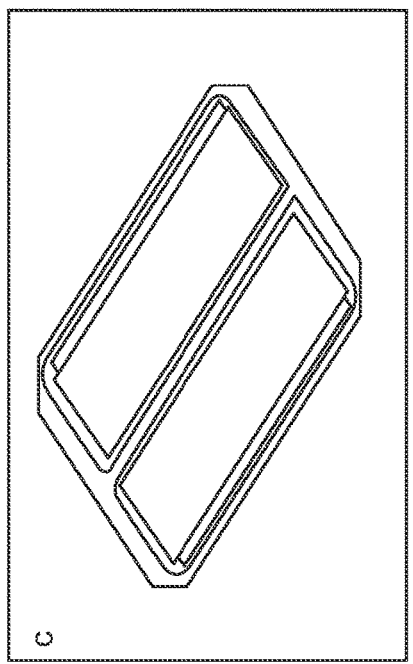

FIG. 59D shows a transmitted light image of an engineered strain growing exponentially within the trapping chambers of a single strain bank.

Figure 60:
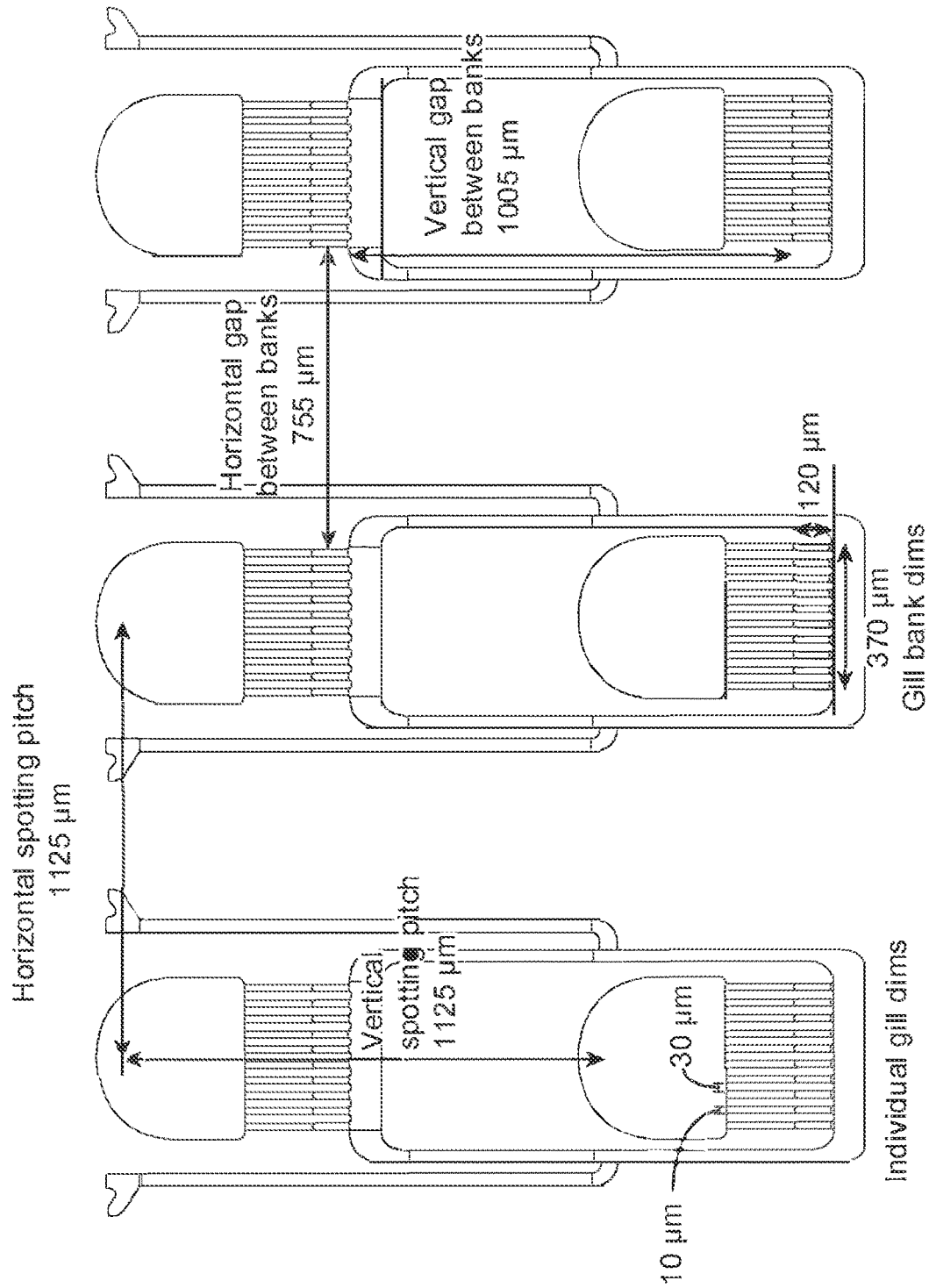
FIG. 60 shows a microfluidic strain bank format compatible with a 6,144-well SBS microplate.

The format of the array of strain banks within our microfluidic device is shown in FIG. 60. The horizontal and vertical spotting pitch is 1.125 mm, which is compatible with the well spacing of a 6,144-format SBS microplate. Our adherence to the 6,144-format microplate standard allows us to easily spot up to 6,144 unique engineered strains within the 85.48×127.76 mm footprint of a standard SBS microplate. The robotic tool used to spot strains into the cell reservoirs may be either (1) a pin tool designed to transfer cells from solid or liquid medium or (2) a liquid handling tool designed to transfer cells from a liquid culture.

As shown in FIG. 60, in various embodiments, the microfluidic device may be fabricated from PDMS, glass, and/or thermoplastics using photolithography, molding, etching, and/or embossing processes. The microfluidic device is assembled by sealing a monolith with recessed strain banks and channels against a flat compatible material. Following fabrication of the monolith, strains are robotically spotted into the recessed strain banks. Finally, the monolith is bonded to a flat material using a compatible method such as thermal fusion, chemical or plasma surface activation, or the addition of an adhesive layer.

For the Sensor Strains, the pLB-Hg-i and pLB-Pb-i plasmids can also be used in some embodiments. These are not specifically sensor plasmids on their own, but can also be combined with any of our single-plasmid sensor strains, to make additional 2-plasmid sensor strains.

More Embodiments

In some embodiments, a microfluidic device comprising one or more colonies or cultures of microorganism cells at one or more predetermined addressable locations, wherein each of the cells within the one or more colonies or cultures comprises an expression cassette comprising a biosensor or promoter operably linked to a polynucleotide encoding a detectable agent, wherein transcription of the biosensor or promoter is modulated by the presence of an analyte. In some embodiments, the detectable agent is a nucleic acid, detectable protein, antibody-linked reporter protein, enzymatic assay product, or electrochemical reaction product. In some embodiments, the detectable protein comprises an activity that is increased or decreased in the presence of an analyte. In some embodiments, the detectable agent is a detectable protein, wherein the detectable protein provides a detectable signal. In some embodiments, the detectable protein is a fluorescent protein or a luminescent protein. In some embodiments, the nucleic acid is RNA or DNA. In some embodiments, the microfluidic device further comprises microfluidic channels or lumens arranged in a rotationally symmetric gill cell trapping configuration. In some embodiments, the microfluidic channels or lumens are arranged in 16 or 18 rotationally symmetric gills. In some embodiments, the device comprises about 20,000 chambers or gill traps. In some embodiments, transcription of the biosensor or promoter is induced, promoted or increased by the presence of an analyte. In some embodiments, wherein transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the biosensor or promoter comprises a polynucleotide having a sequence identity of at least about 90% to a polynucleotide sequence selected from the group consisting of SEQ ID NOs: 1-43. In some embodiments, the biosensor or promoter comprises a polynucleotide having a sequence identity of at least about 90% to a polynucleotide sequence selected from the group consisting of SEQ ID NOs: 2, 5, 8, 11, 12, 13, 14, 15, 16, 17, 20, 23, 25, 28, 29, 30 and 33. In some embodiments, transcription of the biosensor or promoter is decreased or inhibited by the presence of an analyte. In some embodiments, the biosensor or promoter is decreased or inhibited by the presence of ammonia. In some embodiments, the biosensor or promoter is decreased or inhibited by the presence of ammonia is selected from the group consisting of PnasA (ammonia), PnasB (ammonia), Pspo1-tnrA1 (ammonia) and Pspo1-tnrA2 (ammonia). In some embodiments, the biosensor or promoter comprises a polynucleotide sequence having at least about 90% sequence identity to SEQ ID NO:1. In some embodiments, the device detects or monitors the presence or levels of one or more analytes at the following concentrations: a) at least about 0.2 nM arsenic; b) at least about 0.44 µM cadmium; c) at least about 2.5 µM chromium (VI); d) at least about 5 µM copper; e) at least about 1 µM mercury; 0 at least about 1.8 µM lead; g) at least about 72.5 mg/l malathion; and/or h) at least about 1 ppm ammonia. In some embodiments, the microorganism cells are selected from the group consisting of bacteria, cyanobacteria, microalgae and fungi. In some embodiments, the microorganism cells comprise a bacteria selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans*, and *Staphylococcus aureus*. In some embodiments, the microorganism cells comprise a fungus selected from the group consisting of *Saccharomyces cerevisiae* and *Trichosporon cutaneum*. In some embodiments, the microorganism cells comprise *Synechocystis* sp. In some embodiments, the device is capable of culturing at least about 4,000 individual strains of microorganism cells. In some embodiments, the expression cassette is in a plasmid transformed into the microorganism. In some embodiments, the expression cassette is integrated into the genome of the microorganism. In some embodiments, the one or more colonies or cultures of microorganisms are lyophilized (freeze-dried). In some embodiments, the one or more colonies or cultures of microorganisms are one or more different species. In some embodiments, the one or more colonies or cultures of microorganisms are the same species. In some embodiments, the detectable protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the detectable protein is a luminescent protein. In some embodiments, the luminescent protein is bacterial luciferase (Lux). In some embodiments, said microfluidic device comprises a plurality of said colonies or cultures and wherein each of said plurality of colonies or cultures comprises an expression cassette comprising a biosensor or promoter operably linked to a polynucleotide encoding a detectable agent wherein transcription of the biosensor or promoter is modulated by the presence of a different analyte than the biosensor or promoter in the other of said plurality of colonies or cultures. In some embodiments, the plurality of colonies or cultures comprises at least 2 colonies or cultures, 3 colonies or cultures, 4 colonies or cultures, 5 colonies or cultures, 6 colonies or cultures or 7 colonies or cultures. In some embodiments, the colonies or cultures comprise microorganism cells are selected from the group consisting of bacteria, cyanobacteria, microalgae and fungi. In some embodiments, the transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc).

In some embodiments, a system comprising the microfluidic device of any one of the embodiments described herein, is provided. In some embodiments, the microfluidic device comprises one or more colonies or cultures of microorganism cells at one or more predetermined addressable locations, wherein each of the cells within the one or more colonies or cultures comprises an expression cassette comprising a biosensor or promoter operably linked to a polynucleotide encoding a detectable agent, wherein transcription of the biosensor or promoter is modulated by the presence of an analyte. In some embodiments, the detectable agent is a nucleic acid, detectable protein, antibody-linked reporter protein, enzymatic assay product, or electrochemical reaction product. In some embodiments, the detectable protein comprises an activity that is increased or decreased in the presence of an analyte. In some embodiments, the detectable agent is a detectable protein, wherein the detectable protein provides a detectable signal. In some embodiments, the detectable protein is a fluorescent protein or a luminescent protein. In some embodiments, the nucleic acid is RNA or DNA. In some embodiments, the microfluidic device further comprises microfluidic channels or lumens arranged in a rotationally symmetric gill cell trapping configuration. In some embodiments, the microfluidic channels or lumens are arranged in 16 or 18 rotationally symmetric gills. In some embodiments, the device comprises about 20,000 chambers or gill traps. In some embodiments, transcription of the biosensor or promoter is induced, promoted or increased by the presence of an analyte. In some embodiments, wherein transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the biosensor or promoter comprises a polynucleotide having a sequence identity of at least about 90% to a polynucleotide sequence selected from the group consisting of SEQ ID NOs: 1-43. In some embodiments, the biosensor or promoter comprises a polynucleotide having a sequence identity of at least about 90% to a polynucleotide sequence selected from the group consisting of SEQ ID NOs: 2, 5, 8, 11, 12, 13, 14, 15, 16, 17, 20, 23, 25, 28, 29, 30 and 33. In some embodiments, transcription of the biosensor or promoter is decreased or inhibited by the presence of an analyte. In some embodiments, the biosensor or promoter is decreased or inhibited by the presence of ammonia. In some embodiments, the biosensor or promoter is decreased or inhibited by the presence of ammonia is selected from the group consisting of PnasA (ammonia), PnasB (ammonia), Pspo1-tnrA1 (ammonia) and Pspo1-tnrA2 (ammonia). In some embodiments, the biosensor or promoter comprises a polynucleotide sequence having at least about 90% sequence identity to SEQ ID NO:1. In some embodiments, the device detects or monitors the presence or levels of one or more analytes at the following concentrations: a) at least about 0.2 nM arsenic; b) at least about 0.44 µM cadmium; c) at least about 2.5 µM chromium (VI); d) at least about 5 µM copper; e) at least about 1 µM mercury; f) at least about 1.8 µM lead; g) at least about 72.5 mg/l malathion; and/or h) at least about 1 ppm ammonia. In some embodiments, the microorganism cells are selected from the group consisting of bacteria, cyanobacteria, microalgae and fungi. In some embodiments, the microorganism cells comprise a bacteria selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans*, and *Staphylococcus aureus*. In some embodiments, the microorganism cells comprise a fungus selected from the group consisting of *Saccharomyces cerevisiae* and *Trichosporon cutaneum*. In some embodiments, the microorganism cells comprise *Synechocystis* sp. In some embodiments, the device is capable of culturing at least about 4,000 individual strains of microorganism cells. In some embodiments, the expression cassette is in a plasmid transformed into the microorganism. In some embodiments, the expression cassette is integrated into the genome of the microorganism. In some embodiments, the one or more colonies or cultures of microorganisms are lyophilized (freeze-dried). In some embodiments, the one or more colonies or cultures of microorganisms are one or more different species. In some embodiments, the one or more colonies or cultures of microorganisms are the same species. In some embodiments, the detectable protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the detectable protein is a luminescent protein. In some embodiments, the luminescent protein is bacterial luciferase (Lux). In some embodiments, said microfluidic device comprises a plurality of said colonies or cultures and wherein each of said plurality of colonies or cultures comprises an expression cassette comprising a biosensor or promoter operably linked to a polynucleotide encoding a detectable agent wherein transcription of the biosensor or promoter is modulated by the presence of a different analyte than the biosensor or promoter in the other of said plurality of colonies or cultures. In some embodiments, the plurality of colonies or cultures comprises at least 2 colonies or cultures, 3 colonies or cultures, 4 colonies or cultures, 5 colonies or cultures, 6 colonies or cultures or 7 colonies or cultures. In some embodiments, the colonies or cultures comprise microorganism cells are selected from the group consisting of bacteria, cyanobacteria, microalgae and fungi. In some embodiments, the transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the system further comprises a housing enclosing the device, comprising within the housing: i) a peristaltic pump in fluid communication with the microfluidic device; ii) a fluorescent or luminescent signal sensor or detector comprising a platform to accommodate the microfluidic device; and iii) electronics for acquiring and processing data in electronic communication with the fluorescent or luminescent signal sensor or detector. In some embodiments, the system is configured as depicted in FIG. 7. In some embodiments, the housing is temperature and/or humidity controlled.

In some embodiments, a method of detecting the presence or levels of an analyte in an aqueous sample is provided, wherein the method comprises a) inputting into the microfluidic lumens of a microfluidic device of any one of the embodiments described herein, an aqueous test sample suspected of comprising one or more analytes of interest such that the aqueous test sample contacts the one or more colonies or cultures of microorganism cells; b) measuring the amount of a detectable agent that can correspond to a quantifiable level of analyte. In some embodiments, the detectable agent is a detectable protein, antibody-linked reporter protein, enzymatic assay product, or electrochemical reaction product and the measuring comprises detecting the detectable protein, antibody-linked reporter protein, enzymatic assay product, or electrochemical reaction product. In some embodiments, the detectable protein is a fluorescent protein or a luminescent protein. In some embodiments, measuring comprises measuring the transcription and/or activation levels of the detectable agent, wherein the transcription and/or activation levels of the detectable protein expressed by the one or more colonies or cultures at the predetermined addressable locations correspond to a quantifiable level of analyte. In some embodiments, the method further comprises measuring the fluorescence and/or the luminescence of the one or more detectable proteins expressed by the one or more colonies or cultures at the predetermined addressable locations within the device.

In some embodiments, a collection is provided, wherein the collection comprises a plurality of different nucleic acids, wherein each nucleic acid within said collection comprises a first sequence comprising a promoter responsive to an analyte different from the analyte to which the other promoters in the other nucleic acids are responsive; and a second sequence comprising a reporter protein. In some embodiments, the promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the reporter protein is a fluorescent protein or a luminescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG.

In some embodiments, a method of making a plurality of cell strains for the detection of an analyte is provided, wherein the method comprises introducing into a plurality of cell strains the collection of anyone of the embodiments described herein. In some embodiments, the collection comprises a plurality of different nucleic acids, wherein each nucleic acid within said collection comprises a first sequence comprising a promoter responsive to an analyte different from the analyte to which the other promoters in the other nucleic acids are responsive; and a second sequence comprising a reporter protein. In some embodiments, the promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the reporter protein is a fluorescent protein or a luminescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG.

In some embodiments, cell strains for the detection of an analyte are provided. The cell strains can comprise the nucleic acid of anyone of the embodiments described herein, or can be made by the method of anyone of the embodiments described herein. In some embodiments, the cell is of bacteria, cyanobacteria, microalgae and fungi. In some embodiments, the bacteria is selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans*, and *Staphylococcus aureus*. In some embodiments, the cell is a fungus selected from the group consisting of *Saccharomyces cerevisiae* and *Trichosporon cutaneum*. In some embodiments, the cell comprises *Synechocystis* sp.

In some embodiments, a microfluidic device is provided. The microfluidic device can comprise a plurality of lyophilized cell strains wherein each of said plurality of lyophilized cells strains has been genetically engineered to produce an increased or decreased amount of a detectable agent in the presence of an analyte relative to the amount produced in the absence of said analyte. In some embodiments, the detectable agent is a nucleic acid, detectable protein, antibody-linked reporter protein, enzymatic assay product, or electrochemical reaction product. In some embodiments, the detectable protein is a fluorescent protein or a luminescent protein. In some embodiments, the detectable protein comprises an activity that is increased or decreased in the presence of an analyte. In some embodiments, the detectable agent is a detectable protein, wherein the detectable protein provides a detectable signal. In some embodiments, the nucleic acid is RNA or DNA. In some embodiments, tge microfluidic channels or lumens are arranged in a rotationally symmetric gill cell trapping configuration. In some embodiments, the microfluidic channels or lumens are arranged in 16 or 18 rotationally symmetric gills. In some embodiments, the device comprises about 20,000 chambers or gill traps. In some embodiments, transcription of the biosensor or promoter is induced, promoted or increased by the presence of an analyte. In some embodiments, transcription of the biosensor or promoter is induced, promoted or increased by the presence of an analyte selected from the group consisting of arsenic, cadmium, chromium VI, cobalt, copper, lead, malathion, mercury and zinc. In some embodiments, the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), PybiI (lead), PyjjZ (lead), PcusC (malathion), PnemR (malathion), PmerR (mercury), PmntH (zinc), PshiA (zinc), PyjjZ (zinc), PzntA (zinc) and PzraP (zinc). In some embodiments, the biosensor or promoter comprises a polynucleotide having a sequence identity of at least about 90% to a polynucleotide sequence selected from the group consisting of SEQ ID NOs: 1-43. In some embodiments, the biosensor or promoter comprises a polynucleotide having a sequence identity of at least about 90% to a polynucleotide sequence selected from the group consisting of SEQ ID NOs: 2, 5, 8, 11, 12, 13, 14, 15, 16, 17, 20, 23, 25, 28, 29, 30 and 33. In some embodiments, transcription of the biosensor or promoter is decreased or inhibited by the presence of an analyte. In some embodiments, the biosensor or promoter is decreased or inhibited by the presence of ammonia. In some embodiments, the biosensor or promoter which is decreased or inhibited by the presence of ammonia is selected from the group consisting of PnasA (ammonia), PnasB (ammonia), Pspo1-tnrA1 (ammonia) and Pspo1-tnrA2 (ammonia). In some embodiments, the biosensor or promoter comprises a polynucleotide sequence having at least about 90% sequence identity to SEQ ID NO:1. In some embodiments, the device detects or monitors the presence or levels of one or more analytes at the following concentrations: a) at least about 0.2 nM arsenic; b) at least about 0.44 μM cadmium; c) at least about 2.5 μM chromium (VI); d) at least about 5 μM copper; e) at least about 1 μM mercury; f) at least about 1.8 μM lead; g) at least about 72.5 mg/l malathion; and/or h) at least about 1 ppm ammonia. In some embodiments, the microorganism cells are selected from the group consisting of bacteria, cyanobacteria, microalgae and fungi. In some embodiments, the microorganism cells comprise a bacteria selected from the group consisting of *Escherichia coli, Bacillus subtilis, Salmonella* sp., *Aliivibrio fischeri, Pseudomonas fluorescens, Bacillus* sp., *Cupriavidus metallidurans, Deinococcus radiodurans*, and *Staphylococcus aureus*. In some embodiments, the microorganism cells comprise a fungus selected from the group consisting of *Saccharomyces cerevisiae* and *Trichosporon cutaneum*. In some embodiments, the microorganism cells comprise *Synechocystis* sp. In some embodiments, the device is capable of culturing at least about 4,000 individual strains of microorganism cells. In some embodiments, the expression cassette is in a plasmid which has been introduced into the microorganism. In some embodiments, the expression cassette is integrated into the genome of the microorganism. In some embodiments, the one or more colonies or cultures of microorganisms are one or more different species. In some embodiments, the one or more colonies or cultures of microorganisms are the same species. In some embodiments, the detectable protein is a fluorescent protein. In some embodiments, the fluorescent protein is selected from the group consisting of green fluorescent protein, a yellow fluorescent protein, a cyan fluorescent protein, a red-shifted green fluorescent protein (rs-GFP), and miniSOG. In some embodiments, the detectable protein is a luminescent protein. In some embodiments, the luminescent protein is bacterial luciferase (Lux).

APPENDIX A

| | | | | | | |
|---|---|---|---|---|---|---|
| | | | Candidate toxin-responsive promoters | | | |
| Toxin | Gene/Promoter | Source | RBS | Host Strain/Plasmid | Concentration Sensed in Microfluidic Device (μM) | SNR after 6 h |
| Ammonia | $p_{nasA}$ | *B. subtilis* genome | native | | | |
| Ammonia | $p_{nasA}$ | *B. subtilis* genome | synthetic | | | |
| Ammonia | $p_{nasB}$ | *B. subtilis* genome | native | | | |
| Ammonia | $p_{nasB}$ | *B. subtilis* genome | synthetic | | | |
| Ammonia | $p_{spo1-tnrA1}$ | *B. subtilis* genome | synthetic | | | |
| Ammonia | $p_{spo1-tnrA2}$ | *B. subtilis* genome | synthetic | | | |
| Arsenic | arsR/$p_{arsR}$ | *E. coli* plasmid | native | *E. coli* MG1655/As1 | 0.13 | 20 |
| Arsenic | arsR/$p_{arsR}$ | *E. coli* genome | synthetic | *E. coli* LABEC01/As3 | | |
| Arsenic | arsR/$p_{arsR}$ | *E. coli* genome | synthetic | *E. coli* MG1655/As3 | 0.13 | 33 |
| Arsenic | arsR/$p_{arsR}$ | *S. aureus* plasmid | native | *E. coli* MG1655/As5 | | |
| Arsenic | $p_{arsR}$ | *E. coli* RNA-Seq | | | | |
| Cadmium | cadC/$P_{cadC}$ | *S. aureus* plasmid | native | *E. coli* MG1655/Cd1 | 0.04 | 17 |
| Cadmium | cadC/$P_{cadC}$ | *S. aureus* plasmid | synthetic | *E. coli* MG1655/Cd2 | | |
| Cadmium | cadR/$p_{cadR}$ | *P. putida* genome | native | *E. coli* MG1655/Cd4 | | |
| Cadmium | cadR/$p_{cadR}$ | *P. putida* genome | synthetic | *E. coli* MG1655/Cd3 | | |
| Cadmium | $p_{antA}$ | *E. coli* RNA-Seq | | | | |
| Chromium(VI) | chrB/$p_{chrB}$ | *C. metallidurans* plasmid | native | *E. coli* MG1655/Cr3 | | |
| Chromium(VI) | chrB/$p_{chrB}$ | *C. metallidurans* plasmid | synthetic | *E. coli* MG1655/Cr2 | | |
| Chromium(VI) | chrB/$p_{chrB}$ | *O. tritici* transposon | native | *E. coli* LABEC01/Cr5 | 5 | 5 |
| Chromium(VI) | chrB/$p_{chrB}$ | *O. tritici* transposon | native | *E. coli* MG1655/Cr5 | | |
| Chromium(VI) | chrB/$p_{chrB}$ | *O. tritici* transposon | synthetic | *E. coli* LABEC01/Cr4 | | |
| Chromium(VI) | chrB/$p_{chrB}$ | *O. tritici* transposon | synthetic | *E. coli* MG1655/Cr4 | | |
| Chromium(VI) | chrS/$p_{chrS}$ | *B. subtilis* genome | synthetic | *E. coli* MG1655/Cr1 | | |
| Chromium(VI) | $p_{recN}$ | *E. coli* RNA-Seq | | | | |
| Chromium(VI) | $p_{sulA}$ | *E. coli* RNA-Seq | | | | |
| Chromium(VI) | $p_{umuD}$ | *E. coli* RNA-Seq | | | | |
| Cobalt | $p_{dadA}$ | *E. coli* RNA-Seq | | | | |
| Cobalt | $p_{hmp}$ | *E. coli* RNA-Seq | | | | |
| Cobalt | $p_{ilvB}$ | *E. coli* RNA-Seq | | | | |
| Cobalt | $p_{lipA}$ | *E. coli* RNA-Seq | | | | |
| Cobalt | $p_{mmuP}$ | *E. coli* RNA-Seq | native | *E. coli* MG1655/Co7 | | |
| Cobalt | $p_{mmuP}$ | *E. coli* RNA-Seq | synthetic | *E. coli* MG1655/Co8 | | |
| Cobalt | nmtR/$p_{nmtR}$ | *M. tuberculosis* genome | native | *E. coli* MG1655/Co1 | | |
| Cobalt | nmtR/$p_{nmtR}$ | *M. tuberculosis* genome | synthetic | *E. coli* MG1655/Co2 | | |
| Cobalt | $p_{soxR}$ | *E. coli* RNA-Seq | | | | |
| Cobalt | $p_{tehA}$ | *E. coli* RNA-Seq | | | | |
| Cobalt | $p_{ygbA}$ | *E. coli* RNA-Seq | native | *E. coli* MG1655/Co3 | | |
| Cobalt | $p_{ygbA}$ | *E. coli* RNA-Seq | synthetic | *E. coli* MG1655/Co4 | | |
| Cobalt | $p_{yjbJ}$ | *E. coli* RNA-Seq | native | *E. coli* MG1655/Co5 | | |
| Cobalt | $p_{yjbJ}$ | *E. coli* RNA-Seq | synthetic | *E. coli* MG1655/Co6 | | |
| Cobalt | $p_{yqfA}$ | *E. coli* RNA-Seq | | | | |
| Copper | cueR/$p_{copA}$ | *E. coli* genome | native | *E. coli* MG1655/Cu1 | 25 | 65 |
| Copper | (cusS/R)/$p_{cusC}$ | *E. coli* genome | native | *E. coli* MG1655/Cu2 | | |
| Copper | $p_{cusC}$ | *E. coli* RNA-Seq | | | | |
| Copper | $p_{cusR}$ | *E. coli* RNA-Seq | | | | |
| Lead | pbrR/$p_{pbrR}$ | *C. metallidurans* plasmid | native | *E. coli* LABEC01/Pb1 | | |

APPENDIX A-continued

Candidate toxin-responsive promoters

| Toxin | Gene/Promoter | Source | RBS | Host Strain/Plasmid | Concentration Sensed in Microfluidic Device (µM) | SNR after 6 h |
|---|---|---|---|---|---|---|
| Lead | pbrR/$p_{pbrR}$ | C. metallidurans plasmid | native | E. coli MG1655/Pb1 | | |
| Lead | pbrR/$p_{pbrR}$ | C. metallidurans plasmid | synthetic | E. coli LABEC01/Pb2 | 7 | 18 |
| Lead | pbrR/$p_{pbrR}$ | C. metallidurans plasmid | synthetic | E. coli MG1655/Pb2 | | |
| Lead | $p_{mntH}$ | E. coli RNA-Seq | | | | |
| Lead | $p_{shtA}$ | E. coli RNA-Seq | | | | |
| Lead | $p_{ybtI}$ | E. coli RNA-Seq | | | | |
| Lead | $p_{yjjz}$ | E. coli RNA-Seq | | | | |
| Malathion | $p_{cusC}$ | E. coli RNA-Seq | | | | |
| Malathion | $p_{nemR}$ | E. coli RNA-Seq | | | | |
| Mercury | merR/$p_{merR}$ | E. coli plasmid | native | E. coli MG1655/Hg4 | | |
| Mercury | merR/$p_{merR}$ | E. coli plasmid | synthetic | E. coli MG1655/Hg3 | 0.1 | 20 |
| Mercury | merR/$p_{merR}$ | S. aureus plasmid | native | E. coli MG1655/Hg2 | | |
| Mercury | merR/$p_{merR}$ | S. aureus plasmid | synthetic | E. coli MG1655/Hg1 | | |
| Mercury | merR/$p_{merR}$ | S. marcescens plasmid | native | E. coli MG1655/Hg6 | | |
| Mercury | merR/$p_{merR}$ | S. marcescens plasmid | synthetic | E. coli MG1655/Hg5 | | |
| Zinc | $p_{mntH}$ | E. coli RNA-Seq | | | | |
| Zinc | $p_{shtA}$ | E. coli RNA-Seq | | | | |
| Zinc | $p_{yjjz}$ | E. coli RNA-Seq | | | | |
| Zinc | $p_{zntA}$ | E. coli RNA-Seq | | | | |
| Zinc | $p_{zraP}$ | E. coli RNA-Seq | | | | |

As shown in Appendix A, All candidate toxin-responsive promoters identified in this work, ordered by the toxin of expected sensitivity. In the case of promoters identified by RNA-Seq, the gene is unknown. For promoters that have been expressed in a synthetic construct, the selected RBS and host strain are shown. If this synthetic construct has been used to sense the toxin within a microfluidic device, the concentration sensed and SNR after 6 h are shown.

Appendix B

RNA-Seq Results for Promoter Activation in E. coli MG1655 in Response to Single and Multiple Toxin Exposures at Low and High Concentrations:

Our analysis of the sequencing data from RNA-Seq experiments to determine candidate genes that are induced upon toxin exposure consisted of three main tasks: sequence alignment, quantification of gene expression, and identification of differentially expressed genes.

Sequence Alignment:

Reads were aligned to the reference E. coli K-12 substr. MG1655 genome using a tolerance of at most two mismatches per alignment to protect against sequencing errors. The alignment was performed using Bowtie software, 27 which is known to be very efficient in aligning reads to a reference genome.

Quantification of Gene Expression:

The expression level of each gene was determined as a function of the number of aligned reads mapping to the gene. After analyzing several approaches adopted in the literature to tabulate the number of reads mapping to each gene, we implemented our own software capable of reproducing the counting algorithms behind some of the standard toolboxes such as Bedtools28 and HTSeq.29 In particular, we counted the number of reads mapping to each gene regardless of whether the read mapped to several genes, taking into account the strand-specificity of each read. Additionally, we implemented our own algorithms for sequence alignment and quantification of gene expression in order to crosscheck all results.

Identification of Differentially Expressed Genes:

Finally, a set of statistical and information theory algorithms were applied in order to extract not only differentially expressed (DE) genes for each toxin with respect to the control samples (pure water) but also toxin-specific genes. DESeq is a standard tool for identifying DE genes that allowed us to select sensitive genes with differential expression between the control samples (pure water) and the cells exposed to toxin. It assumes that the number of counts for each gene across experimental replicates follows a negative binomial distribution. 30, 31 We considered genes with a False Discovery Rate (FDR) lower than 1% as DE in order to ensure statistically robust DE genes. We note that some genes showed high variability in the control samples across different batches of RNA-Seq experiments, indicating that these genes are very sensitive to environmental conditions. We identified 846 of these genes by performing a DESeq differential analysis (FDR<1%) between the control samples in different batches and subsequently removed them from the candidate pool. The number of DE genes (FDR<1%) identified for each condition when compared to the negative samples in the same batch and after removing genes that are DE between control samples is given in Table 9.

Ideally, good candidate specific genes are those with a significant fold-change with respect to the control samples but with a negligible fold-change with respect to the other toxins. Additionally, genes with the largest number of counts and expression levels are preferable in order to maximize the signal-to-noise ratio. When it is not possible to find toxin-specific genes, the next generation of good candidates is formed by those genes satisfying the above properties for a small subset of toxins (multiple-toxin response). It is desirable to have single-toxin-specific genes for several of the toxins in the combination in order to determine toxin-specific multi-gene-responses by means of logical operations.

In rare cases, shared genes are differentially expressed. Therefore, we have developed information theoretic measures to improve the toxin separability. The core idea of the approach is that low entropies (or highly informative genes) correspond to toxin-specific genes, while large entropies (low information) are associated with scenarios in which DE fold-changes across different toxins are similar and should be discarded. The result of the analysis shows that toxins can easily be discriminated by using simple boolean rules as shown in the main report.

All references listed herein are incorporated herein by reference in their entireties, including the following references:

REFERENCES

1. Corinna Cortes and Vladimir Vapnik. Support-vector networks. Machine learning, 20(3):273-297, 1995.
2. Richard O Duda, Peter E Hart, and David G Stork. Pattern classification. John Wiley & Sons, 2012.
3. Irene Rodriguez-Lujan, Ramon Huerta, Charles Elkan, and Carlos Santa Cruz. Quadratic programming feature selection. The Journal of Machine Learning Research, 11:1491-1516, 2010.
4. Ramon Huerta, Shankar Vembu, J Amigo, Thomas Nowotny, and Charles Elkan. Inhibition in multiclass classification. Neural computation, 24(9):2473-2507, 2012.
5. Ben Langmead, Cole Trapnell, Mihai Pop, and Steven L. Salzberg. Ultrafast and memory-efficient alignment of short DNA sequences to the human genome. Genome Biol, 10 (3): R25, 2009.
6. Aaron R. Quinlan and Ira M. Hall. BEDTools: a flexible suite of utilities for comparing genomic features. Bioinformatics, 26(6):841-842, March 2010.
7. Simon Anders, Paul Theodor Pyl, and Wolfgang Huber. HTSeq-a Python framework to work with high-throughput sequencing data. bioRxiv, 2014.
8. Simon Anders and Wolfgang Huber. Differential expression analysis for sequence count data. Genome Biol, 11 (10): R106, 2010.
9. Simon Anders, Davis J. McCarthy, Yunshun Chen, Michal Okoniewski, Gordon K. Smyth, Wolfgang Huber, and Mark D. Robinson. Count-based differential expression analysis of RNA sequencing data using R and Bioconductor. Nat Protoc, 8(9):1765-1786, September 2013.
10. C. Xu, W. Shi, and B. P. Rosen. The chromosomal arsr gene of *Escherichia coli* encodes a trans-acting metalloregulatory protein. J Biol Chem, 271(5):2427-2432, February 1996.
11. J. Wu and B. P. Rosen. Metalloregulated expression of the ars operon. J Biol Chem, 268(1):52-58, January 1993.
12. Judith Stocker, Denisa Balluch, Monika Gsell, Hauke Harms, Jessika Feliciano, Sylvia Daunert, Khurseed A. Malik, and Jan Roelof van der Meer. Development of a set of simple bacterial biosensors for quantitative and rapid measurements of arsenite and arsenate in potable water. Environ Sci Technol, 37(20):4743-4750, October 2003.
13. Laura S. Busenlehner, Mario A. Pennella, and David P. Giedroc. The smtb/arsr family of metalloregulatory transcriptional repressors: Structural insights into prokaryotic metal resistance. FEMS Microbiol Rev, 27 (2-3): 131-143, June 2003.
14. E. A. Permina, A. E. Kazakov, 0. V. Kalinina, and M. S. Gelfand. Comparative genomics of regulation of heavy metal resistance in eubacteria. BMC Microbiol, 6:49, 2006.
15. G. Endo and S. Silver. Cadc, the transcriptional regulatory protein of the cadmium resistance system of *Staphylococcus aureus* plasmid pi258. J Bacteriol, 177(15): 4437-4441, August 1995.
16. S. W. Lee, E. Glickmann, and D. A. Cooksey. Chromosomal locus for cadmium resistance in *Pseudomonas putida* consisting of a cadmium-transporting atpase and a merr family response regulator. Appl Environ Microbiol, 67(4):1437-1444, April 2001.
17. Rita Branco, Ana Paula Chung, Tatiana Johnston, Volkan Gurel, Paula Morais, and Anatoly Zhitkovich. The chromate-inducible chrbacf operon from the transposable element tnotchr confers resistance to chromium (vi) and superoxide. J Bacteriol, 190(21):6996-7003, November 2008.
18. Rita Branco, Armando Cristovao, and Paula V. Morais. Highly sensitive, highly specific whole-cell bioreporters for the detection of chromate in environmental samples. PLoS One, 8 (1): e54005, 2013.
19. Esther Aguilar-Barajas, Selene Jacobo-Arreola, Luis A. Verduzco-Rosas, Rafael Jimenez-Mejia, Martha I. Ramirez-Diaz, Adriana Julian-Sanchez, Hector Riveros-Rosas, and Carlos Cervantes. An lrp-type transcriptional regulator controls expression of the *Bacillus subtilis* chromate transporter. Antonie Van Leeuwenhoek, 104(6):941-948, December 2013.
20. Christopher Rensing and Gregor Grass. *Escherichia coli* mechanisms of copper homeostasis in a changing environment. FEMS Microbiol Rev, 27 (2-3): 197-213, June 2003.
21. Anna Jaroslawiecka and Zofia Piotrowska-Seget. Lead resistance in microorganisms. Microbiology, 160 (Pt 1): 12-25, January 2014.
22. Jon L. Hobman, Daniel J. Julian, and Nigel L. Brown. Cysteine coordination of pb (ii) is involved in the pbrr-dependent activation of the lead-resistance promoter, ppbra, from *Cupriavidus metallidurans* ch34. BMC Microbiol, 12:109, 2012. 46
23. A. Ivask, K. Hakkila, and M. Virta. Detection of organomercurials with sensor bacteria. Anal Chem, 73(21): 5168-5171, November 2001.
24. G. Nucifora, L. Chu, S. Silver, and T. K. Misra. Mercury operon regulation by the merr gene of the organomercurial resistance system of plasmid pdu1358. J Bacteriol, 171(8):4241-4247, August 1989.
25. S. J. Park, J. Wireman, and A. O. Summers. Genetic analysis of the tn21 mer operatorpromoter. J Bacteriol, 174(7):2160-2171, April 1992.
26. L. Chu, D. Mukhopadhyay, H. Yu, K. S. Kim, and T. K. Misra. Regulation of the *Staphylococcus aureus* plasmid pi258 mercury resistance operon. J Bacteriol, 174(21): 7044-7047, November 1992.
27. D. Rother, R. Mattes, and J. Altenbuchner. Purification and characterization of merr the regulator of the broad-spectrum mercury resistance genes in *Streptomyces lividans* 1326. Mol Gen Genet, 262(1):154-162, August 1999.
28. Dennis J. Paustenbach, Brent L. Finley, Fionna S. Mowat, and Brent D. Kerger. Human health risk and exposure assessment of chromium (vi) in tap water. J Toxicol Environ Health A, 66(14):1295-1339, July 2003.
29. Matthew D. Stout, Ronald A. Herbert, Grace E. Kissling, Bradley J. Collins, Gregory S. Travlos, Kristine L. Witt, Ronald L. Melnick, Kamal M. Abdo, David E. Malarkey, and Michelle J. Hooth. Hexavalent chromium is carcinogenic to f344/n rats and b6c3f1 mice after chronic oral exposure. Environ Health Perspect, 117(5):716-722, May 2009.
30. Tor Norseth. The carcinogenicity of chromium. Environmental health perspectives, 40:121, 1981.
31. Corinna Cortes and Vladimir Vapnik. Support-vector networks. Machine learning, 20(3):273-297, 1995.

32. Richard O Duda, Peter E Hart, and David G Stork. Pattern classification. John Wiley & Sons, 2012.
33. Ramon Huerta, Shankar Vembu, J Amigo, Thomas Nowotny, and Charles Elkan. Inhibition in multiclass classification. Neural computation, 24(9):2473-2507, 2012.
34. Alexander Vergara, Jordi Fonollosa, Jonas Mahiques, Marco Trincavelli, Nikolai Rulkov, and Ramon Huerta. On the performance of gas sensor arrays in open sampling systems using inhibitory support vector machines. Sensors and Actuators B: Chemical, 185:462-477, 2013.
35. Alexander Vergara, Shankar Vembu, Tuba Ayhan, Margaret A Ryan, Margie L Homer, and Ramon Huerta. Chemical gas sensor drift compensation using classifier ensembles. Sensors and Actuators B: Chemical, 166:320-329, 2012.
36. Ben Langmead, Cole Trapnell, Mihai Pop, and Steven L. Salzberg. Ultrafast and memory-efficient alignment of short DNA sequences to the human genome. Genome Biol, 10 (3): R25, 2009.
37. Aaron R. Quinlan and Ira M. Hall. BEDTools: a flexible suite of utilities for comparing genomic features. Bioinformatics, 26(6):841-842, March 2010.
38. Simon Anders, Paul Theodor Pyl, and Wolfgang Huber. HTSeq-a Python framework to work with high-throughput sequencing data. bioRxiv, 2014. Simon Anders and Wolfgang Huber. Differential expression analysis for sequence count data. Genome Biol, 11 (10): R106, 2010.
39. Simon Anders, Davis J. McCarthy, Yunshun Chen, Michal Okoniewski, Gordon K. Smyth, Wolfgang Huber, and Mark D. Robinson. Count-based differential expression analysis of RNA sequencing data using R and Bioconductor. Nat Protoc, 8(9):1765-1786, September 2013.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A microfluidic device comprising a plurality of colonies or cultures of microorganism cells in an array connected in parallel at predetermined addressable locations that each comprise a trapping chamber connected in parallel to a microfluidic medium delivery channel, each trapping chamber being connected by a feeder channel to a cell reservoir, wherein the horizontal and vertical spotting pitch of the cell reservoirs is compatible with spotting of microorganism cells by a robotic pin tool or liquid handling instrument, wherein the colonies or cultures of microorganism cells are each spotted within the cell reservoir and expand via growth through the feeder channel into the trapping chamber, and wherein each of the cells within the colonies or cultures comprises an expression cassette comprising a biosensor or promoter operably linked to a polynucleotide encoding a detectable agent, wherein transcription of the biosensor or promoter is modulated by the presence of an analyte.

2. The microfluidic device of claim 1, wherein the detectable agent is a nucleic acid, detectable protein, antibody-linked reporter protein, enzymatic assay product, or electrochemical reaction product.

3. The microfluidic device of claim 2, wherein the detectable agent is a fluorescent protein or a luminescent protein.

4. The microfluidic device of claim 1, wherein transcription of the biosensor or promoter is induced, promoted or increased by the presence of an analyte selected from the group consisting of arsenic, cadmium, chromium VI, cobalt, copper, lead, malathion, mercury and zinc.

5. The microfluidic device of claim 1, wherein the biosensor or promoter is selected from the group consisting of ParsR (arsenic), PcadC (cadmium), PcadR (cadmium), PzntA (cadmium), PchrB (chromium VI), PchrS (chromium VI), PrecN (chromium VI), PsulA (chromium VI), PumuD (chromium VI), PdadA (cobalt), Phmp (cobalt), PilvB (cobalt), PilvB (cobalt), PlipA (cobalt), PmmuP (cobalt), PnmtR (cobalt), PsoxR (cobalt), PtehA (cobalt), PygbA (cobalt), PyjbJ (cobalt), PyqfA (cobalt), PcopA (copper), PcusC (copper), PcusR (copper), PpbrR (lead), PmntH (lead), PshiA (lead), Pybil (lead), PyjjZ (lead), PcusC (malathion), PnemR (malathion), PmerR (mercury), PmntH (zinc), PshiA (zinc), PyjjZ (zinc), PzntA (zinc) and PzraP (zinc).

6. The microfluidic device of claim 1, wherein the biosensor or promoter comprises a polynucleotide having a sequence identity of at least about 90% to a polynucleotide sequence selected from the group consisting of SEQ ID NOs: 1-43.

7. The microfluidic device of claim 1, wherein the biosensor or promoter is decreased or inhibited by the presence of ammonia.

8. The microfluidic device of claim 7 wherein the biosensor or promoter which is decreased or inhibited by the presence of ammonia is selected from the group consisting of PnasA (ammonia), PnasB (ammonia), Pspo1-tnrA1 (ammonia) and Pspo1-tnrA2 (ammonia).

9. The microfluidic device of claim 1, wherein the device detects or monitors the presence or levels of one or more analytes at the following concentrations:
    a) at least about 0.2 nM arsenic;
    b) at least about 0.44 µM cadmium;
    c) at least about 2.5 µM chromium(VI);
    d) at least about 5 µM copper;
    e) at least about 1 µM mercury;
    f) at least about 1.8 µM lead;
    g) at least about 72.5 mg/l malathion; and/or
    h) at least about 1 ppm ammonia.

10. The microfluidic device of claim 1, wherein the microorganism cells are selected from the group consisting of bacteria, cyanobacteria, microalgae and fungi.

11. The microfluidic device of claim 1, wherein the device is capable of culturing at least about 4,000 individual strains of microorganism cells.

12. The microfluidic device of claim 1, wherein the one or more colonies or cultures of microorganisms are lyophilized (freeze-dried).

13. The microfluidic device of claim 3, wherein the detectable agent is a fluorescent protein selected from the group consisting of green fluorescent protein, a yellow fluorescent protein, a cyan fluorescent protein, a red-shifted green fluorescent protein (rs-GFP), and miniSOG.

14. The microfluidic device of claim 1, wherein for each of said plurality of colonies or cultures transcription of the biosensor or promoter for such colony or culture is modulated by the presence of a different analyte than the biosensor or promoter in the other of said plurality of colonies or cultures.

15. A system comprising the microfluidic device of claim 1.

16. The system of claim 15, wherein the system further comprises a housing enclosing the device, comprising within the housing:
    i) a peristaltic pump in fluid communication with the microfluidic device; ii) a fluorescent or luminescent signal sensor or detector comprising a platform to accommodate the microfluidic device; and
    iii) electronics for acquiring and processing data in electronic communication with the fluorescent or luminescent signal sensor or detector.

17. A method of detecting the presence or levels of an analyte in an aqueous sample, comprising:
    a) inputting into the microfluidic lumens of a microfluidic device of claim 1 an aqueous test sample suspected of comprising one or more analytes of interest such that the aqueous test sample contacts the plurality of colonies or cultures of microorganism cells;
    b) measuring the amount of a detectable agent that can correspond to a quantifiable level of analyte.

18. The method of claim 17, wherein measuring comprises measuring the transcription and/or activation levels of the detectable agent, wherein the transcription and/or activation levels of the detectable agent expressed by the plurality of colonies or cultures at the predetermined addressable locations correspond to a quantifiable level of analyte.

* * * * *